United States Patent
Haketa et al.

(10) Patent No.: US 10,622,569 B2
(45) Date of Patent: Apr. 14, 2020

(54) COMPOUND, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Tasuku Haketa, Chiba (JP); Masahiro Kawamura, Ichihara (JP); Yumiko Mizuki, Basel (CH); Hirokatsu Ito, Ichihara (JP); Tomoharu Hayama, Utsunomiya (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 194 days.

(21) Appl. No.: 14/917,174

(22) PCT Filed: Oct. 1, 2014

(86) PCT No.: PCT/JP2014/076326
§ 371 (c)(1),
(2) Date: Mar. 7, 2016

(87) PCT Pub. No.: WO2015/050173
PCT Pub. Date: Apr. 9, 2015

(65) Prior Publication Data
US 2016/0218299 A1    Jul. 28, 2016

(30) Foreign Application Priority Data

Oct. 3, 2013 (JP) .................................. 2013-208532

(51) Int. Cl.
*H01L 51/00* (2006.01)
*C07D 401/04* (2006.01)
(Continued)

(52) U.S. Cl.
CPC ........ *H01L 51/0072* (2013.01); *C07D 209/86* (2013.01); *C07D 401/04* (2013.01);
(Continued)

(58) Field of Classification Search
CPC combination set(s) only.
See application file for complete search history.

(56) References Cited

U.S. PATENT DOCUMENTS

2008/0122344 A1    5/2008  Shin et al.
2008/0131731 A1*   6/2008  Igawa ................. H01L 51/0072
                                                       428/690
(Continued)

FOREIGN PATENT DOCUMENTS

CN    103319535 A    9/2013
JP    11-149987 A    6/1999
(Continued)

OTHER PUBLICATIONS

Machine translatino of KR 20120044523 Generated Jun. 2017.*
International Search Report dated Dec. 22, 2014 in PCT/JP2014/076326 filed on Oct. 1, 2014.

*Primary Examiner* — Jennifer A Chriss
*Assistant Examiner* — Sean M DeGuire
(74) *Attorney, Agent, or Firm* — Oblon, McClelland, Maier & Neustadt, L.L.P.

(57) ABSTRACT

The present invention provides a compound having a fluoranthene skeleton represented by the formula (1); an organic electroluminescence device having plural organic thin film layers including a light-emitting layer between a cathode and an anode, wherein at least one layer of the organic thin film layers contains the compound; and an electronic equipment provided with the organic electroluminescence device. The organic electroluminescence device realizes further lower voltage driving and has high emission efficiency. [In (Continued)

the formula (1), $X^1$ to $X^{10}$, L, $R^1$ to $R^9$, and n are as stated in the description.]

32 Claims, 1 Drawing Sheet

(51) Int. Cl.
    *C07D 209/86*     (2006.01)
    *C09K 11/02*     (2006.01)
    *C09K 11/06*     (2006.01)
    *H01L 51/50*     (2006.01)

(52) U.S. Cl.
    CPC ............ C09K 11/025 (2013.01); C09K 11/06 (2013.01); H01L 51/0054 (2013.01); H01L 51/0058 (2013.01); H01L 51/0059 (2013.01); H01L 51/0067 (2013.01); H01L 51/0085 (2013.01); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *C09K 2211/185* (2013.01); *H01L 51/5008* (2013.01); *H01L 51/5016* (2013.01); *H01L 51/5056* (2013.01); *H01L 51/5064* (2013.01); *H01L 51/5092* (2013.01)

(56) References Cited

U.S. PATENT DOCUMENTS

| | | |
|---|---|---|
| 2009/0102371 A1 | 4/2009 | Hashimoto et al. |
| 2009/0247753 A1 | 10/2009 | Takasu et al. |
| 2009/0278118 A1 | 11/2009 | Ohrui et al. |
| 2012/0223295 A1 | 9/2012 | Inoue et al. |
| 2012/0275421 A1 | 11/2012 | Vukovic et al. |
| 2014/0048784 A1 | 2/2014 | Inoue et al. |
| 2014/0100367 A1 | 4/2014 | Yoon et al. |
| 2014/0107338 A1 | 4/2014 | Ahn et al. |
| 2014/0114069 A1 | 4/2014 | Kim et al. |
| 2015/0108449 A1* | 4/2015 | Huang ................ C07F 9/5325 548/310.7 |
| 2015/0280139 A1* | 10/2015 | Ichihashi ............ C07D 213/74 257/40 |

FOREIGN PATENT DOCUMENTS

| | | | |
|---|---|---|---|
| JP | 2002-69044 | A | 3/2002 |
| JP | 2005-104981 | A | 4/2005 |
| JP | 2007-314510 | A | 12/2007 |
| JP | 2008-137978 | A | 6/2008 |
| JP | 2008-156315 | A | 7/2008 |
| JP | 2009-256348 | A | 11/2009 |
| JP | 2012-140365 | A | 7/2012 |
| KR | 10-2012-0044523 | A | 5/2012 |
| KR | 20120044523 | A * | 5/2012 |
| WO | 2009/099133 | A1 | 8/2009 |
| WO | 2012/036482 | A1 | 3/2012 |
| WO | 2012/108388 | A1 | 8/2012 |
| WO | 2012/108389 | A1 | 8/2012 |
| WO | 2012/121561 | A1 | 9/2012 |
| WO | 2012/134124 | A1 | 10/2012 |
| WO | 2012/165844 | A1 | 12/2012 |
| WO | 2013/032278 | A1 | 3/2013 |
| WO | 2013/146942 | A1 | 10/2013 |
| WO | 2013/182046 | A1 | 12/2013 |
| WO | 2014/057874 | A1 | 4/2014 |

* cited by examiner

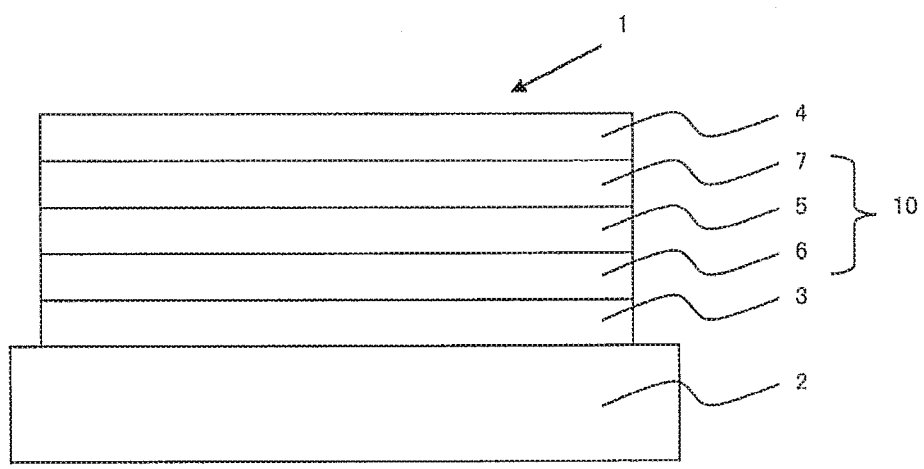

COMPOUND, ORGANIC ELECTROLUMINESCENT ELEMENT, AND ELECTRONIC DEVICE

TECHNICAL FIELD

The present invention relates to a compound, an organic electroluminescence device using the compound, and an electronic equipment provided with the organic electroluminescence device.

BACKGROUND ART

An organic electroluminescence (EL) device is generally composed of an anode, a cathode, and one or more organic thin film layers sandwiched between the anode and the cathode. When a voltage is applied between the electrodes, electrons are injected from the cathode and holes are injected from the anode each into a light emitting region. The injected electrons recombine with the injected holes in the light emitting region to form excited states. When the excited states return to the ground state, the energy is released as light.

Many researches have been made on the applications of organic EL device to display, etc. because of its possibility of a wide selection of emission colors by using various emitting materials in a light emitting layer. Particularly, the research on the materials which emit three primary red, green, blue colors has been made most actively, and the intensive research has been made to improve their properties.

One of the biggest challenges in organic EL devices is to satisfy both high emission efficiency and low driving voltage. As a means for obtaining high-efficiency light-emitting devices, there is known a method of forming a light-emitting layer by doping a host material with a few % of a dopant material. The host material is required to satisfy high carrier mobility and uniform film formability, and the dopant material is required to satisfy high fluorescence quantum yield and uniform dispersibility.

Heretofore, as materials for organic EL devices, there are known compounds having a fluoranthene derivative substituted at the 9-position of a carbazole group (see PTLs 1 to 5), bisfluoranthene derivatives having a carbazolyl group (see PTLs 6 and 7), etc. However, the compounds disclosed in these patent publications still have room for improvement especially in driving voltage and emission efficiency.

CITATION LIST

Patent Literature

PTL 1: WO 2012/108388
PTL 2: WO 2012/108389
PTL 3: JP 11-149987 A
PTL 4: US Patent Application Publication No. 2008/0122344
PTL 5: JP 2012-140365 A
PTL 6: JP 2005-104981 A
PTL 7: JP 2002-69044 A

SUMMARY OF INVENTION

Technical Problem

The present invention has been made under the situation, and its object is to provide an organic electroluminescence device capable of realizing a further lower driving voltage and having high emission efficiency and an electronic equipment provided with the organic electroluminescence device, and as a compound for realizing these.

Solution to Problem

The present inventors have made assiduous studies for attaining the above-mentioned objects and, as a result, have found that a compound having a specific structure with a fluoranthene skeleton can attain the objects. The inventors have completed the present invention on the basis of this finding.

One aspect of the present invention includes the following [1] to [4].

[1] A compound represented by the following formula (1);

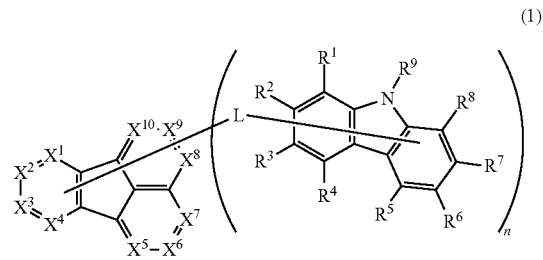

wherein $X^1$ to $X^{10}$ each independently represent C—R (where R represents a hydrogen atom, a substituent or a single bond bonding to L), or a nitrogen atom;

L represents a single bond, a substituted or unsubstituted arylene group having 6 to 30 ring carbon atoms, a substituted or unsubstituted heteroarylene group having 5 to 30 ring carbon atoms, or a divalent group composed of 2 to 4 of the arylene group and the heteroarylene group bonding to each other;

$R^1$ to $R^8$ each independently represent a hydrogen atom, a fluorine atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group from 6 to 30 ring carbon atoms, a substituted or unsubstituted alkylthio group having 1 to 20 carbon atoms, a substituted or unsubstituted arylthio group having 6 to 30 ring carbon atoms, a silyl group represented by —Si($R^{100}$)$_3$ [where $R^{100}$ represents a hydrogen atom, an alkyl group having 1 to 30 carbon atoms, or an aromatic hydrocarbon group having 6 to 60 ring carbon atoms, three $R^{100}$'s may be the same or different], a substituted or unsubstituted alkylamino group having 2 to 30 carbon atoms, a substituted or unsubstituted arylamino group having 6 to 60 ring carbon atoms, a substituted or unsubstituted aryl group having 6 to 30 ring carbon atoms, or a heteroaryl group selected from the group consisting of a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group and a xanthenyl group which each may be substituted or unsubstituted, or a single bond bonding to L;

$R^9$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring carbon atoms; and n indicates an integer of 1 to 4, and when n is an integer of 2 to 4, plural parenthesized groups may be the same or different, provided that the number of the fluoranthene structure that the compound represented by the general formula (1) has is one.

[2] A material for organic electroluminescence devices containing the compound of the above [1].

[3] An organic electroluminescence device having plural organic thin film layers including a light-emitting layer between a cathode and an anode, wherein at least one layer of the organic thin film layers contains the compound of the above [1].

[4] An electronic equipment provided with the organic electroluminescence device of the above [3].

Advantageous Effects of Invention

According to the present invention, there can be provided an organic electroluminescence device capable of realizing a further lower driving voltage and having high emission efficiency and an electronic equipment provided with the organic electroluminescence device, as well as a compound for realizing these.

BRIEF DESCRIPTION OF DRAWING

The Figure shows a schematic illustration of an example of an organic EL device according to one embodiment of the present invention.

DESCRIPTION OF EMBODIMENTS

The term of "a to b carbon atoms" referred to by "a substituted or unsubstituted group X having a to b carbon atoms" used herein is the number of carbon atoms of the unsubstituted group X and does not include any carbon atom in the substituent of the substituted group X.

The term of "ring carbon atoms" means carbon atoms constituting a saturated ring, an unsaturated ring, or an aromatic ring, and does not include any carbon atom in the substituent bonding to the ring.

The terms of "ring atoms" means atoms constituting a saturated ring, an unsaturated ring, an aromatic ring or a hetero ring, and does not include any hydrogen atom and any atom in the substituent bonding to the ring.

The definition of "hydrogen atom" includes isotopes different in the neutron numbers, i.e., light hydrogen (protium), heavy hydrogen (deuterium), and tritiated hydrogen (tritium).

The "substituent" and the optional substituent referred to by "substituted or unsubstituted" are, unless otherwise defined, preferably selected from the group consisting of an alkyl group having 1 to 20 (preferably 1 to 10, more preferably 1 to 6) carbon atoms; a cycloalkyl group having 3 to 20 (preferably 3 to 6, more preferably 5 or 6) ring carbon atoms; an aryl group having 6 to 30 (preferably 6 to 24, more preferably 6 to 12) ring carbon atoms; an aralkyl group having 7 to 30 (preferably 7 to 10, more preferably 7 to 12) carbon atoms and having an aryl group having 6 to 30 (preferably 6 to 24, more preferably 6 to 12) ring carbon atoms; an amino group; a mono- or dialkylamino group having an alkyl group having 1 to 20 (preferably 1 to 10, more preferably 1 to 6) carbon atoms; a mono- or diarylamino group having an aryl group having 6 to 30 (preferably 6 to 24, more preferably 6 to 12) ring carbon atoms; an alkoxy group having an alkyl group having 1 to 30 (preferably 1 to 10, more preferably 1 to 6) carbon atoms; an aryloxy group having an aryl group having 6 to 30 (preferably 6 to 24, more preferably 6 to 12) ring carbon atoms; a mono-, di- or tri-substituted silyl group having a group selected from an alkyl group having 1 to 20 (preferably 1 to 10, more preferably 1 to 6) carbon atoms and an aryl group having 6 to 30 (preferably 6 to 24, more preferably 6 to 12) ring carbon atoms; a heteroaryl group having 5 to 30 (preferably 5 to 24, more preferably 5 to 12) ring carbon atoms and containing 1 to 5 (preferably 1 to 3, more preferably 1 or 2) hetero atoms (nitrogen atom, oxygen atom, sulfur atom); a haloalkyl group having 1 to 20 (preferably 1 to 10, more preferably 1 to 6) carbon atoms; a halogen atom (fluorine atom, chlorine atom, bromine atom, iodine atom); a cyano group; and a nitro group.

Among the above-mentioned substituents, those selected from the group consisting of an alkyl group having 1 to 6 carbon atoms, a cycloalkyl group having 5 or 6 carbon atoms and an aryl group having 6 to 12 ring carbon atoms are especially preferred.

These optional substituents may be further substituted with the substituent mentioned above.

The number of the optional substituents in the term of "substituted or unsubstituted" may be one or may be 2 or more. When the number of the substituents is 2 or more, these substituents may be the same or different.

In this description, those which are defined as being preferred can be selected arbitrarily and a combination thereof is a more preferred embodiment.

The organic EL device of the present invention has plural organic thin film layers including a light-emitting layer between a cathode and an anode, wherein at least one layer of the organic thin film layers contains the compound represented by the following general formula (1) of the present invention.

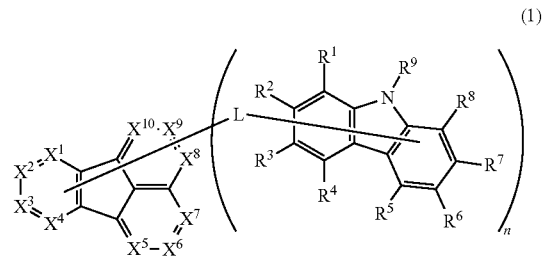

(1)

In the formula (1), $X^1$ to $X^{10}$ each independently represent C—R (where R represents a hydrogen atom, a substituent or a single bond bonding to L), or a nitrogen atom.

L represents a single bond, a substituted or unsubstituted arylene group having 6 to 30 ring carbon atoms, a substituted or unsubstituted heteroarylene group having 5 to 30 ring carbon atoms, or a divalent group composed of 2 to 4 such arylene groups and heteroarylene groups bonding to each other.

$R^1$ to $R^8$ each independently represent a hydrogen atom, a fluorine atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a silyl group represented by $-Si(R^{100})_3$ [where $R^{100}$ represents a hydrogen atom, an alkyl group having 1 to 30 carbon atoms, or an aromatic hydrocarbon group having 6 to 60 ring carbon atoms, three $R^{100}$'s may be the same or different], a substituted or unsubstituted alkylamino group having 2 to 30 carbon atoms, a substituted or unsubstituted arylamino group having 6 to 60 ring carbon atoms, a substituted or unsubstituted aryl group having 6 to 30 ring carbon atoms, or a heteroaryl group selected from the group consisting of a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group and a xanthenyl group which each may be substituted or unsubstituted, or a single bond bonding to L.

$R^9$ represents a hydrogen atom, a substituted or unsubstituted alkyl group having 1 to 20 carbon atoms, a substituted or unsubstituted cycloalkyl group having 3 to 20 ring carbon atoms, a substituted or unsubstituted aryl group having 6 to 30 ring carbon atoms, or a substituted or unsubstituted heteroaryl group having 5 to 30 ring carbon atoms.

n indicates an integer of 1 to 4. When n is an integer of 2 to 4, plural parenthesized groups may be the same or different. However, the number of the fluoranthene structure that the compound represented by the general formula (1) has is one.

It is desirable that $X^1$ to $X^{10}$ each are independently C—R (where R represents a hydrogen atom, a substituent or a single bond bonding to L), and except those where R is a single bond bonding to L, R is preferably a hydrogen atom.

Examples of the arylene group having 6 to 30 (preferably 6 to 24, more preferably 6 to 18, even more preferably 6 to 12) ring carbon atoms that is represented by L include a phenylene group, a naphthylene group, a biphenylylene group, an anthrylene group, an acenaphthylylene group, an anthranylene group, a phenanthlylene group, a phenarenylene group, a xylylene group, an isoquinolylene group, an s-indacenylene group, an as-indacenylene group, a chrysenylene group, etc. Among these, a phenylene group, a naphthylene group and a biphenylene group are preferred, a phenylene group is more preferred, and a 1,4-phenylene group is even more preferred.

Preferred examples of the heteroarylene group having 5 to 30 (preferably 5 to 24, more preferably 5 to 12) ring carbon atoms that is represented by L include a pyrrolylene group, a furylene group, a thienylene group, a pyridylene group, an imidazopyridylene group, a pyridazinylene group, a pyrimidinylene group, a pyrazinylene group, a triazinylene group, an imidazolylene group, an oxazolylene group, a thiazolylene group, a pyrazolylene group, an isoxazolylene group, an isothiazolylene group, an oxadiazolylene group, a thiadiazolylene group, a triazolylene group, a tetrazolylene group, an indolylene group, an isoindolylene group, a benzofuranylene group, an isobenzofuranylene group, a benzothiophenylene group, an isobenzothiophenylene group, an indolydinylene group, a quinolidinylene group, an quinolylene group, an isoquinolylene group, a cinnolylene group, a phthalzinylene group, a quinazolinylene group, a quinoxalinylene group, a benzimidazolylene group, a benzoxazolylene group, a benzothiazolylene group, an indazolylene group, a benzisoxazolylene group, a benzisothiazolylene group, a dibenzofuranylene group, a dibenzothiophenylene group, a phenanthridinylene group, an acrydinylene group, a phenantrolinylene group, a phenadinylene group, a phenothiazinylene group, a phenoxazinylene group and a xanthenylene group. Among these, a furylene group, a thienylene group, a pyridylene group, an imidazopyridylene group, a pyridazinylene group, a pyrimidinylene group, a pyrazinylene group, a benzimidazolylene group, a dibenzofuranylene group, a dibenzothiophenylene group and a phenanthrolinylene group are preferred.

As described above, L may be a divalent group composed of 2 to 4 of the above-mentioned arylene group and the above-mentioned heteroarylene group bonding to each other. Specifically, the divalent group includes a heteroarylene group-arylene group, an arylene group-heteroarylene group, an arylene group-heteroarylene group-arylene group, a heteroarylene group-arylene group-heteroarylene group, an arylene group-heteroarylene group-arylene group-heteroarylene group, a heteroarylene group-arylene group-heteroarylene group-arylene group, etc. Preferably, the group is a divalent group composed of the above-mentioned one arylene group and the above-mentioned one heteroarylene group bonding to each other, that is, a heteroarylene group-arylene group, and an arylene group-heteroarylene group. Specific examples of the arylene group and the heteroarylene group may be arbitrarily selected from the above-mentioned specific examples of the arylene group and the heteroarylene group.

L is preferably a single bond, or a substituted or unsubstituted arylene group having 6 to 30 ring carbon atoms, more preferably a single bond or a substituted or unsubstituted arylene group having 6 to 12 ring carbon atoms, even more preferably a single bond, a substituted or unsubstituted phenylene group, a substituted or unsubstituted biphenylylene group, a substituted or unsubstituted terphenylylene group, a substituted or unsubstituted naphthylene group, a substituted or unsubstituted anthrylene group, a substituted or unsubstituted pyrenylene group, and especially preferably a single bond, a phenylene group, a naphthylene group or a biphenylylene group.

Examples of the alkyl group having 1 to 20 (preferably 1 to 10, more preferably 1 to 6) carbon atoms that is represented by $R^1$ to $R^9$ include a methyl group, an ethyl group, an n-propyl group, an isopropyl group, an n-butyl group, an isobutyl group, an s-butyl group, a t-butyl group, a pentyl group (including isomer groups), a hexyl group (including isomer groups), a heptyl group (including isomer groups), an octyl group (including isomer groups), a nonyl group (including isomer groups), a decyl group (including isomer groups), an undecyl group (including isomer groups), a dodecyl group (including isomer groups), etc. Among these, a methyl group, an ethyl group, an n-propyl group, an isopropyl group, an n-butyl group, an isobutyl group, an s-butyl group, a t-butyl group, and a pentyl group (including isomer groups) are preferred, a methyl group, an ethyl group, an n-propyl group, an isopropyl group, an n-butyl group, an isobutyl group, an s-butyl group and a t-butyl group are more preferred, and a methyl group, an ethyl group, an isopropyl group and t-butyl group are especially preferred.

Examples of the cycloalkyl group having 3 to 20 (preferably 3 to 6, more preferably 5 or 6) ring carbon atoms that is represented by $R^1$ to $R^9$ include a cyclopropyl group, a cyclobutyl group, a cyclopentyl group, a cyclohexyl group, a cycloheptyl group, a cyclooctyl group, an adamantyl group, etc. Among these, a cyclopentyl group and a cyclohexyl group are preferred.

The alkoxy group having 1 to 20 (preferably 1 to 10, more preferably 1 to 6) carbon atoms that is represented $R^1$ to $R^8$ includes an alkoxy group in which the alkyl moiety is the above-mentioned alkyl group having 1 to 20 carbon atoms. Preferred examples of the alkoxy group include those in which the alkyl moiety is the above-mentioned preferred alkyl group.

The aryloxy group having 6 to 30 (preferably 6 to 24, more preferably 6 to 18, even more preferably 6 to 10) ring carbon atoms that is represented $R^1$ to $R^8$ includes those in which the aryl group moiety is an aryl group having 6 to 30 ring carbon atoms to be mentioned hereinunder. Preferred examples of the aryloxy group include those where the aryl group moiety is a preferred aryl group to be mentioned hereinunder.

The alkylthio group having 1 to 20 (preferably 1 to 10, more preferably 1 to 6) carbon atoms that is represented $R^1$ to $R^8$ includes an alkylthio group where the alkyl group moiety is the above-mentioned alkyl group having 1 to 20 carbon atoms. Preferred examples of the thioalkyl group include those where the alkyl group moiety is the above-mentioned preferred alkyl group.

The arylthio group having 6 to 30 (preferably 6 to 24, more preferably 6 to 18, even more preferably 6 to 10) ring carbon atoms that is represented $R^1$ to $R^8$ includes those where the aryl group moiety is an aryl group having 6 to 30 ring carbon atoms to be mentioned hereinunder. Preferred examples of the arylthio group include those where the aryl group moiety is a preferred aryl group to be mentioned hereinunder.

$R^{100}$ that the silyl group represented by $-Si(R^{100})_3$ for $R^1$ to $R^8$ has is a hydrogen atom, an alkyl group having 1 to 30 carbon atoms or an aryl group having 6 to 60 ring carbon atoms. Three $R^{100}$'s substituting on the silicon atom may be the same or different. The silyl group having an alkyl group with 1 to 30 carbon atoms concretely includes a monoalkylsilyl group, dialkylsilyl group, and a trialkylsilyl group.

Examples of the monoalkylsilyl group include a monoalkylsilyl group having two hydrogen atoms and having the above-mentioned one alkyl group having 1 to 30 carbon atoms. The carbon number of the monoalkylsilyl group is preferably 1 to 30, more preferably 1 to 10, even more preferably 1 to 5.

Examples of the dialkylsilyl group include a dialkylsilyl group having one hydrogen atom and having the above-mentioned two alkyl groups each having 1 to 30 carbon atoms. The total carbon number of the dialkylsilyl group is preferably 2 to 30, more preferably 2 to 20, even more preferably 2 to 10.

The trialkylsilyl group concretely includes a trimethylsilyl group, a triethylsilyl group, a tri-n-butylsilyl group, a tri-n-octylsilyl group, a triisobutylsilyl group, a dimethylethylsilyl group, a dimethylisopropylsilyl group, a dimethyl-n-propylsilyl group, a dimethyl-n-butylsilyl group, a dimethyl-t-butylsilyl group, a diethylisopropylsilyl group, a vinyldimethylsilyl group, a propyldimethylsilyl group, a triisopropylsilyl group, etc. The total carbon number of the trialkylsilyl group is preferably 3 to 30, more preferably 3 to 15.

Plural alkyl groups in the dialkylsilyl group and the trialkylsilyl group may be the same or different.

The silyl group having an aryl group with 6 to 60 ring carbon atoms concretely includes a monoarylsilyl group, a diarylsilyl group, a dialkylarylsilyl group, an alkyldiarylsilyl group and a triarylsilyl group.

Examples of the monoarylsilyl group include a monoarylsilyl group having 2 hydrogen atoms and having one aryl group with 6 to 30 ring carbon atoms to be mentioned hereinunder.

Examples of the diarylsilyl group include a diarylsilyl group having one hydrogen atom and having two aryl groups each with 6 to 30 ring carbon atoms to be mentioned hereinunder. The total carbon number of the diarylsilyl group is preferably 12 to 30.

Examples of the dialkylarylsilyl group include a dialkylarylsilyl group having two alkyl groups exemplified for the above-mentioned alkyl group having 1 to 30 carbon atoms and having one aryl group with 6 to 30 ring carbon atoms to be mentioned hereinunder. The total carbon number of the dialkylarylsilyl group is preferably 8 to 30.

Examples of the alkyldiarylsilyl group include an alkyldiarylsilyl group having one alkyl group exemplified for the above-mentioned alkyl group having 1 to 30 carbon atoms and having two aryl groups each having 6 to 30 ring carbon atoms to be mentioned hereinunder. The total carbon number of the alkyldiarylsilyl group is preferably 13 to 30.

Examples of the triarylsilyl group include triarylsilyl group having three aryl groups each having 6 to 30 ring carbon atoms to be mentioned hereinunder. The total carbon number of the triarylsilyl group is preferably 18 to 30.

Plural aryl groups in the diarylsilyl group, the alkyldiarylsilyl group and the triarylsilyl group may be the same or different.

The alkylamino group having 2 to 30 carbon atoms that is represented by $R^1$ to $R^8$ is expressed as $-NHR^V$ or $-N(R^V)_2$. Two $R^V$'s in $-N(R^V)_2$ may be the same or different. $R^V$ includes the above-mentioned alkyl group having 1 to 30 carbon atoms. The carbon number of the alkyl group moiety is preferably 1 to 20, more preferably 1 to 10, even more preferably 1 to 6. The alkylamino group is preferably a dimethylamino group, a diethylamino group or a diisopropylamino group.

The arylamino group having 6 to 60 ring carbon atoms that is represented by $R^1$ to $R^8$ is expressed as $-NHR^W$ or $-N(R^W)_2$. Two $R^w$'s in $-N(R^w)_2$ may be the same or different. $R^w$ includes the above-mentioned aromatic hydrocarbon group having 6 to 30 ring carbon atoms. The ring carbon number of the aryl group moiety is preferably 6 to 30, more preferably 6 to 24, even more preferably 6 to 18, especially preferably 6 to 10. The arylamino group is preferably a diphenylamino group.

The aryl group having 6 to 30 (preferably 6 to 24, more preferably 6 to 18, even more preferably 6 to 10) ring carbon atoms that is represented by by $R^1$ to $R^9$ may be a condensed ring or a non-condensed ring. Examples of the aryl group include a phenyl group, a naphthylphenyl group, a biphenylyl group, a terphenylyl group, a naphthyl group, an acenaphthylenyl group, an anthryl group, a benzanthryl group, an aceanthryl group, a phenanthryl group, a benzo[c]phenanthryl group, a phenalenyl group, a fluorenyl group, a picenyl group, a pentaphenyl group, a pyrenyl group, a chrysenyl group, a benzo[g]chrysenyl group, an s-indacenyl group, an as-indacenyl group, a fluoranthenyl group, a benzo[k]fluoranthenyl group, a triphenylenyl group, a benzo[b]triphenylenyl group, a perylenyl group, etc. Among these, a phenyl group, a biphenylyl group, a terphenylyl group, a naphthyl group, an anthryl group, a pyrenyl group and a fluoranthenyl group are preferred, a phenyl group, a biphenylyl group and a terphenylyl group are more preferred, and a phenyl group is even more preferred.

The heteroaryl group having 5 to 30 (preferably 5 to 24, more preferably 5 to 12) ring atoms that is represented by by $R^9$ includes at least one, preferably 1 to 5, more preferably 1 to 4, and even more preferably 1 to 3 hetero atoms. Examples of the hetero atom include a nitrogen atom, a sulfur atom and an oxygen atom. A nitrogen atom and an oxygen atom are preferred, and a nitrogen atom is more preferred.

Examples of the heteroaryl group include a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group and a xanthenyl group. Among these, a furyl group, a thienyl group, a pyridyl group, an imidazopyridyl group, a pyridazinyl group, a pyrimidinyl group, a pirazinyl group, a benzimidazolyl group, a dibenzofuranyl group, a dibenzothiophenyl group and a phenanthrolinyl group are preferred.

As described above, $R^1$ to $R^8$ each may represent a single bond bonding to L, but $R^9$ does not represent a single bond bonding to L. $R^1$ to $R^9$ do not bond to each other to form a ring.

n indicates an integer of 1 to 4, preferably 1 or 2, more preferably 1. When n is an integer of 2 to 4, plural parenthesized groups, that is, the following groups may be the same or different.

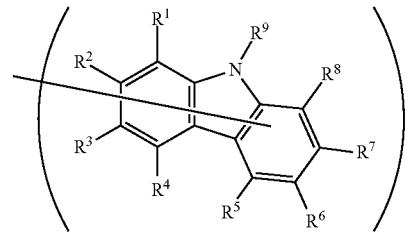

[Chem.3]

[A] In the compound represented by the above formula (1), where at least one of $X^1$ to $X^{10}$ is a nitrogen atom, it is preferable that at least one selected from $X^1$ to $X^4$, $X^5$, $X^7$, $X^8$ and $X^9$ is a nitrogen atom. Above all, it is more preferable that $X^7$ or $X^8$ is a nitrogen atom, or $X^1$ and $X^3$, $X^2$ and $X^4$, $X^5$ and $X^7$, or $X^8$ and $X^{10}$ are nitrogen atoms. In particular, in the case where $X^7$ is a nitrogen atom, it is even more preferable that $X^6$ represents C—R and R is a single bond bonding to L. Also in particular, in the case where $X^1$ and $X^3$ are nitrogen atoms, it is more preferable that $X^2$ is C—R and R is a single bond bonding to L; in the case where $X^2$ and $X^4$ are nitrogen atoms, it is more preferable that $X^3$ is C—R and R is a single bond bonding to L; in the case where $X^5$ and $X^7$ are nitrogen atoms, it is more preferable that $X^6$ is C—R and R is a single bond bonding to L; and in the case where $X^8$ and $X^{10}$ are nitrogen atoms, it is more preferable that $X^9$ is C—R and R is a single bond bonding to L.

[B] Regarding the compound represented by the above formula (1), those represented by the following formula (1-1) where $X^8$ is C—R and R is a single bond bonding to L are preferred from the viewpoint of low-voltage driving and emission efficiency.

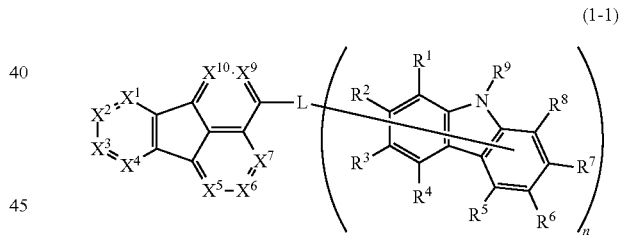

(1-1)

(In the formula (1-1), $X^1$ to $X^7$, X9, $X^{10}$, L, $R^1$ to $R^9$ and n are as defined above.)

[C] Regarding the compound of the present invention, those represented by the following formula (1-2) where $X^2$ is C—R and R is a single bond bonding to L are also preferred from the viewpoint of low-voltage driving and emission efficiency.

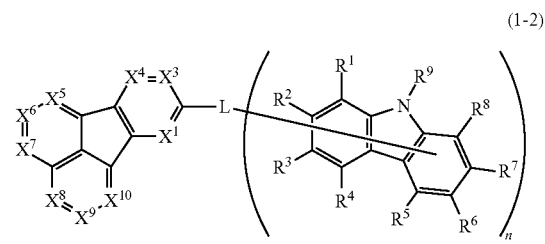

(1-2)

(In the formula (1-2), $X^1$, $X^3$ to $X^{10}$, L, $R^1$ to $R^9$ and n are as defined above.)

Regarding the compound of the present invention, those where 8 or more of $X^1$ to $X^{10}$ are C—R (where R is a hydrogen atom or a single bond bonding to L) are preferred from the viewpoint of low-voltage driving and emission efficiency, and those where 9 or more are C—R (where R is a hydrogen atom or a single bond bonding to L) are more preferred, and as represented by the following formula (1'), those where all are C—R (where R is a single bond bonding to a hydrogen atom or L) are even more preferred.

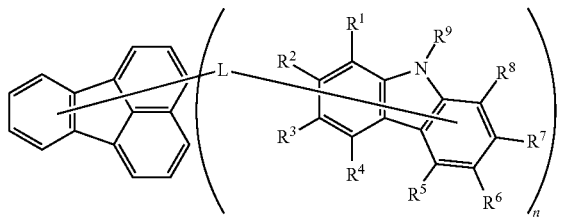

In the above formula (1'), $R^1$ to $R^9$, L and n are the same as those in the formula (1), and preferred ones are also the same.

Among the compound represented by the above formula (1') of the present invention, those represented by the following formula (1'-1) or (1'-2) are preferred from the viewpoint of low-voltage driving and emission efficiency.

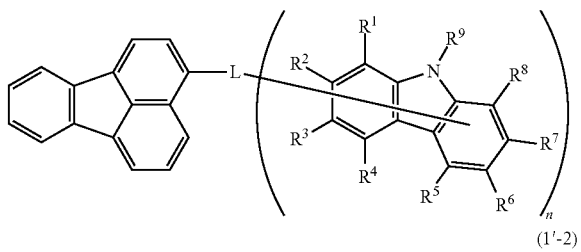

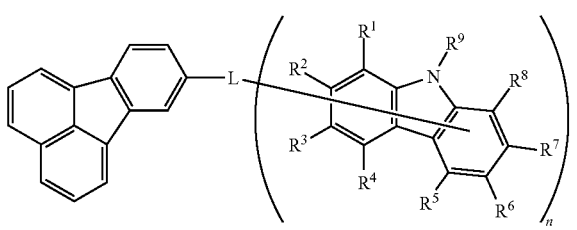

In the above formulae (1'-1) and (1'-2), $R^1$ to $R^9$, L and n are the same as those in the formulae (1) and (1'), and preferred ones are also the same.

In the above formulae (1), (1-1), (1-2), (1'), (1'-1) and (1'-2), the following compounds are preferred from the viewpoint of low-voltage driving and emission efficiency.

[D] Compounds where n is 1 or 2.

[E] Compounds where $R^3$ is a single bond bonding to L. Further in the case, those where $R^9$ is a substituted or unsubstituted aryl group having 6 to 30 (preferably 6 to 24, more preferably 6 to 18, even more preferably 6 to 10) ring carbon atoms are more preferred, and those where it is a substituted or unsubstituted phenyl group, a substituted or unsubstituted biphenylyl group, or a substituted or unsubstituted naphthyl group are even more preferred, and those where it is a phenyl group, a biphenylyl group or a naphthyl group are especially more preferred.

[F] Compounds where $R^2$ is a single bond bonding to L. Further in the case, those where $R^9$ is a substituted or unsubstituted aryl group having 6 to 30 (preferably 6 to 24, more preferably 6 to 18, even more preferably 6 to 10) ring carbon atoms are more preferred, and those where it is a substituted or unsubstituted phenyl group, a substituted or unsubstituted biphenylyl group, or a substituted or unsubstituted naphthyl group are even more preferred, and those where it is a phenyl group, a biphenylyl group or a naphthyl group are especially more preferred.

[G] Compounds where $R^9$ is a substituted or unsubstituted aryl group having 6 to 30 ring carbon atoms. Further in the case, the aryl group is preferably a phenyl group, a biphenylyl group, a terphenylyl group, a naphthyl group, an anthryl group or a pyrenyl group.

[H] Compounds where $R^9$ is a substituted or unsubstituted heteroaryl group having 5 to 30 ring carbon atoms. Further in the case, the heteroaryl group is preferably a furyl group, a thienyl group, a pyridyl group, an imidazopyridyl group, a pyridazinyl group, a pyrimidinyl group, a pyrazinyl group, a benzimidazolyl group, a dibenzofuranyl group, a dibenzothiophenyl group or a phenanthrolyl group.

[I] Compounds where L is a single bond, or a substituted or unsubstituted arylene group having 6 to 30 (more preferably 6 to 12) ring carbon atoms. Further in the case, the arylene group is preferably a phenylene group, a biphenylylene group, a terphenylylene group, a naphthylene group, an anthrylene group or a pyrenylene group.

[J] Further, as the compound of the present invention, compounds represented by any of the following formulae (1-3), (1-4), (1-5), (1-5-1), (1-6), (1-6-1), (1-7), (1-8), (1-9) and (1-10) are more preferred.

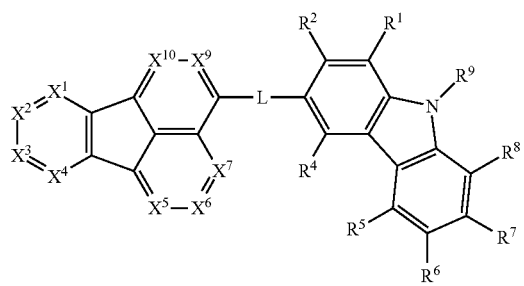

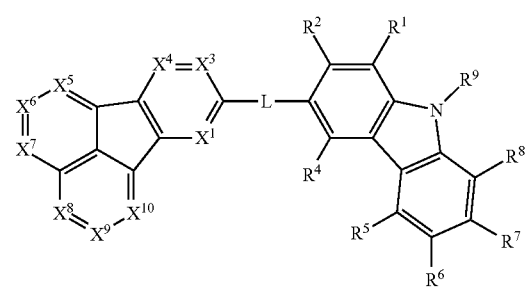

-continued
(1-5)
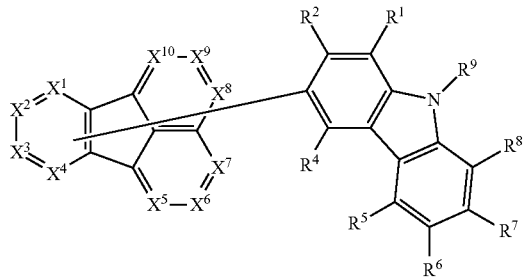
(1-5-1)
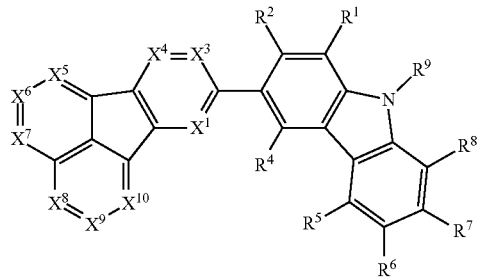
(1-6)
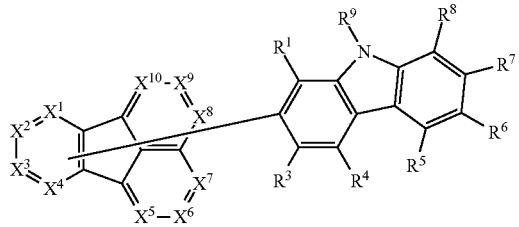
(1-6-1)
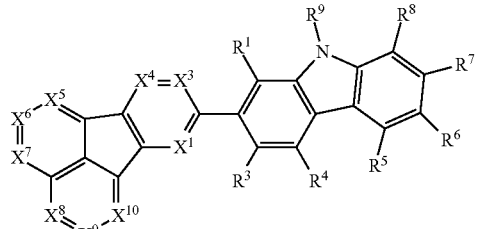
(1-7)
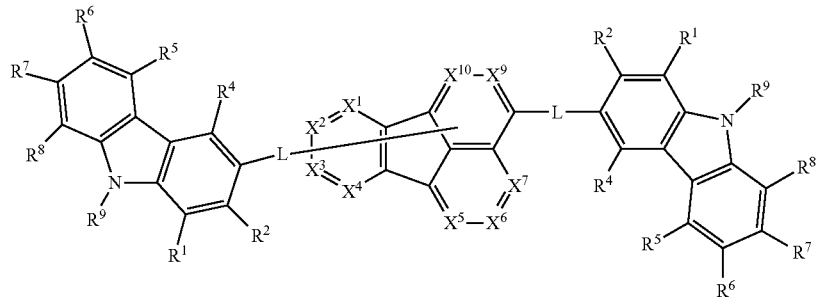
(1-8)
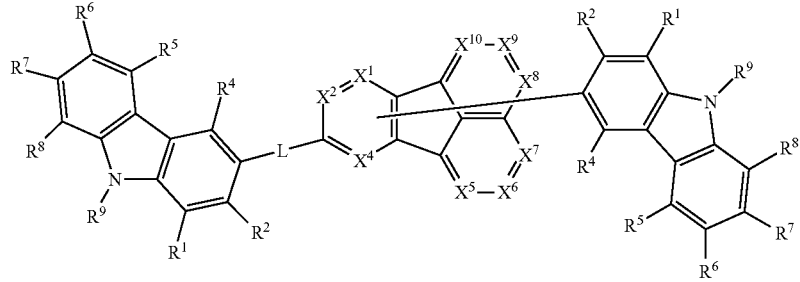
(1-9)
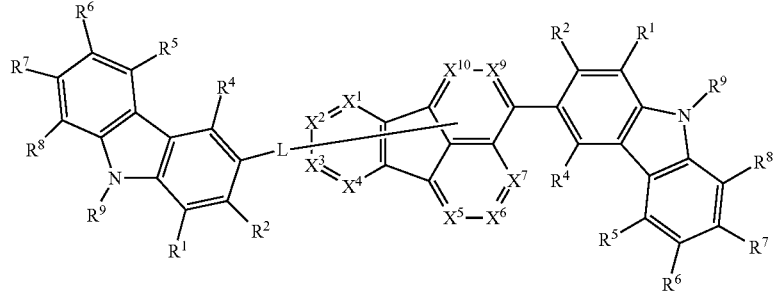

-continued
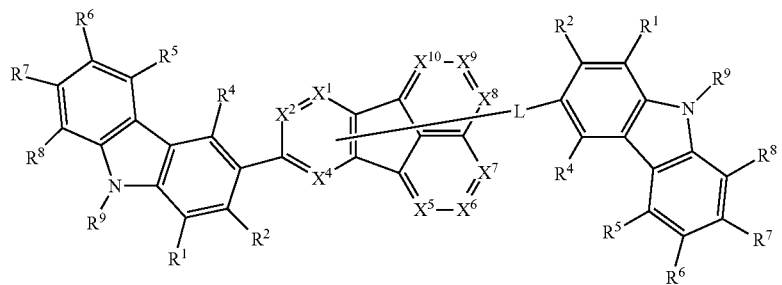
(1-10)
(In the above formulae (1-3), (1-4), (1-5), (1-5-1), (1-6), (1-6-1), (1-7), (1-8), (1-9) and (1-10), the definition of each group is the same as in the formula (1), and the preferred ones are also the same.)
Specific examples of the compound of the present invention are shown below, however, the compound is not limited to these.
[Chem. 19]
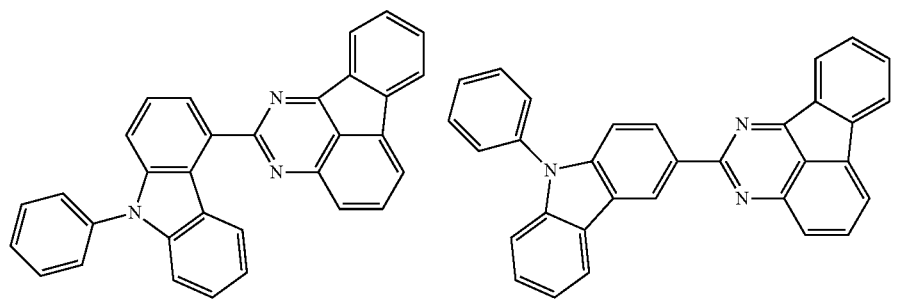
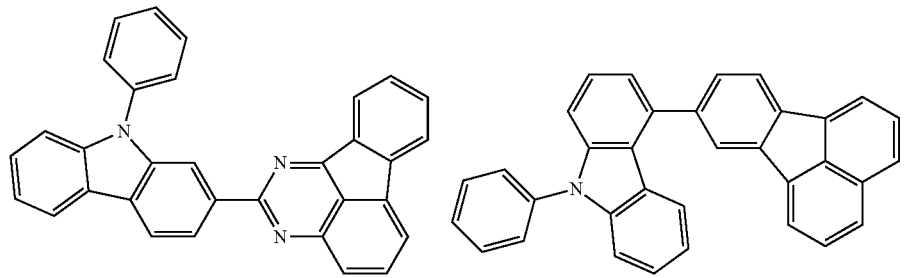
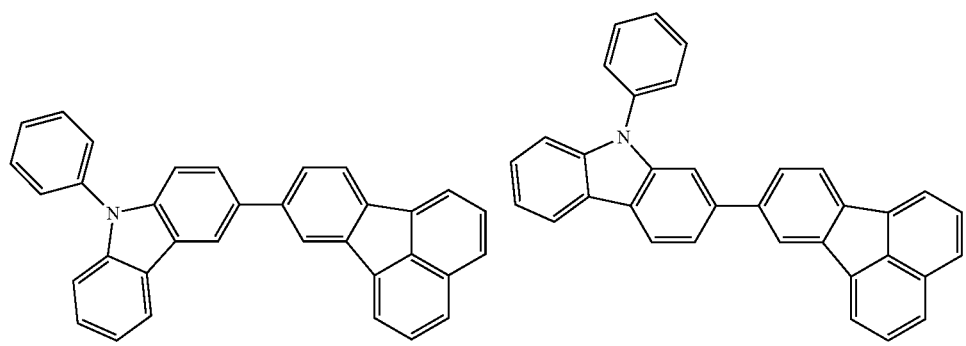

-continued
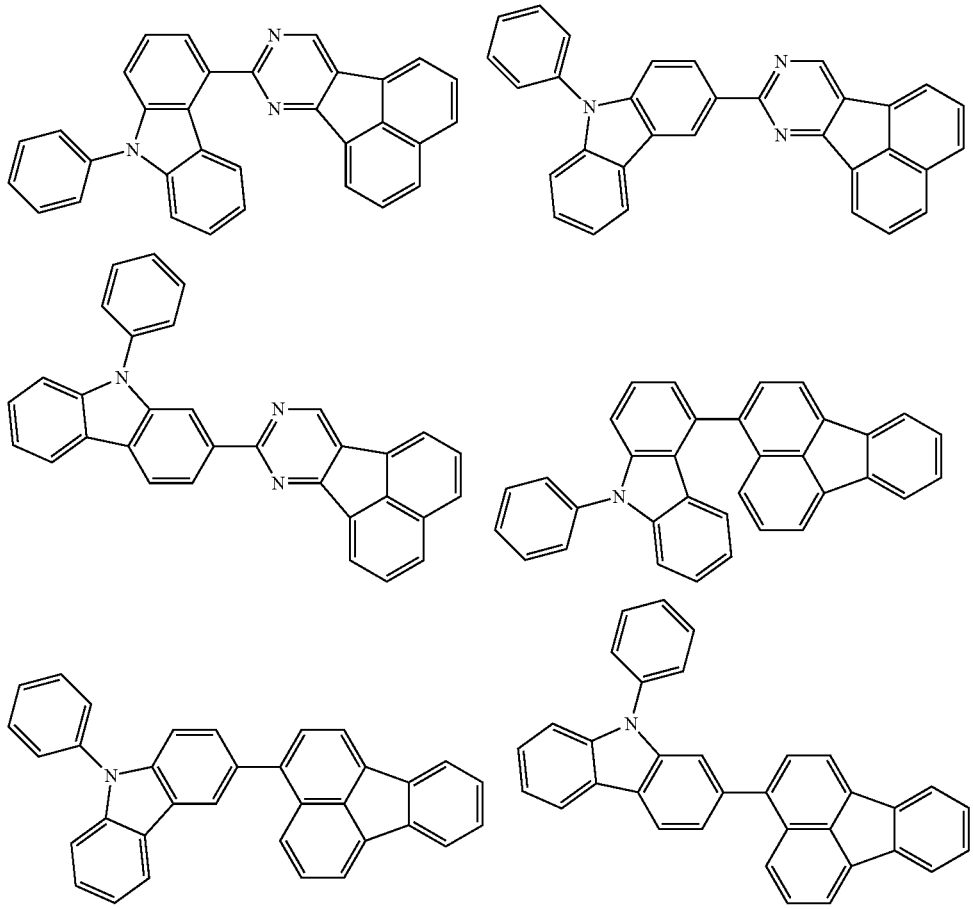
[Chem. 20]
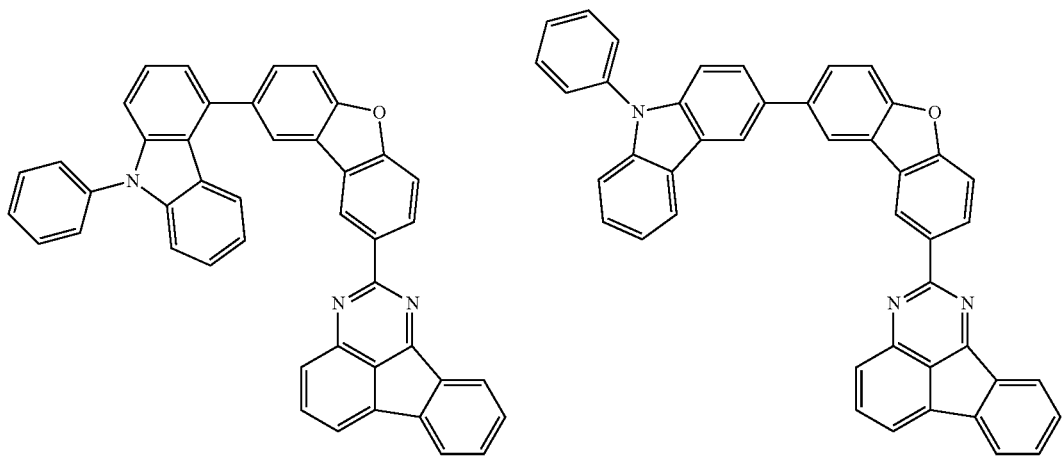

-continued
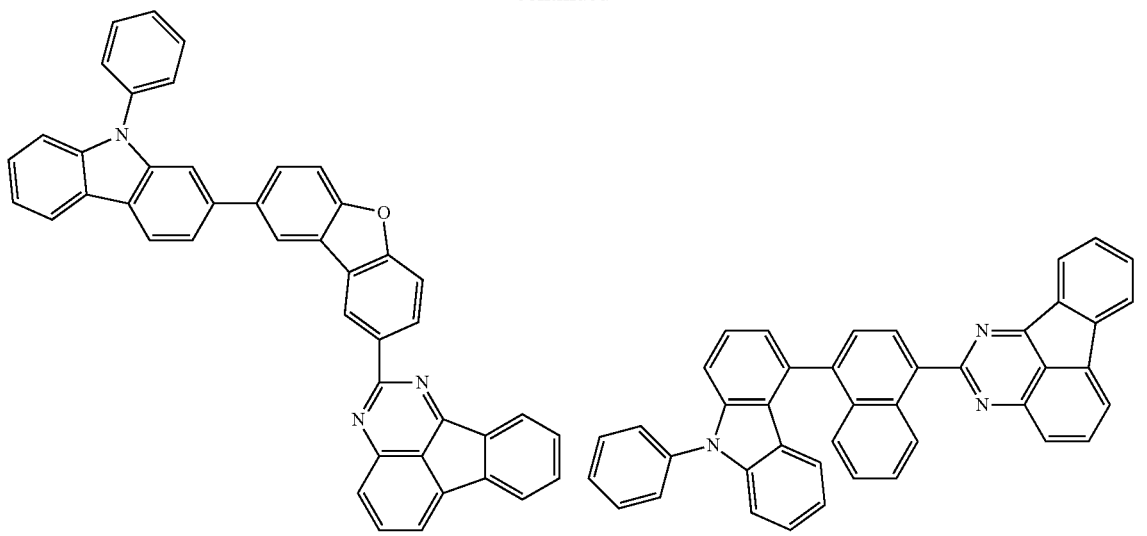
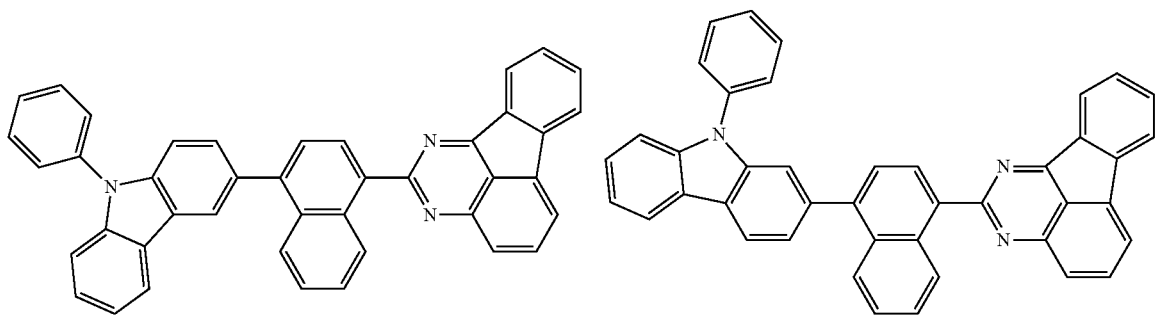
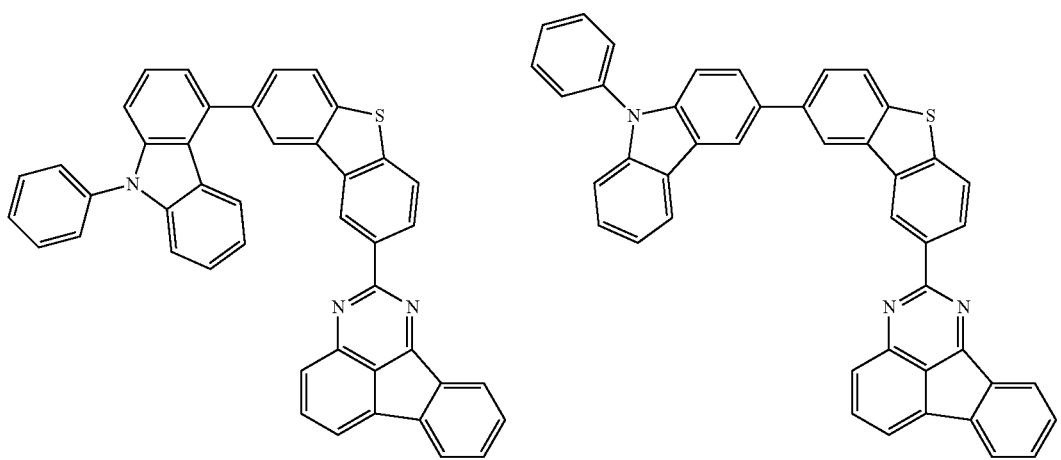

-continued
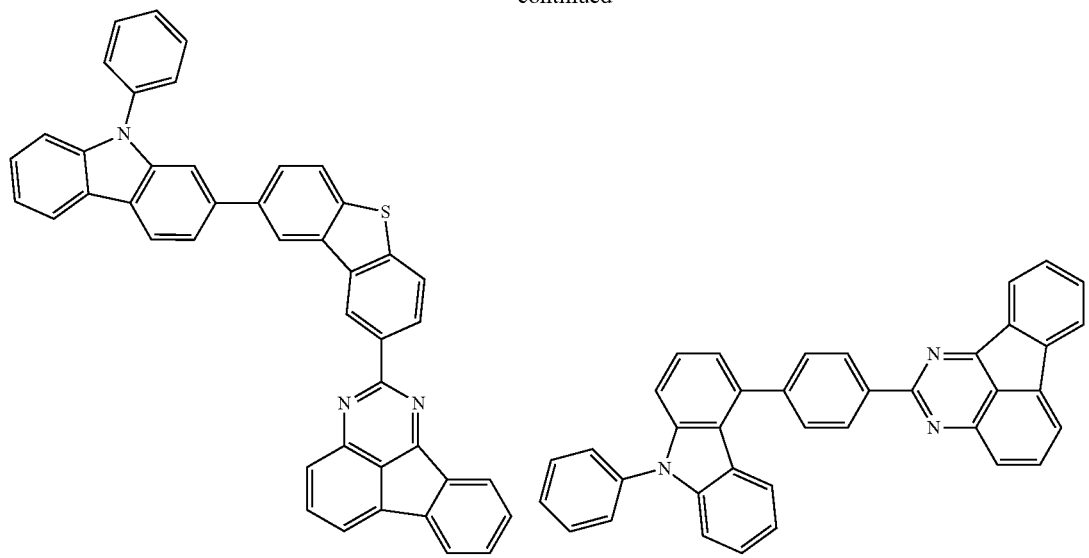
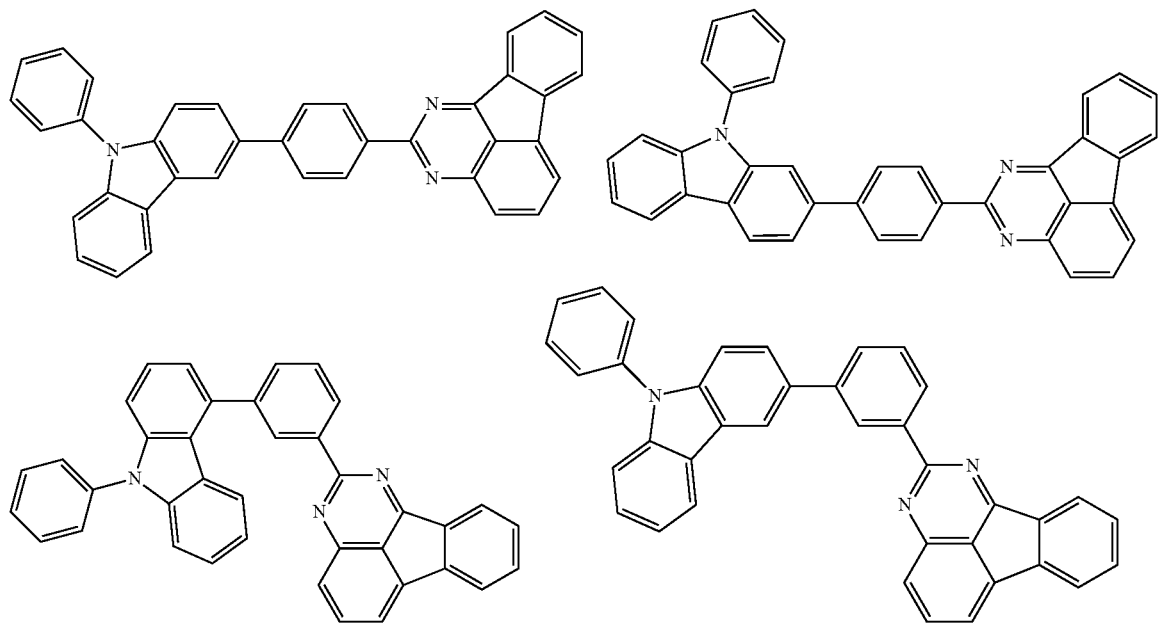
[Chem. 21]
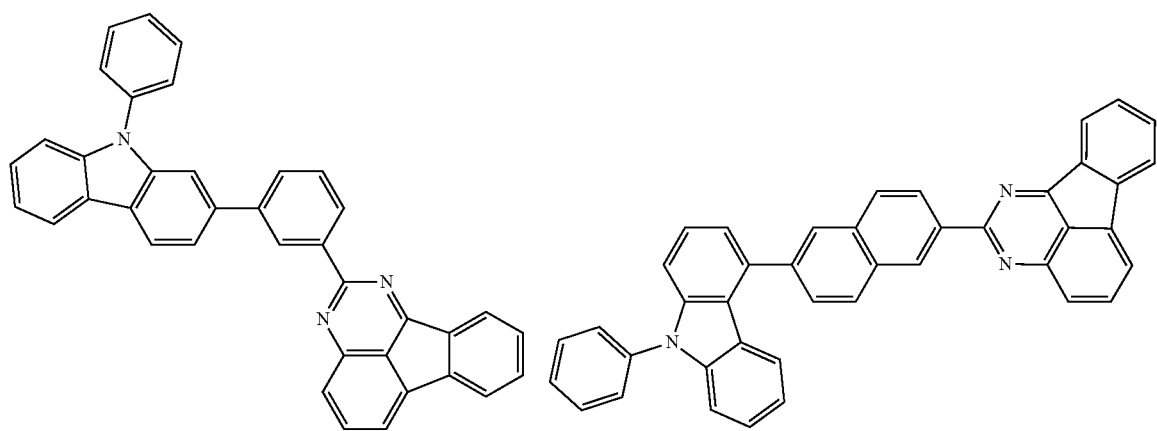

-continued
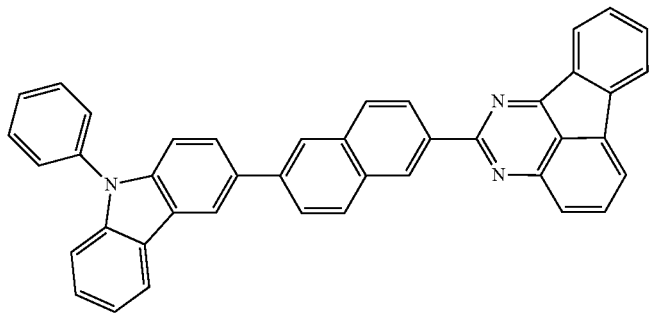
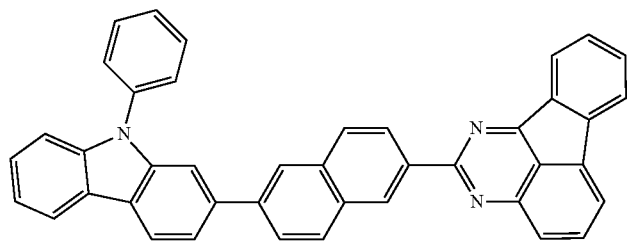
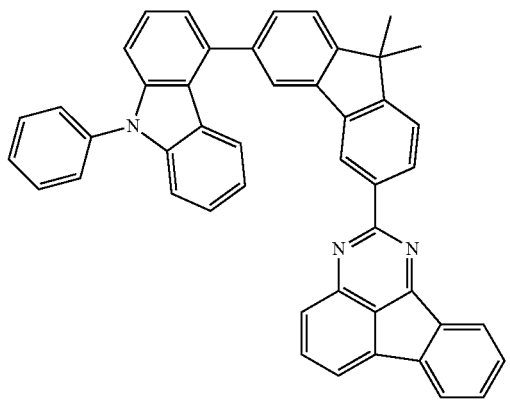
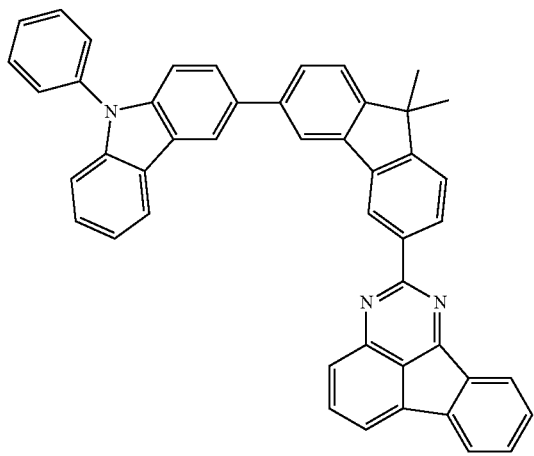 [SMILES: CC1(C)c2ccc(-c3ccc4c(c3)c3ccccc3n4-c3ccccc3)cc2-c2cc(-c3nc4c5c(cccc5n3)-c3ccccc3-4)ccc21]

[Chem. 22]
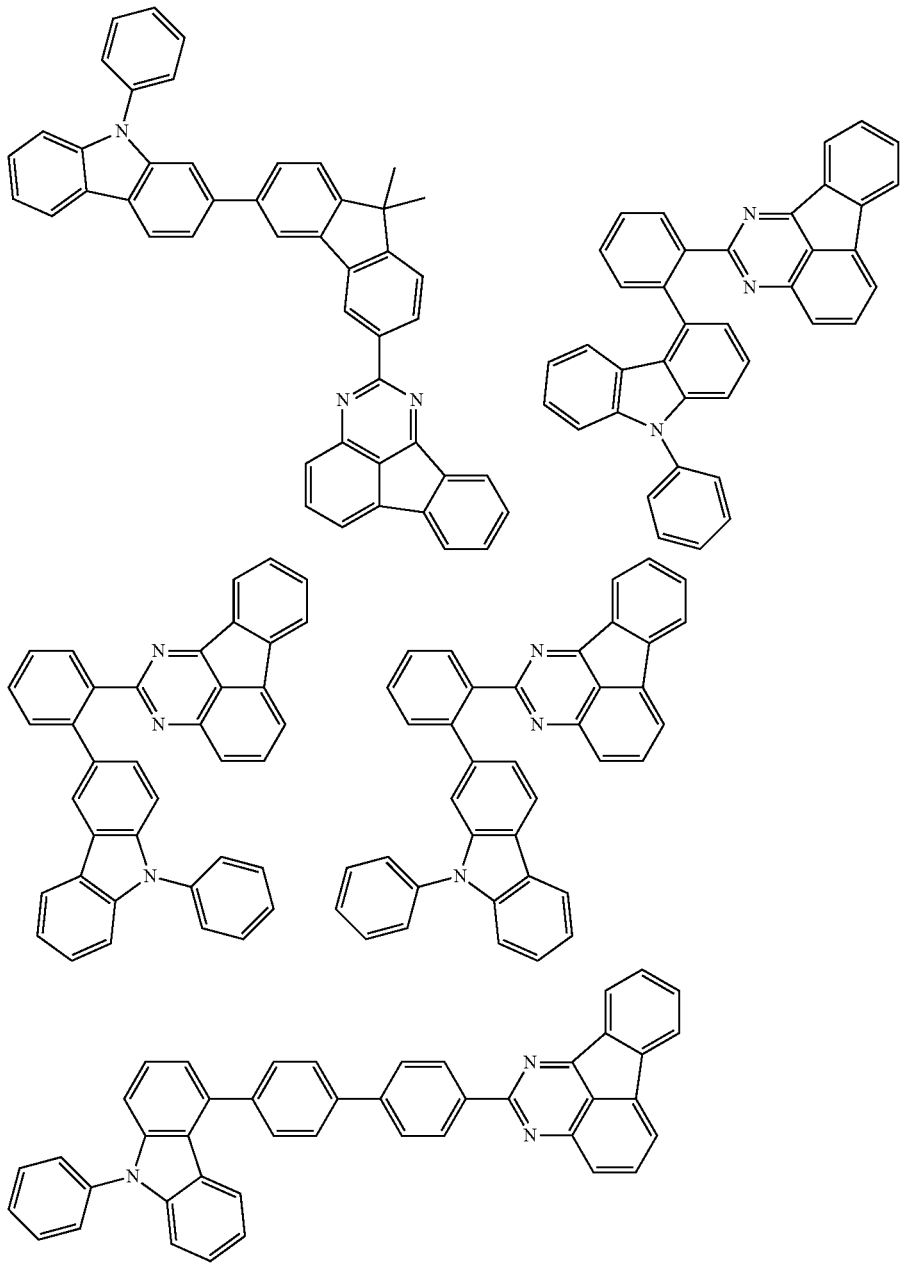
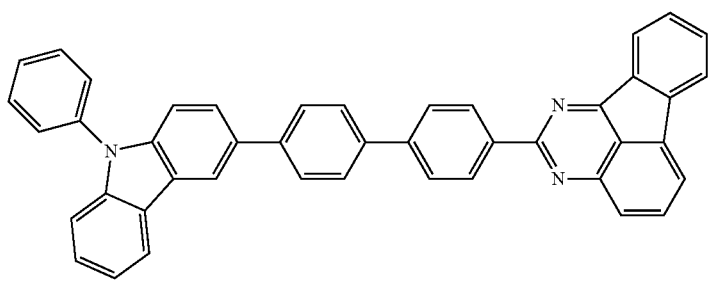

-continued
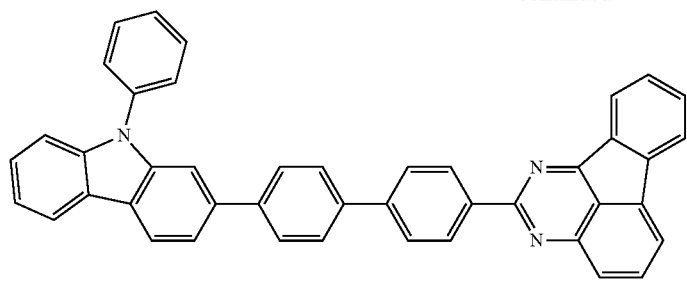
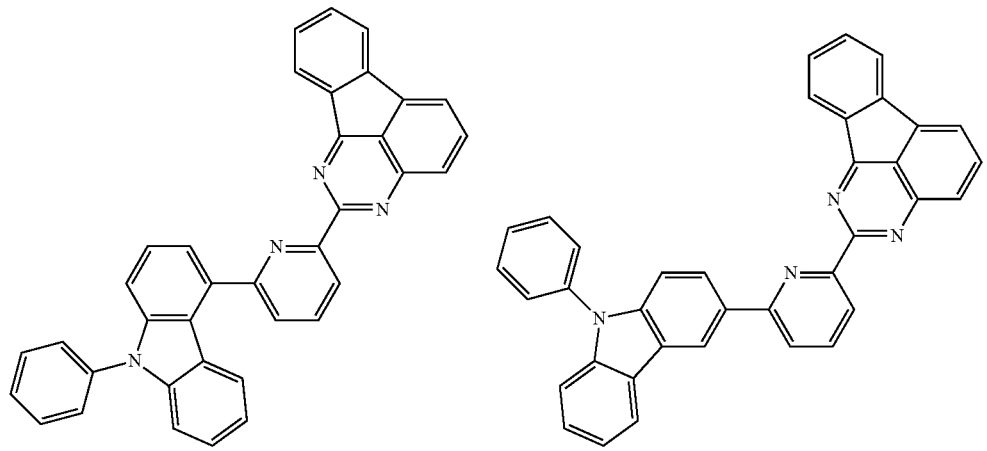
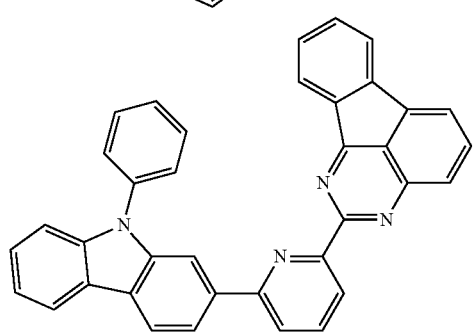
[Chem. 23]
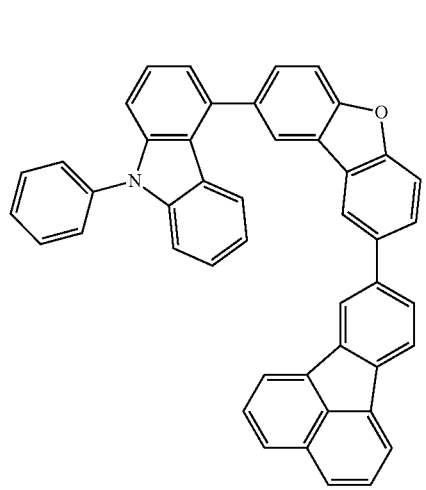
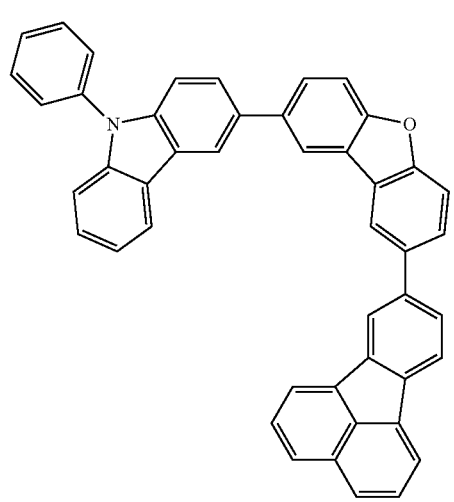

-continued
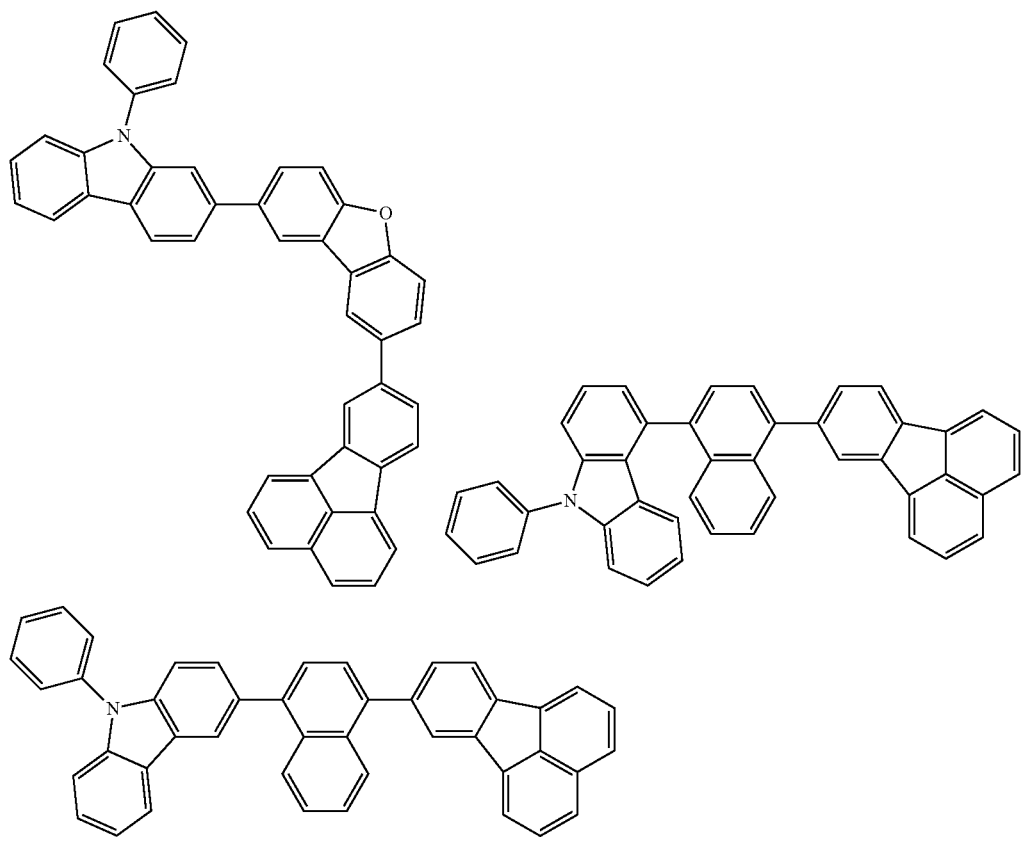
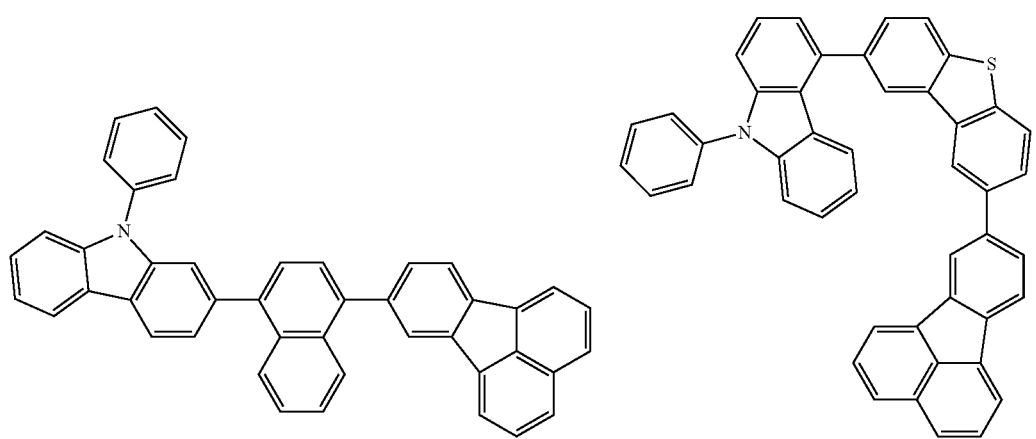

-continued
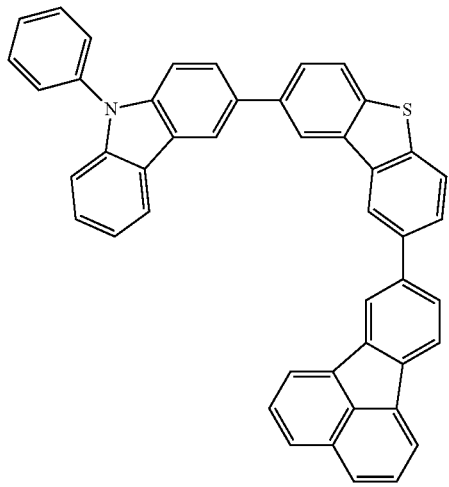
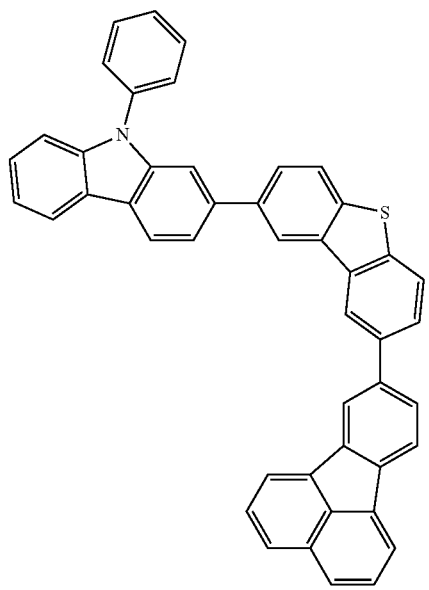
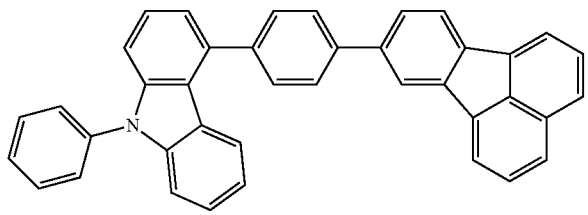
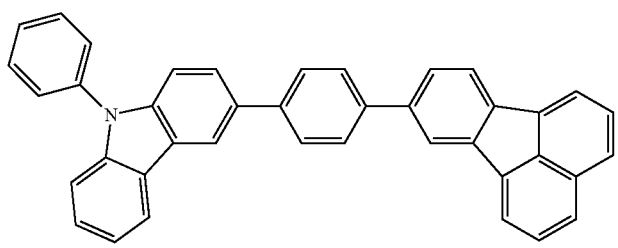
[Chem. 24]
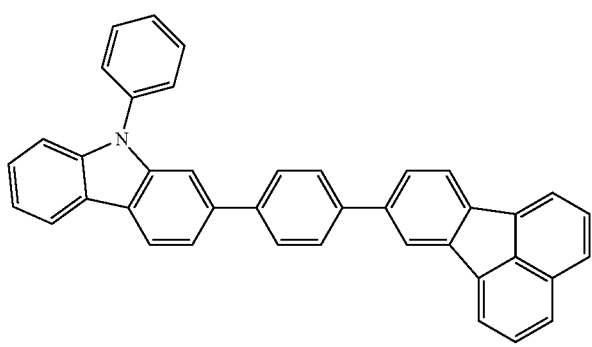
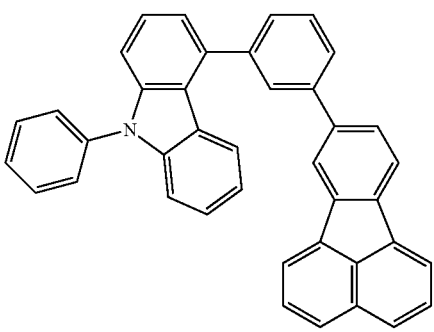

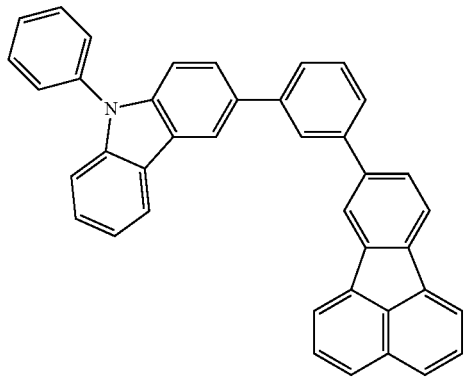
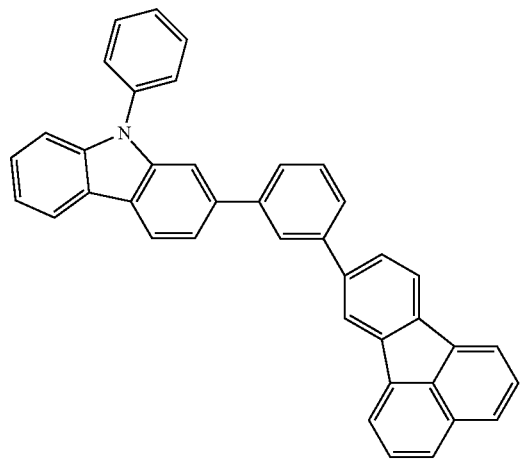
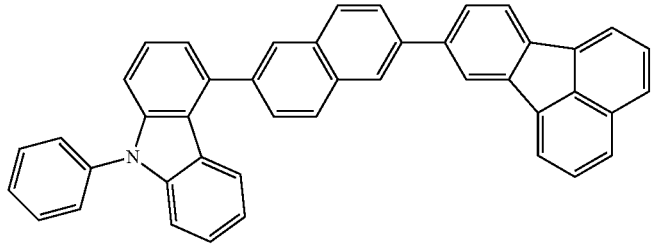
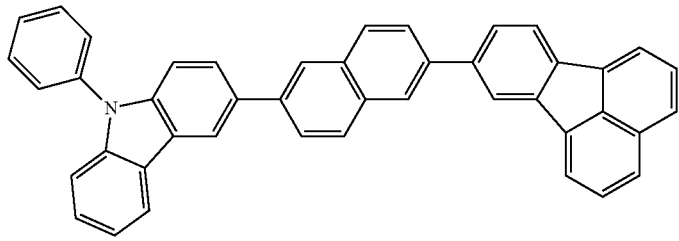
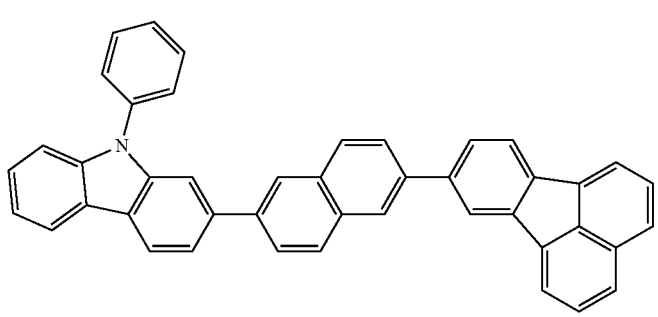
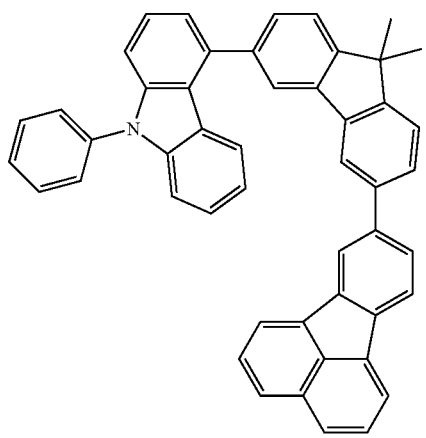

-continued
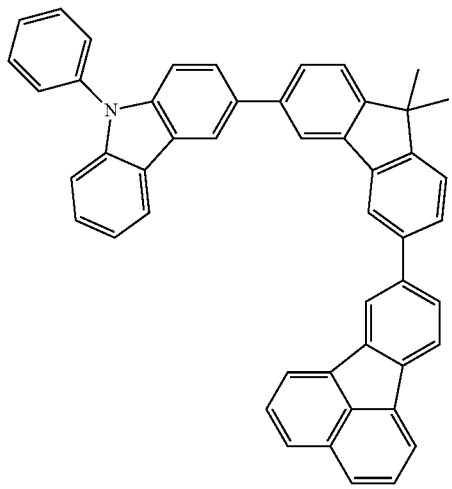
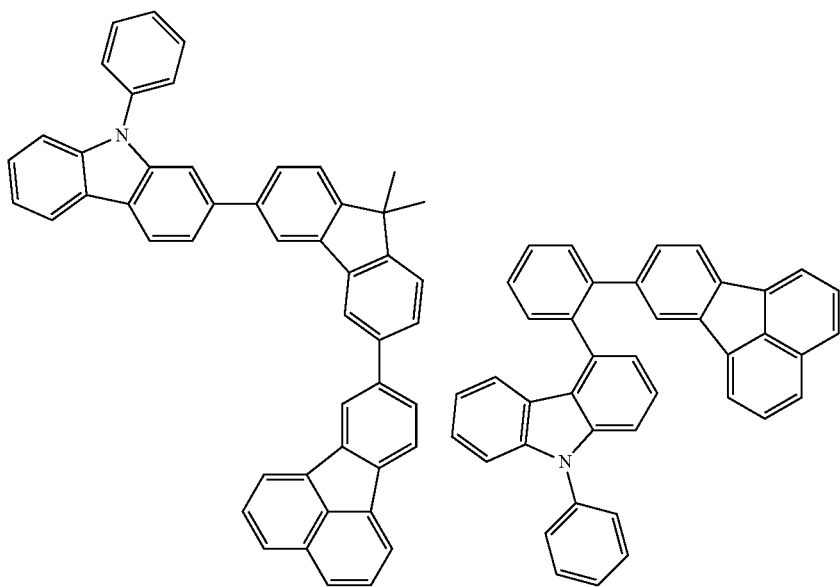
[Chem. 25]
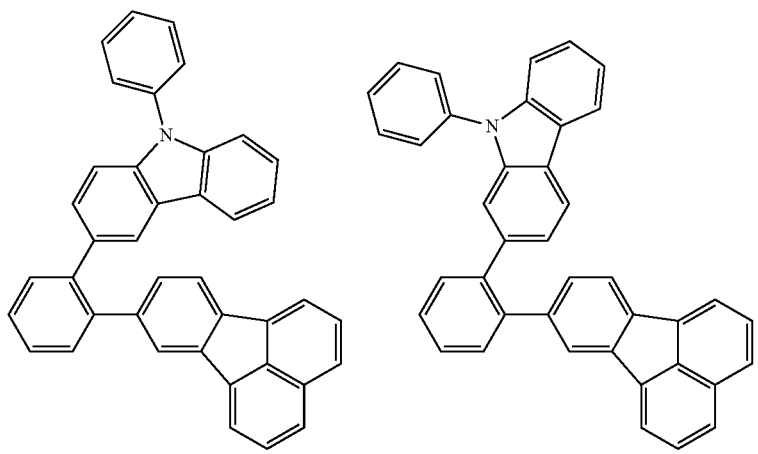

-continued
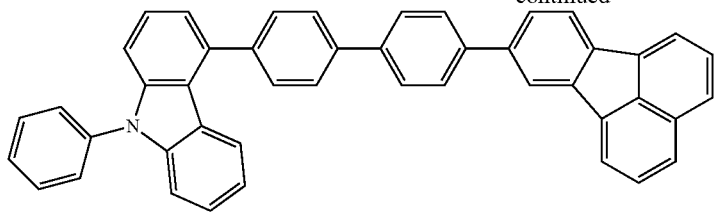
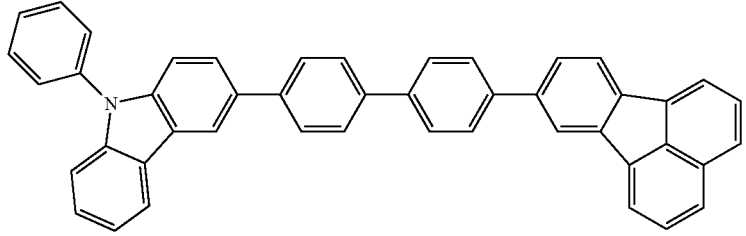
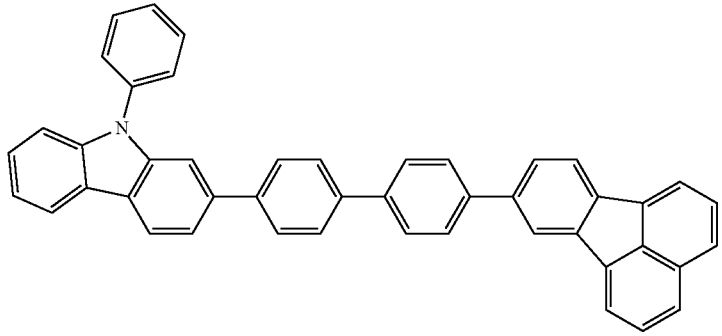
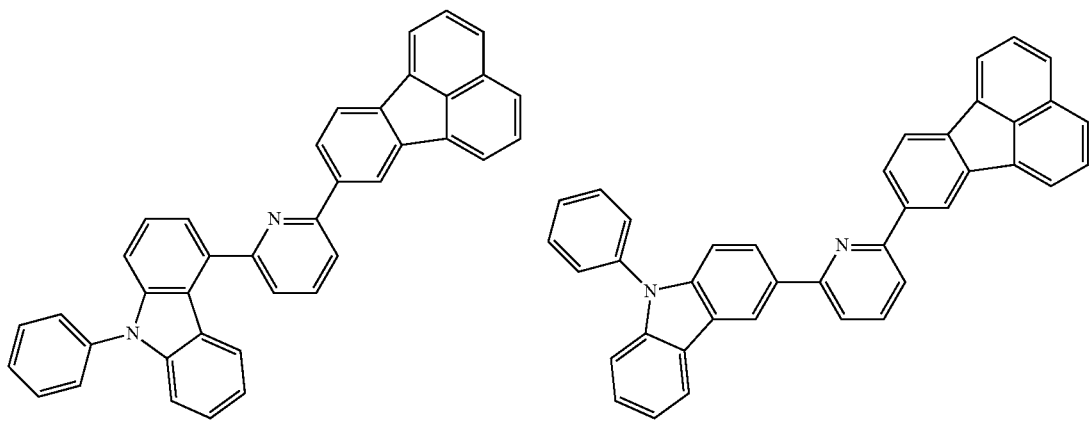
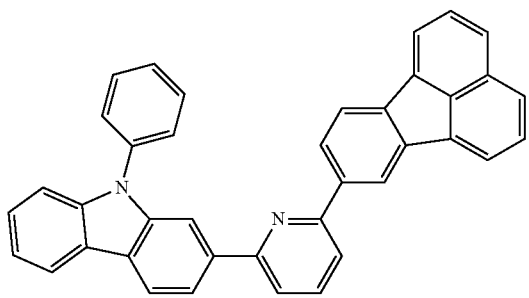

-continued
[Chem. 26]
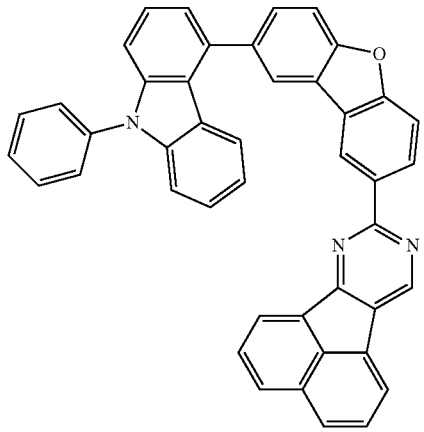
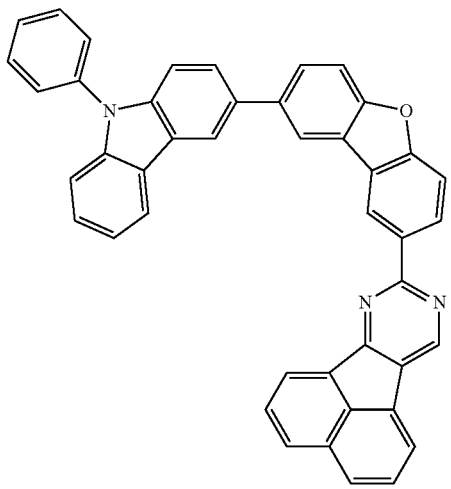
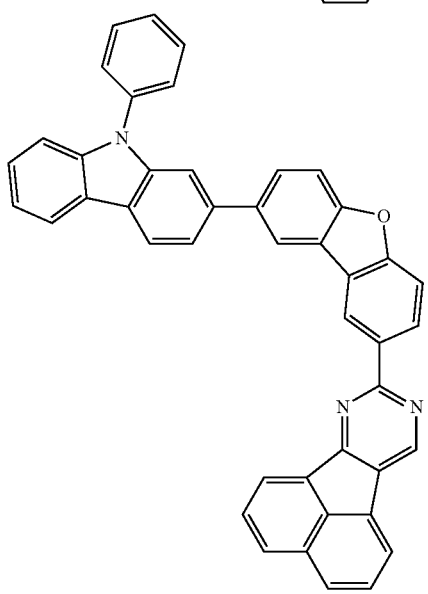
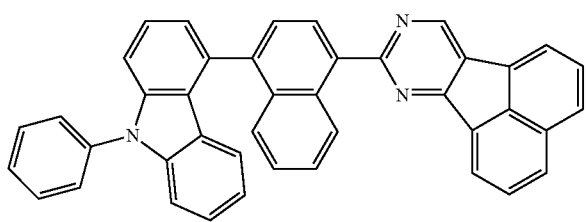
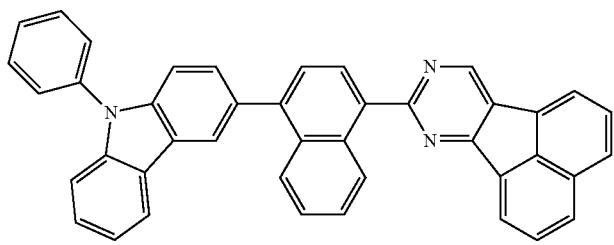

-continued
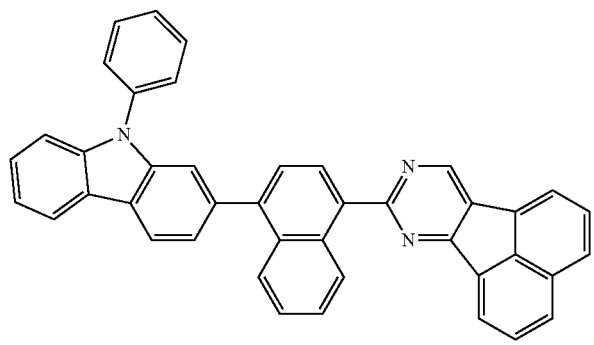
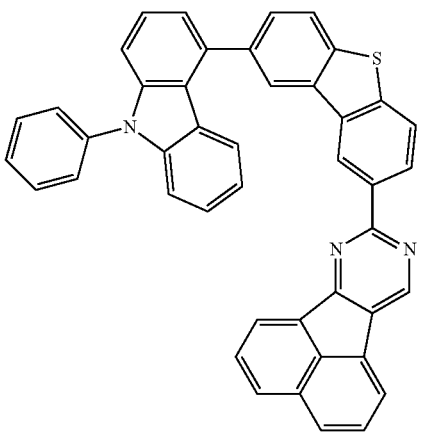
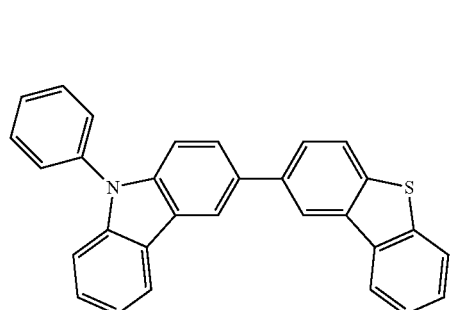
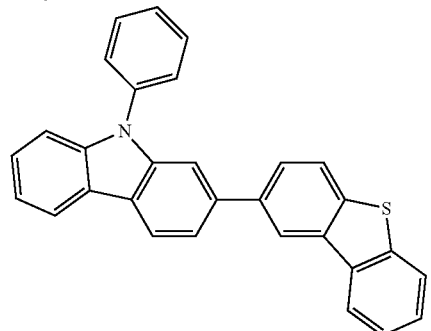
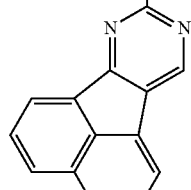
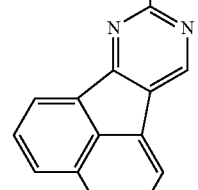
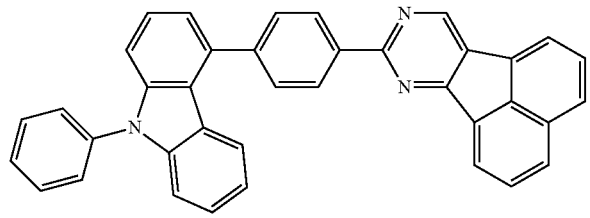
[Chem. 27]
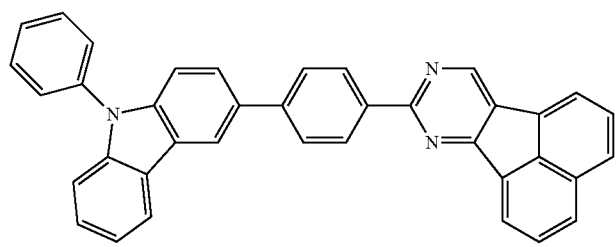

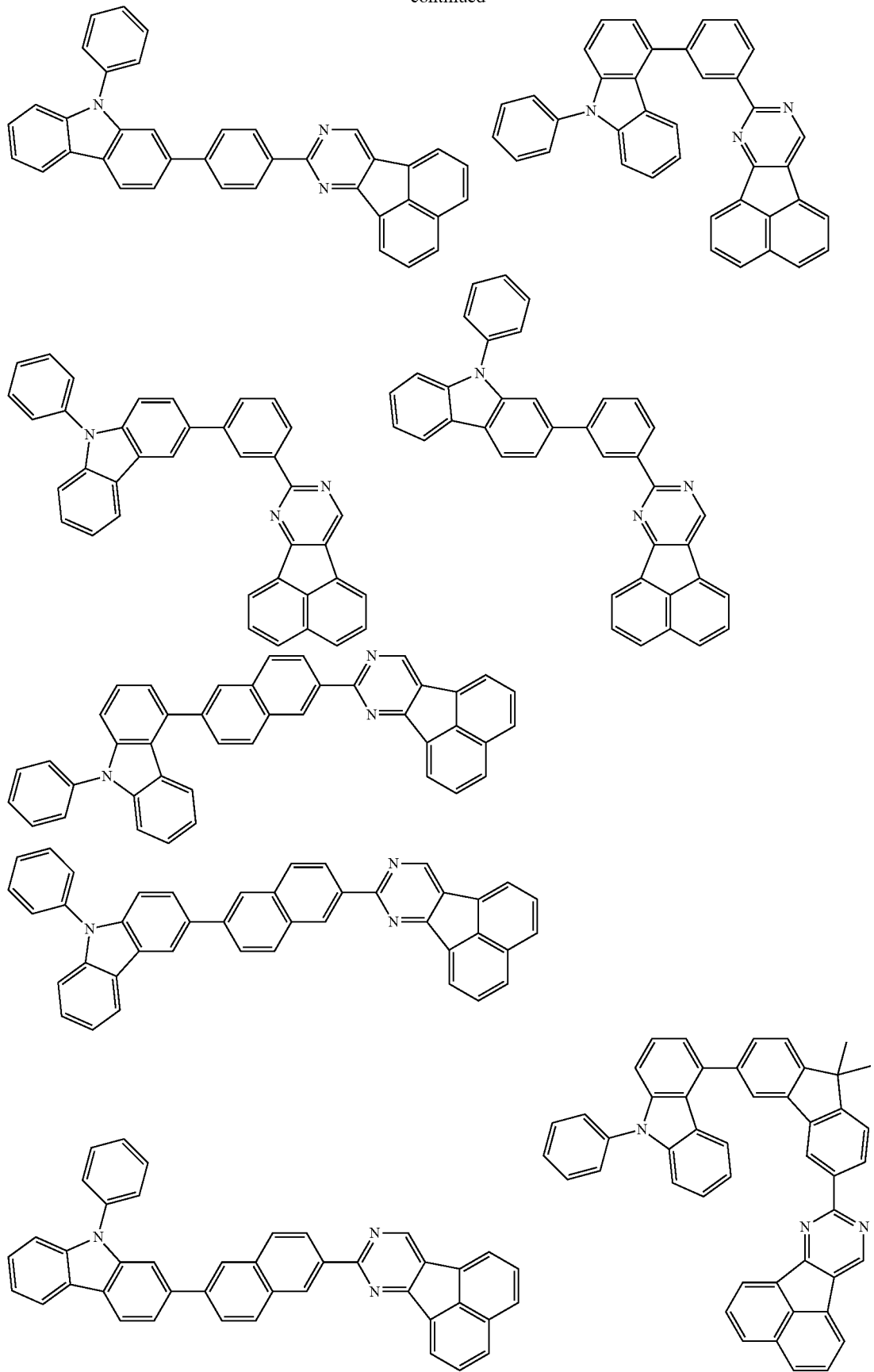

-continued
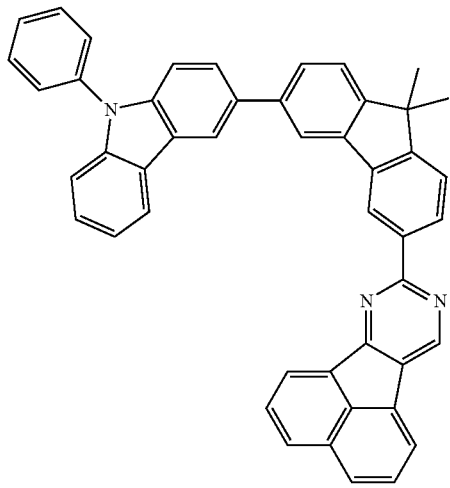
[Chem. 28]
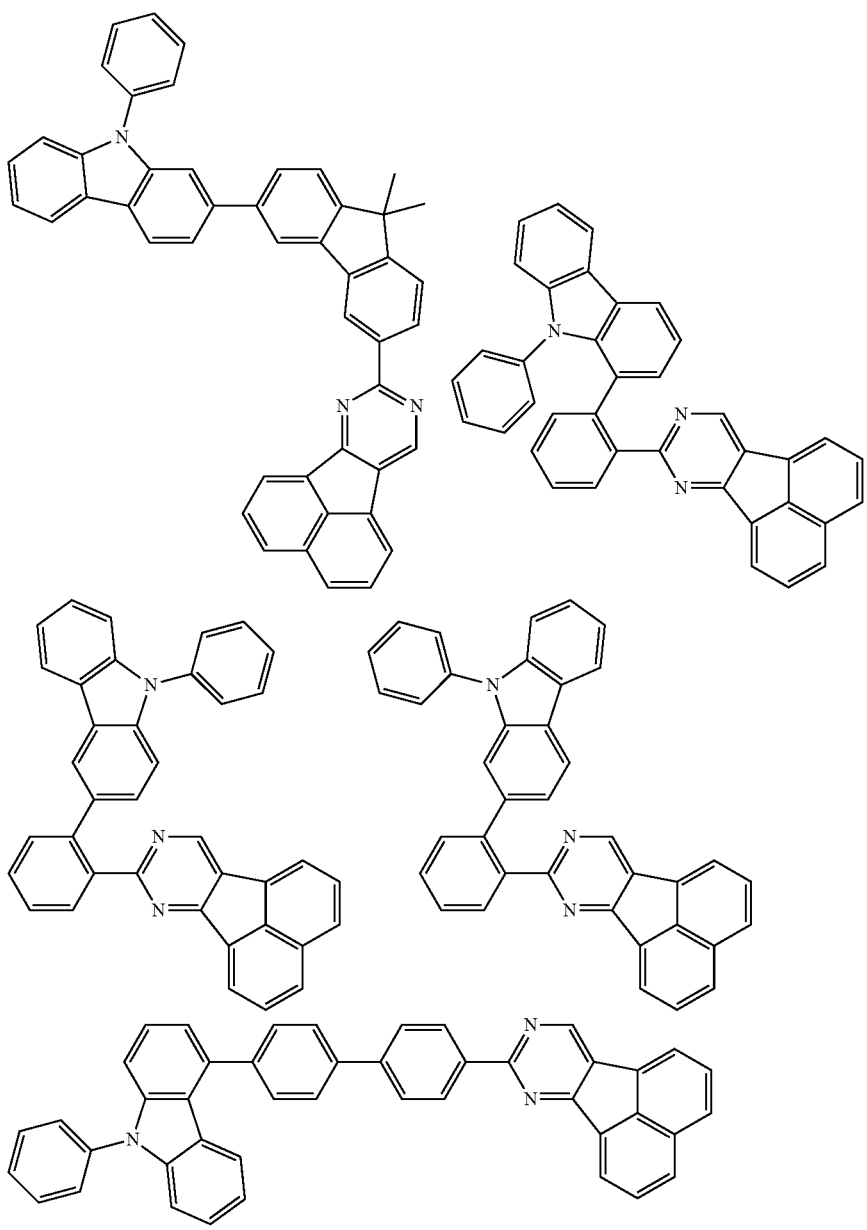

-continued
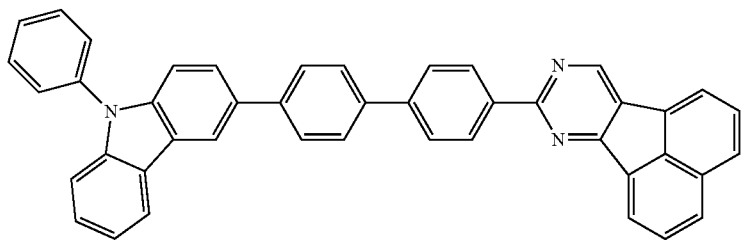
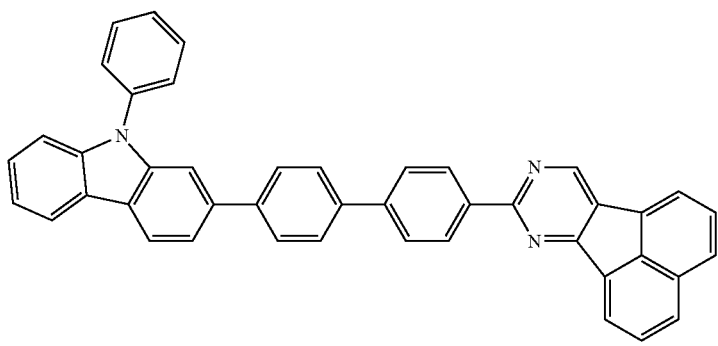
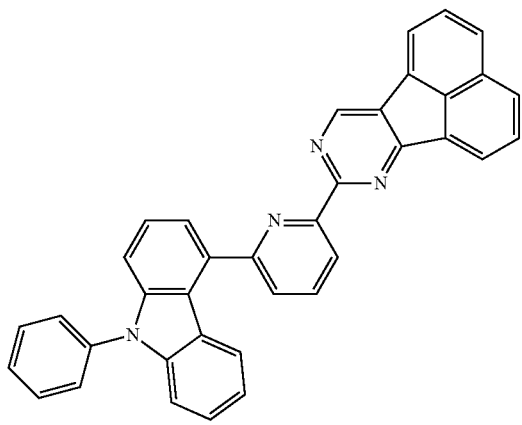
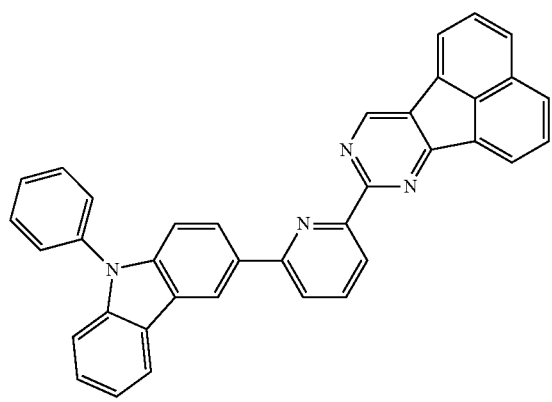
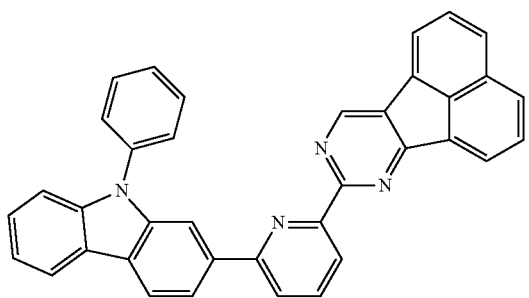

[Chem. 29]
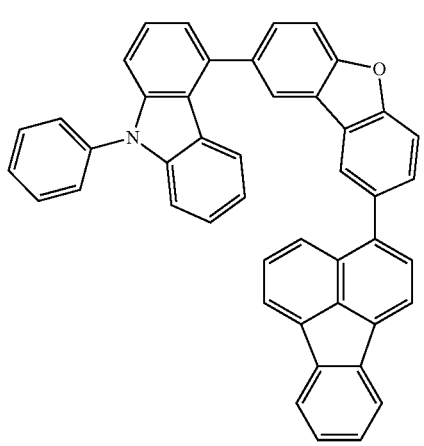
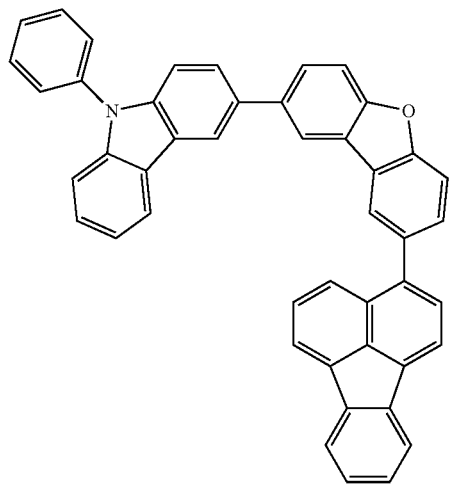
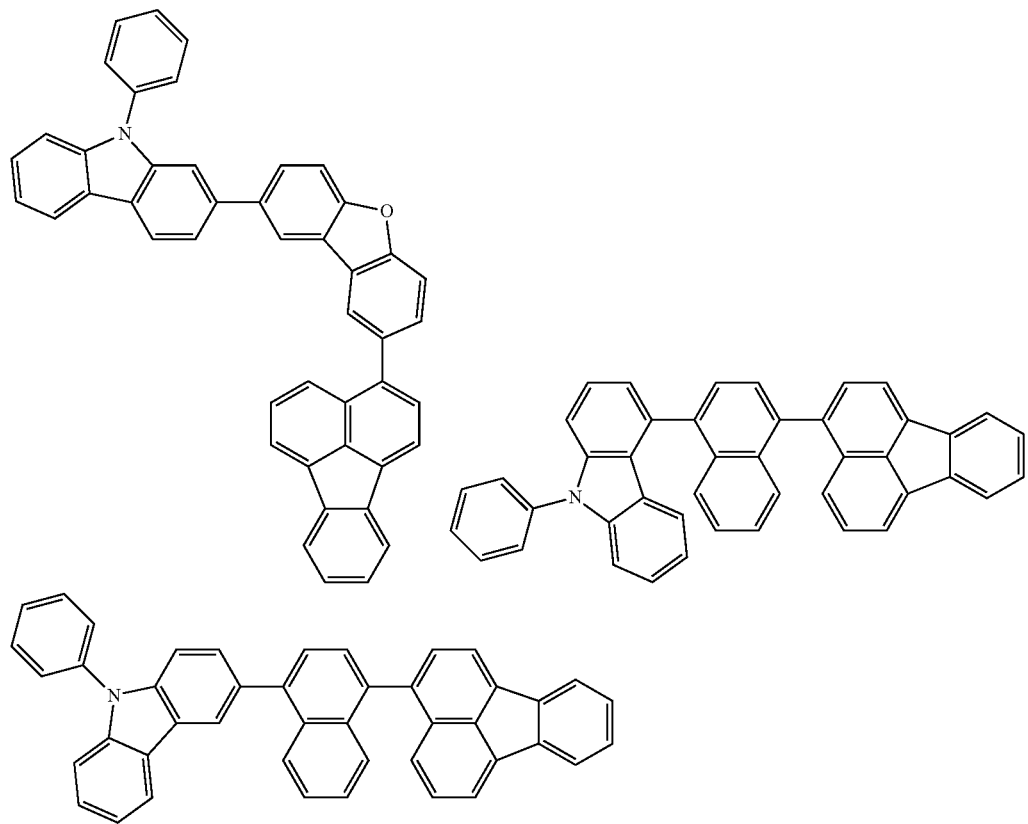

-continued
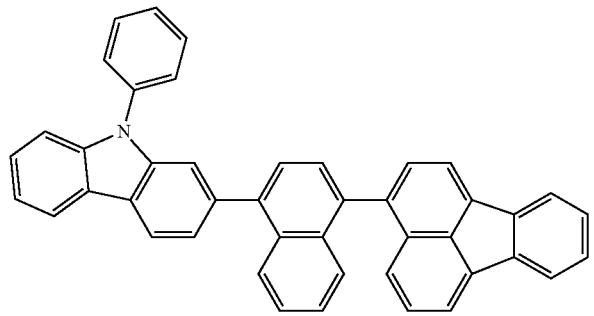
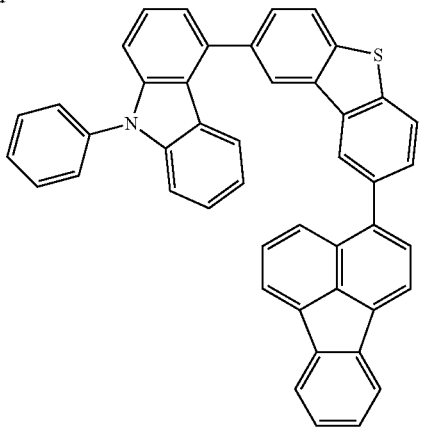
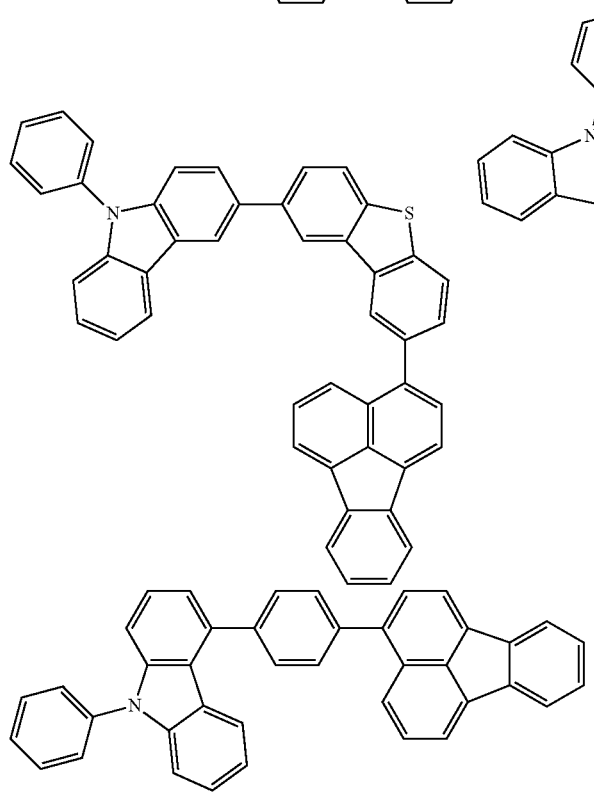
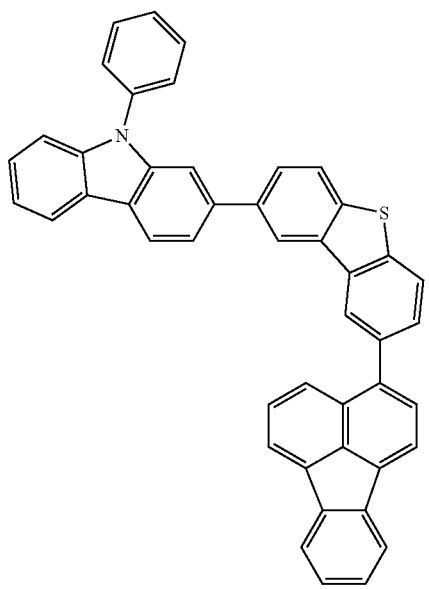
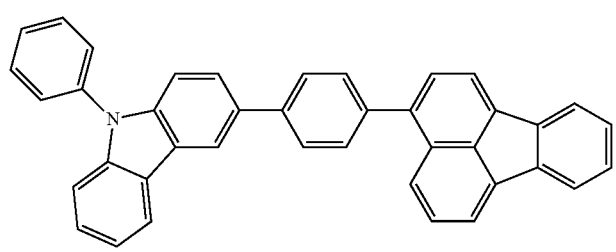
[Chem. 30]

-continued
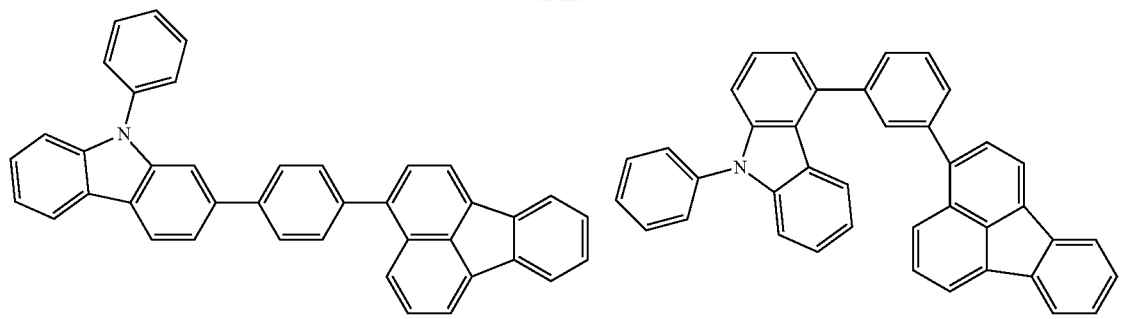
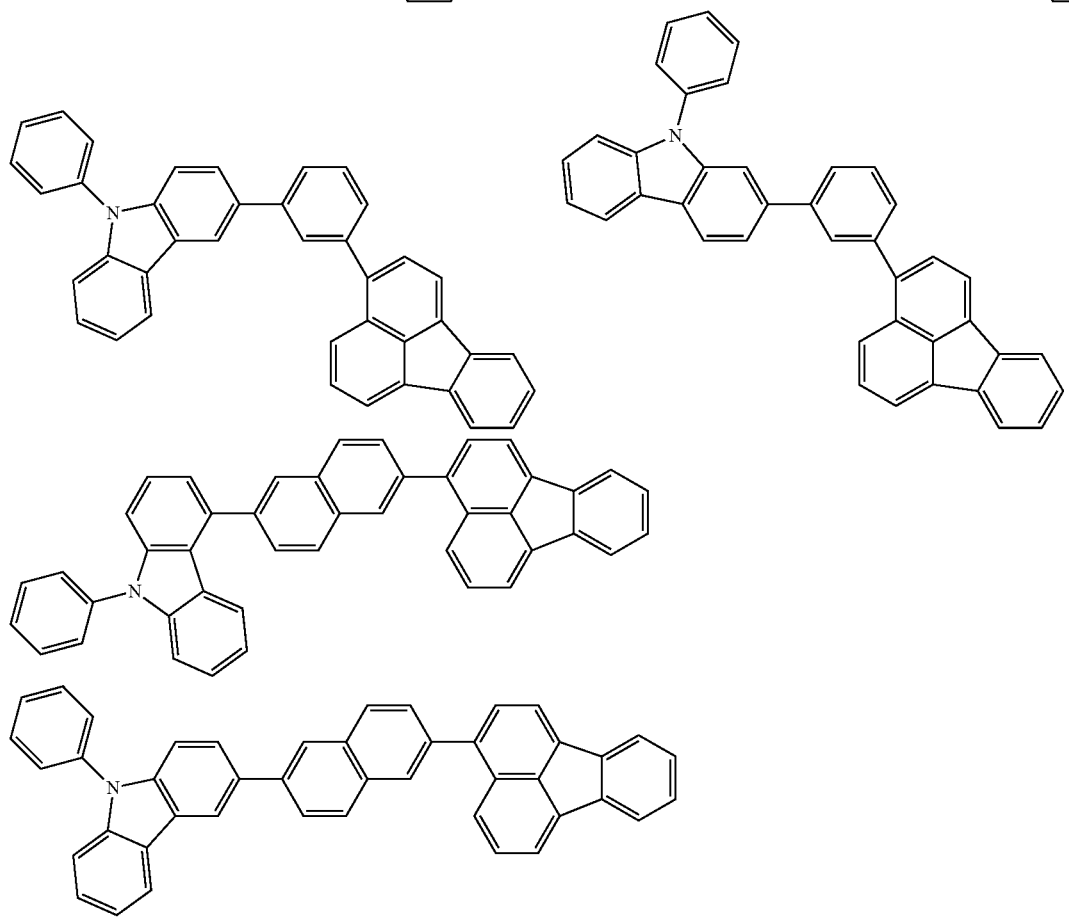
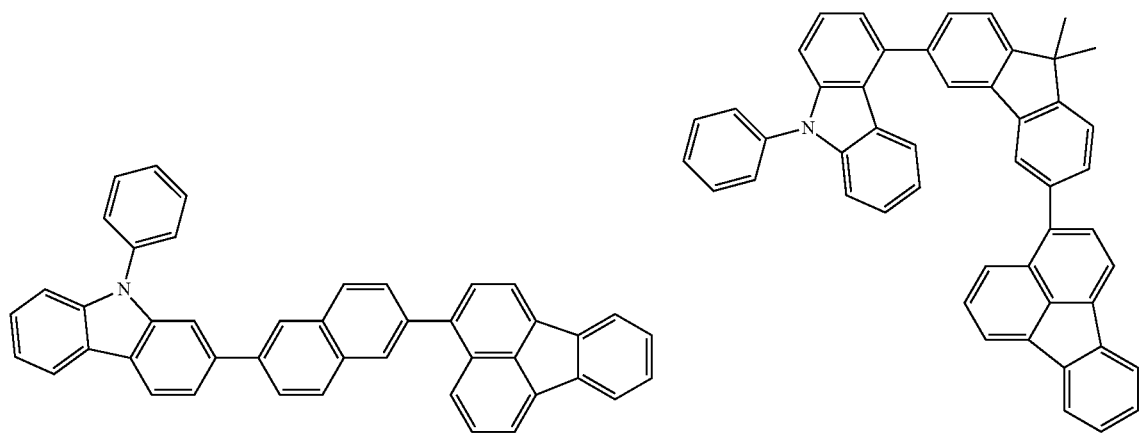

-continued
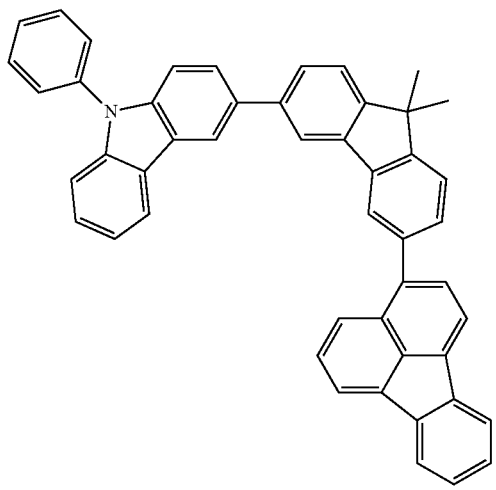
[Chem. 31]
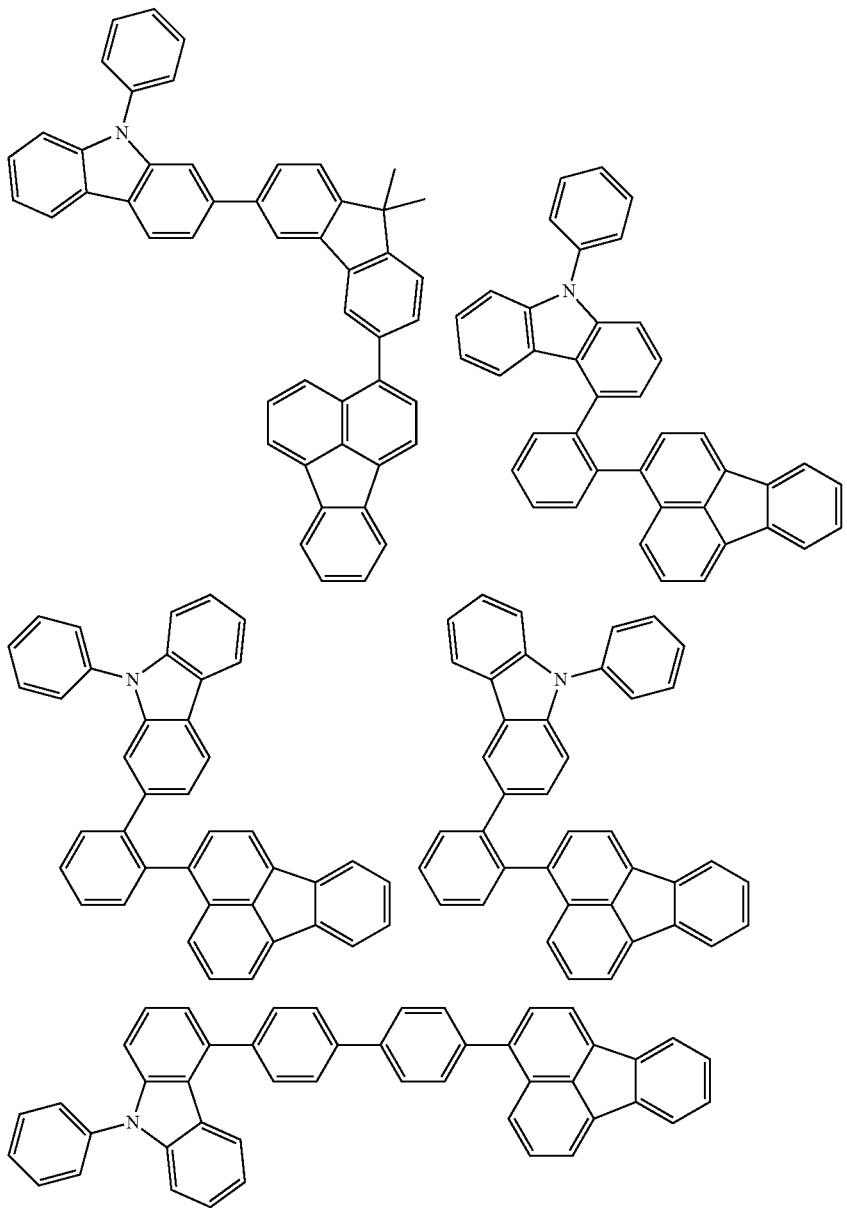

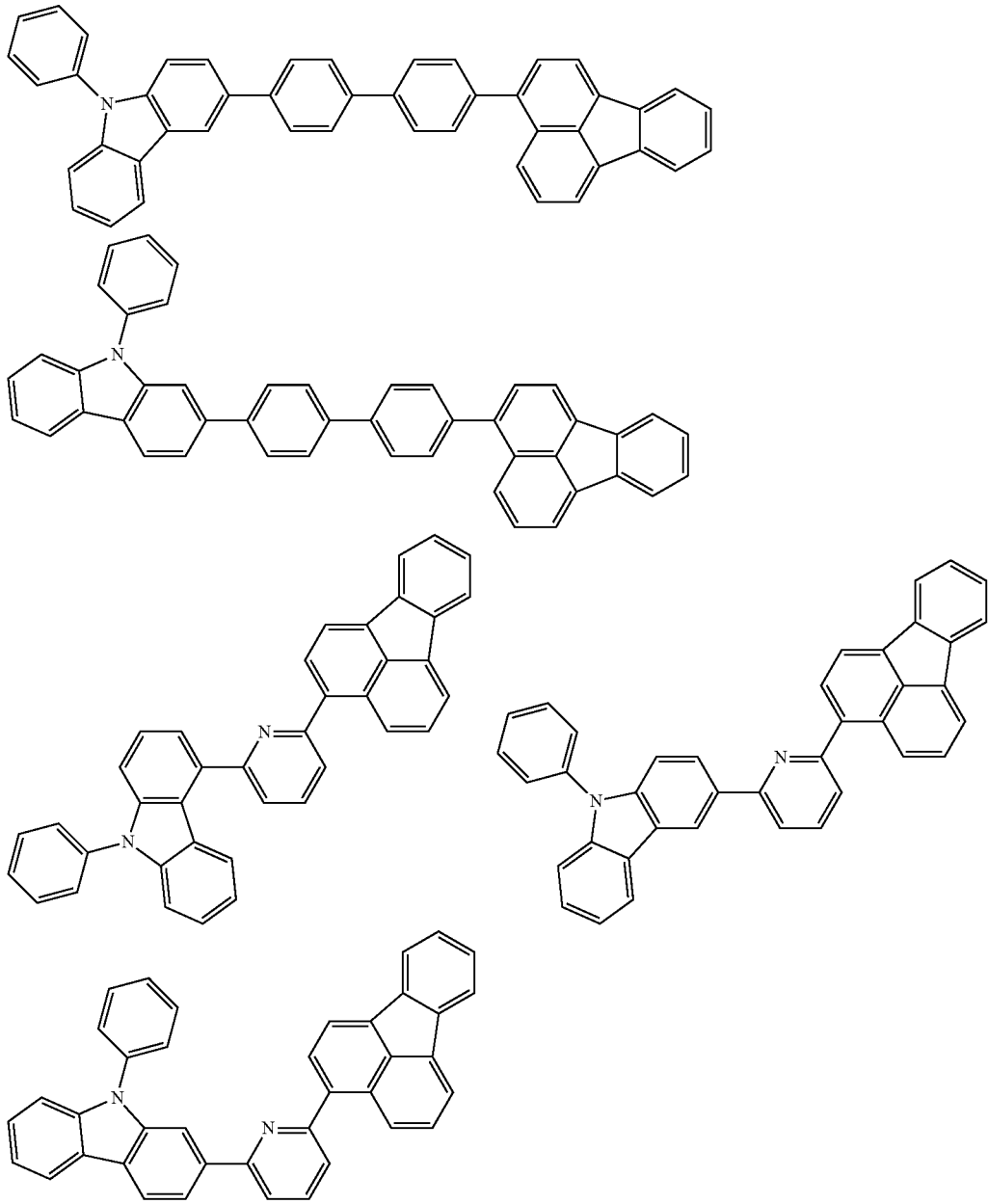
[Chem. 32]
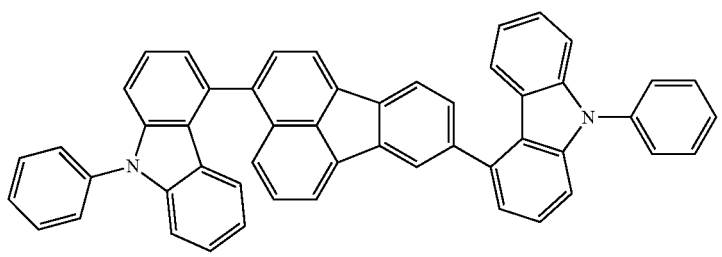

-continued
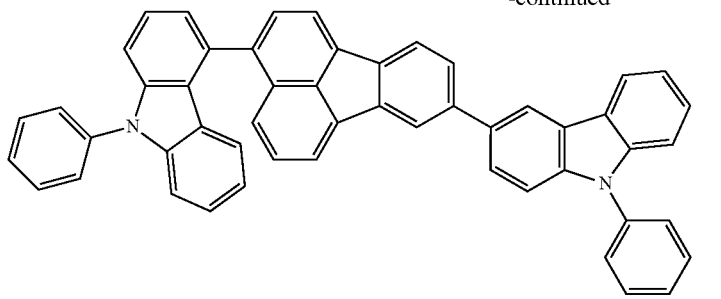
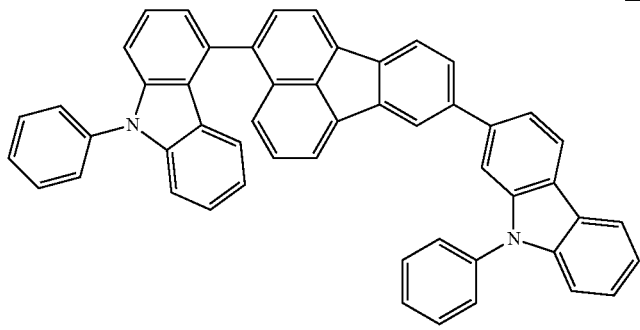
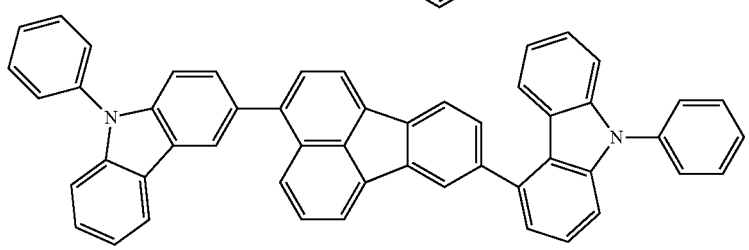
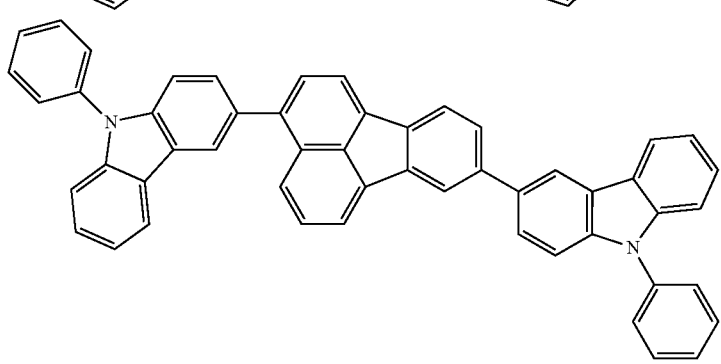
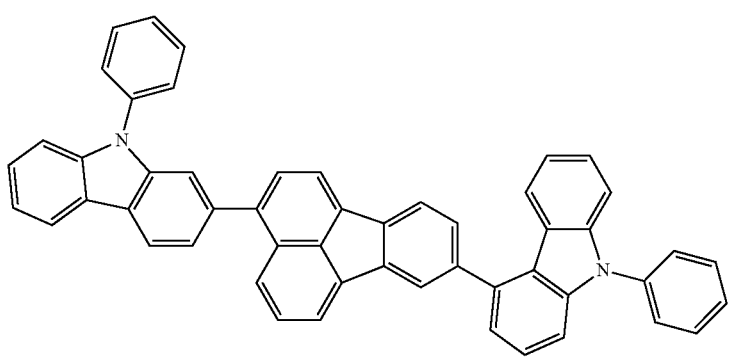

-continued
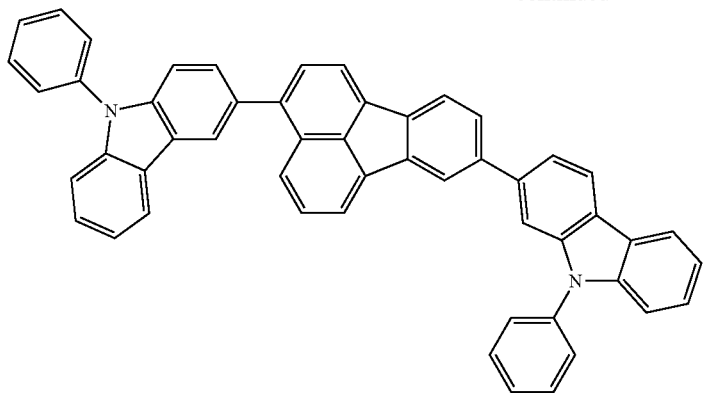
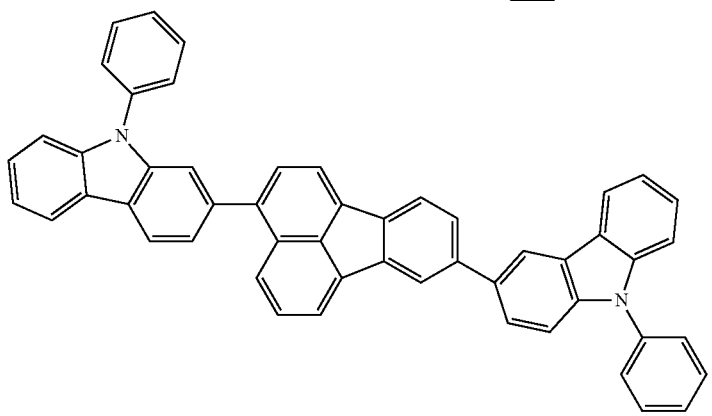
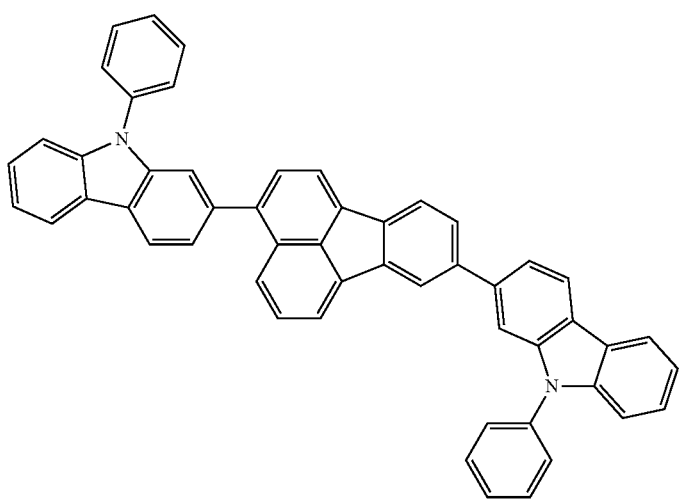

[Chem. 33]
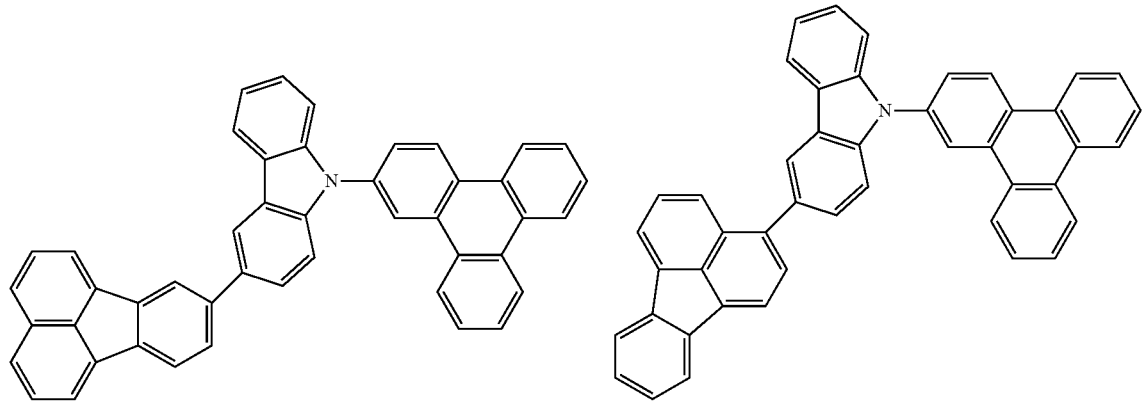
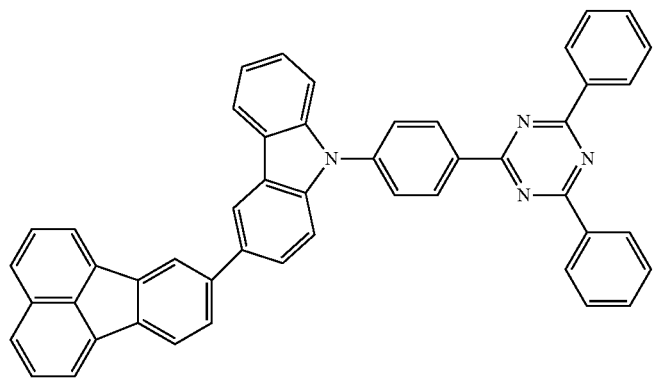
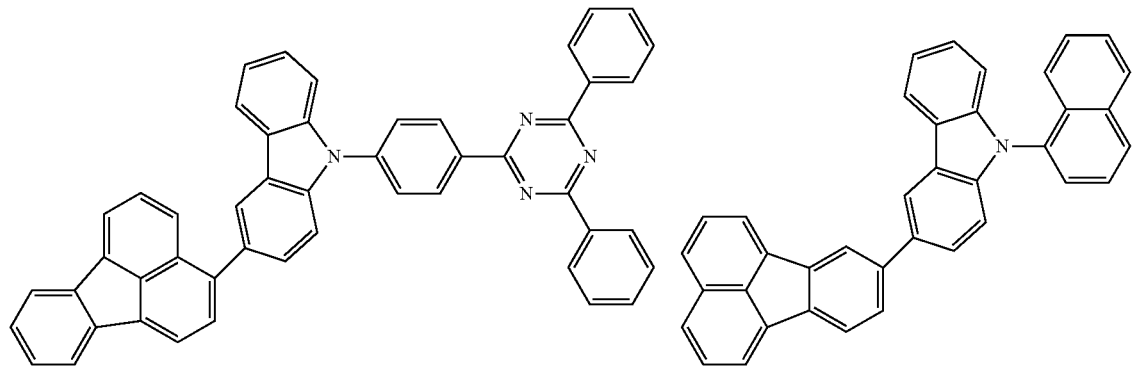
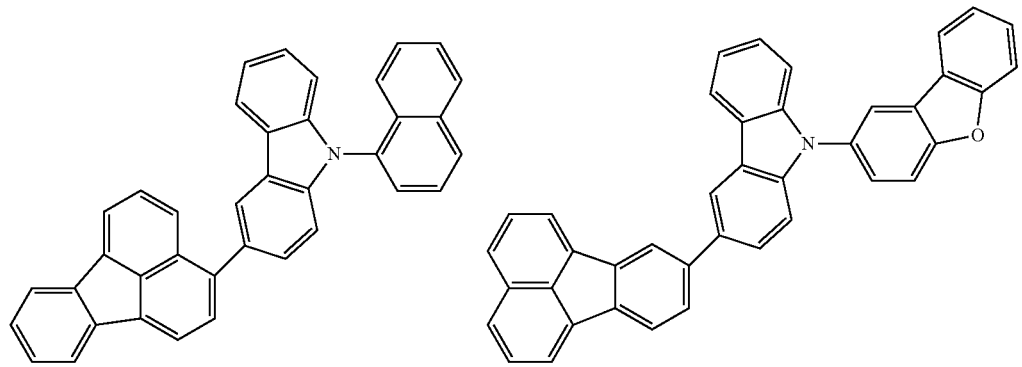

-continued
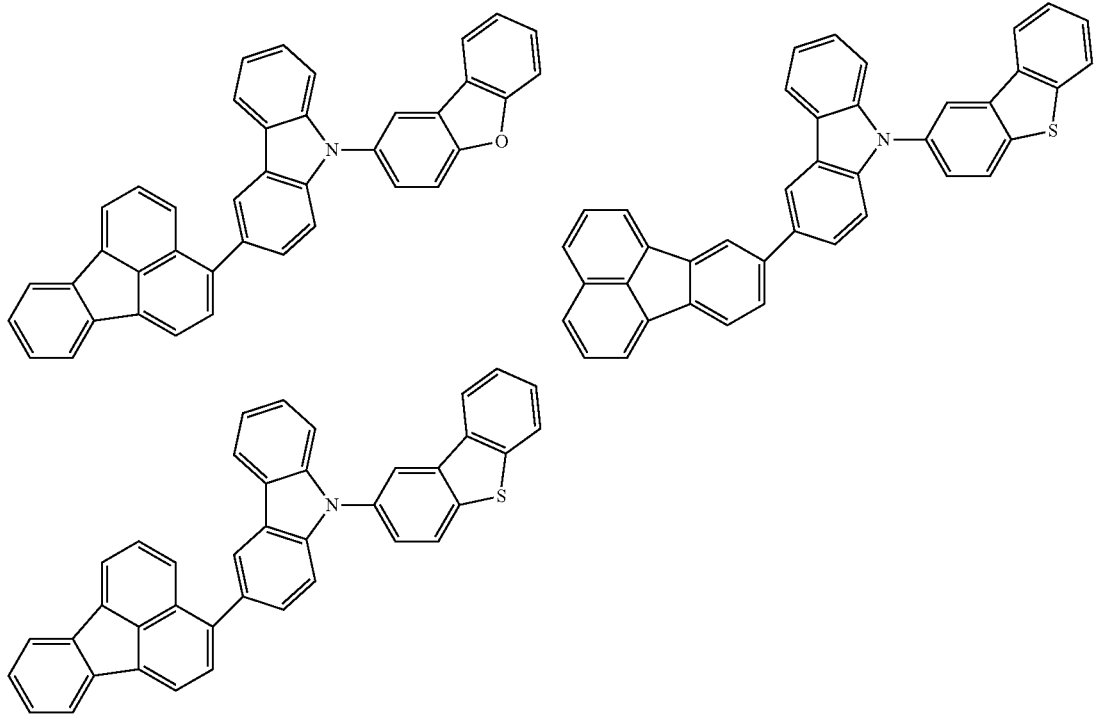
[Chem. 34]
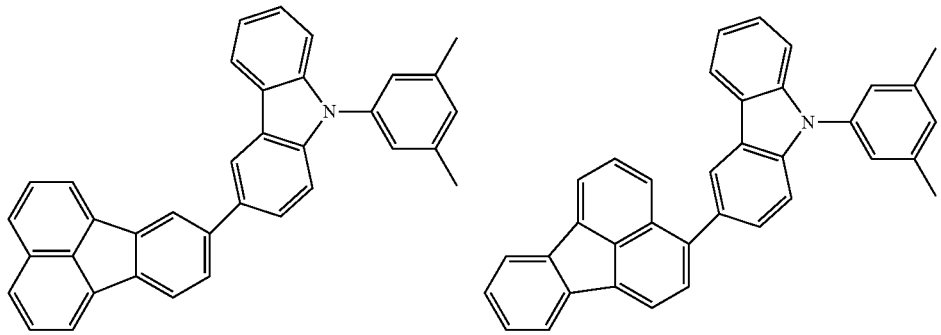
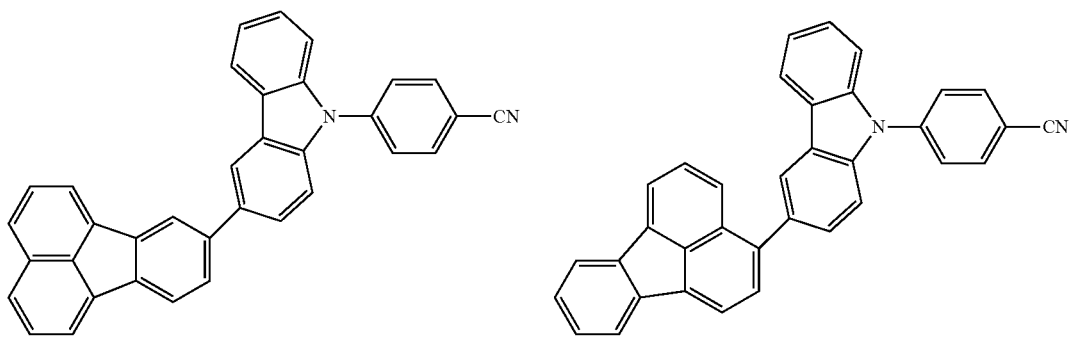

-continued
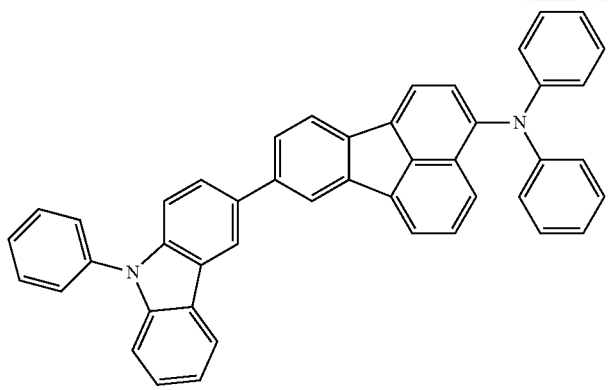
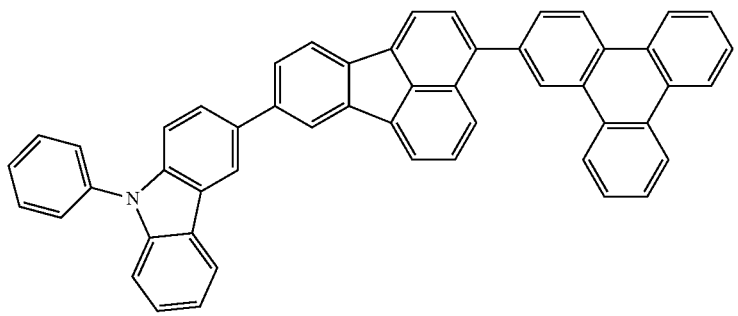
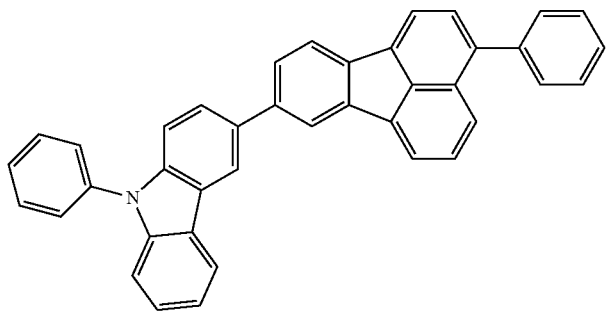
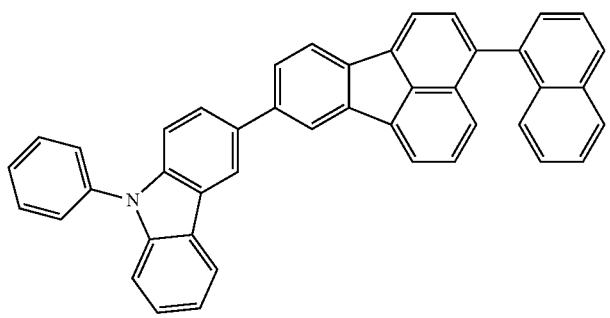
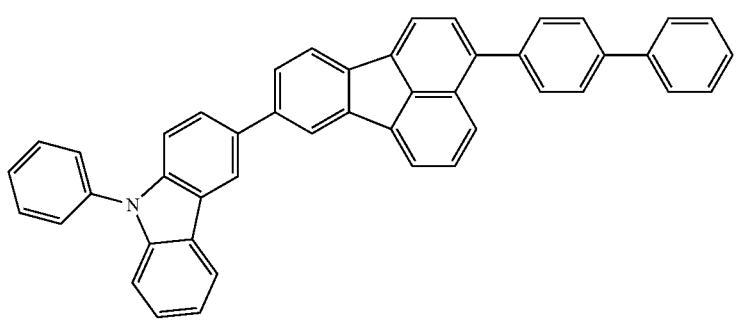

-continued
[Chem. 35]
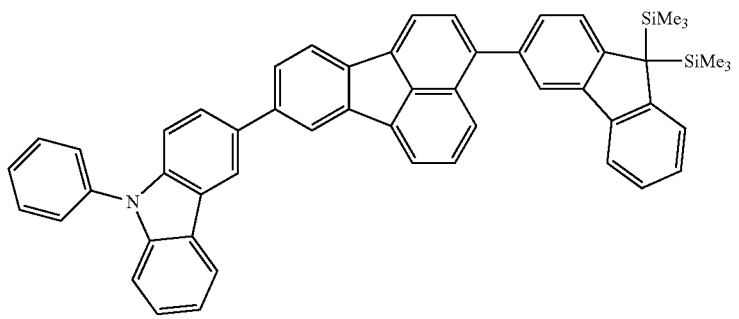
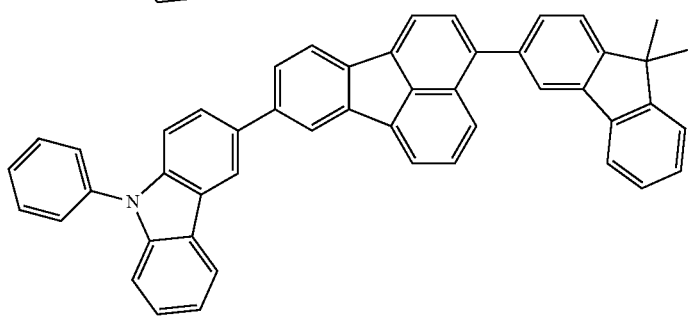
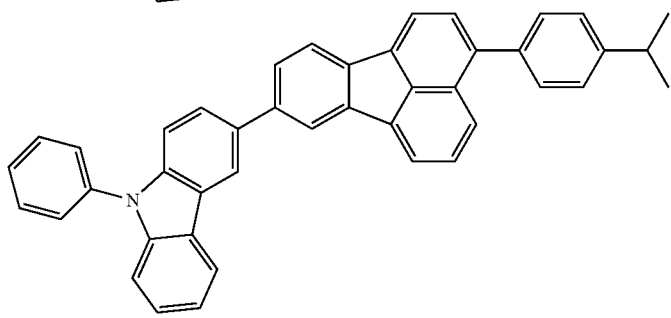
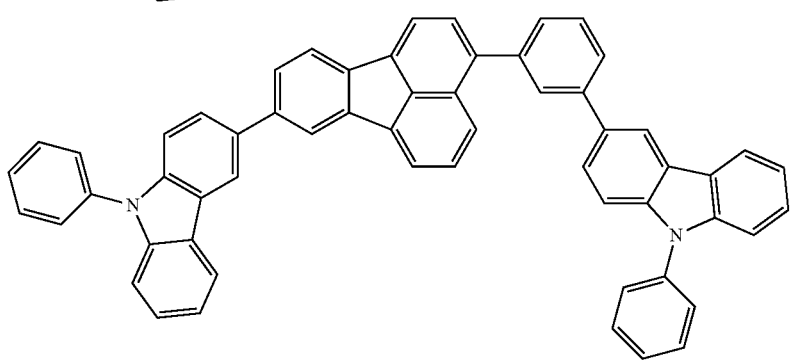
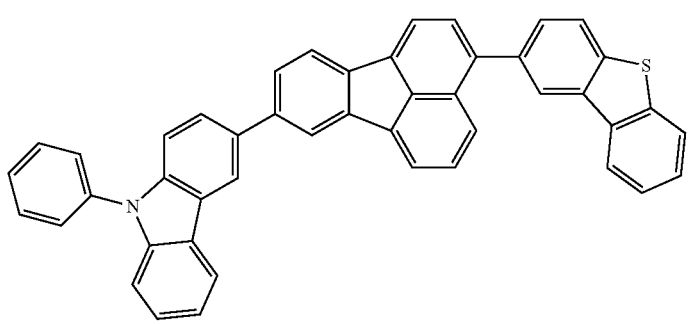

-continued
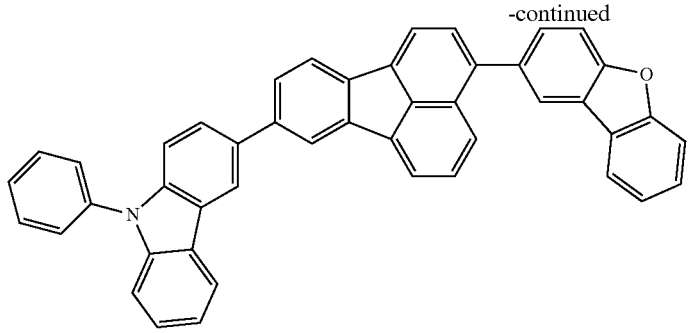
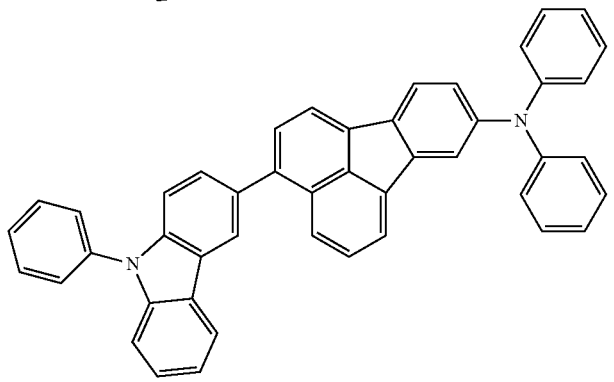
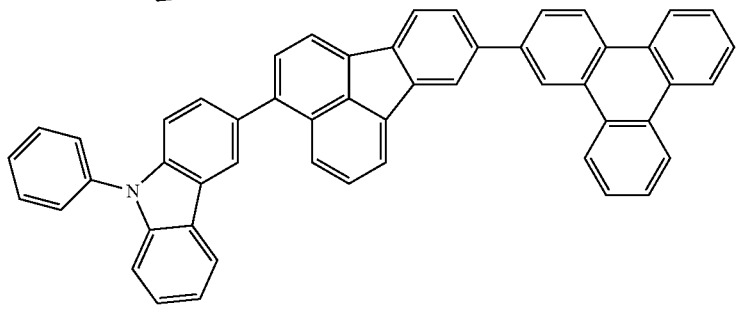
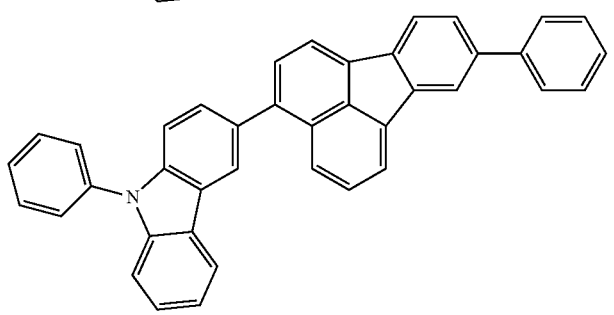
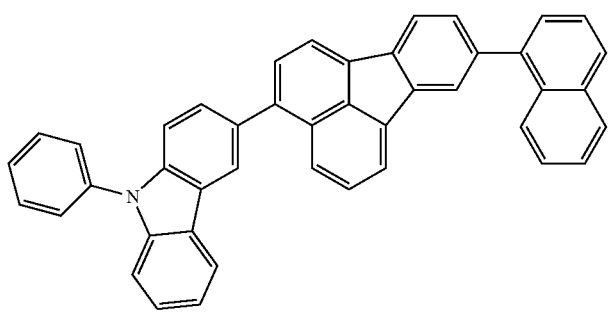

-continued
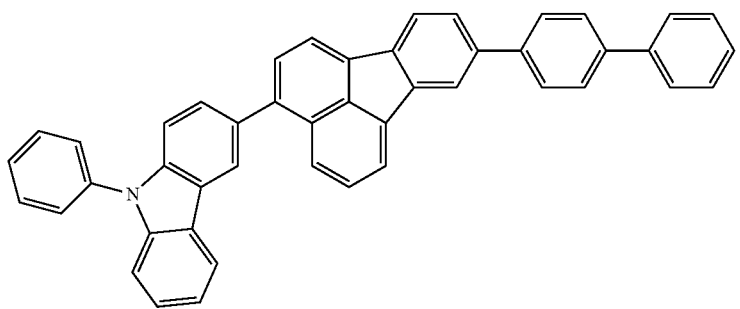
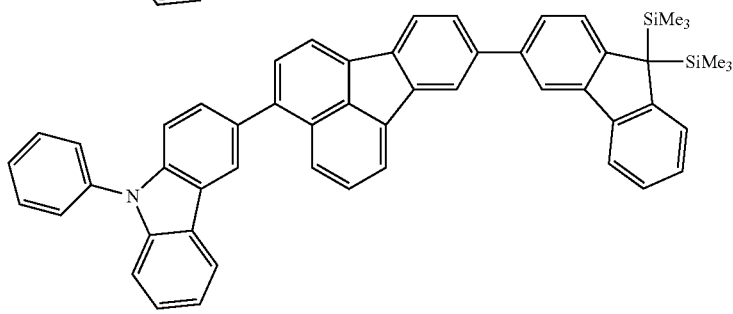
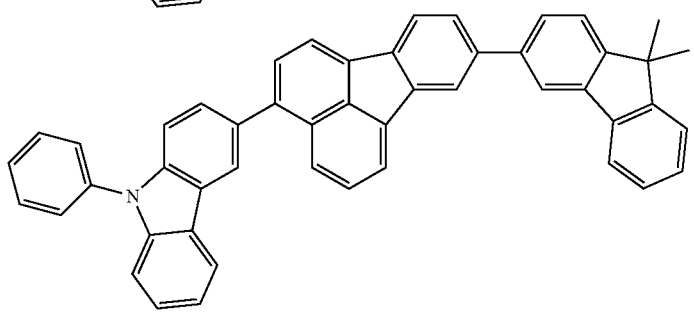
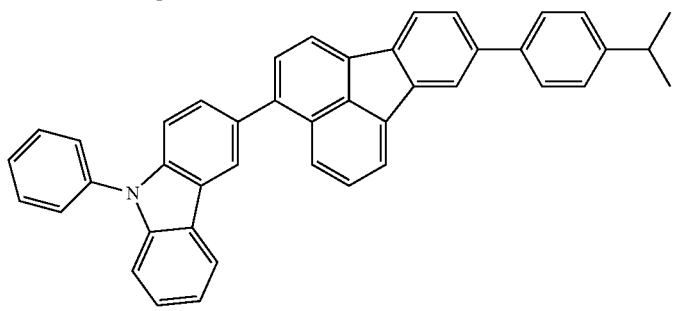
[Chem. 36]
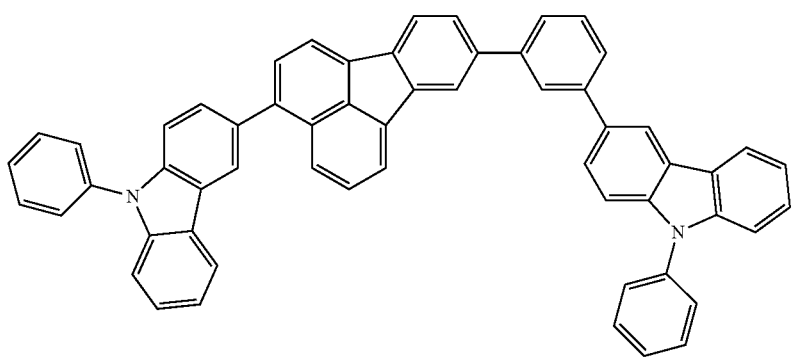

-continued
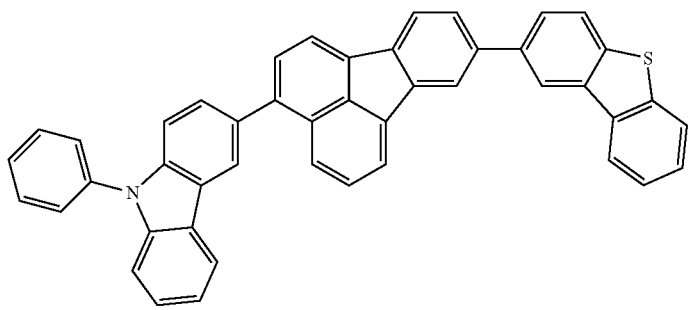
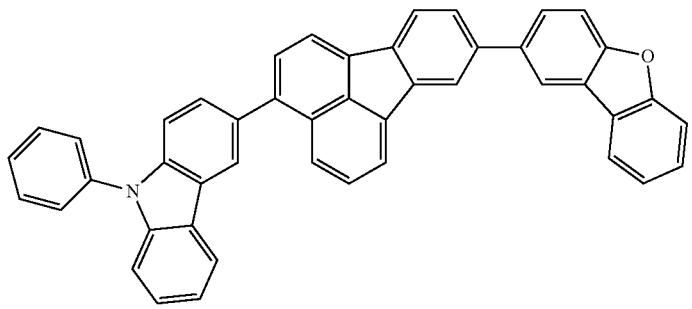
[Chem. 37]
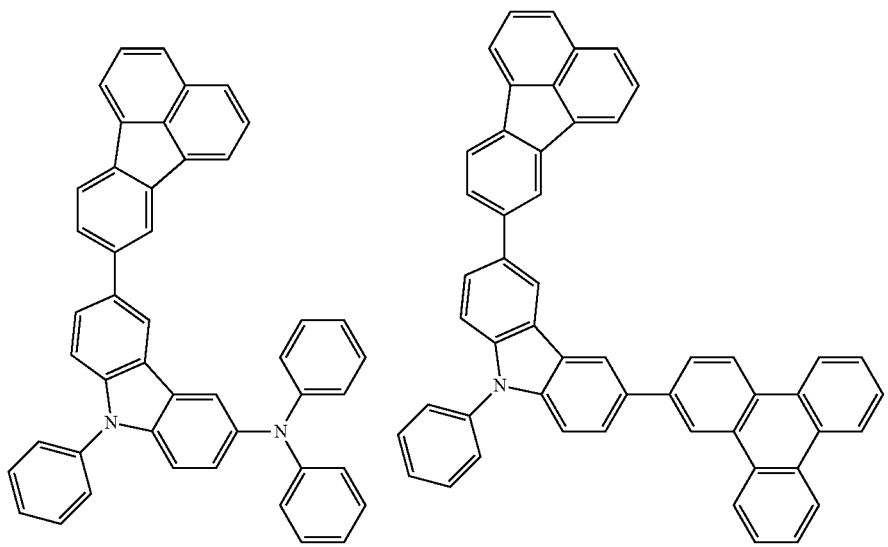
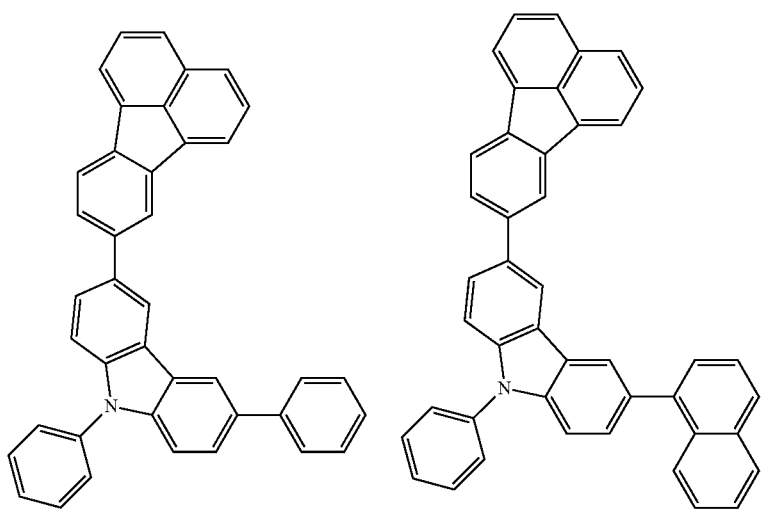

-continued
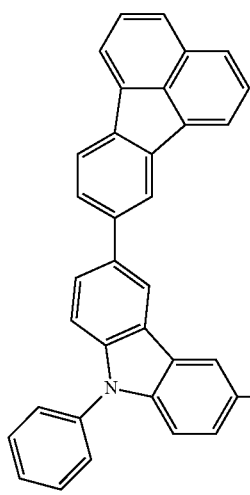
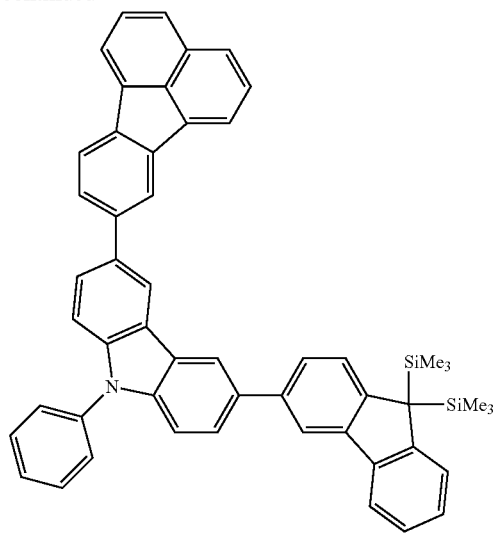
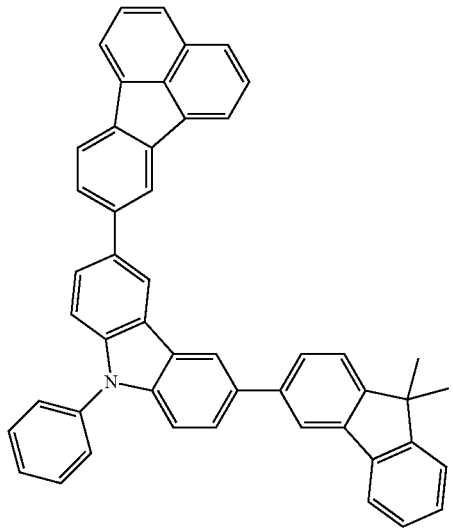
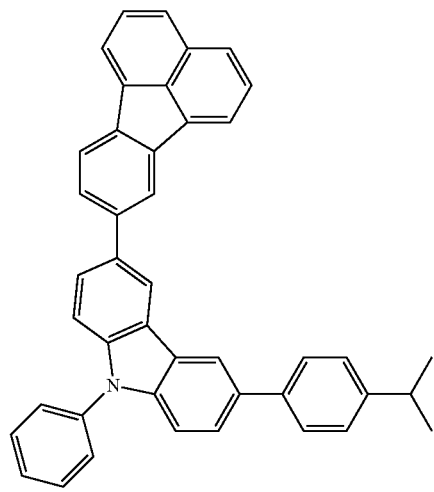
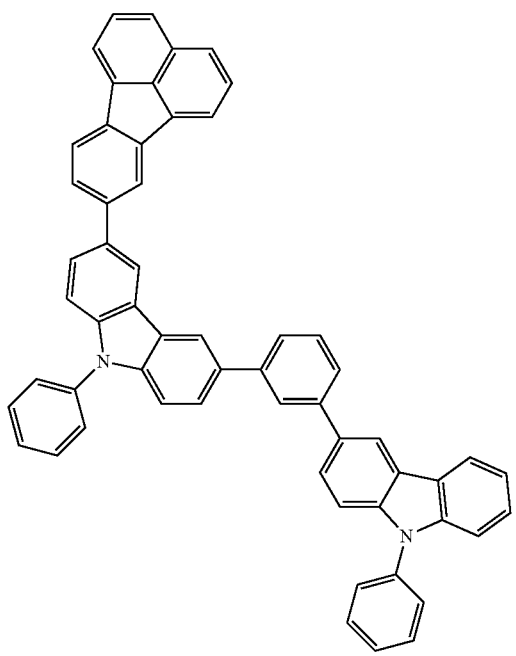
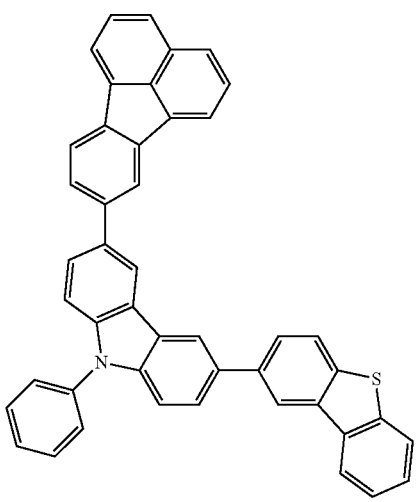

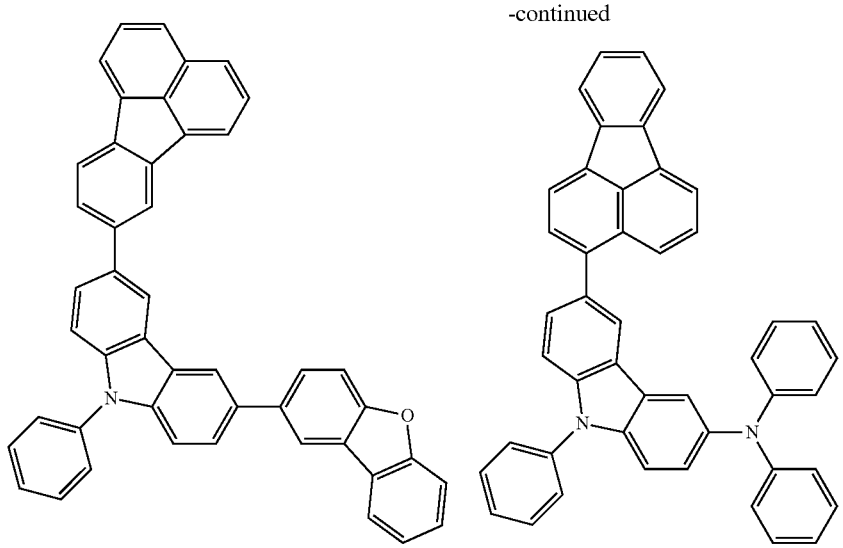
[Chem. 38]
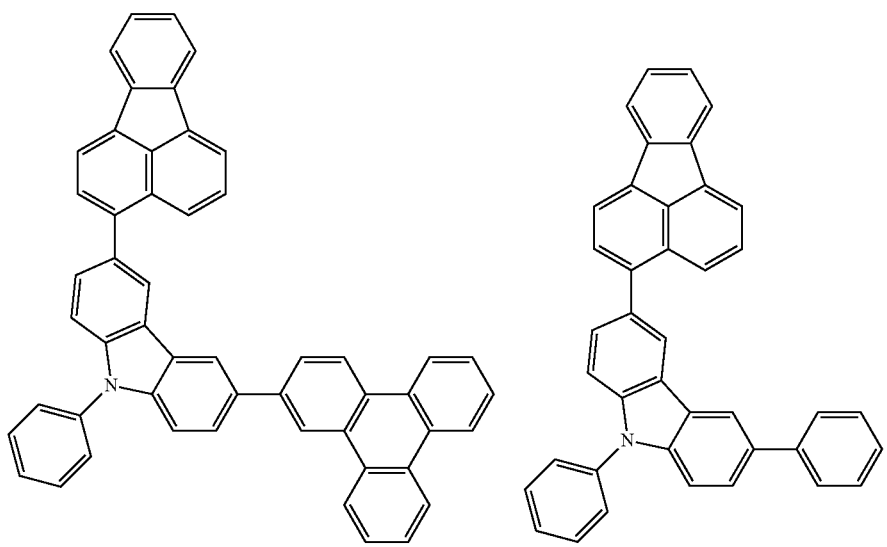
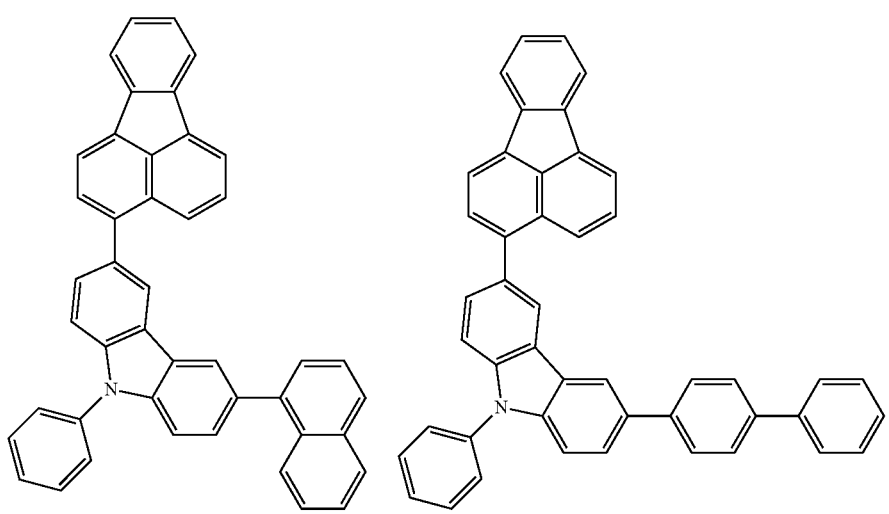

-continued
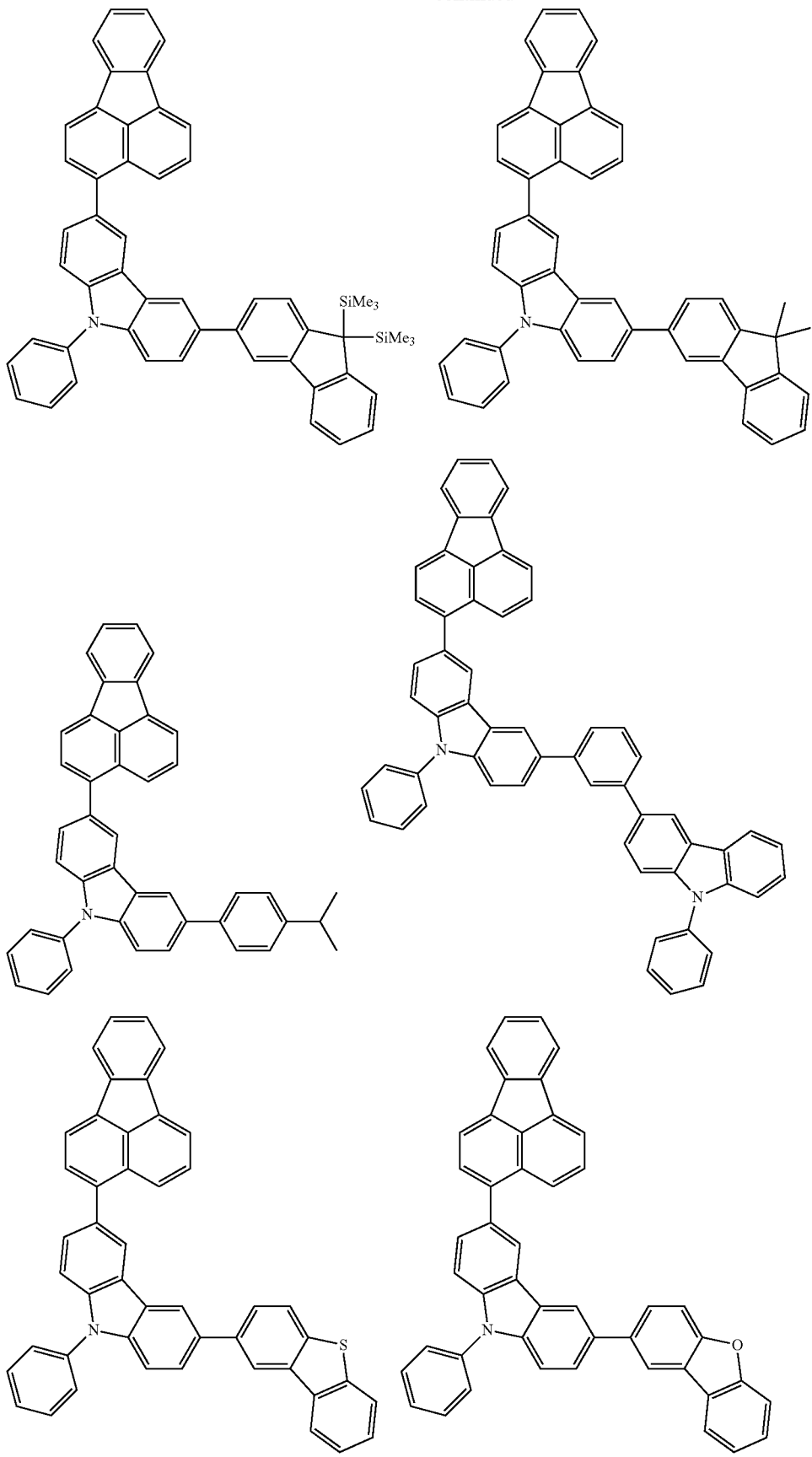

-continued
[Chem. 39]
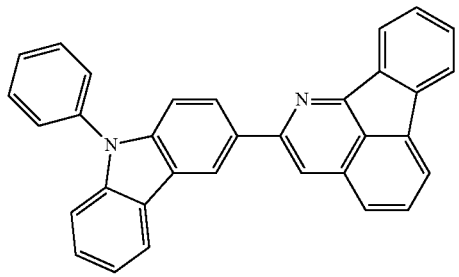
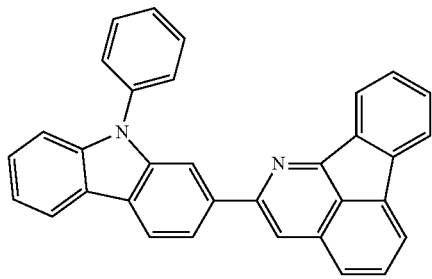
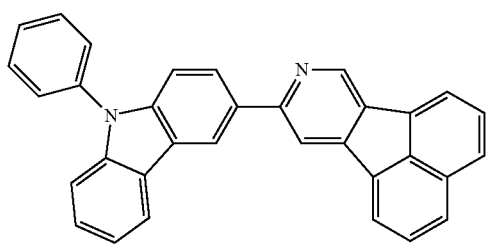
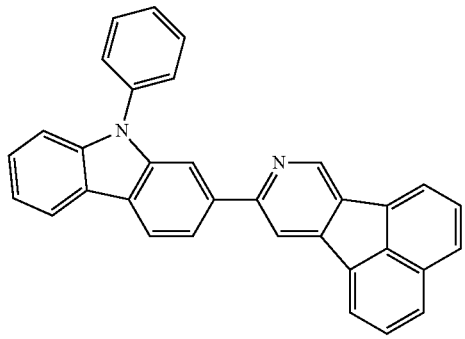
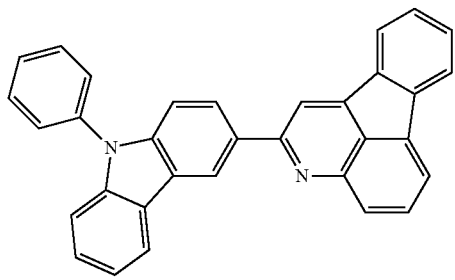
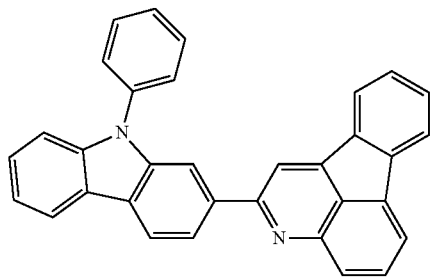
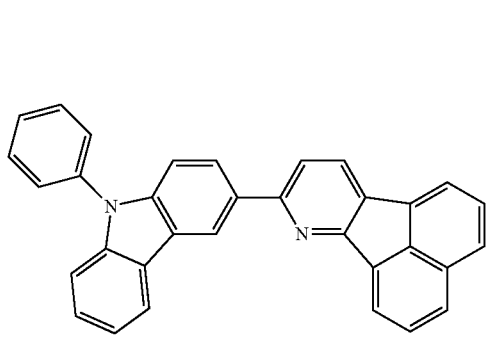
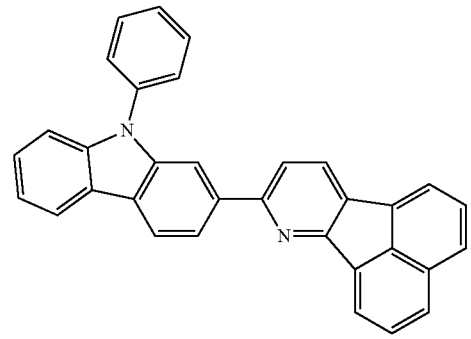
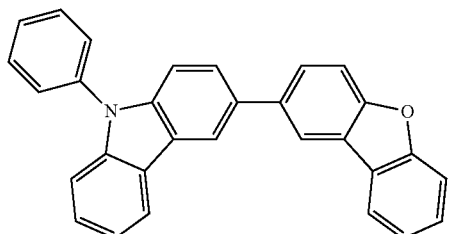
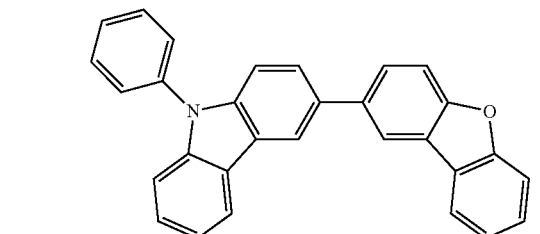
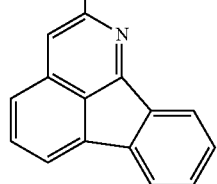
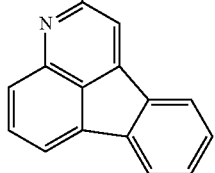

-continued
[Chem. 40]
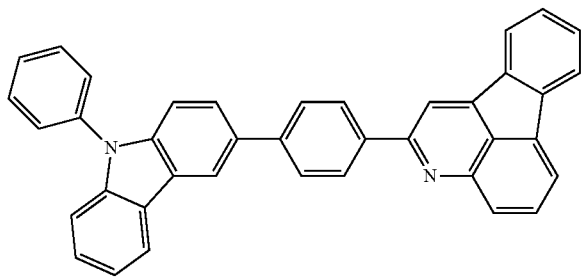
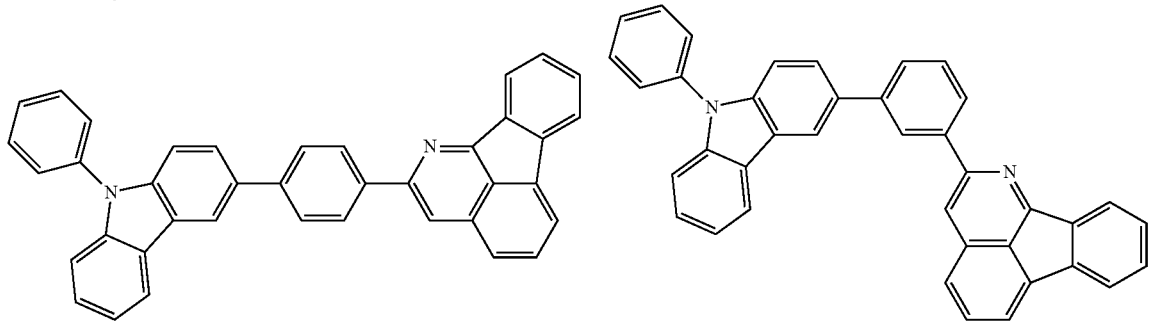
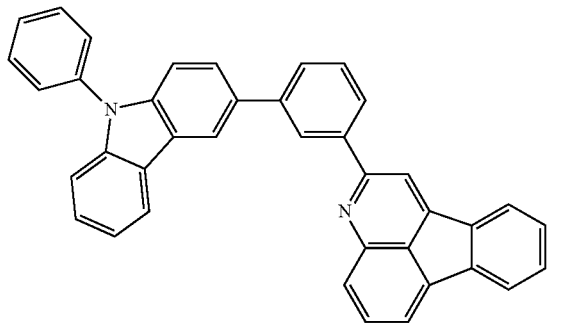
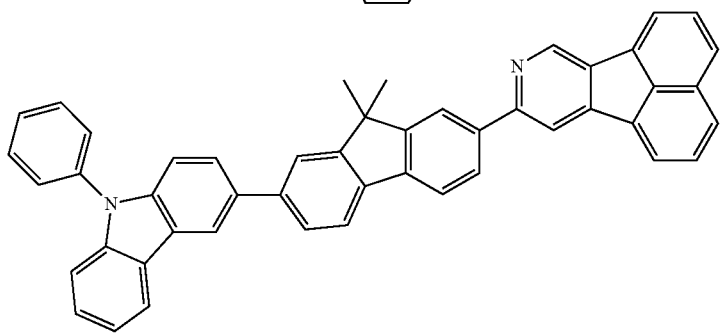
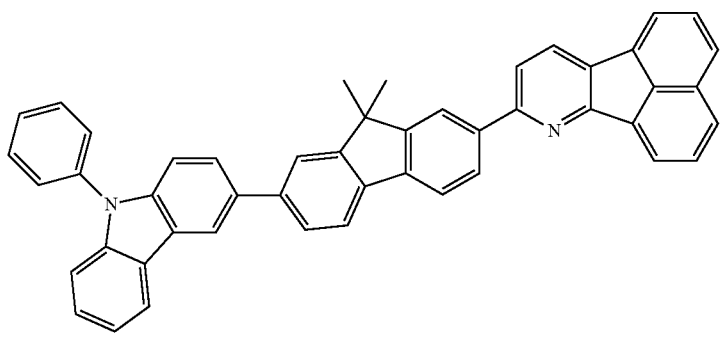

-continued
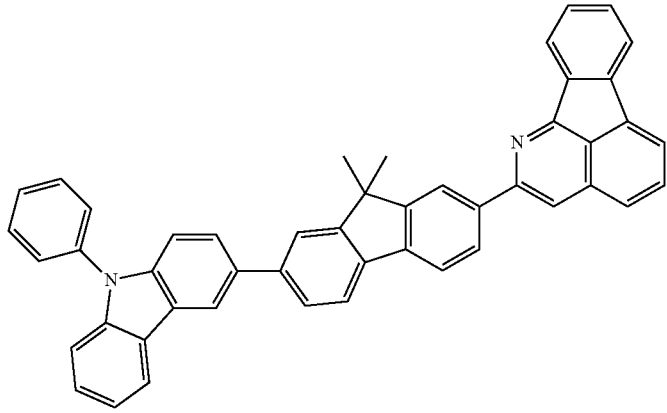
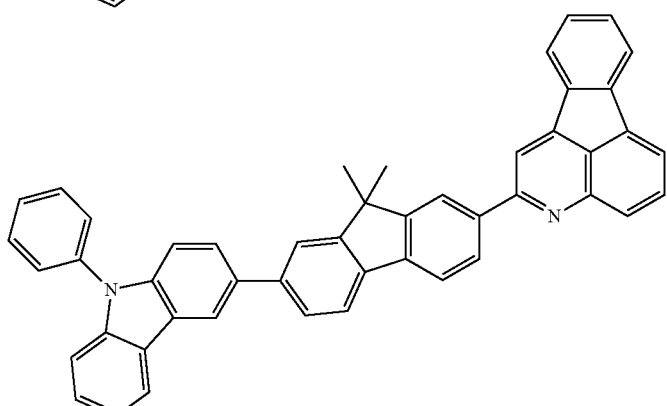
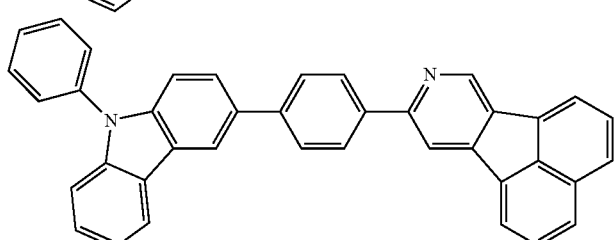
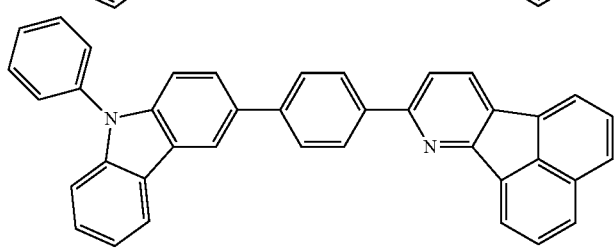
[Chem. 41]
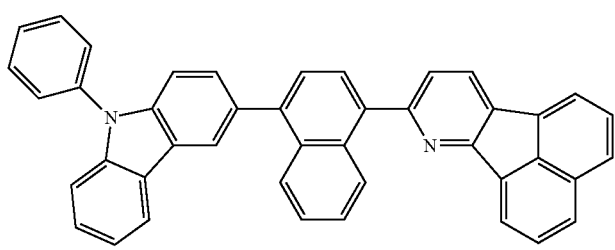

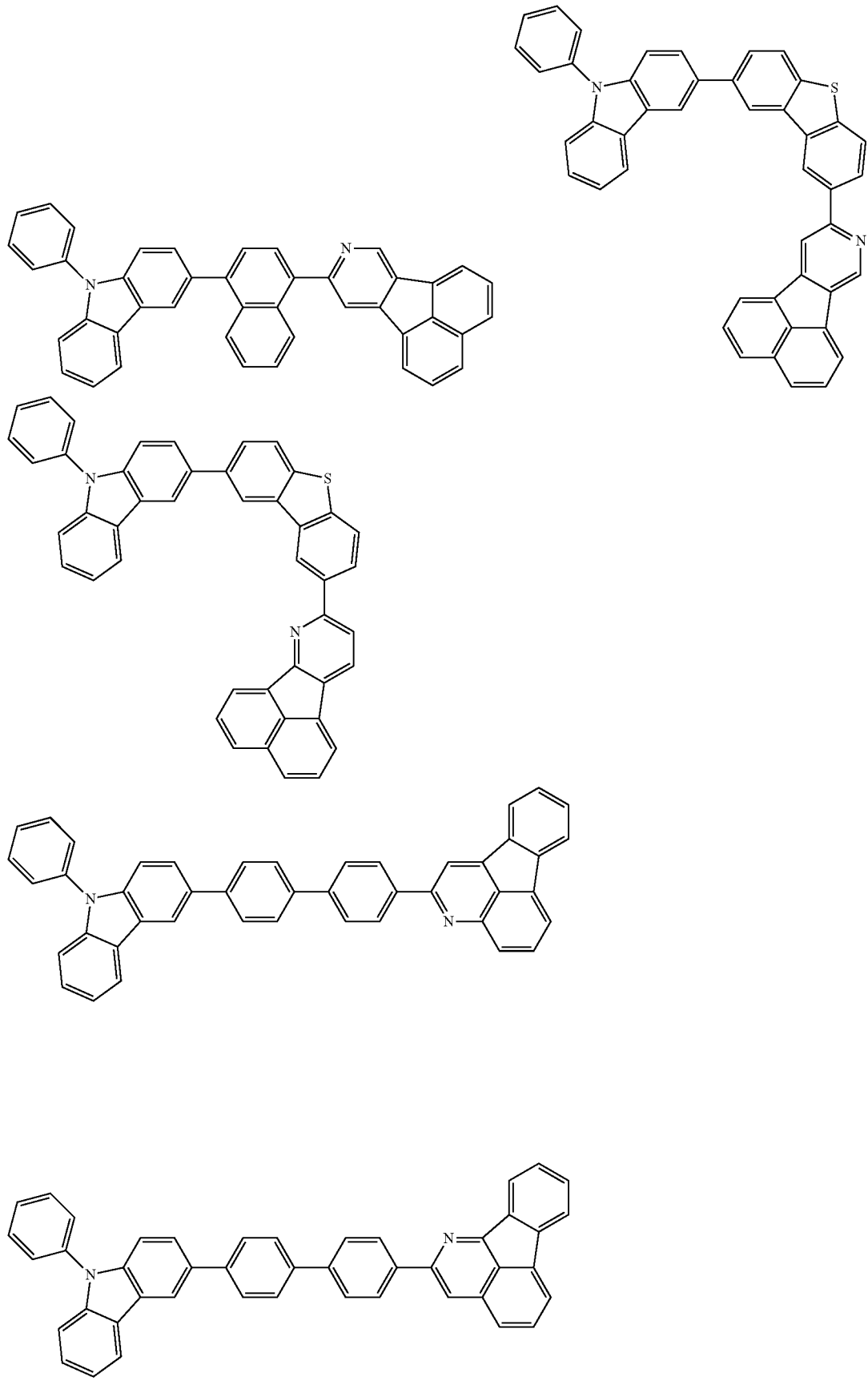

-continued
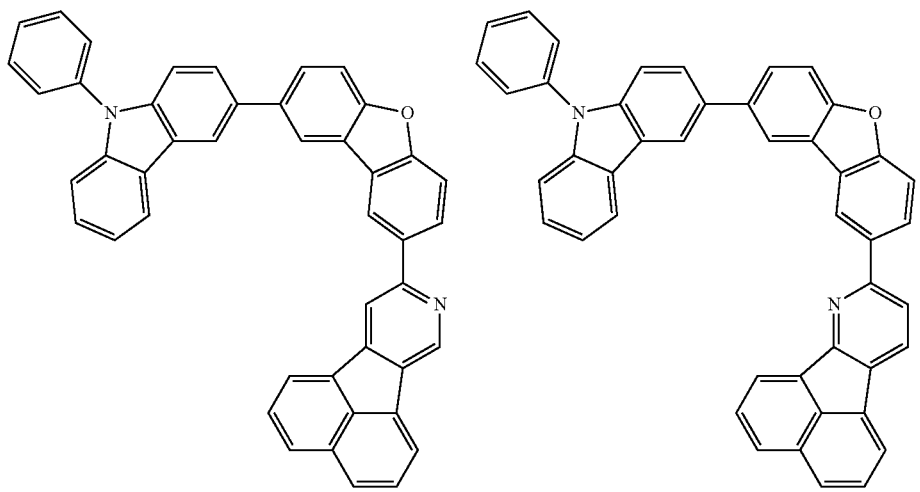
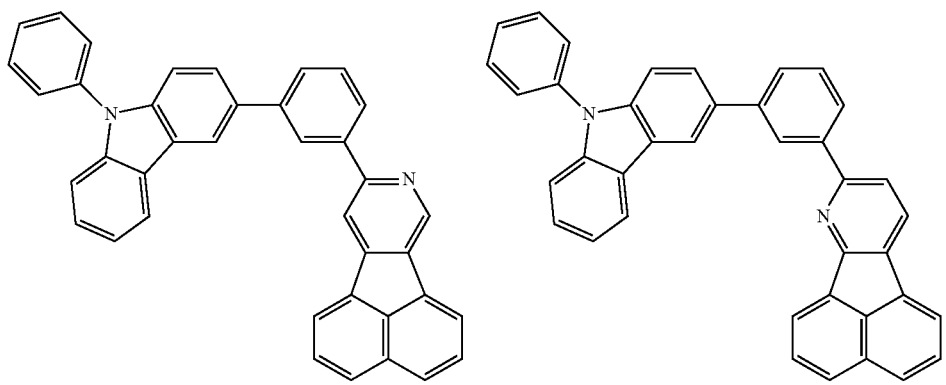
[Chem. 42]
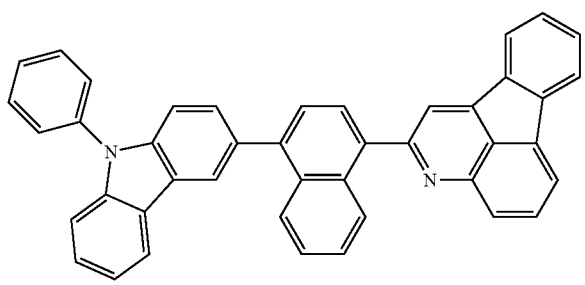
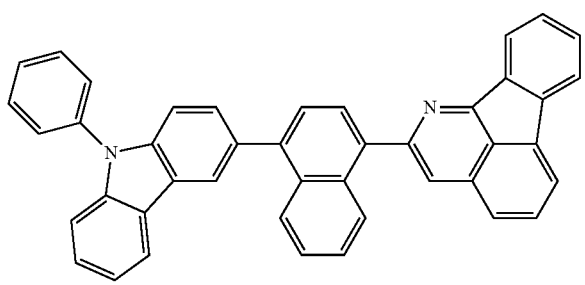
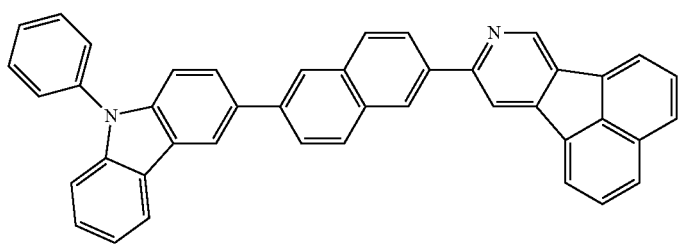

-continued
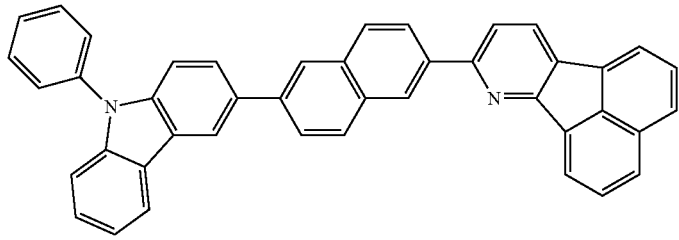
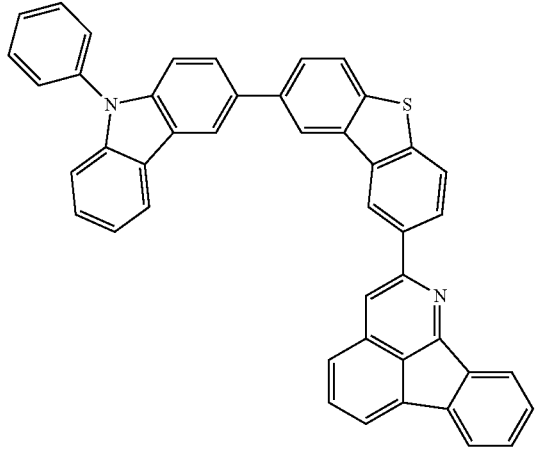
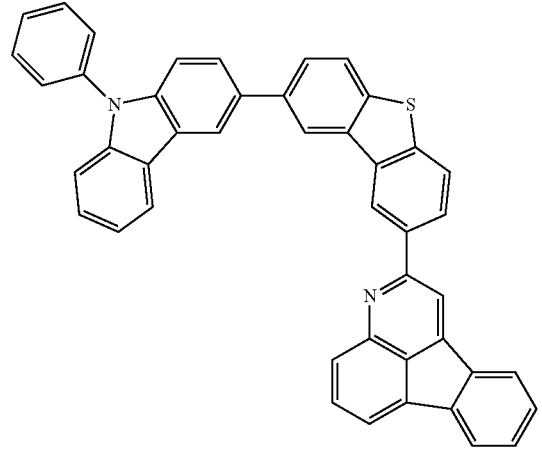
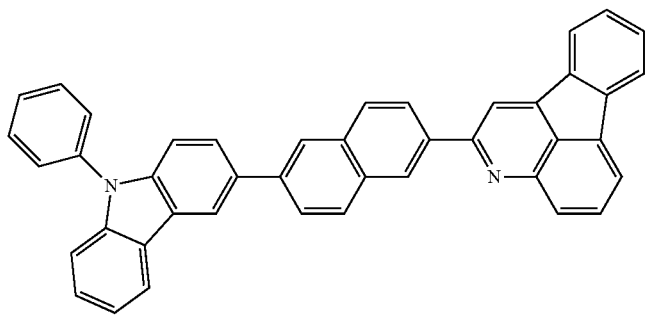
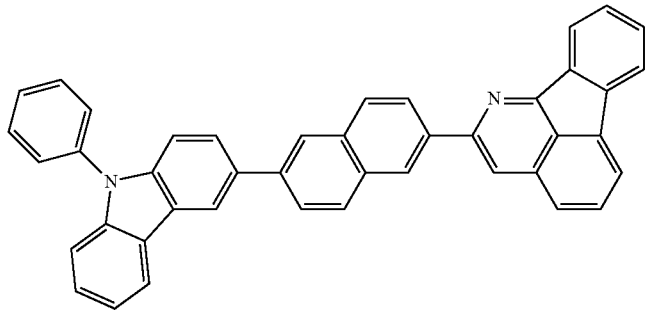
[Chem. 43]
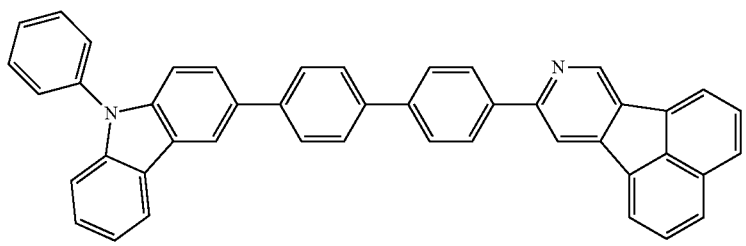

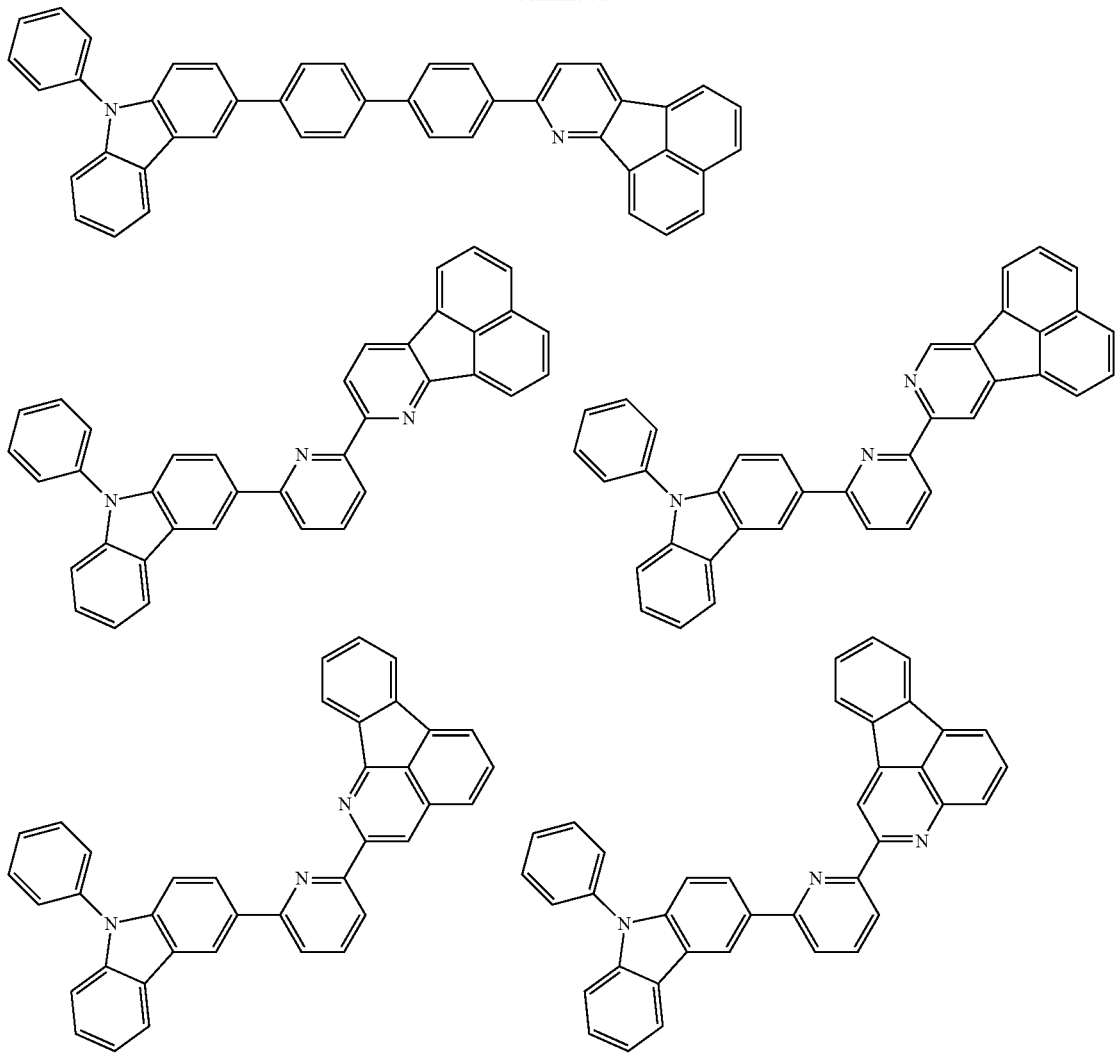
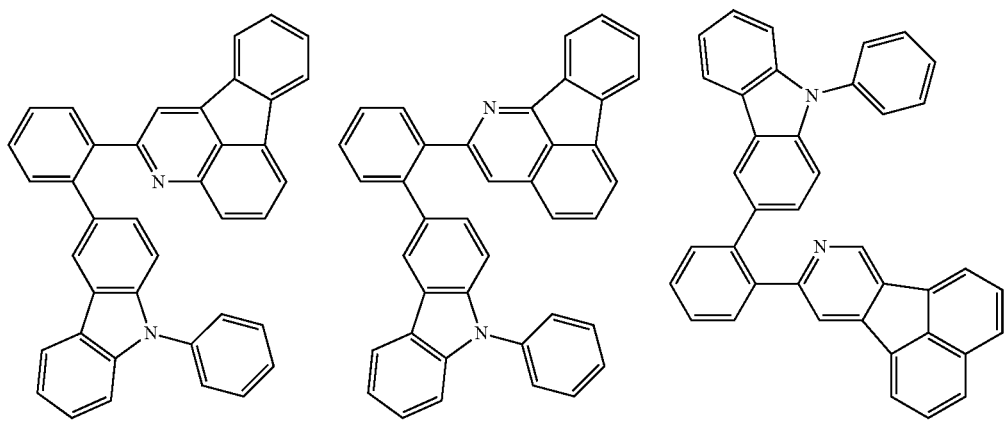

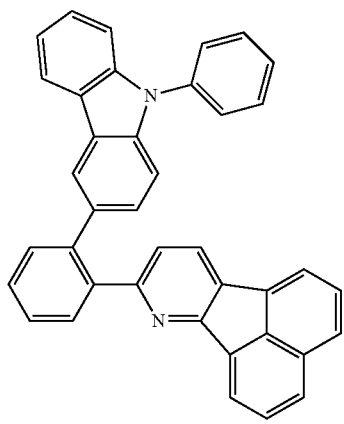
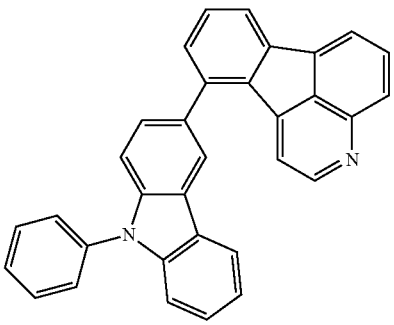
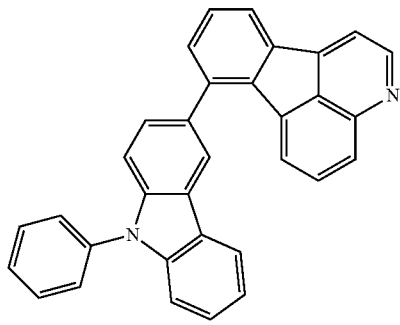
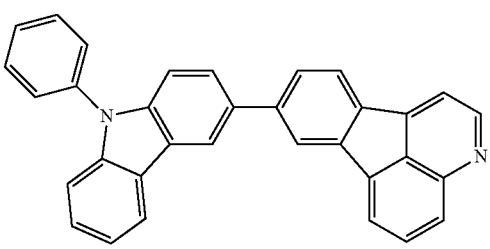
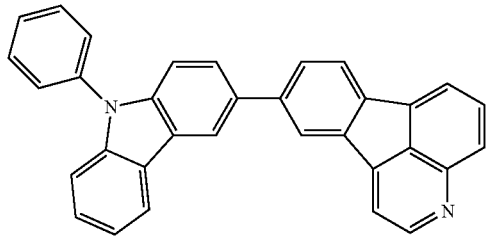
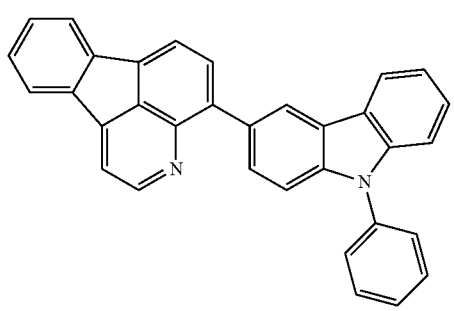
[Chem. 44]
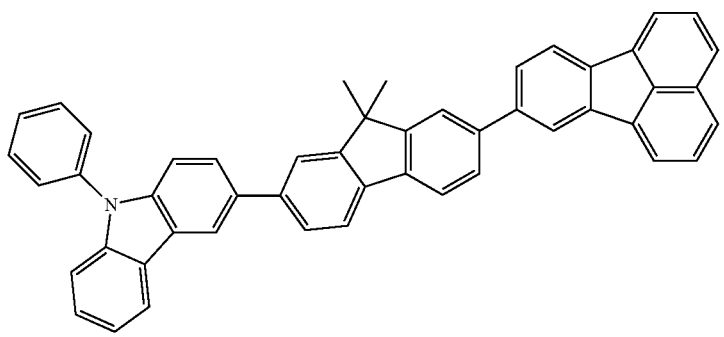

-continued
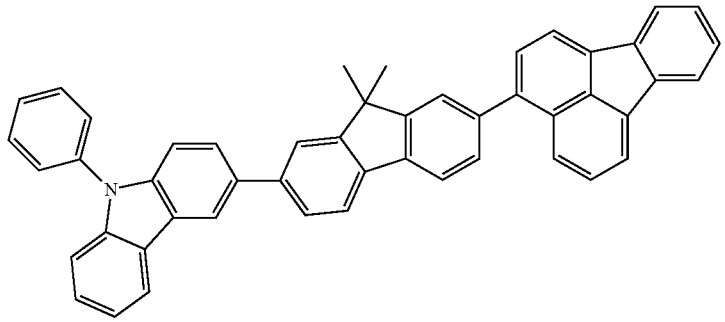
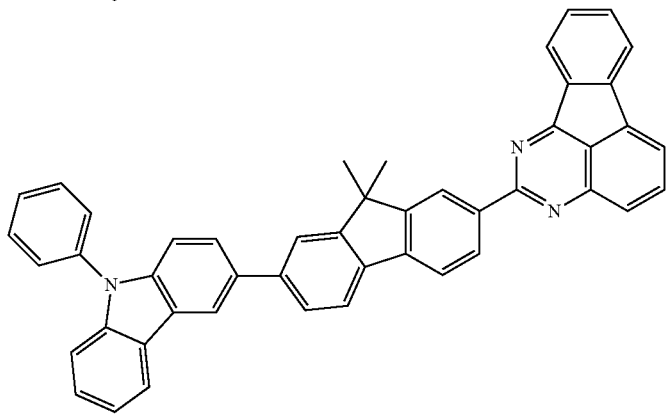
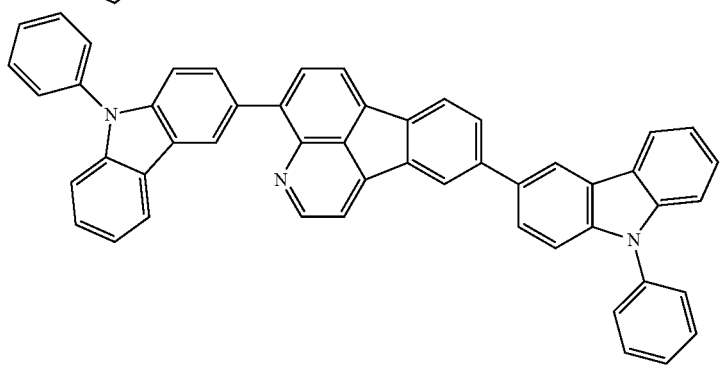
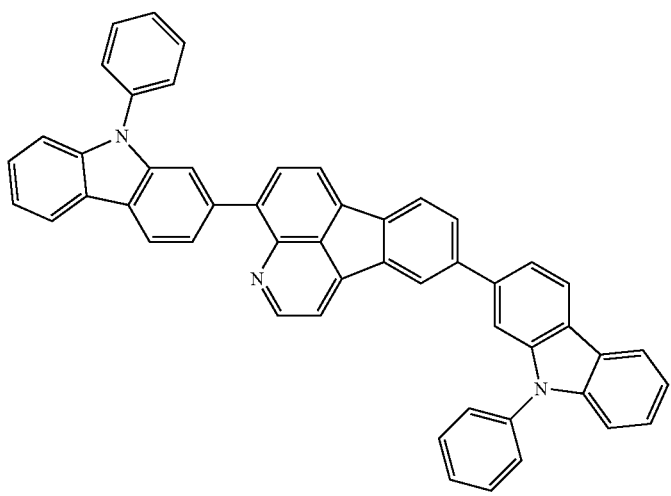

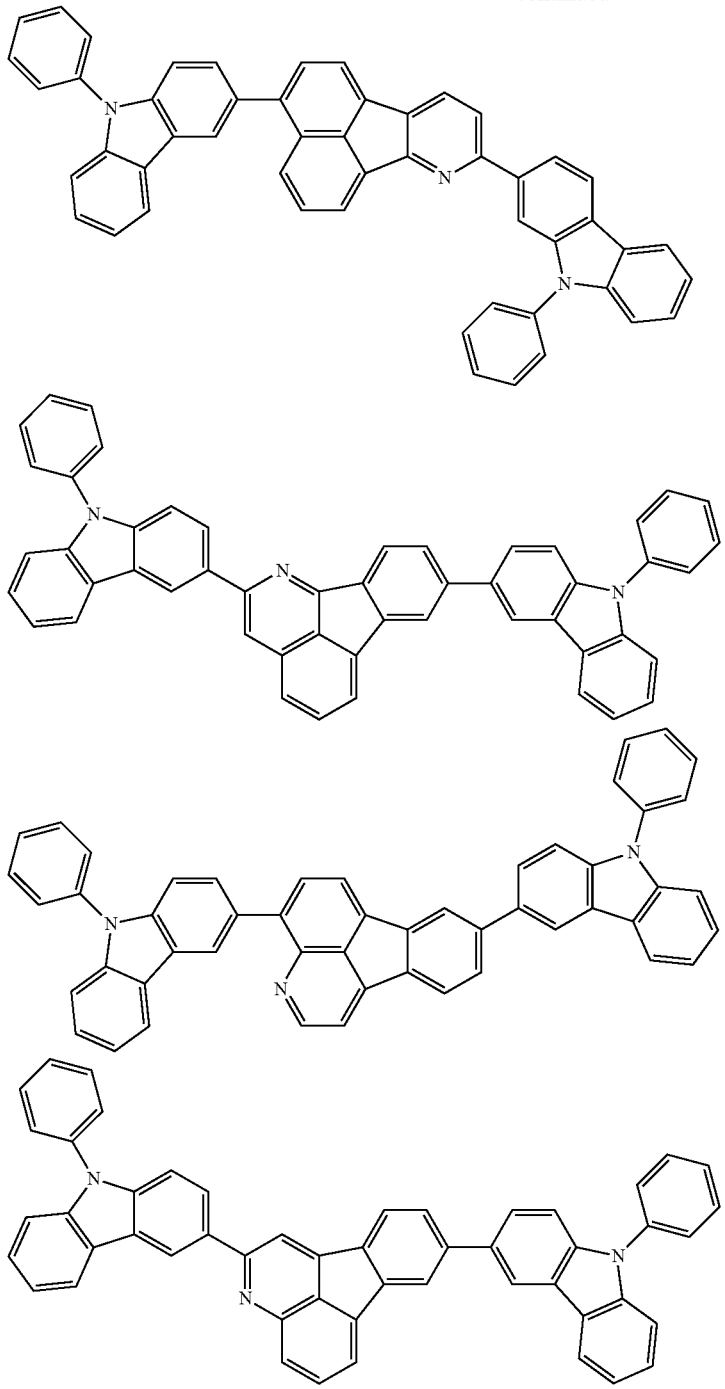

The compound of the present invention is useful as a material for organic EL devices. Preferably, the light-emitting layer of the organic EL device contains the compound of the present invention.

An embodiment of the organic EL device of the present invention having a hole transporting layer (hole injection layer), in which the hole transporting layer (hole injection layer) contains the compound of the present invention, is preferred.

One embodiment of the organic EL device of the present invention is described in detail hereinunder.

(Structure of Organic EL Device)

Representative device structures of the organic EL device are shown below.

(1) anode/light emitting layer/cathode (2) anode/hole transporting layer/light emitting layer/cathode (3) anode/light emitting layer/electron transporting layer/cathode (4) anode/hole transporting layer/light emitting layer/electron transporting layer/cathode (5) anode/organic semiconductor layer/light emitting layer/cathode
(6) anode/organic semiconductor layer/electron blocking layer/light emitting layer/cathode
(7) anode/organic semiconductor layer/light emitting layer/adhesion improving layer/cathode
(8) anode/hole transporting layer/light emitting layer/electron transporting layer/cathode
(9) anode/insulating layer/light emitting layer/insulating layer/cathode
(10) anode/inorganic semiconductor layer/insulating layer/light emitting layer/insulating layer/cathode
(11) anode/organic semiconductor layer/insulating layer/light emitting layer/insulating layer/cathode
(12) anode/insulating layer/hole transporting layer/light emitting layer/insulating layer/cathode
(13) anode/insulating layer/hole transporting layer/light emitting layer/electron transporting layer/cathode Among the above, the structure (8) is preferably used, but needless to say, the device is not limited to the structure.

Between each light emitting layer, a space layer may be provided for the purpose of preventing the exciton formed in a phosphorescent light emitting layer from diffusing into a fluorescent light emitting layer.

A schematic structure of an example of the organic EL device of the present invention is shown in the Figure.

The organic EL device 1 has a transparent substrate 2, an anode 3, a cathode 4, and an organic thin film layer 10 disposed between the anode 3 and the cathode 4.

The organic thin film layer 10 has a phosphorescent light emitting layer 5 containing a phosphorescent host as a host material and a phosphorescent dopant as a phosphorescent material, but may have a hole transporting layer 6 or the like between the phosphorescent light emitting layer 5 and the anode 3, and an electron transporting layer 7 or the like between the phosphorescent light emitting layer 5 and the cathode 4.

In addition, an electron blocking layer may be arranged on the side of the anode 3 of the phosphorescent light emitting layer 5, and a hole blocking layer may be arranged on the side of the cathode 4 of the phosphorescent light emitting layer 5.

Accordingly, electrons and holes may be trapped in the phosphorescent light emitting layer 5 so that the probability of forming excitons in the phosphorescent light emitting layer 5 may be thereby increased.

The organic EL device of the present invention may be a fluorescent or phosphorescent emission-type monochromatic light emitting device or a fluorescent/phosphorescent hybrid-type white light emitting device, and may be a simple-type having a single emission unit, or a tandem-type having plural emission units. Here, "emission unit" means a minimum unit containing one or more organic layers, in which one layer is a light emitting layer and the injected holes and electrons are recombined for light emission. Representative layered structures of the emission unit are shown below.

(a) hole transporting layer/light emitting layer (/electron transporting layer);
(b) hole transporting layer/first phosphorescent light emitting layer/second phosphorescent light emitting layer (/electron transporting layer);
(c) hole transporting layer/phosphorescent light emitting layer/space layer/fluorescent light emitting layer (/electron transporting layer);
(d) hole transporting layer/first phosphorescent light emitting layer/second phosphorescent light emitting layer/space layer/fluorescent light emitting layer (/electron transporting layer);
(e) hole transporting layer/first phosphorescent light emitting layer/space layer/second phosphorescent light emitting layer/space layer/fluorescent light emitting layer (/electron transporting layer);
(f) hole transporting layer/phosphorescent light emitting layer/space layer/first fluorescent light emitting layer/second fluorescent light emitting layer (/electron transporting layer).

A representative device structure of the tandem-type organic EL device is shown below.

Anode/first emission unit/intermediate layer/second emission unit/cathode

Here, the first emission unit and the second emission unit may be selected independently, for example, from those described above with respect to the emission units.

Generally, the intermediate layer is also called an intermediate electrode, an intermediate conductive layer, a charge generation layer, an electron withdrawing layer, a connecting layer, or an intermediate insulating layer. The intermediate layer may be formed by known materials so as to supply electrons to the first emission unit and holes to the second emission unit.

Here, the host material is referred to as a fluorescent host when combinedly used with a fluorescent dopant and referred to as a phosphorescent host when combinedly used with a phosphorescent dopant. Therefore, the fluorescent host and the phosphorescent host are not distinguished from each other merely by the difference in their molecular structures.

Namely, in the present description, the term "phosphorescent host" means a material for constituting a phosphorescent light emitting layer containing a phosphorescent dopant and does not mean a material that can be used only as a host for a phosphorescent material.

(Transparent Substrate)

The organic EL device of the present invention is formed on a light-transmissive substrate. The light-transmissive substrate serves as a support for the organic EL device and is preferably a flat substrate having a transmittance of 50% or more to 400 to 700 nm visible light.

Examples of the substrate include a glass plate and a polymer plate.

The glass plate may include a plate made of soda-lime glass, barium-strontium-containing glass, lead glass, aluminosilicate glass, borosilicate glass, barium borosilicate glass, or quartz.

The polymer plate may include a plate made of polycarbonate, acryl, polyethylene terephthalate, polyether sulfide, or polysulfone.

(Anode and Cathode)

The anode of the organic EL devices plays a role of injecting holes to the hole transporting layer or the light emitting layer, and it is effective to have a work function of 4.5 eV or more.

Examples of the material for anode include indium tin oxide alloy (ITO), tin oxide (NESA), indium zinc oxide, gold, silver, platinum, and cupper.

The anode is formed by making the electrode material into a thin film by a method, such as a vapor deposition method or a sputtering method.

When getting the light emitted from the light emitting layer through the anode as in this embodiment, the transmittance of anode to visible light is preferably 10% or more. The sheet resistance of anode is preferably several hundred Ω/square or less. The film thickness of anode depends upon the kind of the material thereof and generally 10 nm to 1 μm, preferably 10 to 200 nm.

For cathode, a material having a small work function is preferred for the purpose of injecting electrons to the electron transporting layer or the light emitting layer.

Examples of the material for cathode include, but not limited to, indium, aluminum, magnesium, magnesium-indium alloy, magnesium-aluminum alloy, aluminum-lithium alloy, aluminum-scandium-lithium alloy, and magnesium-silver alloy.

Like the anode, the cathode is formed by making the material into a thin film by a method, such as the vapor deposition method and the sputtering method. An embodiment of taking out the emitted light through the cathode side may be employed.

(Light Emitting Layer)

The light emitting layer in the organic EL device has the following functions.

Specifically:

(1) injecting function; function to inject holes from anode or hole transporting layer in electric field application, and to inject electrons from cathode or electron transporting layer;

(2) transporting function; function to move the injected charges (electrons and holes) by the force of electric field;

(3) light emitting function; function to provide a field for recombination of electrons and holes to result in light emission.

However, the easiness of hole injection and the easiness of electron injection may be different from each other. Also, the hole transporting ability and the electron transporting ability each being expressed by mobility of holes and electrons may be different from each other.

The light emitting layer is formed, for example, by a known method, such as a vapor deposition method, a spin coating method, and an LB method (Langmuir Blodgett method).

The light emitting layer is preferably a molecular deposit film.

Here, the molecular deposit film is a thin film formed by depositing a vaporized material compound or a film formed by solidifying a material compound in the state of solution or liquid. In general, the molecular deposit film can be distinguished from a thin film formed by an LB method (molecular build-up film) by the differences in the assembly structures and higher order structures and the functional difference due to the structural differences.

The light emitting layer can be formed also by making a solution of a binder, such as resin, and the material compound in a solvent into a thin film by a method such as spin coating.

The organic EL device of the present invention has one or plural organic thin film layers between cathode and anode. The organic thin film layers have at least one light emitting layer, and at least one of the organic thin film layers contains at least one phosphorescent material and at least one compound of the present invention. Preferably, at least one light emitting layer contains at least one compound of the present invention and at least one phosphorescent material.

—Phosphorescent Material—

In the present invention, the phosphorescent material contains a metal complex, and the metal complex preferably has a metal atom selected from the group consisting of Ir, Pt, Os, Au, Cu, Re, and Ru and a ligand. In particular, the ligand preferably has an ortho-metal bond.

In view of obtaining a high phosphorescent quantum yield and further improving the external quantum efficiency of luminescent device, a compound containing a metal element selected from Ir, Os, and Pt is preferred, and a metal complex such as an iridium complex, an osmium complex or a platinum complex (preferably, orthometalated complex) is more preferred. Above all, an iridium complex and a platinum complex (preferably, both are orthometalated complexes) are more preferred, and an orthometalated iridium complex is the most preferred.

Preferred examples of the metal complex are shown below, but the examples are not particularly limited thereto.

[Chem. 45]

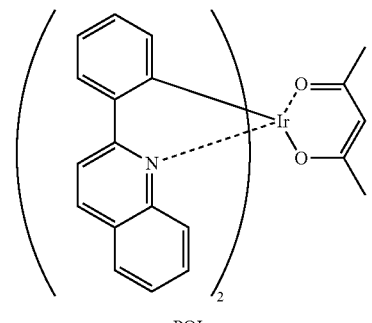

PQIr

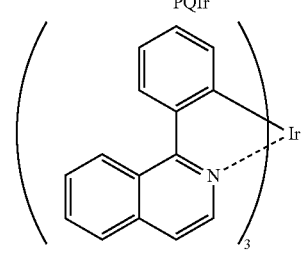

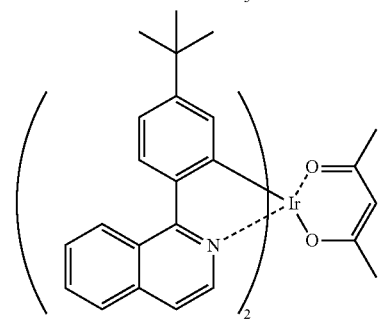

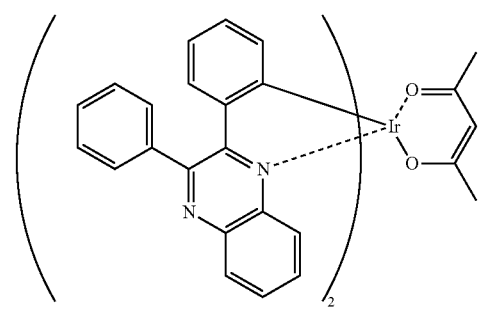

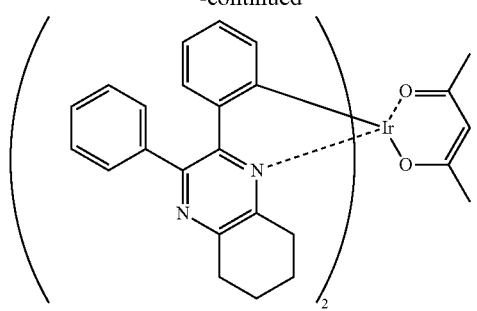
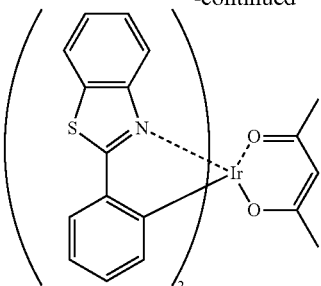
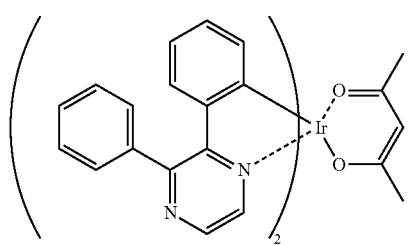
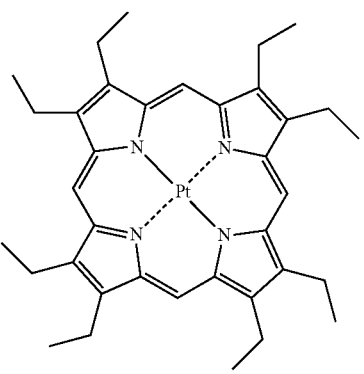
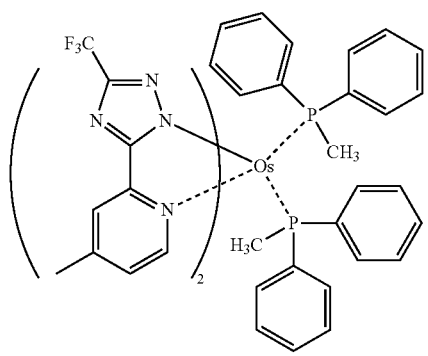
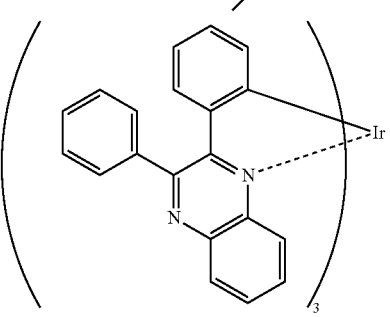
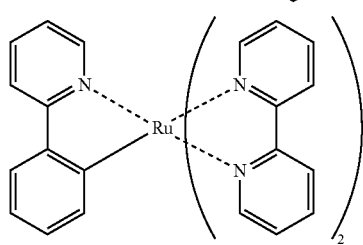
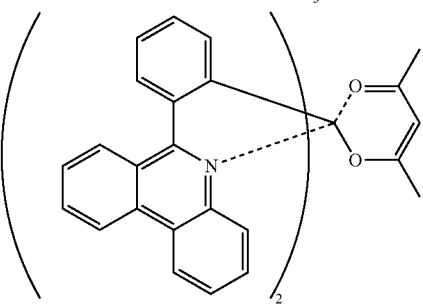
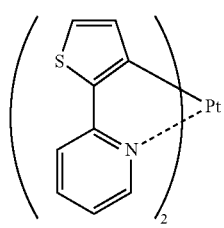
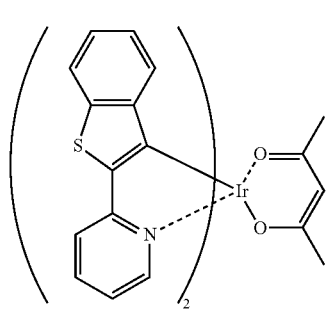
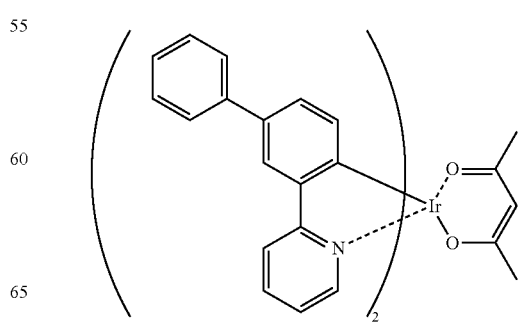

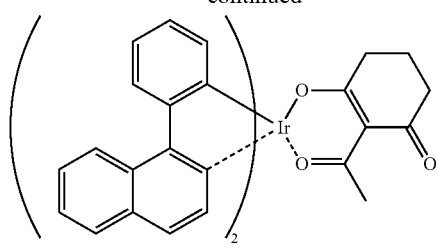
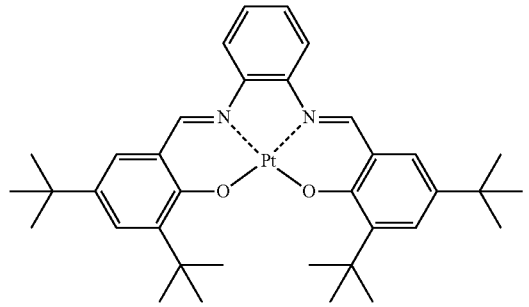
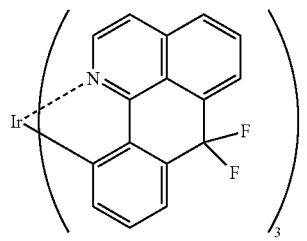
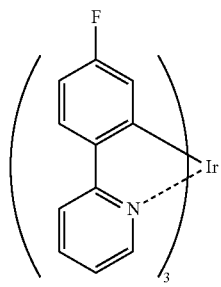
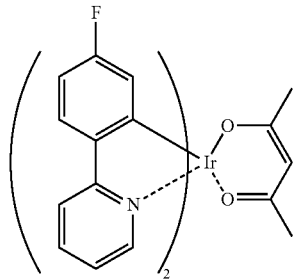
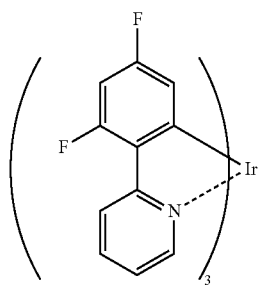
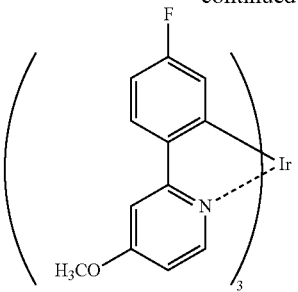
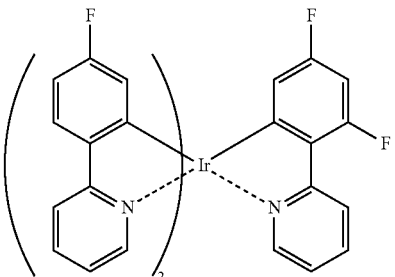
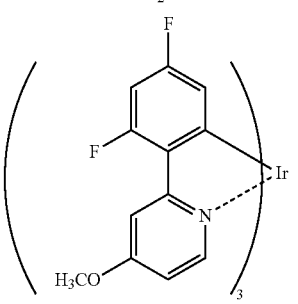
[Chem. 46]
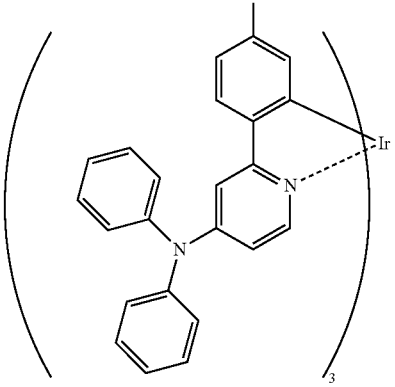
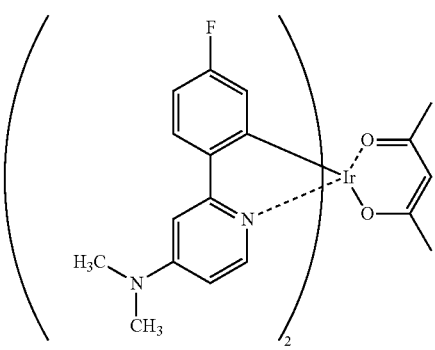

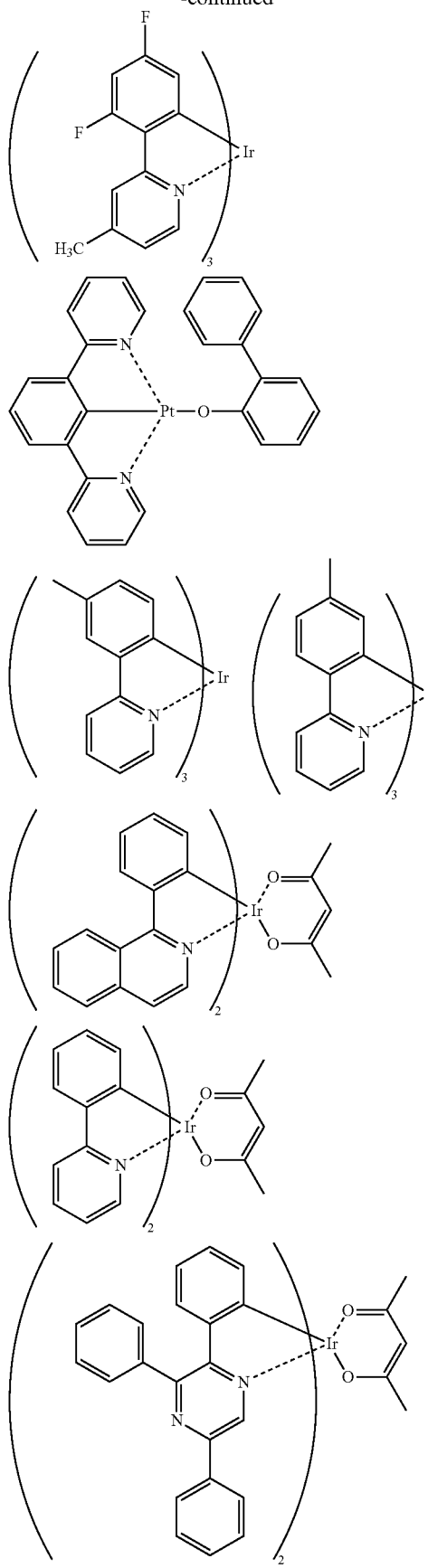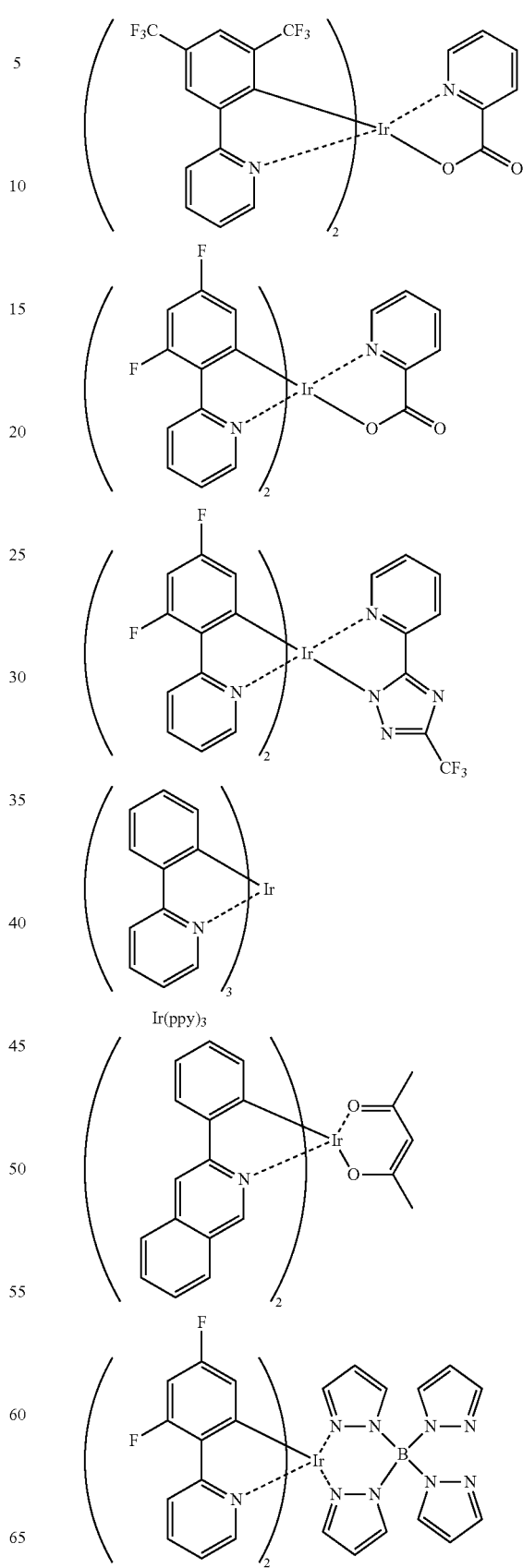

-continued
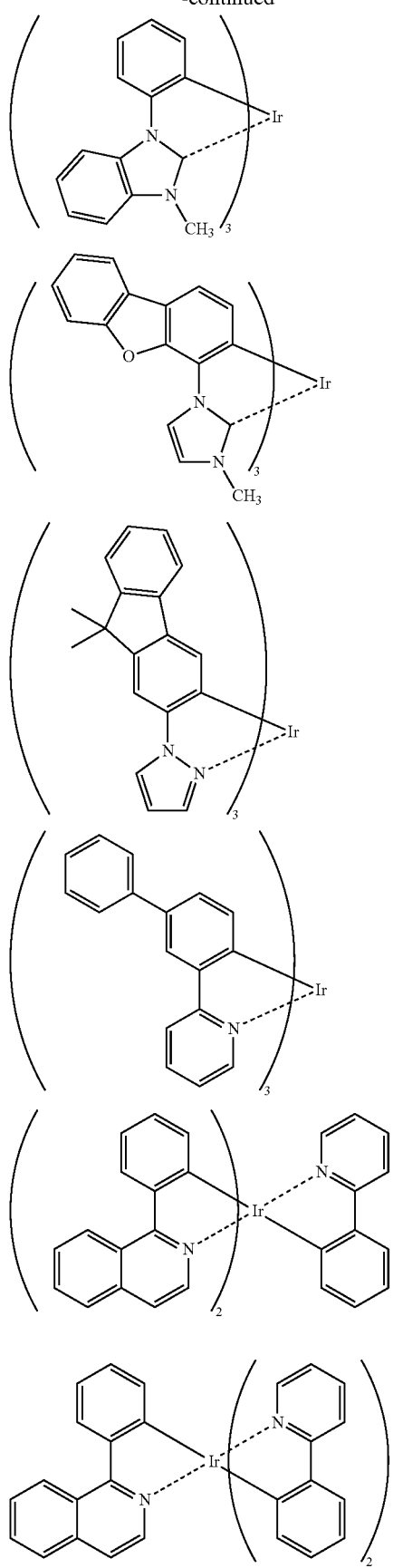
-continued
[Chem. 48]
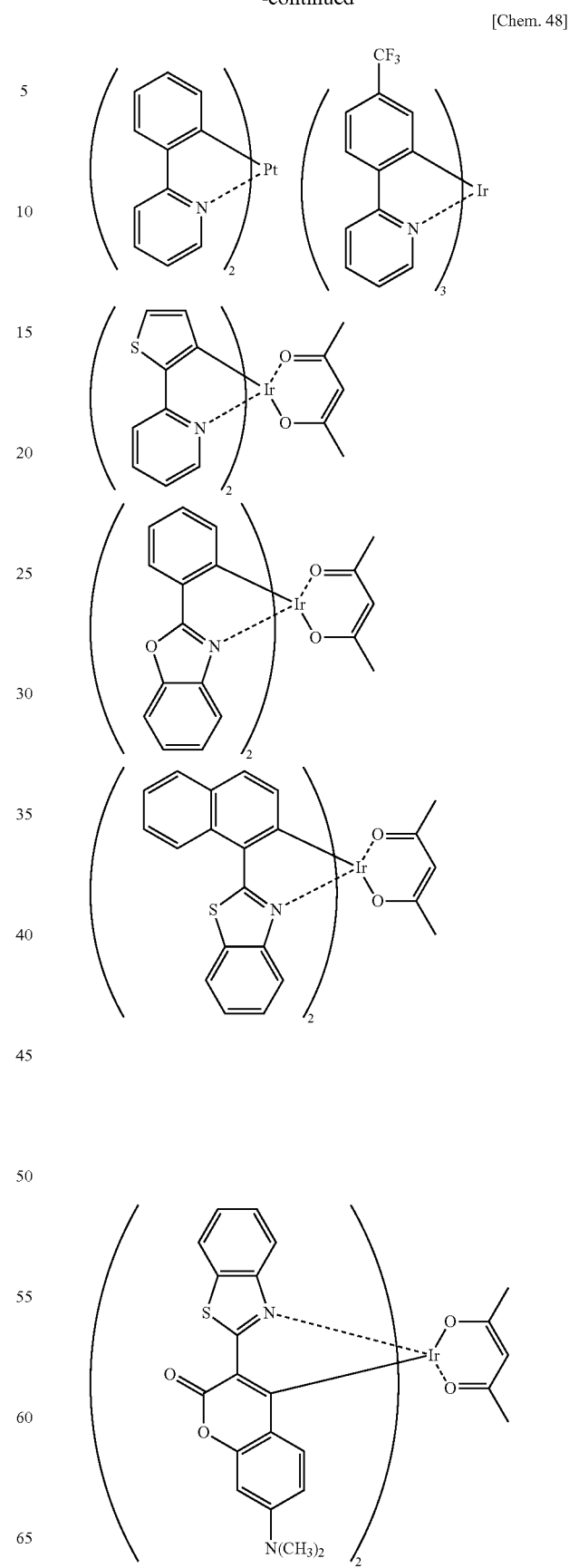

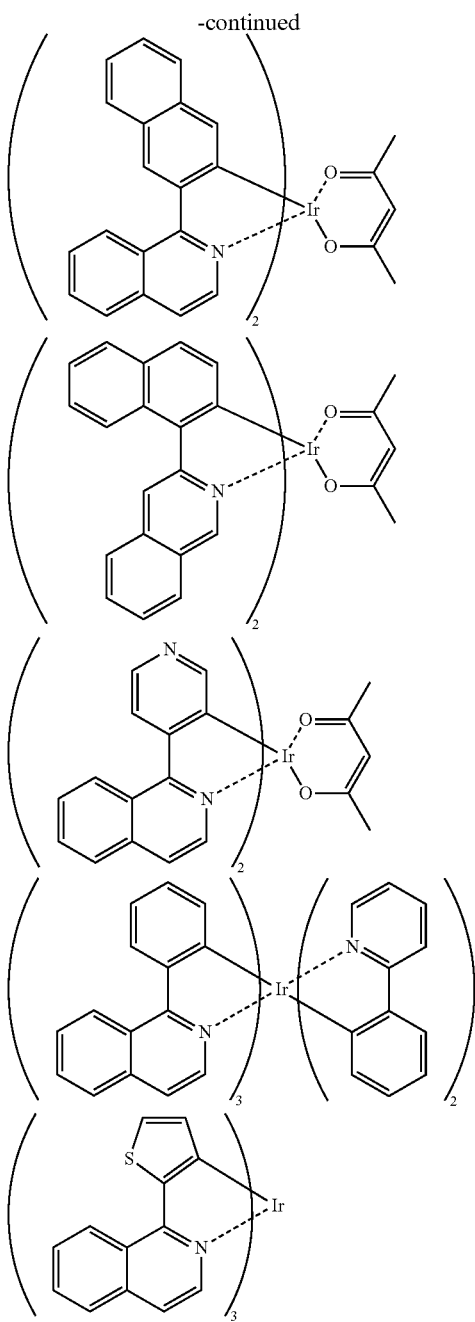

In the present invention, preferably, at least one phosphorescent material contained in the light emitting layer emits light having a maximum value of an emission wavelength falling within the range of 450 nm or more and 750 nm or less. As preferred examples, the maximum value is 450 nm or more and 495 nm or less, 495 nm or more and 590 nm or less, and 590 nm or more and 750 nm or less.

By doping the specific host material for use in the present invention with the phosphorescent material (phosphorescent dopant) having such an emission wavelength to form the light emitting layer, a high-efficiency organic EL device can be produced.

The thickness of the light emitting layer is not specifically limited, but is preferably 5 to 100 nm, more preferably 7 to 70 nm, even more preferably 10 to 50 nm. When the thickness is 5 nm or more, the light emitting layer is easy to form, and when it is 100 nm or less, increase in driving voltage can be avoided.

(Reducing Dopant)

The organic EL device of the present invention preferably has a reducing dopant in an interfacial region between the cathode and the organic thin film layer.

With such a construction, the organic EL device has an improved luminance and an elongated lifetime.

The reducing dopant may be at least one selected from the group consisting of alkali metals, alkali metal complexes, alkali metal compounds, alkaline earth metals, alkaline earth metal complexes, alkaline earth metal compounds, rare earth metals, rare earth metal complexes, and rare earth metal compounds.

Examples of the alkali metal include Na (work function: 2.36 eV), K (work function: 2.28 eV), Rb (work function: 2.16 eV), and Cs (work function: 1.95 eV), with those having a work function of 2.9 eV or less being particularly preferred. Of the above, preferred are K, Rb, and Cs, more preferred are Rb and Cs, and most preferred is Cs.

Examples of the alkaline earth metal include Ca (work function: 2.9 eV), Sr (work function: 2.0 to 2.5 eV), and Ba (work function: 2.52 eV), with those having a work function of 2.9 eV or less being particularly preferred.

Examples of the rare earth metal include Sc, Y, Ce, Tb, and Yb, with those having a work function of 2.9 eV or less being particularly preferred.

The preferred metals among the above metals especially have a high reducing capability and, when a relatively small amount thereof is added to the electron injecting region, the emission luminance of the organic EL device can be increased and the life thereof can be prolonged.

Examples of the alkali metal compound include alkali oxide, such as $Li_2O$, $Cs_2O$, $K_2O$, and alkali halide, such as LiF, NaF, CsF, and KF, with LiF, $Li_2O$, and NaF being preferred.

Examples of the alkaline earth metal compound include BaO, SrO, CaO, and mixture thereof, such as $Ba_xSr_{1-x}O$ (0<x<1) and $Ba_xCa_{1-x}O$ (0<x<1), with BaO, SrO, and CaO being preferred.

Examples of the rare earth metal compound include $YbF_3$, $ScF_3$, $ScO_3$, $Y_2O_3$, $Ce_2O_3$, $GdF_3$, and $TbF_3$, with $YbF_3$, $ScF_3$, and $TbF_3$ being preferred.

Examples of the alkali metal complex, alkaline earth metal complex, and rare earth metal complex are not particularly limited as long as containing at least one metal ion selected from alkali metal ions, alkaline earth metal ions, and rare earth metal ions, respectively. The ligand is preferably, but not limited to, quinolinol, benzoquinolinol, acridinol, phenanthridinol, hydroxyphenyloxazole, hydroxyphenylthiazole, hydroxydiaryloxadiazole, hydroxydiarylthiadiazole, hydroxyphenylpyridine, hydroxyphenylbenzimidazole, hydroxybenzotriazole, hydroxyfulborane, bipyridyl, phenanthroline, phthalocyanine, porphyrin, cyclopentadiene, β-diketones, azomethines, and derivative thereof.

The reducing dopant is added to the interfacial region preferably into a form of layer or island. The reducing dopant is added preferably by depositing an organic material which serves as a light emitting material or an electron injecting material for forming the interfacial region while depositing the reducing agent by a resistance heating deposition method, thereby dispersing the reducing dopant into the organic material. The disperse concentration expressed by the molar ratio of the organic material to the reducing dopant is 100:1 to 1:100 and preferably 5:1 to 1:5.

When the reducing dopant is formed into a form of layer, a light emitting material or an electron transporting material is made into a layer which serves as an organic layer in the interface, and then, the reducing dopant alone is deposited by a resistance heating deposition method into a layer having a thickness preferably 0.1 to 15 nm.

When the reducing dopant is formed into a form of island, a light emitting material or an electron transporting material is made into a form of island which serves as an organic layer in the interface, and then, the reducing dopant alone is deposited by a resistance heating deposition method into a form of island having a thickness preferably 0.05 to 1 nm.

The ratio of the main component to the reducing dopant in the organic EL device of the present invention is preferably 5:1 to 1:5 and more preferably 2:1 to 1:2, as a molar ratio of main component/reducing dopant.

(Electron Transporting Layer)

The electron transporting layer is an organic layer disposed between the light emitting layer and the cathode and transports electrons from the cathode to the light emitting layer. If two or more electron transporting layers are provided, the organic layer closer to the cathode may be called an electron injecting layer in some cases. The electron injecting layer has a function to efficiently inject electrons from the cathode to the organic layer unit.

The compound of the present invention may be used as an electron transporting material to be contained in the electron transporting layer.

An aromatic heterocyclic compound having one or more heteroatoms in the molecule thereof is preferably used as the electron transporting material used in the electron transporting layer, and a nitrogen-containing ring derivative is particularly preferred. In addition, the nitrogen-containing ring derivative is preferably an aromatic ring compound having a nitrogen-containing, 6- or 5-membered ring skeleton, or a condensed aromatic ring compound having a nitrogen-containing, 6- or 5-membered ring skeleton.

The nitrogen-containing ring derivative is preferably, for example, a metal chelate complex of a nitrogen-containing ring represented by the following formula (A).

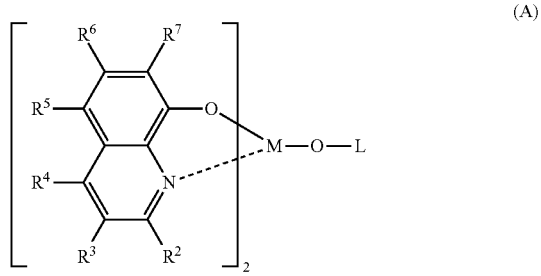

(A)

In the general formula (A), each of $R^2$ to $R^7$ independently represents a hydrogen atom, a halogen atom, a hydroxyl group, an amino group, a hydrocarbon group having 1 to 40 (preferably 1 to 20, more preferably 1 to 10, even more preferably 1 to 6) carbon atoms, an alkoxy group having 1 to 40 (preferably 1 to 20, more preferably 1 to 10, even more preferably 1 to 6) carbon atoms, an aryloxy group having 6 to 40 (preferably 6 to 20, more preferably 6 to 12) ring carbon atoms, an alkoxycarbonyl group having 2 to 40 (preferably 2 to 20, more preferably 2 to 10, even more preferably 2 to 5) carbon atoms, or an aromatic heterocyclic group having 9 to 40 (preferably 9 to 30, more preferably 9 to 20) ring carbon atoms, each being optionally substituted.

The halogen atom may include fluorine, chlorine, bromine, and iodine. Examples of the substituted amino group may include an alkylamino group, an arylamino group, and an aralkylamino group.

The alkoxycarbonyl group is represented by —COOY', wherein examples of Y' may be the same as those of the above-mentioned alkyl group. The alkylamino group and the aralkylamino group are represented by —NQ$^1$Q$^2$. Examples of Q$^1$ and Q$^2$ may include the same ones as those described independently for the above-mentioned alkyl group and the aralkyl group, and preferred examples thereof are also the same. One of Q$^1$ and Q$^2$ may be a hydrogen atom.

The arylamino group is represented by —NAr$^1$Ar$^2$, wherein specific examples of Ar$^1$ and Ar$^2$ may be the same ones as those described independently for the above-mentioned non-condensed aromatic hydrocarbon group and the condensed aromatic hydrocarbon group. One of Ar$^1$ and Ar$^2$ may be a hydrogen atom.

M is aluminum (Al), gallium (Ga), or indium (In), with In being preferred.

L in the above formula (A) is a group represented by the following formula (A') or (A").

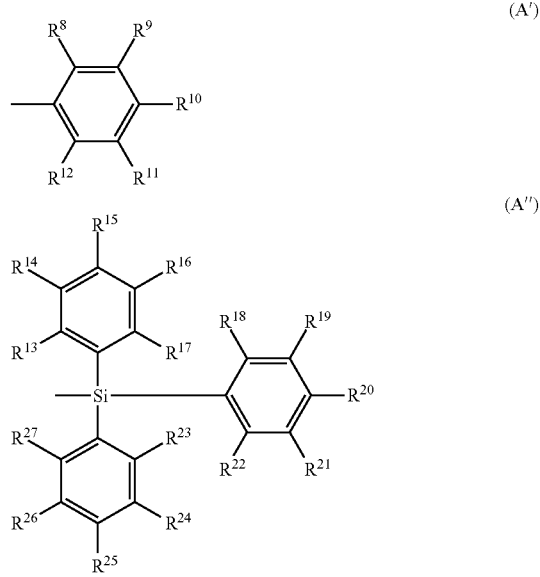

In the above formula (A'), each of $R^8$ to $R^{12}$ independently represents a hydrogen atom, or a substituted or unsubstituted hydrocarbon group having 1 to 40 (preferably 1 to 20, more preferably 1 to 10, even more preferably 1 to 6) carbon atoms; and two neighboring groups may form a ring structure. In the above formula (A"), each of $R^{13}$ to $R^{27}$ independently represents a hydrogen atom, or a substituted or unsubstituted hydrocarbon group having 1 to 40 (preferably 1 to 20, more preferably 1 to 10, even more preferably 1 to 6) carbon atoms; and two neighboring groups may form a ring structure.

Examples of the hydrocarbon group having 1 to 40 carbon atoms represented by $R^8$ to $R^{12}$ and $R^{13}$ to $R^{27}$ in the above formulae (A') and (A") may be the same as those described above with respect to $R^2$ to $R^7$ of the above formula (A).

Examples of the divalent group formed by two neighboring groups of $R^8$ to $R^{12}$ and $R^{13}$ to $R^{27}$ which completes the ring structure include a tetramethylene group, a pentamethylene group, a hexamethylene group, a diphenylmethane-2,2'-diyl group, a diphenylethane-3,3'-diyl group, and a diphenylpropane-4,4'-diyl group.

An electron transmitting compound may be used in the electron transporting layer, and the compound is preferably a metal complex including 8-hydroxyquinoline or its derivative, an oxadiazole derivative, or a nitrogen-containing heterocyclic derivative. Examples of the metal complex including 8-hydroxyquinoline or its derivative include a metal chelate oxinoid compound including a chelated oxine (generally, 8-quinolinol or 8-hydroxyquinoline), for example, tris(8-quinolinol)aluminum. Examples of the oxadiazole derivative are shown below.

or unsubstituted bivalent condensed aromatic hydrocarbon group, and $Ar^{23}$ and $Ar^{24}$ may be the same or different.

Examples of the bivalent aromatic hydrocarbon group or the bivalent condensed aromatic hydrocarbon group include a phenylene group, a naphthylene group, a biphenylene group, an anthranylene group, a perylenylene group, and a pyrenylene group. The optional substituent may be an alkyl group having 1 to 10 carbon atoms, an alkoxyl group having 1 to 10 carbon atoms or a cyano group.

Electron transmitting compounds which have a good thin film-forming property are preferably used. Examples of the electron transmitting compound are shown below.

[Chem. 52]

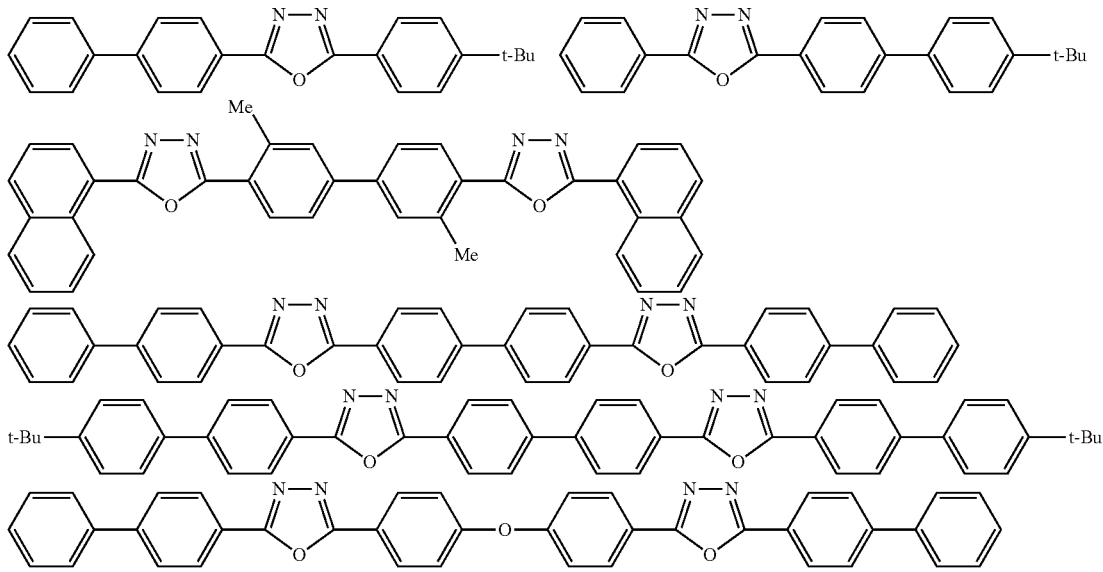

[Chem.51]

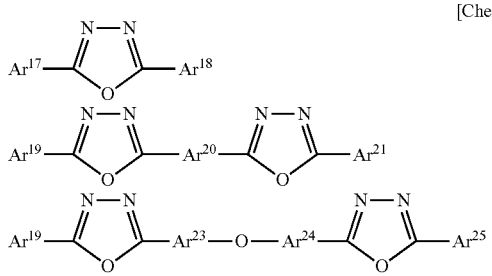

In the above formulae, each of $Ar^{17}$, $Ar^{18}$, $Ar^{19}$, $Ar^{21}$, $Ar^{22}$, and $Ar^{25}$ is a substituted or unsubstituted aromatic hydrocarbon group or a substituted or unsubstituted condensed aromatic hydrocarbon group, and $Ar^{17}$ and $Ar^{18}$, $Ar^{19}$ and $Ar^{21}$, and $Ar^{22}$ and $Ar^{25}$ may be the same or different. Examples of the aromatic hydrocarbon group and the condensed aromatic hydrocarbon group include a phenyl group, a naphthyl group, a biphenyl group, an anthranyl group, a perylenyl group, and a pyrenyl group. The optional substituent may be an alkyl group having 1 to 10 carbon atoms, an alkoxyl group having 1 to 10 carbon atoms or a cyano group.

Each of $Ar^{20}$, $Ar^{23}$, and $Ar^{24}$ is a substituted or unsubstituted bivalent aromatic hydrocarbon group or a substituted Examples of the nitrogen-containing heterocyclic derivative for use as the electron transmitting compound include a nitrogen-containing heterocyclic derivative of an organic compound having any of the following formulae but exclusive of metal complex, for example, a compound having a 5- or 6-membered ring which has the skeleton represented by the following formula (B) or having the structure represented by the following formula (C).

 (B)

 (C)

In the above formula (C), X is a carbon atom or a nitrogen atom. Each of $Z_1$ and $Z_2$ independently represents a group of atoms for completing the nitrogen-containing heterocyclic ring.

The nitrogen-containing heterocyclic derivative is more preferably an organic compound which has a nitrogen-containing aromatic polycyclic ring including a 5-membered ring or a 6-membered ring. If two or more nitrogen atoms are included, the nitrogen-containing aromatic polycyclic organic compound preferably has a skeleton of a combination of the above formulae (B) and (C) or a combination of the above formula (B) and the following formula (D).

(D)

The nitrogen-containing group of the nitrogen-containing aromatic polycyclic organic compound is selected, for example, from nitrogen-containing heterocyclic groups represented by the following formulae.

[Chem. 55]

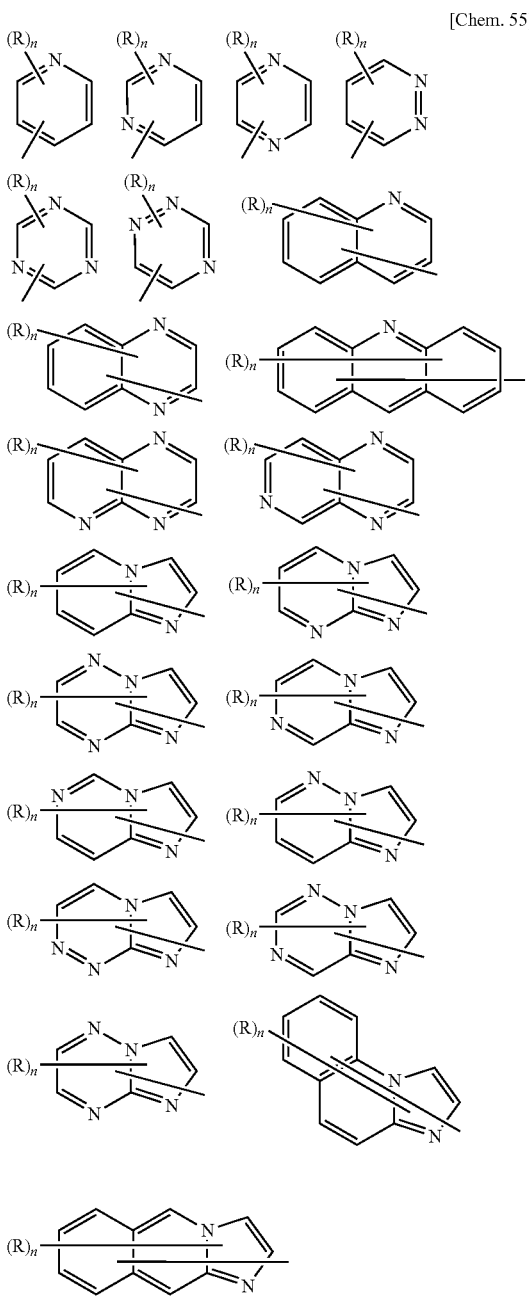

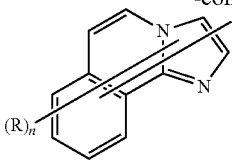
-continued

In the above formulae, R is an aromatic hydrocarbon group having 6 to 40 (preferably 6 to 30, more preferably 6 to 20, even more preferably 6 to 12) ring carbon atoms, a condensed aromatic hydrocarbon group having 6 to 40 (preferably 6 to 30, more preferably 6 to 20, even more preferably 6 to 12) ring carbon atoms, an aromatic heterocyclic group having 5 to 40 (preferably 5 to 30, more preferably 5 to 20, even more preferably 5 to 12) ring atoms, a condensed aromatic heterocyclic group having 5 to 40 (preferably 5 to 30, more preferably 5 to 20, even more preferably 5 to 12) ring atoms, an alkyl group having 1 to 20 (preferably 1 to 10, more preferably 1 to 6) carbon atoms, or an alkoxy group having 1 to 20 (preferably 1 to 10, more preferably 1 to 6) carbon atoms.

n is an integer of 0 to 5, and when 2 is an integer of 2 or more, plural R's may be the same or different.

Further, a nitrogen-containing heterocyclic derivative represented by the following formula is mentioned as a preferred example of the compound.

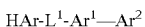
HAr-L$^1$-Ar$^1$—Ar$^2$

In the formula, HAr is a nitrogen-containing heterocyclic group having 5 to 40 (preferably 5 to 30, more preferably 5 to 20, even more preferably 5 to 12) ring atoms and optionally having a substituent.

L$^1$ is a single bond, an aromatic hydrocarbon group or condensed aromatic hydrocarbon group each having 6 to 40 (preferably 6 to 30, more preferably 6 to 20, even more preferably 6 to 12) ring carbon atoms and optionally having a substituent, or an aromatic heterocyclic group having 5 to 40 (preferably 5 to 30, more preferably 5 to 20, even more preferably 5 to 12) ring atoms and optionally having a substituent, or a condensed aromatic heterocyclic group having 6 to 40 (preferably 6 to 30, more preferably 6 to 20, even more preferably 6 to 12) ring carbon atoms and optionally having a substituent.

Ar$^1$ is a single bond, a divalent aromatic hydrocarbon group having 6 to 40 (preferably 6 to 30, more preferably 6 to 20, even more preferably 6 to 12) ring carbon atoms and optionally having a substituent; and Ar$^2$ is an aromatic hydrocarbon group having 6 to 40 (preferably 6 to 30, more preferably 6 to 20, even more preferably 6 to 14) ring carbon atoms and optionally having a substituent, a condensed aromatic hydrocarbon group having 6 to 40 (preferably 6 to 30, more preferably 6 to 20, even more preferably 6 to 12) ring carbon atoms and optionally having a substituent, an aromatic heterocyclic group having 5 to 40 (preferably 5 to 30, more preferably 5 to 20, even more preferably 5 to 12) ring atoms and optionally having a substituent, or a condensed aromatic heterocyclic group having 5 to 40 (preferably 5 to 30, more preferably 5 to 20, even more preferably 5 to 12) ring atoms and optionally having a substituent.

HAr is selected, for example, from the following groups.
[Chem. 56]
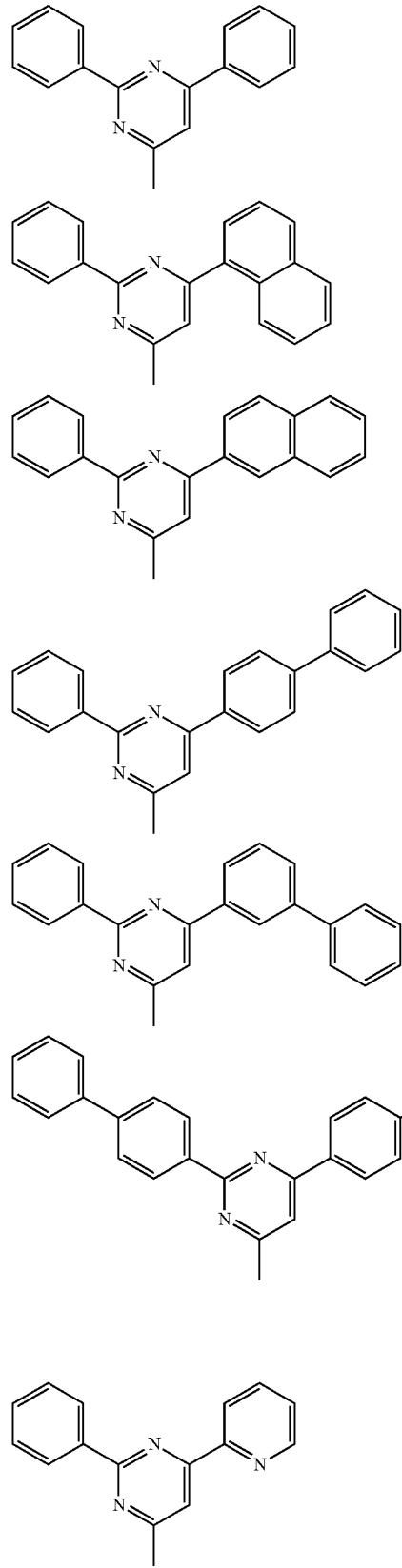
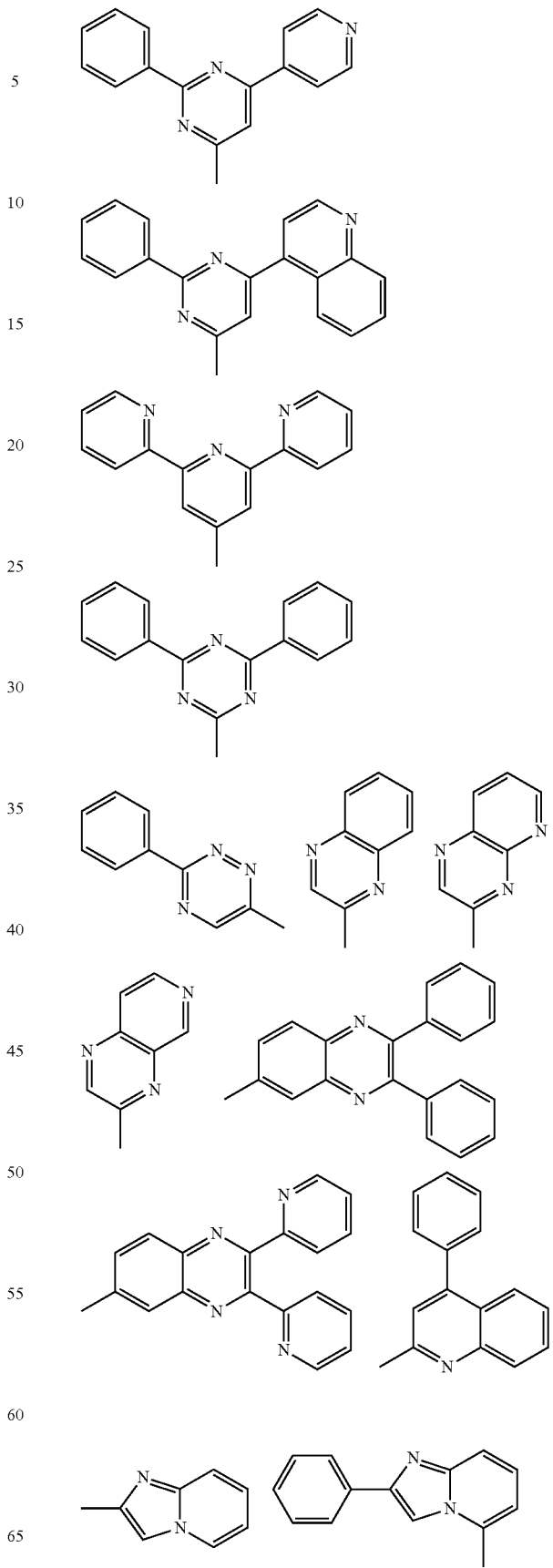

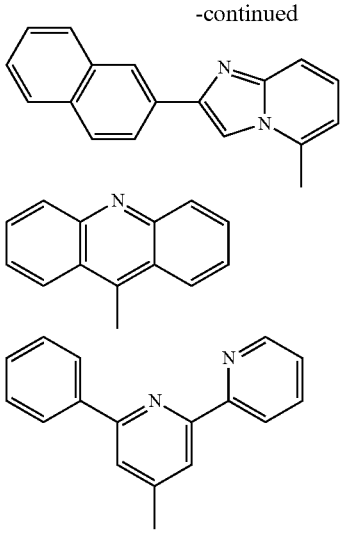

Preferably, $L^1$ is selected, for example, from the following groups, and a phenylene group is more preferred. Also preferably, $L^1$ is one having a carbazolyl group especially a 9-carbazolyl group as a substituent. More preferred is one having two 9-carbazolyl groups.

[Chem. 57]

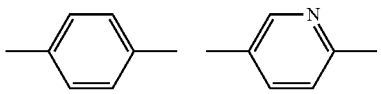

Also preferably, $Ar^1$ is a single bond, or is selected, for example, from the following arylanthranylene groups.

[Chem. 58]

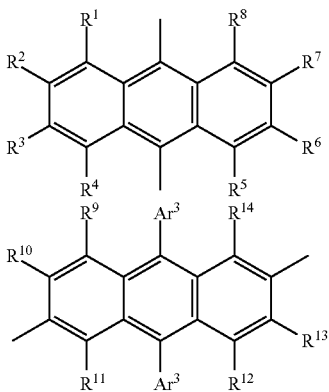

In the above formulae, $R^1$ to $R^{14}$ are each independently a hydrogen atom, a halogen atom, an alkyl group having 1 to 20 (preferably 1 to 10, more preferably 1 to 6) carbon atoms, an alkoxy group having 1 to 20 (preferably 1 to 10, and more preferably 1 to 6) carbon atoms, an aryloxy group having 6 to 40 (preferably 6 to 30, more preferably 6 to 20, even more preferably 6 to 12) ring carbon atoms, an aromatic hydrocarbon group having 6 to 40 (preferably 6 to 30, more preferably 6 to 20, even more preferably 6 to 12) ring carbon atoms and optionally having a substituent, a condensed aromatic hydrocarbon group having 6 to 40 (prefer- ably 6 to 30, more preferably 6 to 20, even more preferably 6 to 12) ring carbon atoms and optionally having a substituent, an aromatic heterocyclic group having 5 to 40 (prefer- ably 5 to 30, more preferably 5 to 20, even more preferably 5 to 12) ring atoms, or a condensed aromatic heterocyclic group having 5 to 40 (preferably 5 to 30, more preferably 5 to 20, even more preferably 5 to 12) ring atoms.

$Ar^3$ is an aromatic hydrocarbon group having 6 to 40 (preferably 6 to 30, more preferably 6 to 20, even more preferably 6 to 12) ring carbon atoms and optionally having a substituent, a condensed aromatic hydrocarbon group having 6 to 40 (preferably 6 to 30, more preferably 6 to 20, even more preferably 6 to 12) ring carbon atoms and optionally having a substituent, an aromatic heterocyclic group having 5 to 40 (preferably 5 to 30, more preferably 5 to 20, even more preferably 5 to 12) ring atoms, or a condensed aromatic heterocyclic group having 5 to 40 (preferably 5 to 30, more preferably 5 to 20, even more preferably 5 to 12) ring atoms.

The compound may also be a nitrogen-containing hetero- cyclic derivative where $R^1$ to $R^8$ are all hydrogen atoms.

Preferably, $Ar^2$ is a group selected, for example, from the following groups, and is also preferably a heterocyclic group such as a carbazolyl group, especially a 9-carbazolyl group.

[Chem. 59]

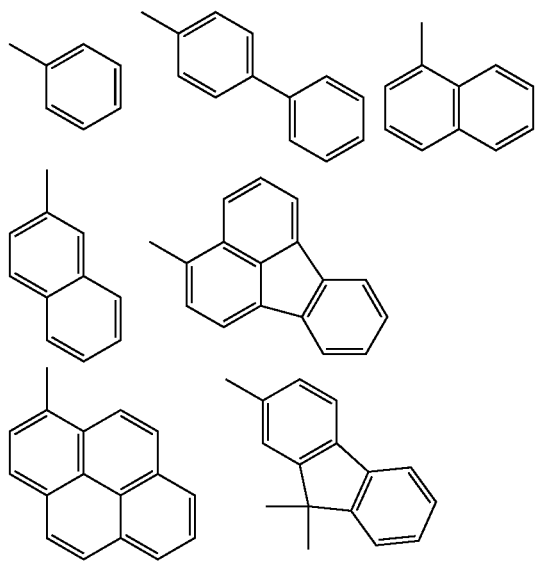

In addition, the following compounds are preferably used as the nitrogen-containing aromatic polycyclic organic com- pound for use as the electron transmitting compound (see JP 9-3448 A).

[Chem. 60]

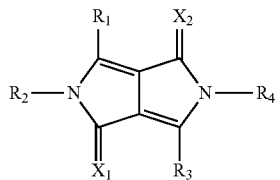

In the above formula, $R_1$ to $R_4$ each independently rep- resent a hydrogen atom, a substituted or unsubstituted aliphatic group, a substituted or unsubstituted alicyclic group having, a substituted or unsubstituted carbocyclic aromatic group, or a substituted or unsubstituted heterocyclic group; and $X_1$ and $X_2$ each independently represent an oxygen atom, a sulfur atom, or a dicyanomethylene group.

Further, the following compounds are also favorably used as the electron transmitting compound (see JP 2000-173774 A).

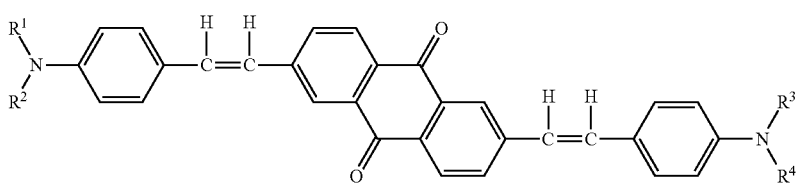

[Chem. 61]

In the above formula, $R^1$, $R^2$, $R^3$ and $R^4$ each independently represent an aromatic hydrocarbon group represented by the following formula, or a condensed aromatic hydrocarbon group.

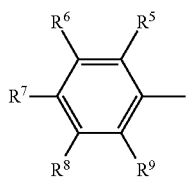

[Chem. 62]

In the above formula, $R^5$, $R^6$, $R^7$, $R^8$ and $R^9$ each independently represent a hydrogen atom, or at least one of these is a saturated or unsaturated alkoxyl group, an alkyl group, an amino group, or an alkylamino group.

Further, a polymer including the above nitrogen-containing heterocyclic group or the above nitrogen-containing heterocyclic derivative is also usable as the electron transmitting compound.

Further, the electron transporting layer preferably contains at least any one of nitrogen-containing heterocyclic derivatives represented by the following formulae (201) to (203).

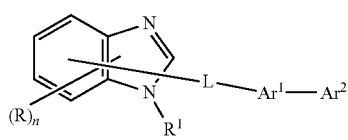
(201)

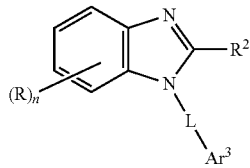
(202)

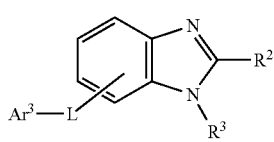
(203)

In the above formulae (201) to (203), R represents a hydrogen atom, an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, a condensed aromatic heterocyclic group having 5 to 60 (preferably 5 to 30, more preferably 5 to 20, even more preferably 5 to 12) ring atoms and optionally having a substituent, an alkyl group having 1 to 20 (preferably 1 to 10, more preferably 1 to 6) carbon atoms and optionally having a substituent, or an alkoxy group having 1 to 20 (preferably 1 to 10, more preferably 1 to 6) carbon atoms and optionally having a substituent.

n indicates an integer of 0 to 4.

In the above formulae (201) to (203), $R^1$ represents an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, a condensed aromatic heterocyclic group having 5 to 60 (preferably 5 to 30, more preferably 5 to 20, even more preferably 5 to 12) ring atoms and optionally having a substituent, an alkyl group having 1 to 20 (preferably 1 to 10, more preferably 1 to 6) carbon atoms and optionally having a substituent, or an alkoxy group having 1 to 20 (preferably 1 to 10, more preferably 1 to 6) carbon atoms and optionally having a substituent.

$R^2$ and $R^3$ each independently represent represents a hydrogen atom, an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, a condensed aromatic heterocyclic group having 5 to 60 (preferably 5 to 30, more preferably 5 to 20, even more preferably 5 to 12) ring atoms and optionally having a substituent, an alkyl group having 1 to 20 (preferably 1 to 10, more preferably 1 to 6) carbon atoms and optionally having a substituent, or an alkoxy group having 1 to 20 (preferably 1 to 10, more preferably 1 to 6) carbon atoms and optionally having a substituent.

In the above formulae (201) to (203), L represents an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, or a condensed aromatic heterocyclic group having 5 to 60 (preferably 5 to 30, more preferably 5 to 20, even more preferably 5 to 12) ring atoms and optionally having a substituent.

$Ar^1$ represents an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, or a condensed aromatic heterocyclic group having 5 to 60 (preferably 5 to 30, more preferably 5 to 20, even more preferably 5 to 12) ring atoms and optionally having a substituent.

$Ar^2$ represents an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, a condensed aromatic heterocyclic group having 5 to 60 (preferably 5 to 30, more preferably 5 to 20, even more preferably 5 to 12) ring atoms and optionally having a substituent, an alkyl group having 1 to 20 (preferably 1 to 10, more preferably 1 to 6) carbon atoms and optionally having a substituent, or an alkoxy group having 1 to 20 (preferably 1 to 10, more preferably 1 to 6) carbon atoms and optionally having a substituent.

$Ar^3$ represents an aromatic hydrocarbon group having 6 to 60 (preferably 6 to 30, more preferably 6 to 20, even more preferably 6 to 12) ring carbon atoms and optionally having a substituent, a condensed aromatic hydrocarbon group having 6 to 60 (preferably 6 to 30, more preferably 6 to 20, even more preferably 6 to 12) ring carbon atoms and optionally having a substituent, an aromatic heterocyclic group having 5 to 60 (preferably 5 to 30, more preferably 5 to 20, even more preferably 5 to 12) ring atoms and optionally having a substituent, a condensed aromatic heterocyclic group having 5 to 60 (preferably 5 to 30, more preferably 5 to 20, even more preferably 5 to 12) ring atoms and optionally having a substituent, an alkyl group having 1 to 20 (preferably 1 to 10, more preferably 1 to 6) carbon atoms and optionally having a substituent, an alkoxy group having 1 to 20 (preferably 1 to 10, more preferably 1 to 6) carbon atoms and optionally having a substituent, or a group represented by —$Ar^1$—$Ar^2$ (where $Ar^1$ and $Ar^2$ each are the same as above).

In the above formulae (201) to (203), R represents a hydrogen atom, an aromatic hydrocarbon group or condensed aromatic hydrocarbon group having 6 to 60 carbon atoms and optionally having a substituent, a pyridyl group optionally having a substituent, a quinolyl group optionally having a substituent, an alkyl group having 1 to 20 carbon atoms and optionally having a substituent, or an alkoxy group having 1 to 20 carbon atoms and optionally having a substituent.

The thickness of the electron transporting layer is not particularly limited, but it is preferably 1 nm to 100 nm.

As the constituent component for the electron injecting layer that may be arranged adjacent to the electron transporting layer, an insulating material or a semiconductor is preferably used as an inorganic compound in addition to the nitrogen-containing cyclic derivative. When the electron injecting layer is formed of an insulating material or a semiconductor, current leak could be effectively prevented to improve electron injection performance.

The insulating material is preferably at least one metal compound selected from the group consisting of an alkali metal chalcogenide, an alkaline earth metal chalcogenide, an alkali metal halide, and an alkaline earth metal halide. The electron injecting layer formed of such an alkali metal chalcogenide or the like is preferred from the viewpoint of further improving electron injection performance. Concretely, preferred examples of the alkali metal chalcogenide include $Li_2O$, $K_2O$, $Na_2S$, $Na_2Se$ and $Na_2O$; and preferred examples of the alkaline earth metal chalcogenide include CaO, BaO, SrO, BeO, BaS and CaSe. Preferred examples of the alkali metal halide include LiF, NaF, KF, LiCl, KCl and NaCl. Preferred examples of the alkaline earth metal halide include fluorides such as $CaF_2$, $BaF_2$, $SrF_2$, $MgF_2$ and $BeF_2$, and other halides than fluorides.

Examples of the semiconductor include oxides, nitrides or oxynitrides of at least one element selected from the group consisting of Ba, Ca, Sr, Yb, Al, Ga, In, Li, Na, Cd, Mg, Si, Ta, Sb and Zn. The semiconductor may be used alone or in combination of two or more. The inorganic compound included in the electron injecting layer preferably forms a microcrystalline or amorphous insulating thin film. If the electron injecting layer is formed from such an insulating thin film, the pixel defects, such as dark spots, can be decreased because a more uniform thin film is formed. Examples of such inorganic compound include the alkali metal chalcogenide, the alkaline earth metal chalcogenide, the alkali metal halide and the alkaline earth metal halide.

When using the insulating material or the semiconductor, the thickness of its layer is preferably about 0.1 to 15 nm. The electron injecting layer may contain the reducing dopant mentioned above.

(Hole Transporting Layer)

The hole transporting layer is an organic layer formed between the light emitting layer and the anode and has a function of transporting holes from the anode to the light emitting layer. When the hole transporting layer is formed into two or more layers, the organic layer closer to the anode may be defined as a hole injecting layer in some cases. The hole injecting layer has a function of efficiently injecting holes from the anode to the organic layer unit. The compound of the present invention may be used as the hole transporting material to be contained in the hole transporting layer (first charge transporting layer).

Another preferred material for the hole transporting layer may include an aromatic amine compound, for example, an aromatic amine derivative represented by formula (H):

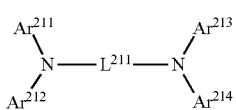

(H)

In the above formula (H), each of $Ar^{211}$ to $Ar^{214}$ represents a substituted or unsubstituted aromatic hydrocarbon group having 6 to 50 (preferably 6 to 30, more preferably 6 to 20, even more preferably 6 to 12) ring carbon atoms, a substituted or unsubstituted, condensed aromatic hydrocarbon group having 6 to 50 (preferably 6 to 30, more preferably 6 to 20, even more preferably 6 to 12) ring carbon atoms, a substituted or unsubstituted aromatic heterocyclic group having 5 to 50 (preferably 5 to 30, more preferably 5 to 20, even more preferably 5 to 12) ring atoms, a substituted or unsubstituted condensed aromatic heterocyclic group having 5 to 50 (preferably 5 to 30, more preferably 5 to 20, even more preferably 5 to 12) ring atoms, or a group formed of such an aromatic hydrocarbon group or a condensed aromatic hydrocarbon group and an aromatic heterocyclic group or a condensed aromatic heterocyclic group as combined. $Ar^{211}$ and $Ar^{212}$, and $Ar^{213}$ and $Ar^{214}$ may form a ring along with the nitrogen atom to which they bond, and examples of the ring include a carbazole ring, etc.

In the above formula (H), $L^{211}$ represents a substituted or unsubstituted aromatic hydrocarbon group having 6 to 50 (preferably 6 to 30, more preferably 6 to 20, even more preferably 6 to 12) ring carbon atoms, a substituted or unsubstituted, condensed aromatic hydrocarbon group having 6 to 50 (preferably 6 to 30, more preferably 6 to 20, even more preferably 6 to 12) ring carbon atoms, a substituted or unsubstituted aromatic heterocyclic group having 5 to 50 (preferably 5 to 30, more preferably 5 to 20, even more preferably 5 to 12) ring atoms, a substituted or unsubstituted condensed aromatic heterocyclic group having 5 to 50 (preferably 5 to 30, more preferably 5 to 20, even more preferably 5 to 12) ring atoms.

Specific examples of the compound of the formula (H) are shown below, although not limited thereto.

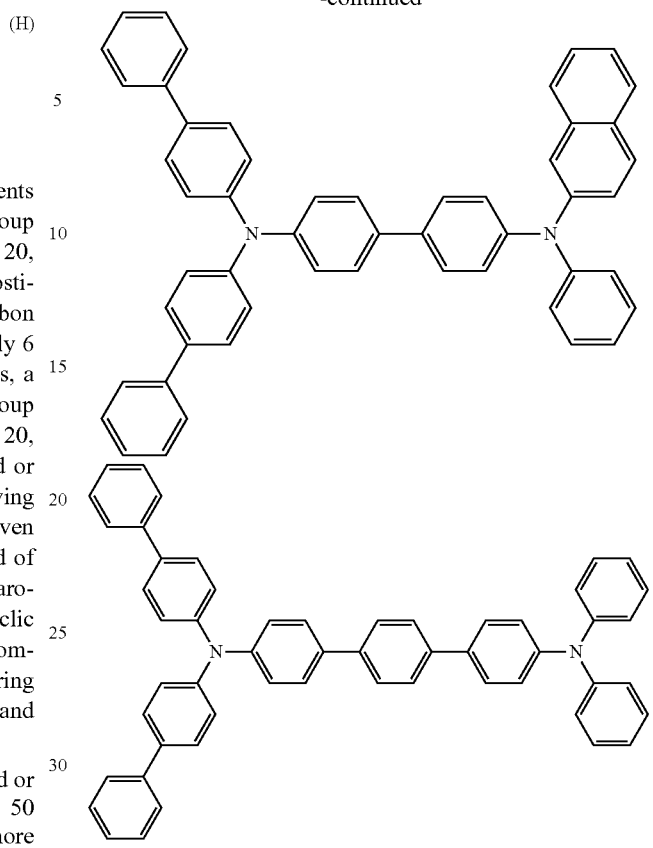

[Chem. 65]

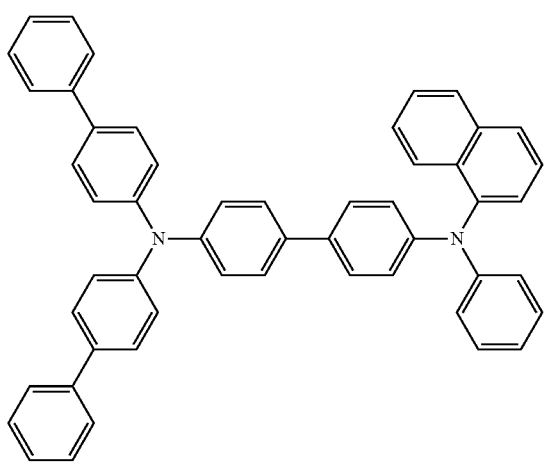

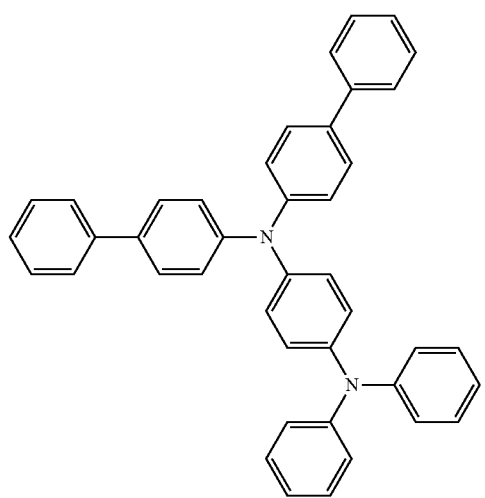

133
-continued
134
-continued
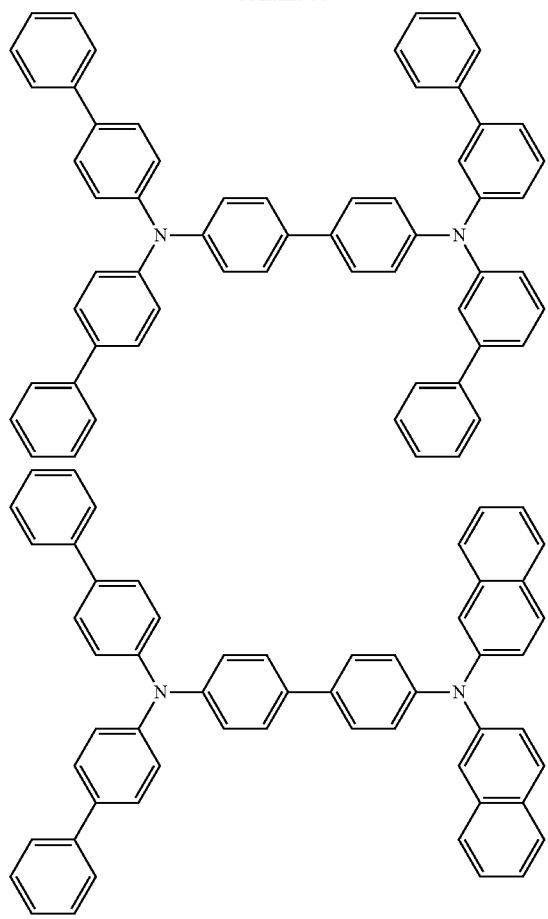
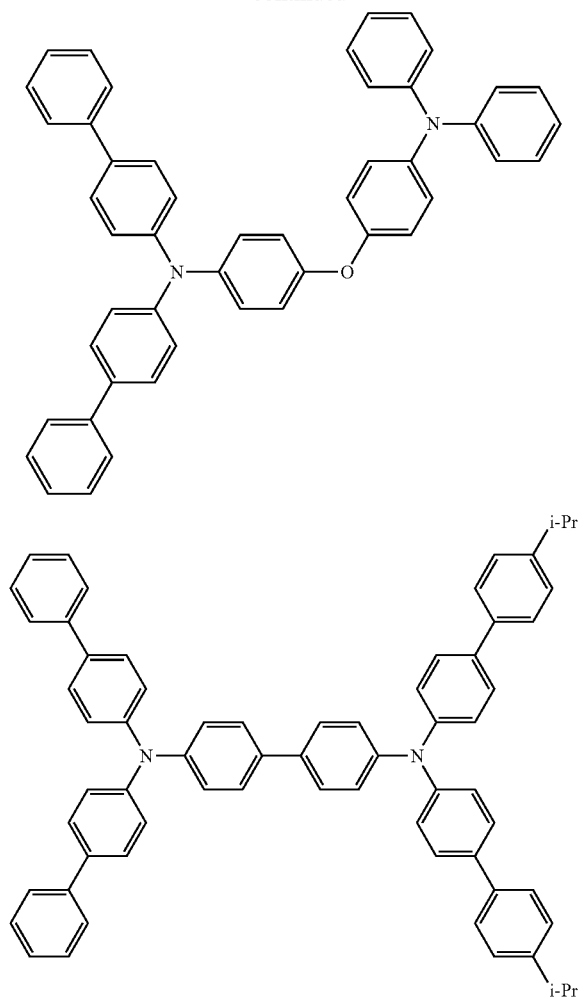
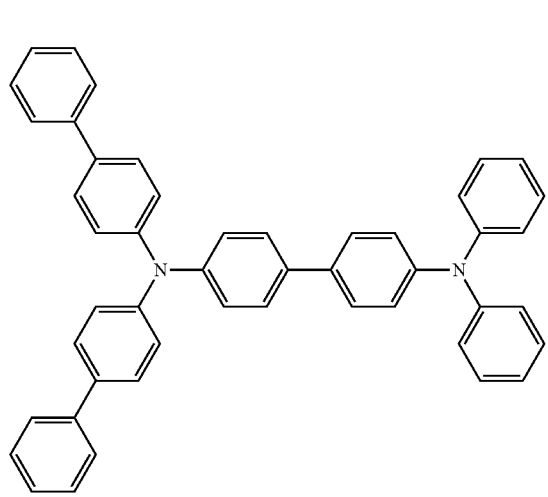

135
-continued
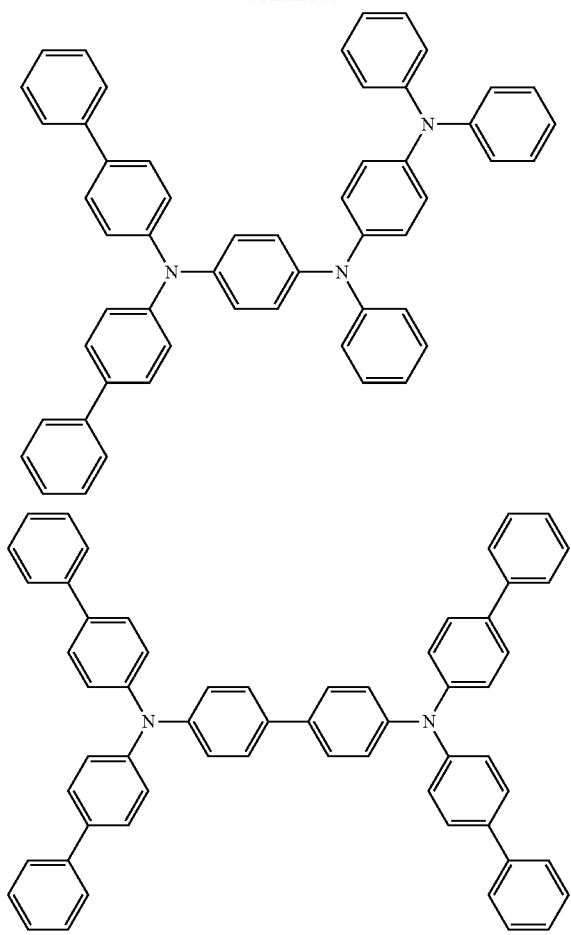
136
-continued
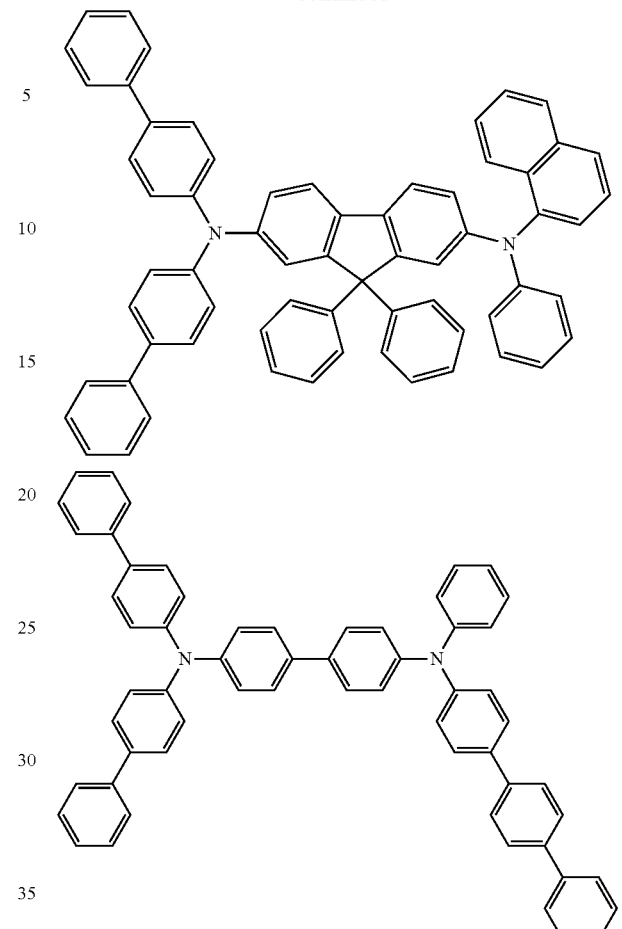
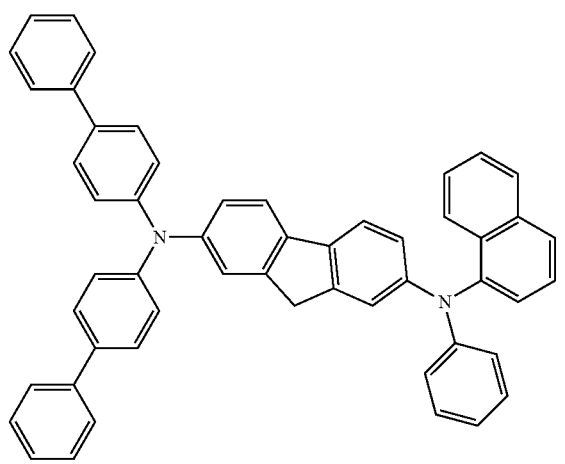
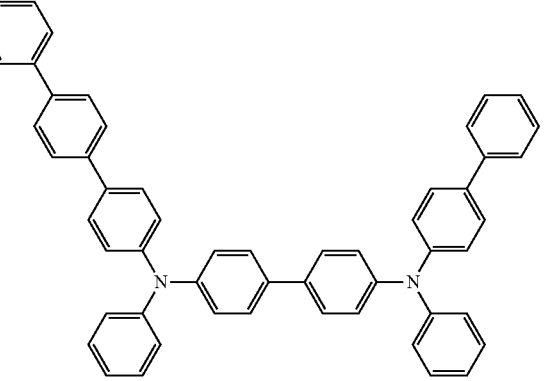

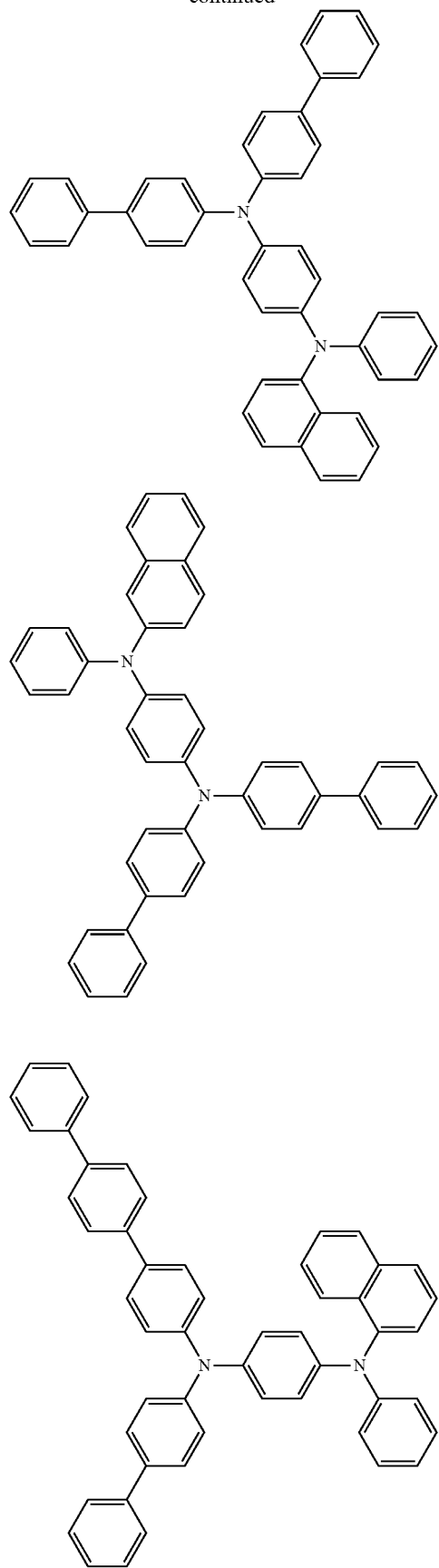
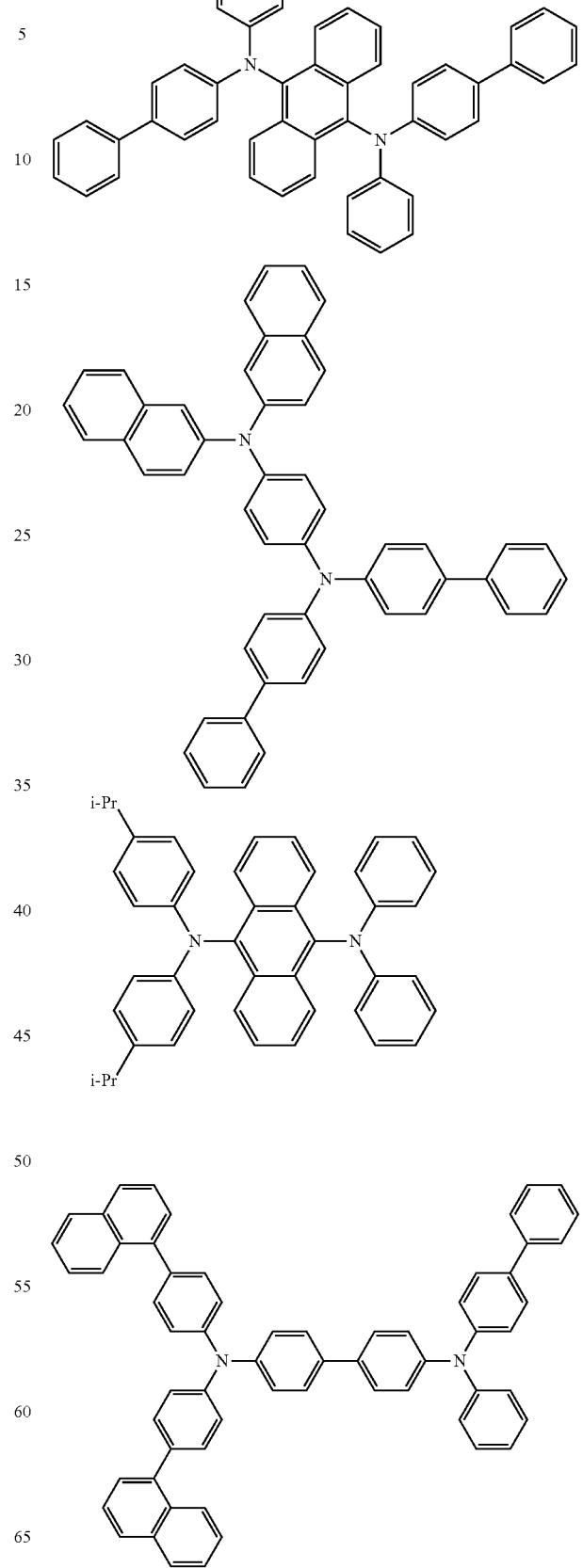

139
-continued
140
-continued
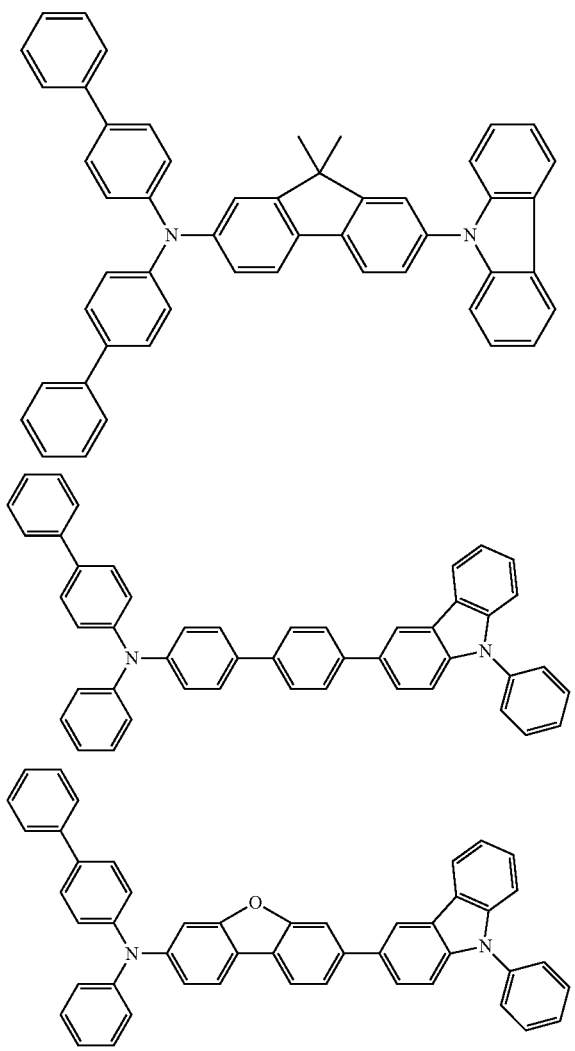
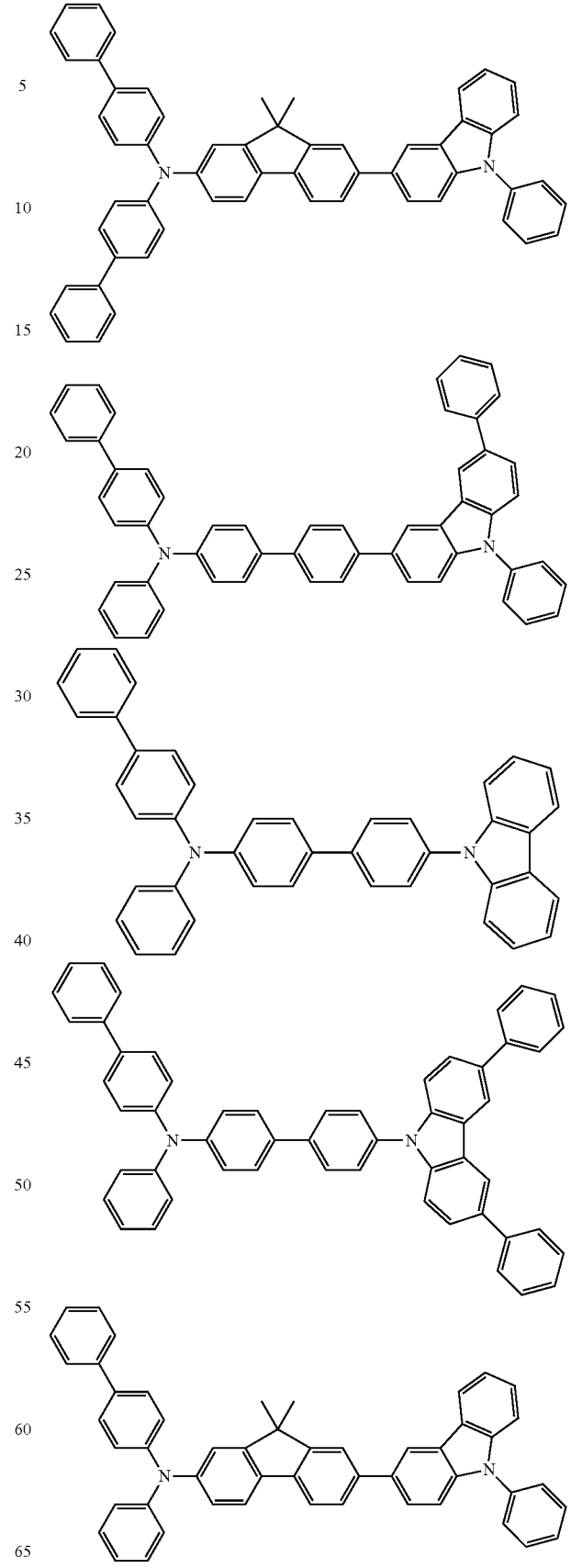

An aromatic amine compound represented by the following formula (J) is also preferably used to form the hole transporting layer.
(J)
In the above formula (J), $Ar^{221}$ to $Ar^{223}$ are as defined above with respect to $Ar^{211}$ to $Ar^{214}$ of formula (H). Examples of the compound represented by formula (J) are shown below, although not limited thereto.
[Chem. 67]
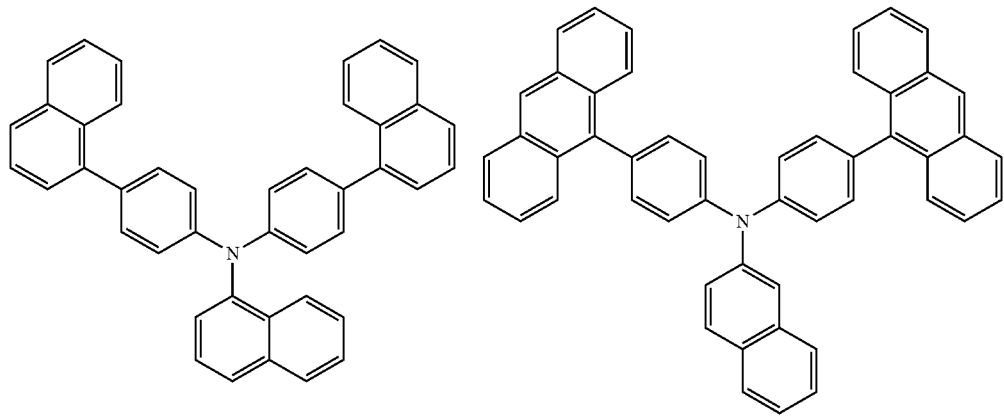
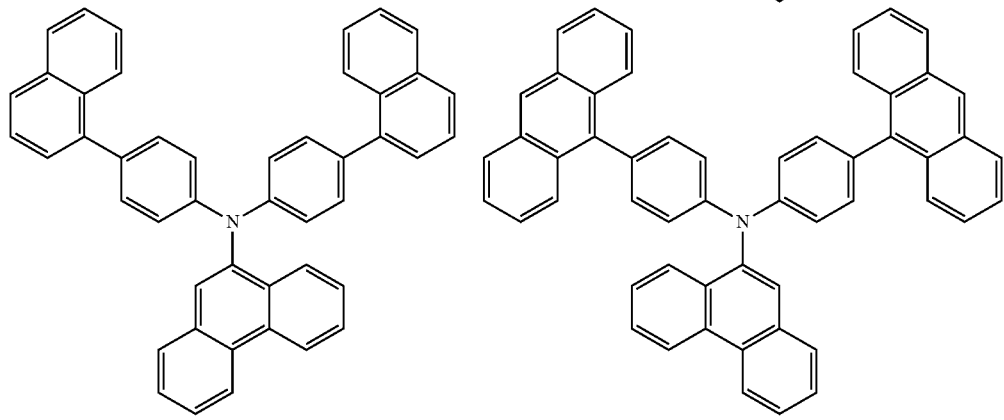
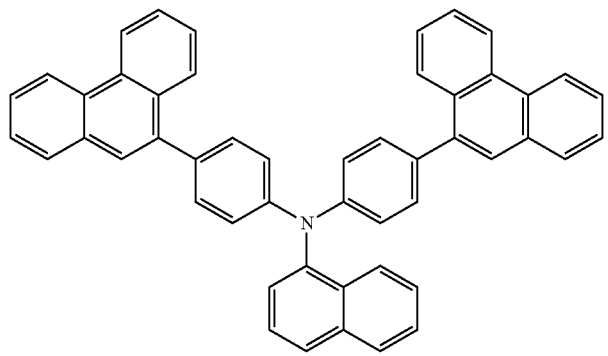

-continued
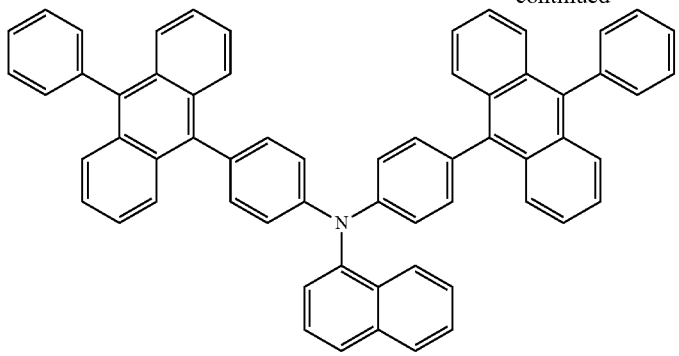
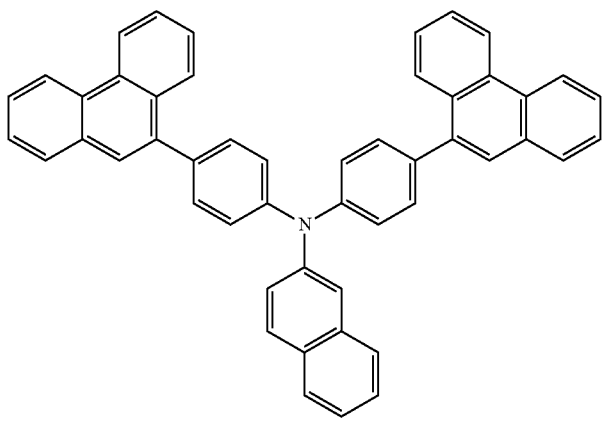
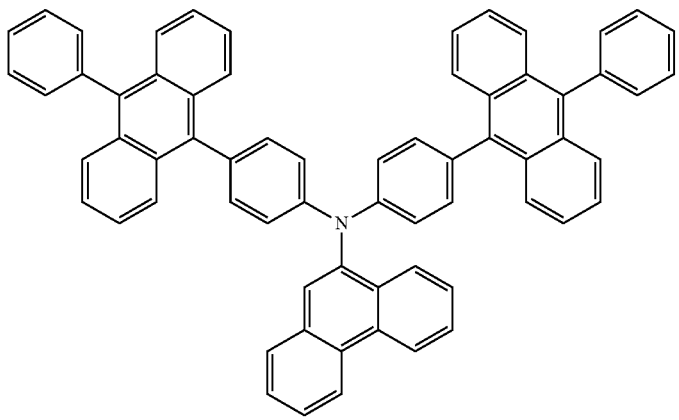
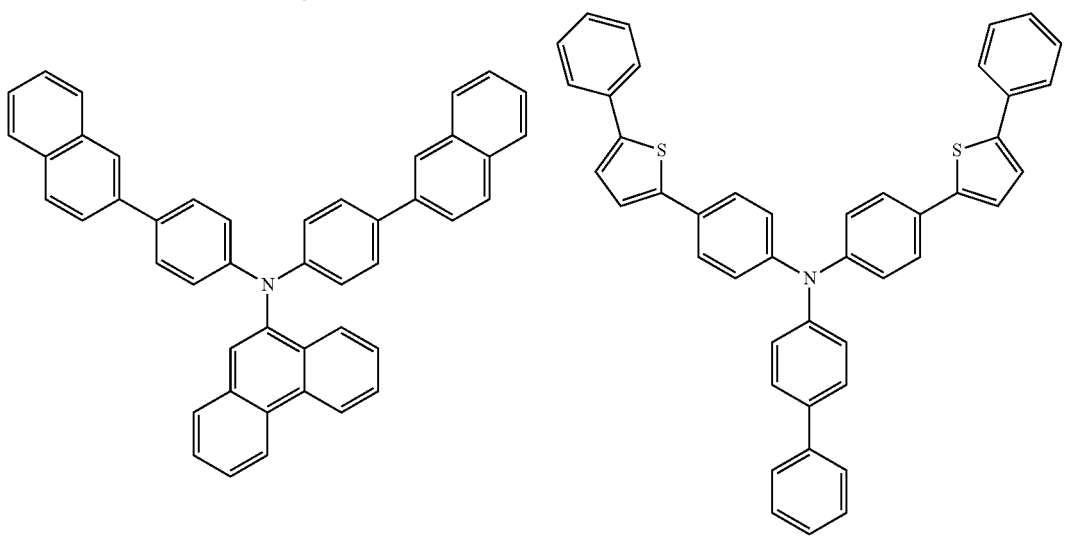

-continued
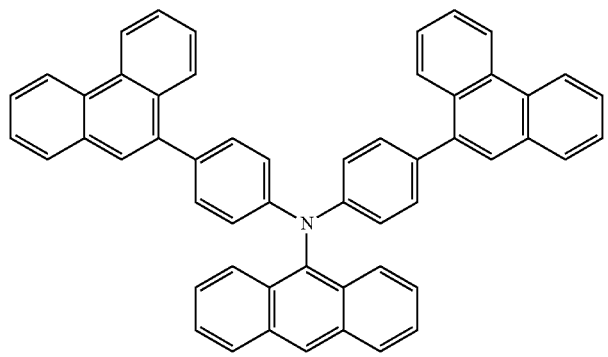
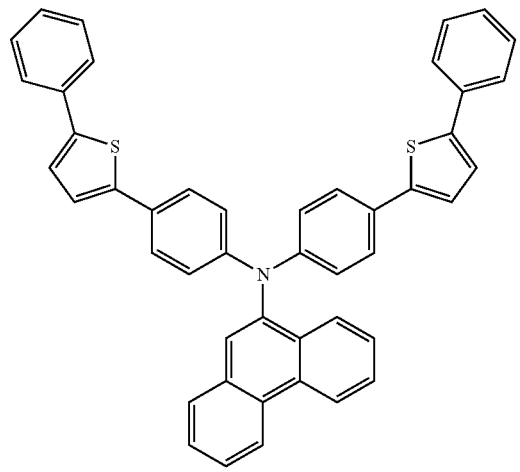
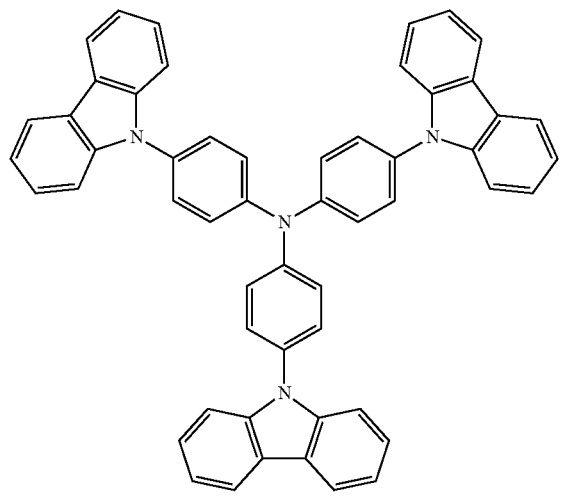
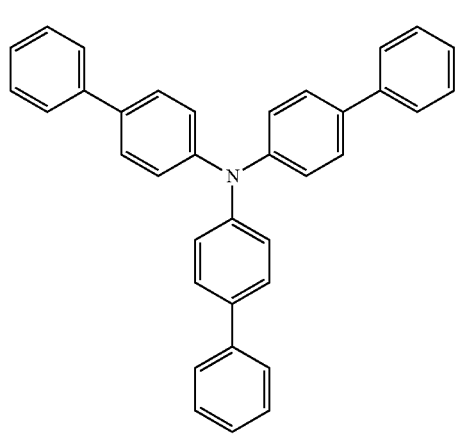
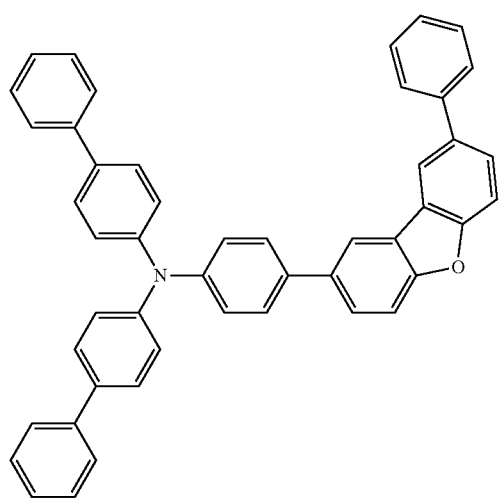
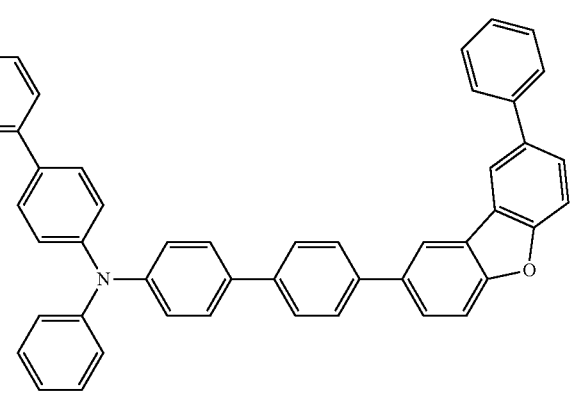

-continued
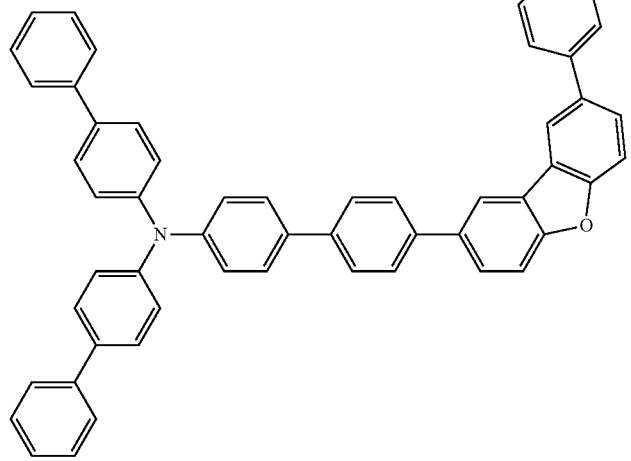
[Chem 68]
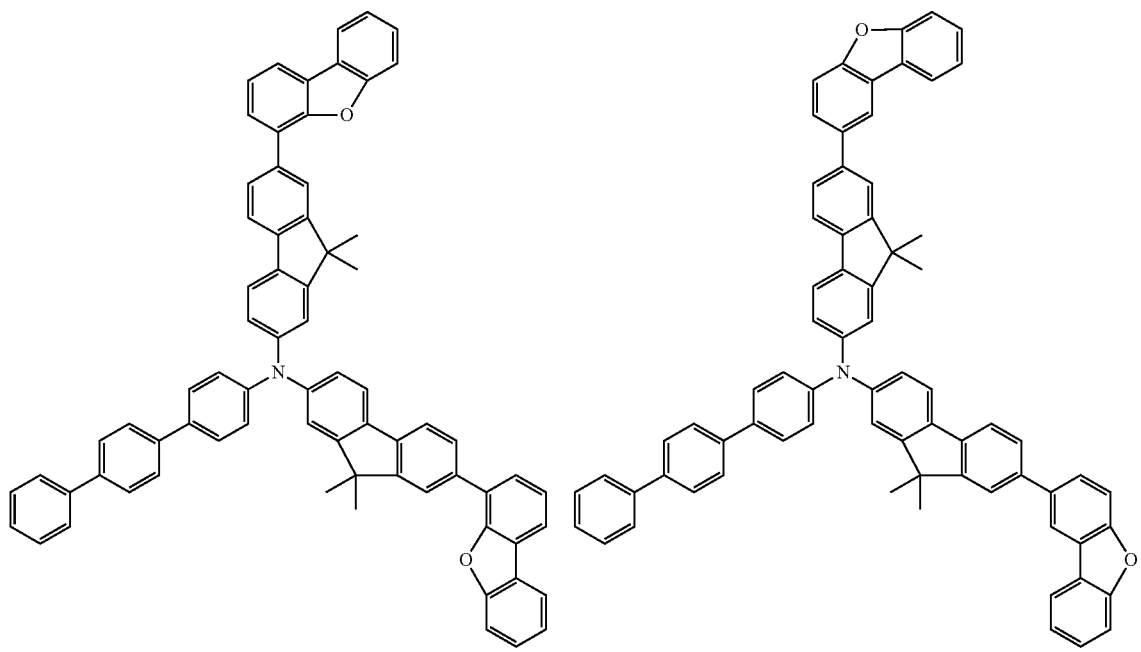

149 150
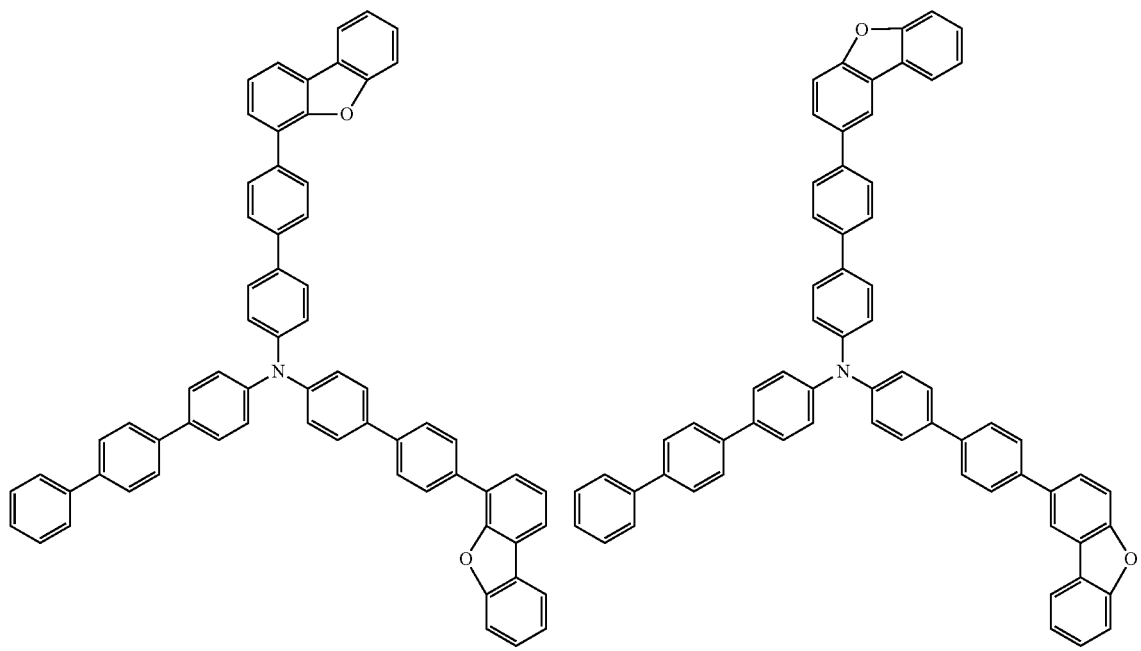
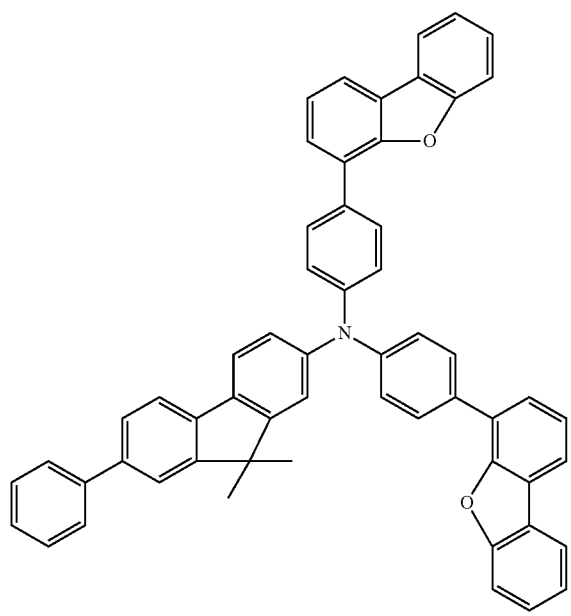

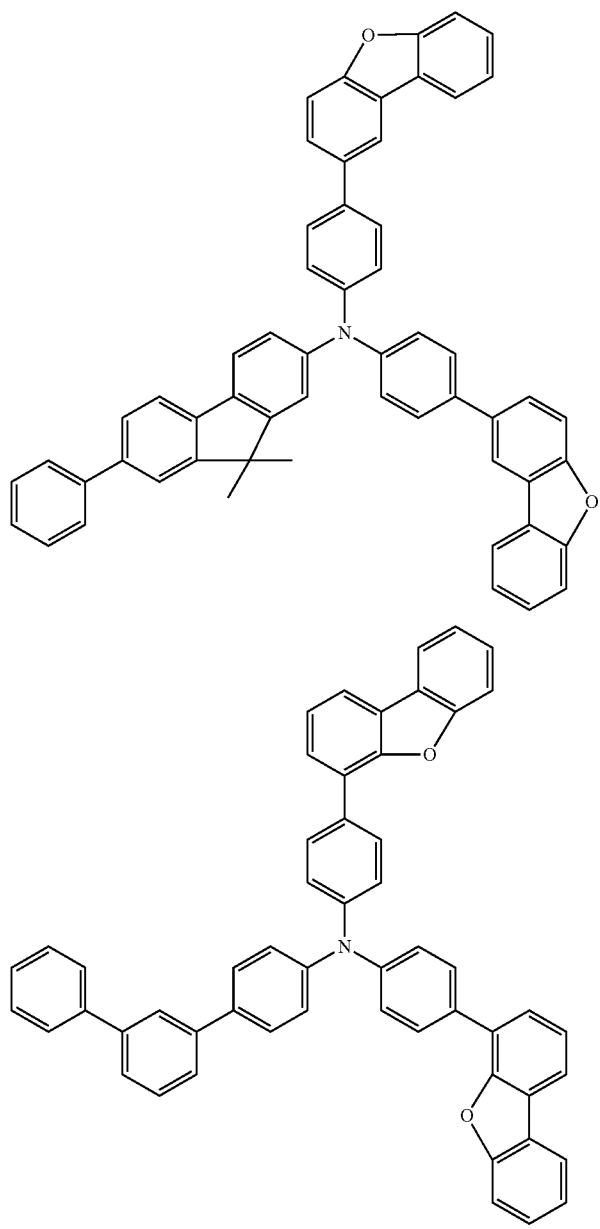

-continued
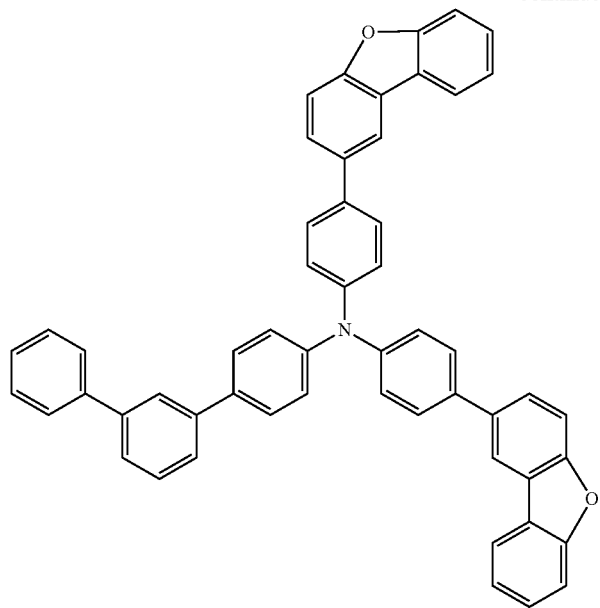
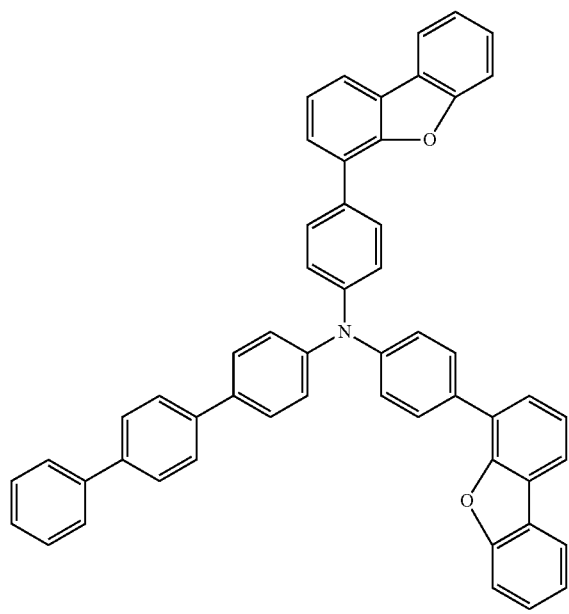

-continued
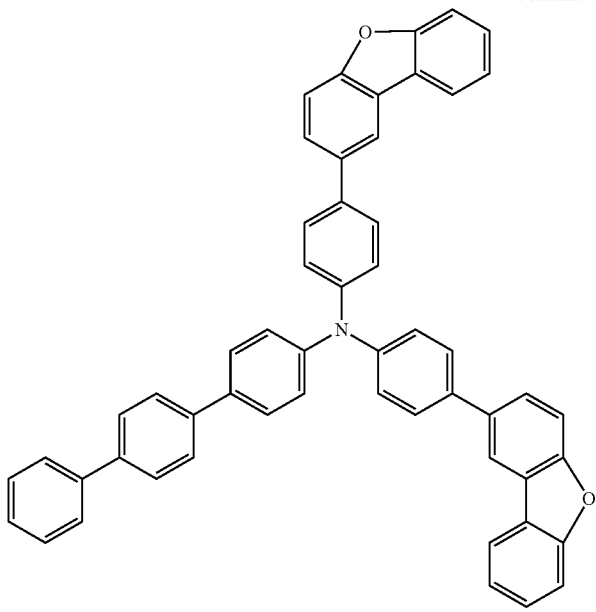
[Chem. 69]

-continued
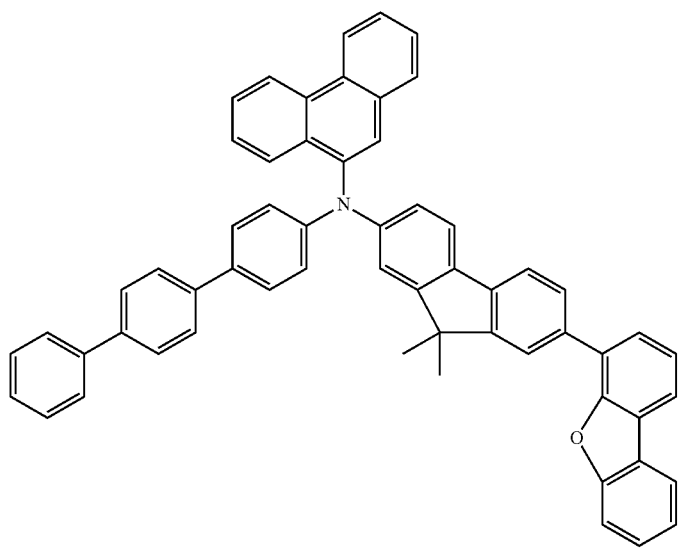
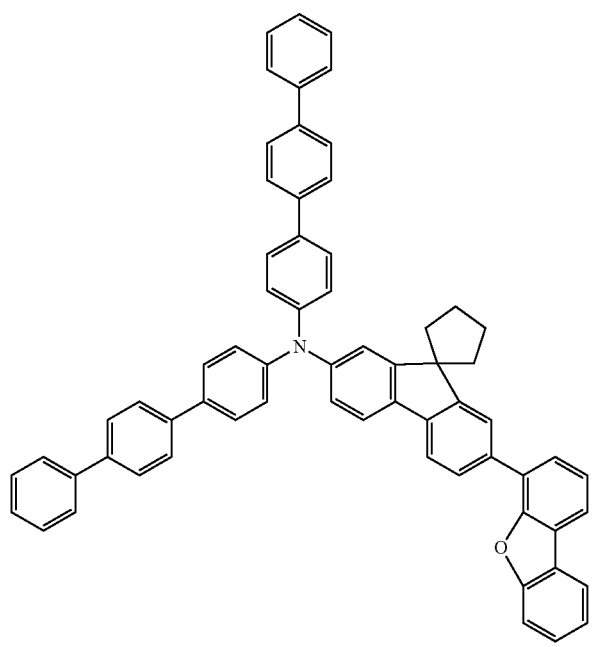

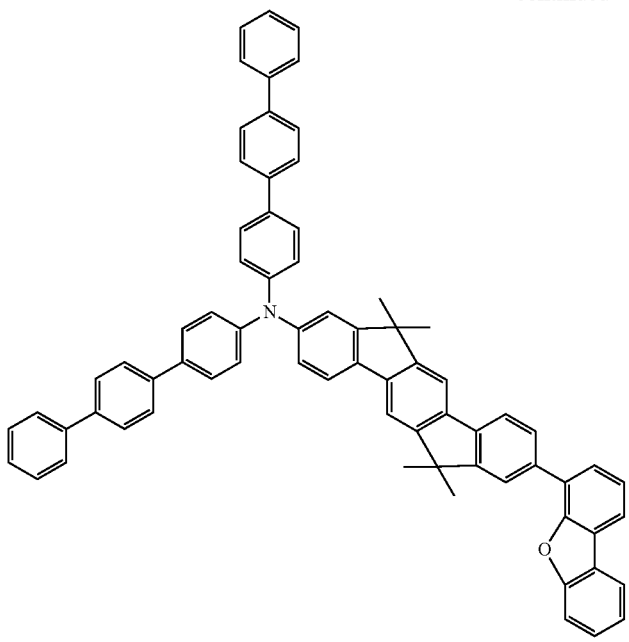
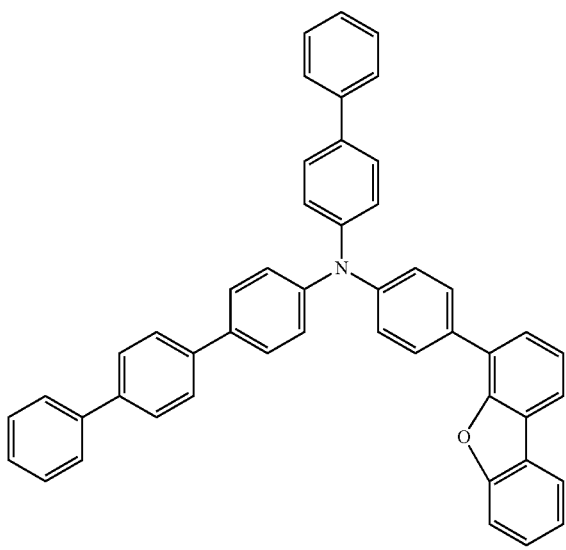

161 162
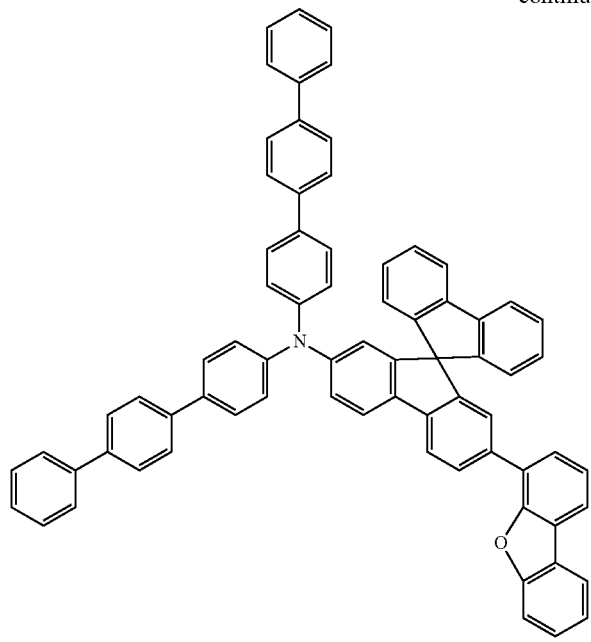
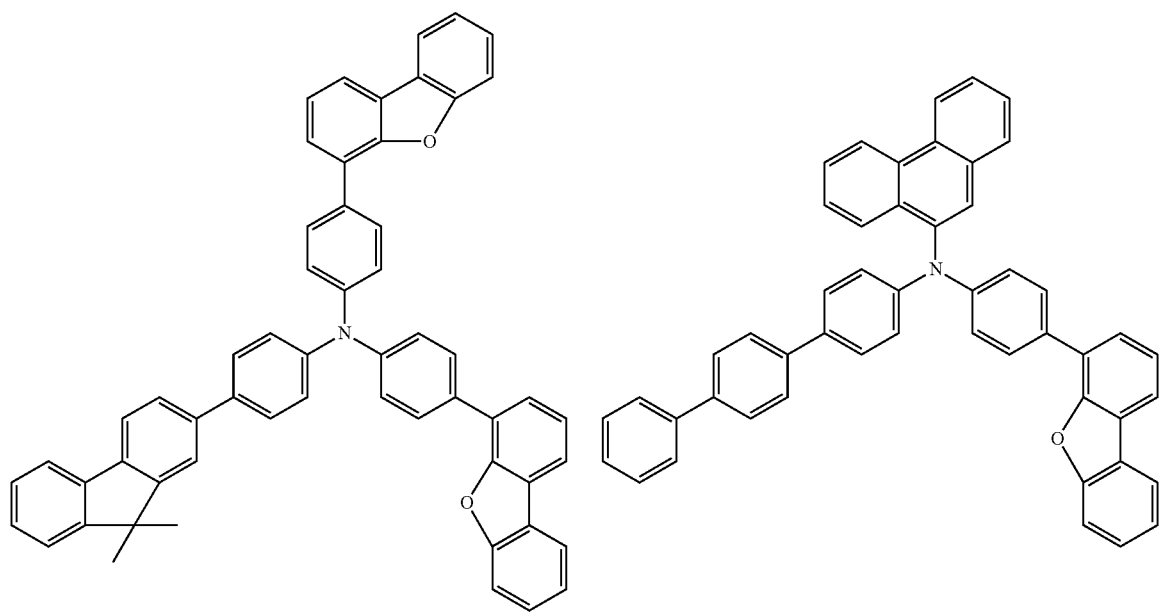

163 164
-continued
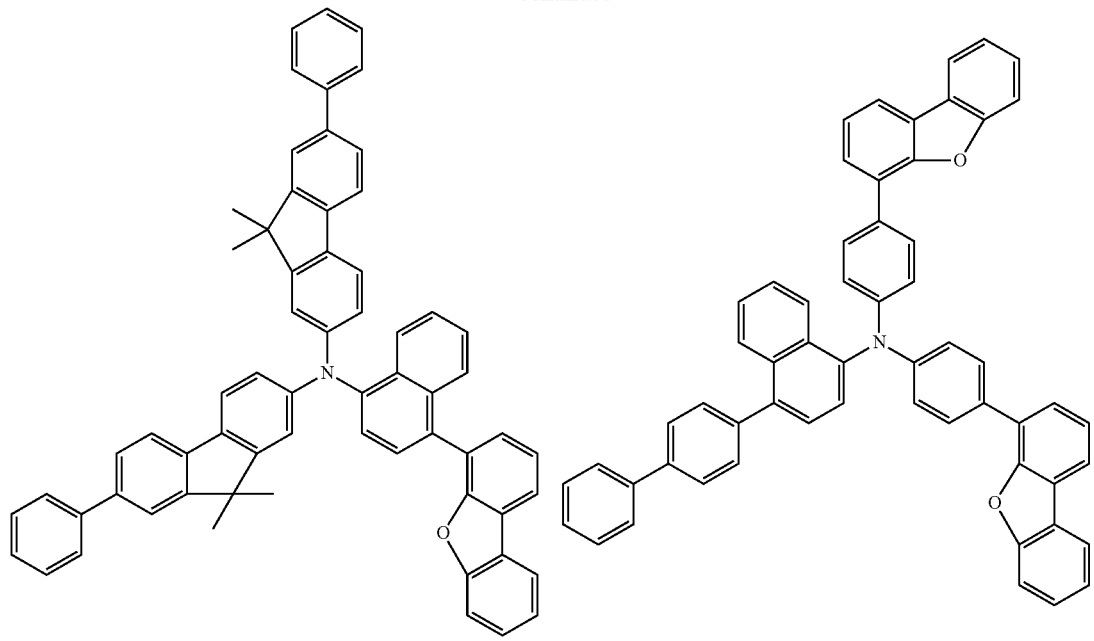
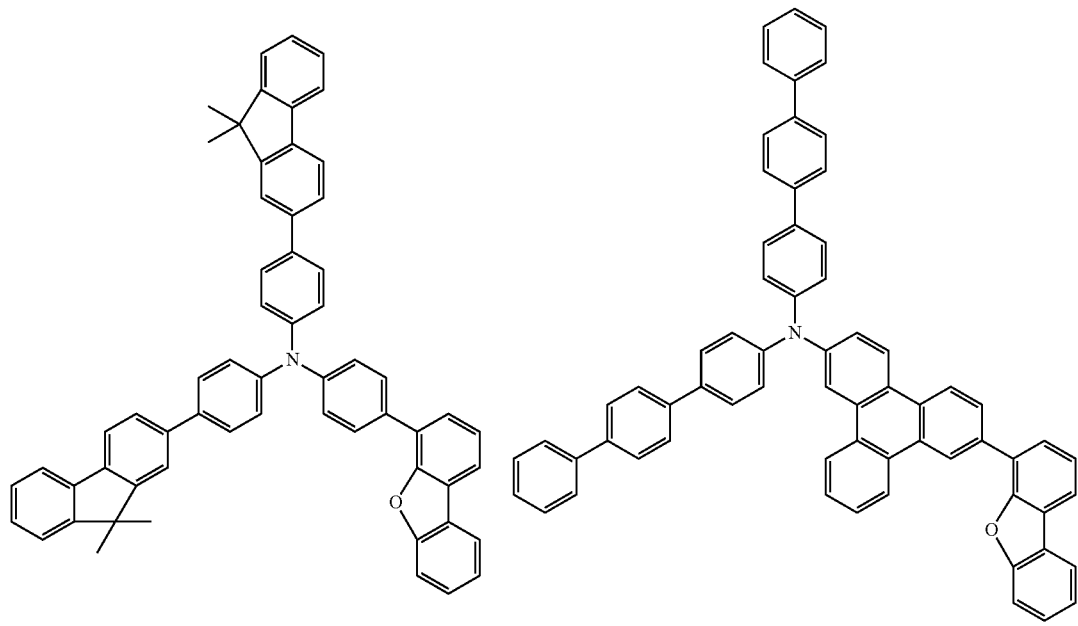

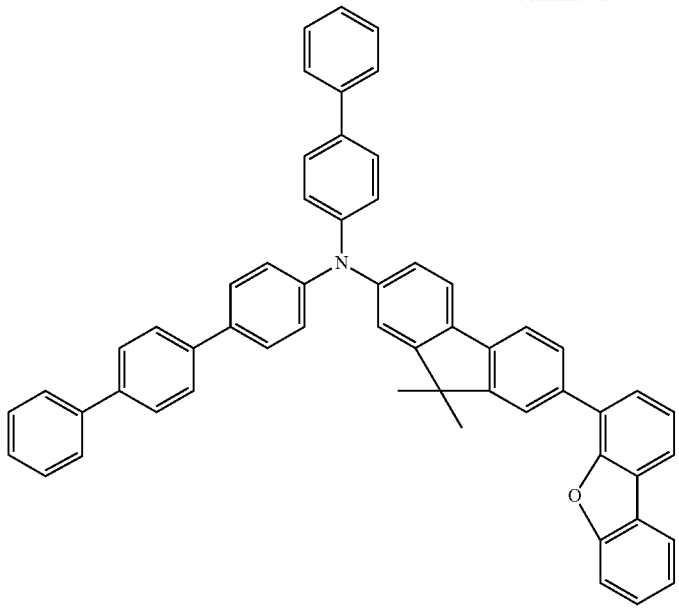 [SMILES: CC1(C)c2cc(-c3cccc4c3oc3ccccc34)ccc2-c2ccc(N(c3ccc(-c4ccccc4)cc3)c3ccc(-c4ccc(-c5ccccc5)cc4)cc3)cc21]

The hole transporting layer of the organic EL device of one embodiment of the present invention may be made into a two-layered structure of a first hole transporting layer (anode side) and a second hole transporting layer (cathode side).

The thickness of the hole transporting layer is not particularly limited, but it is preferably 10 nm to 300 nm. When the hole transporting layer has the above-mentioned two-layered structure, the thickness of the first hole transporting layer is not particularly limited, but it is preferably 50 to 300 nm, more preferably 50 to 250 nm, even more preferably 100 to 250 nm, still more preferably 150 to 250 nm, and the thickness of the second hole transporting layer is not particularly limited, but it is preferably 5 to 100 nm, more preferably 5 to 50 nm, even more preferably 5 to 30 nm, still more preferably 5 to 20 nm.

The organic EL device of one embodiment of the present invention may have a layer containing an acceptor material, which is disposed in contact with the anode side of the hole transporting layer or the first hole transporting layer. With such a layer, it is expected that the driving voltage is lowered and the production cost is reduced.

The acceptor material is preferably a compound represented by the following formula (K).

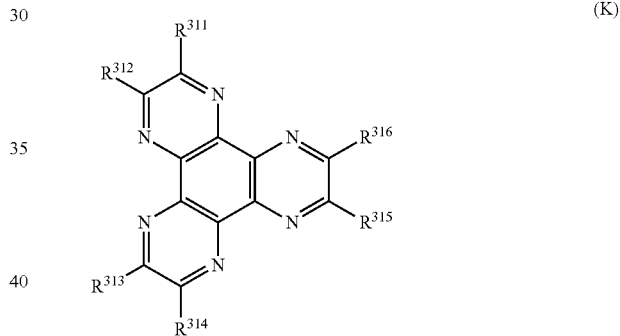

(K)

(In the above formula (K), $R^{311}$ to $R^{316}$ may be the same or different and each independently represent a cyano group, —$CONH_2$, a carboxyl group, or —$COOR^{317}$ wherein $R^{317}$ represents an alkyl group having 1 to 20 carbon atoms or a cycloalkyl group having 3 to 20 carbon atoms. However, one or a pair of two or more of $R^{311}$ and $R^{312}$, $R^{313}$ and $R^{314}$, or $R^{315}$ and $R^{316}$ may bond to each other to form a group represented by —CO—O—CO—.)

$R^{317}$ includes a methyl group, an ethyl group, an n-propyl group, an isopropyl group, an n-butyl group, an isobutyl group, a t-butyl group, a cyclopentyl group, and a cyclohexyl group.

The thickness of the layer containing the acceptor material is preferably 5 to 20 nm, although not particularly limited thereto.

As the acceptor material, the following materials are also preferably used.

[Chem. 71]
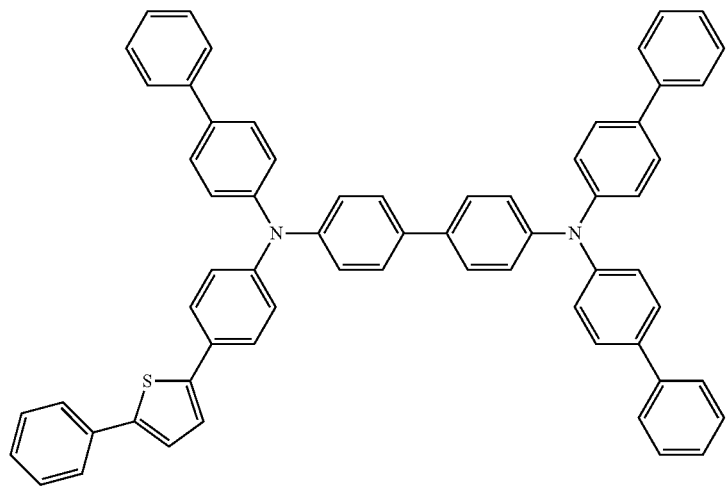
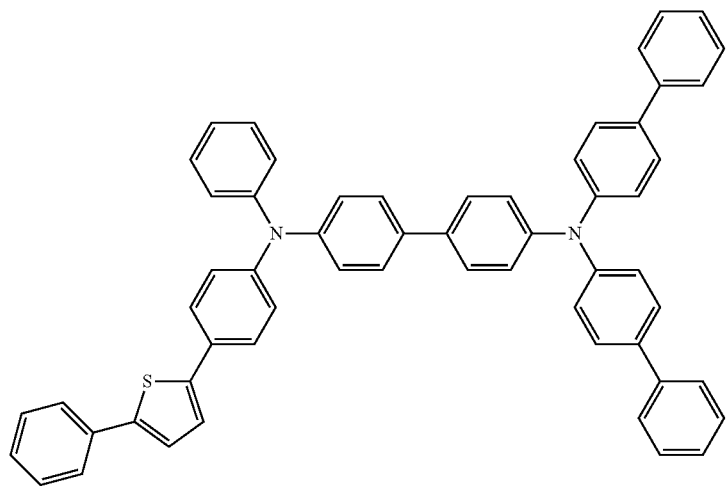
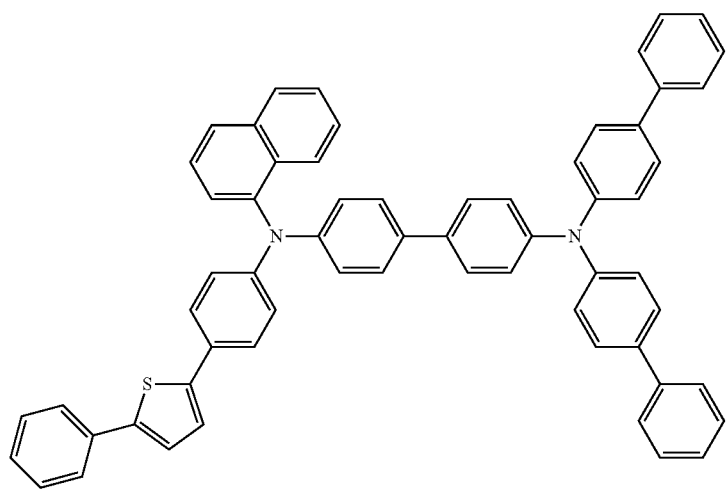

-continued
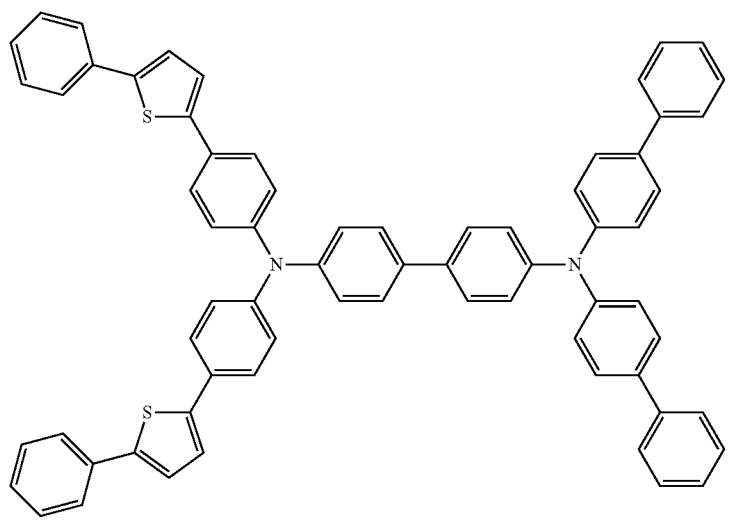
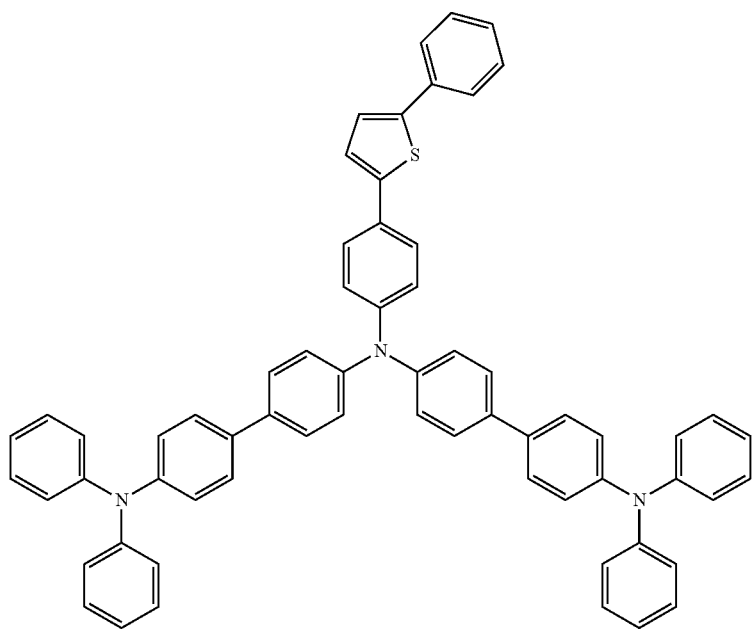
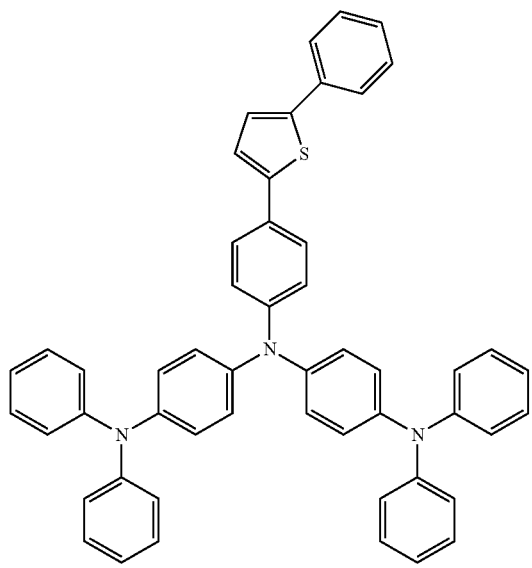

-continued
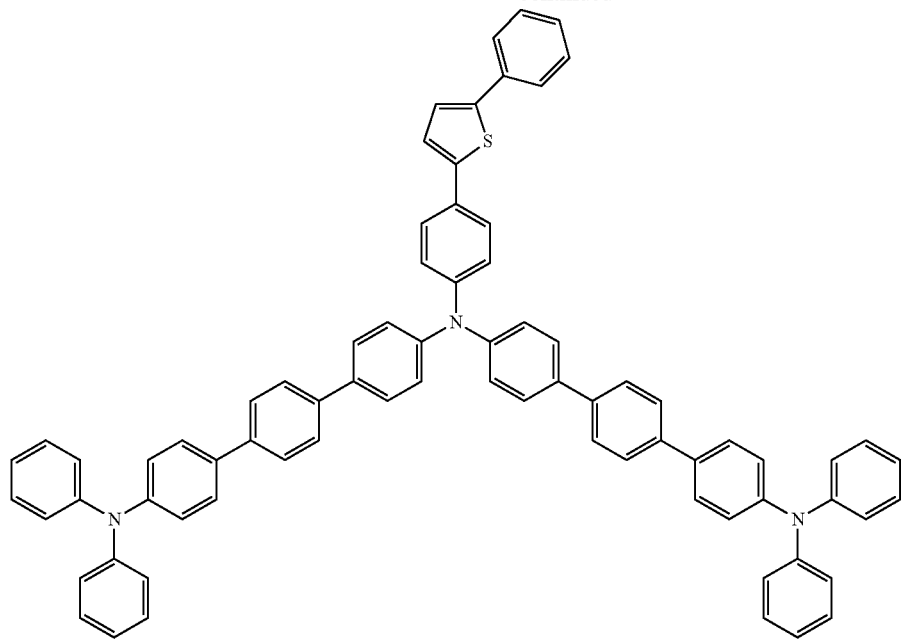
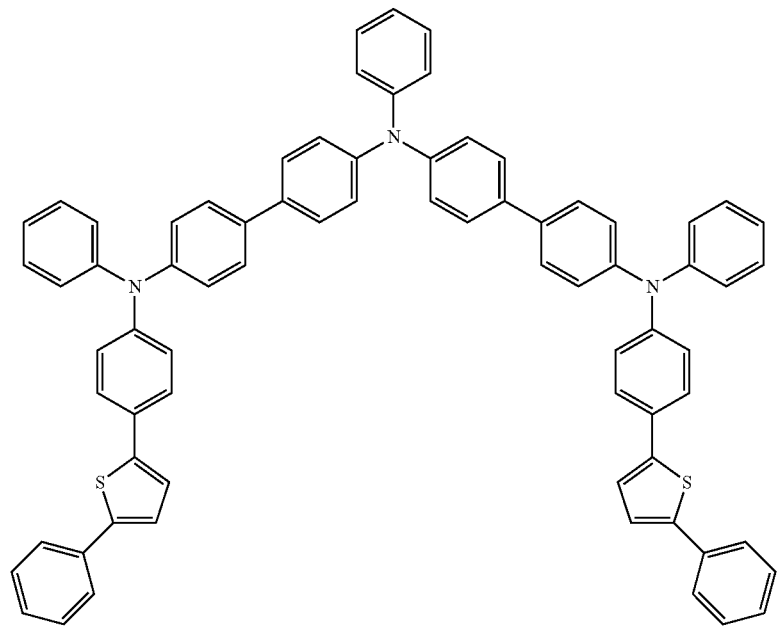

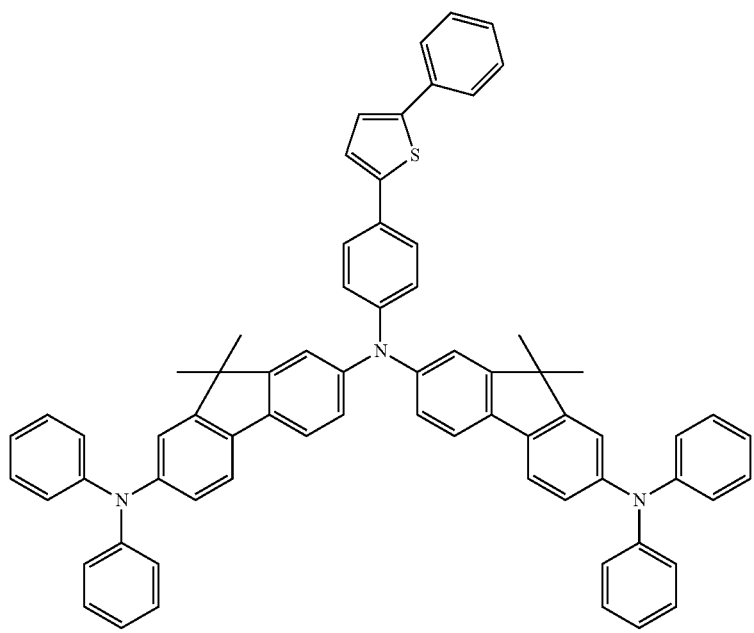
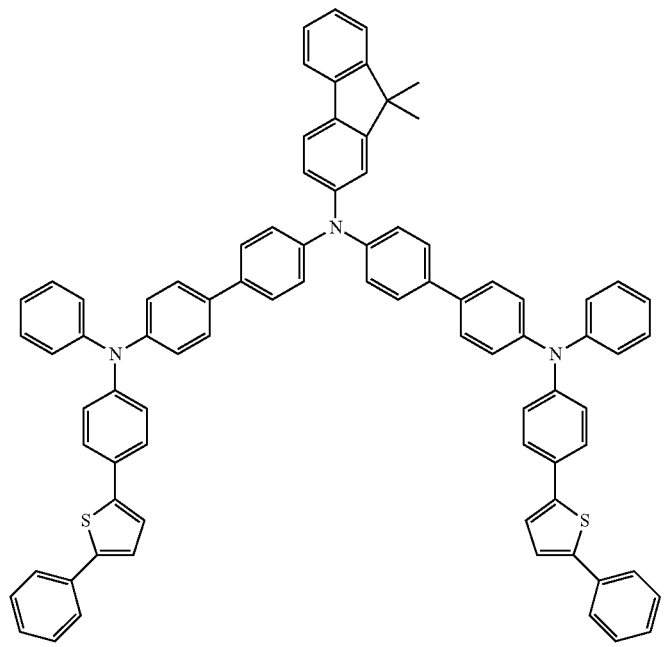

-continued
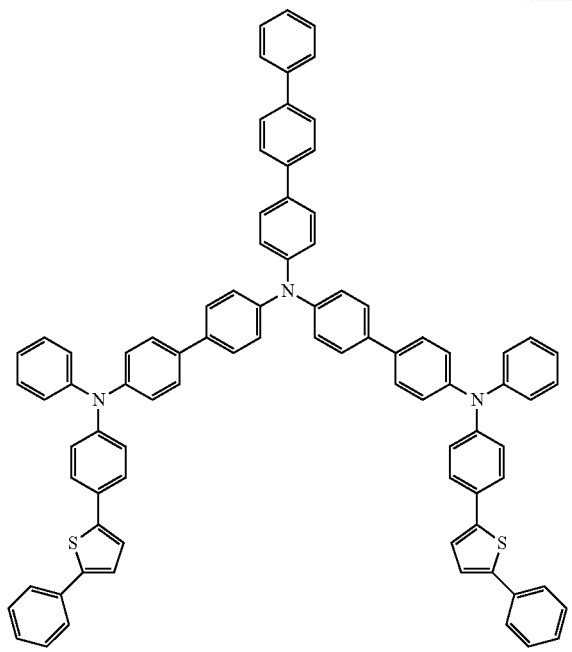
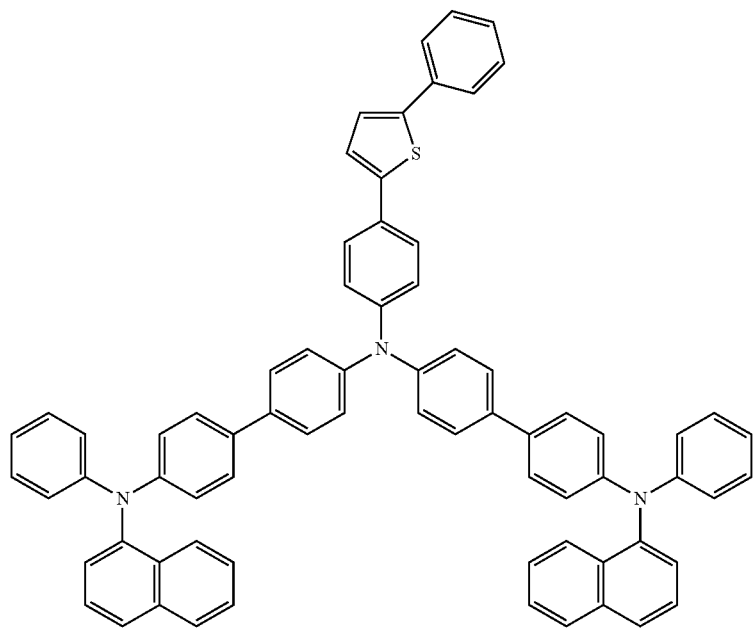

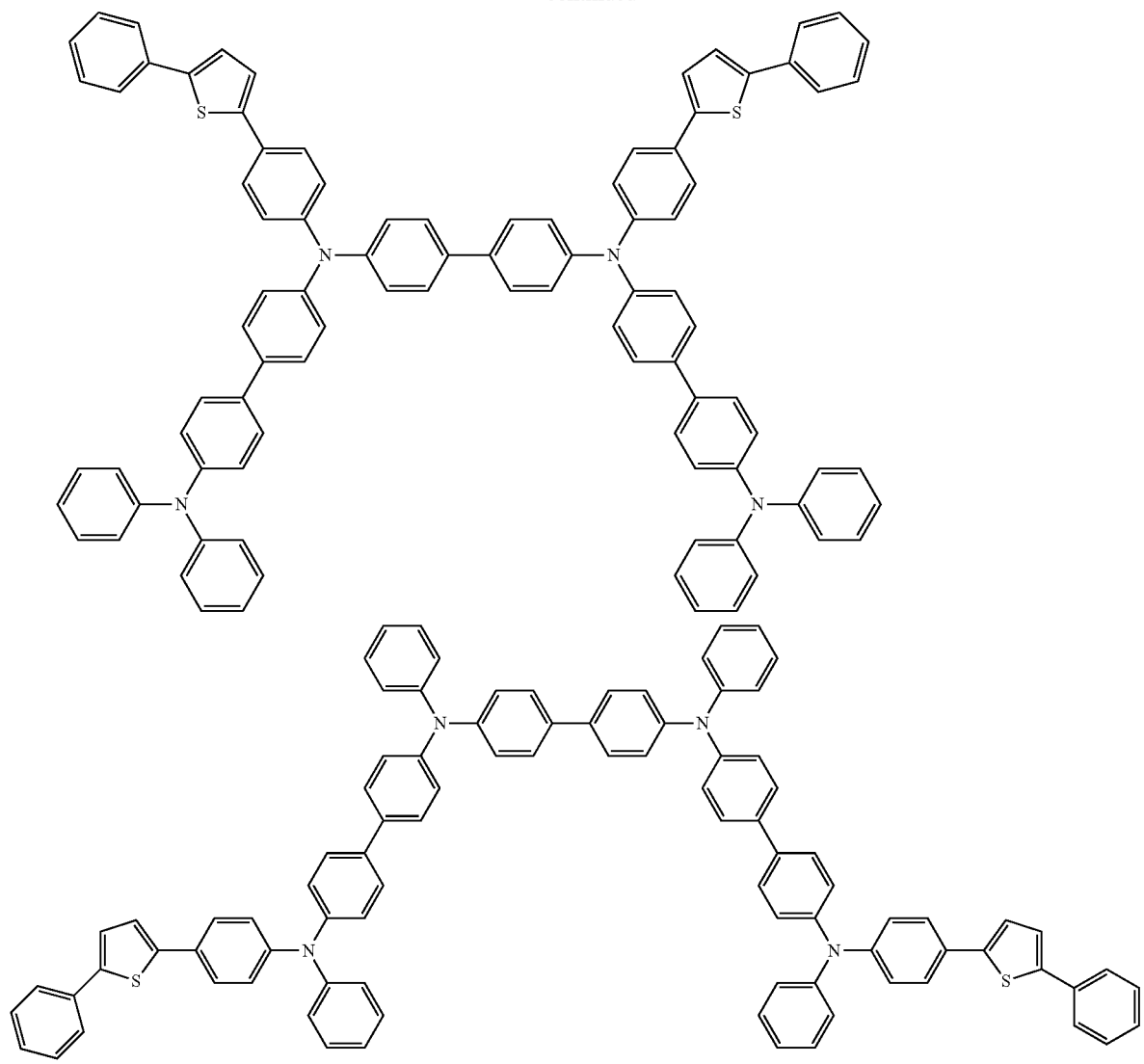
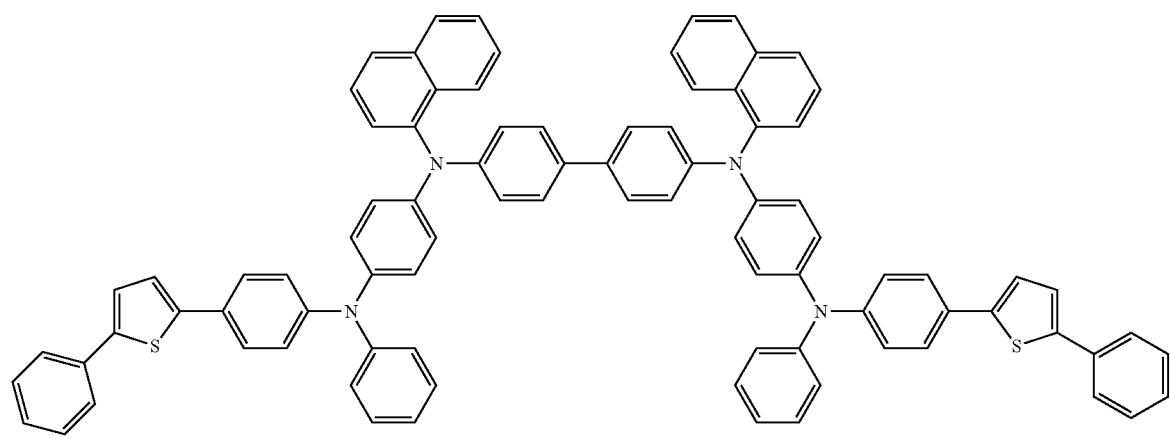

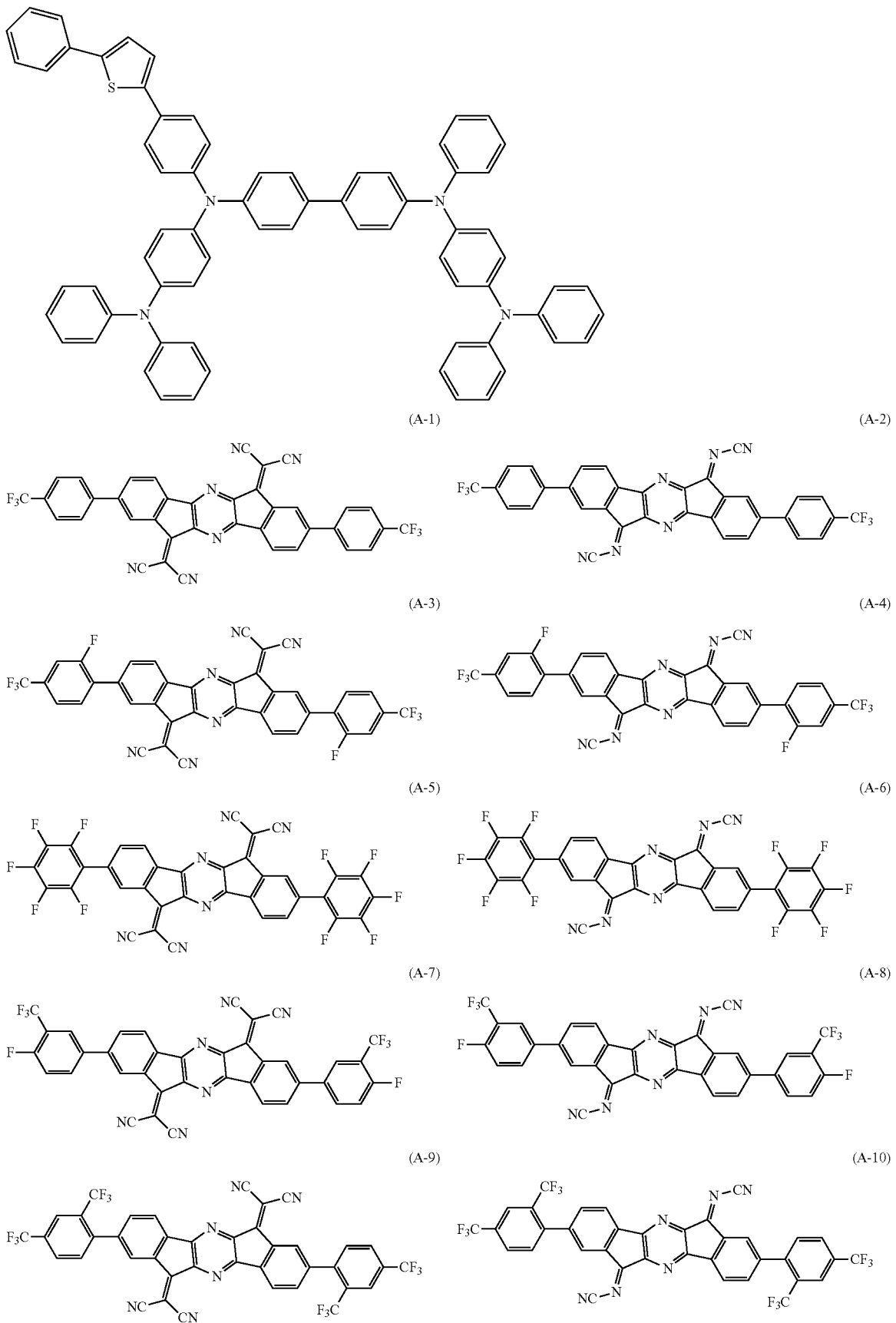

-continued
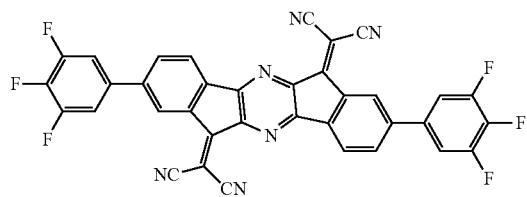
(A-11)
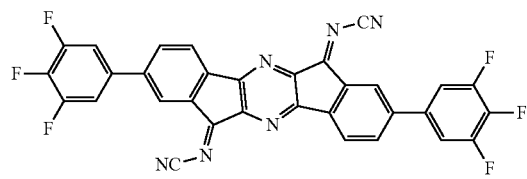
(A-12)
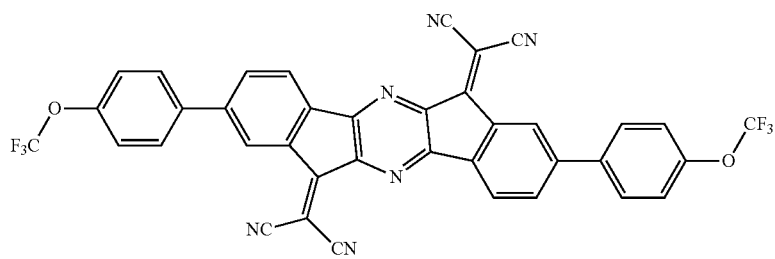
(A-13)
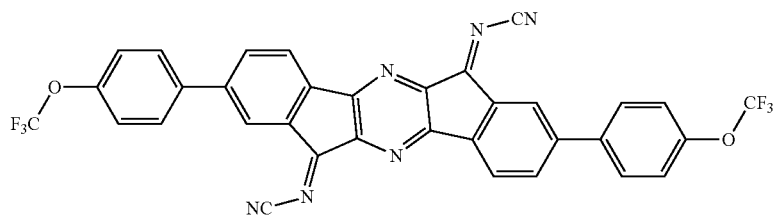
(A-14)
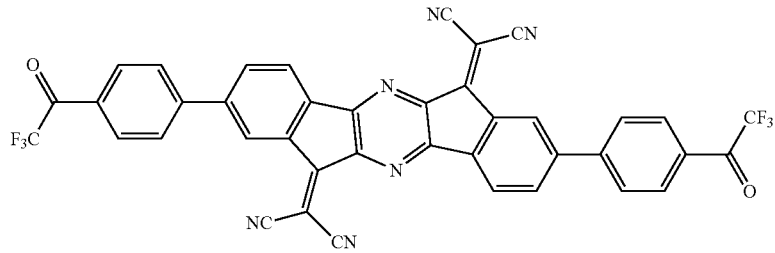
(A-15)
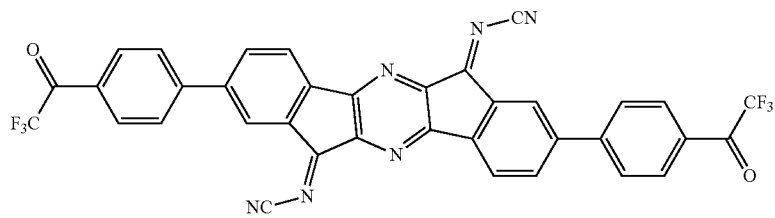
(A-16)
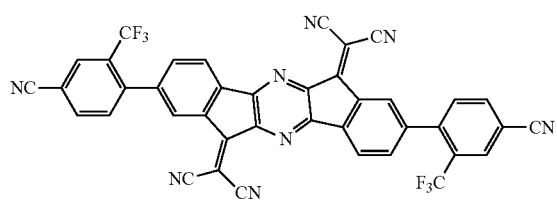
(A-17)
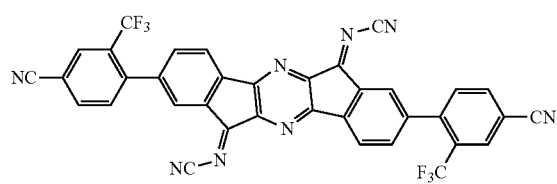
(A-18)

-continued
(A-19) 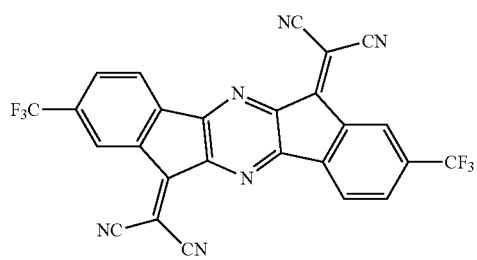
(A-20) 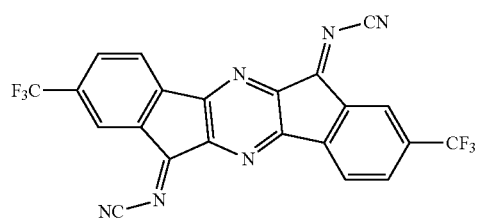
(A-21) 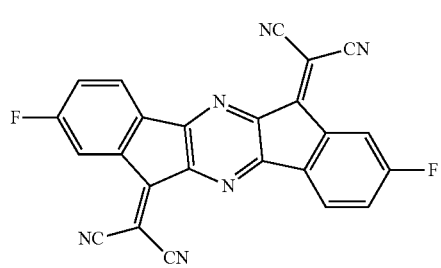
(A-22) 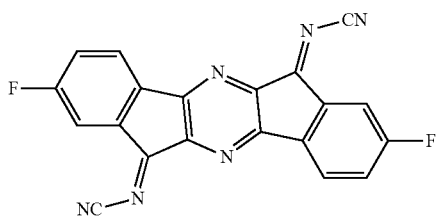
(A-23) 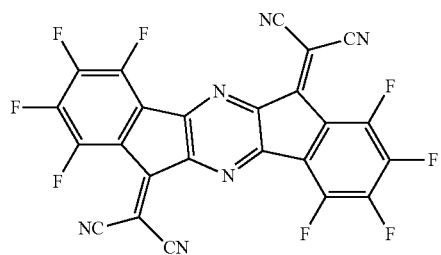
(A-24) 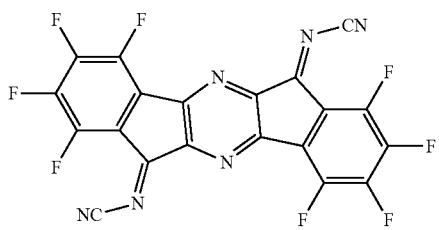
(A-25) 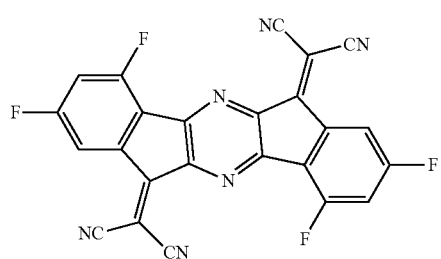
(A-26) 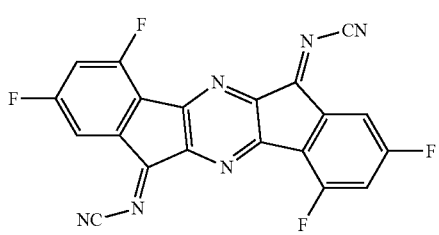
(A-27) 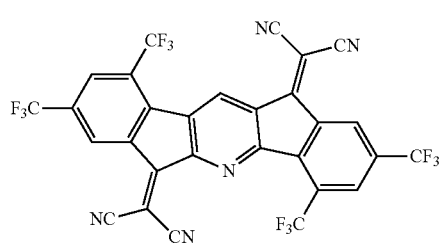
(A-28) 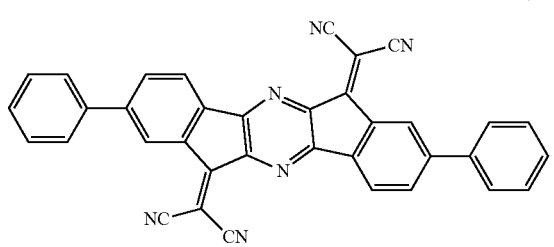

-continued
(A-29)
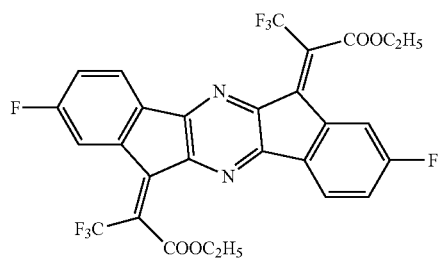
(A-30)
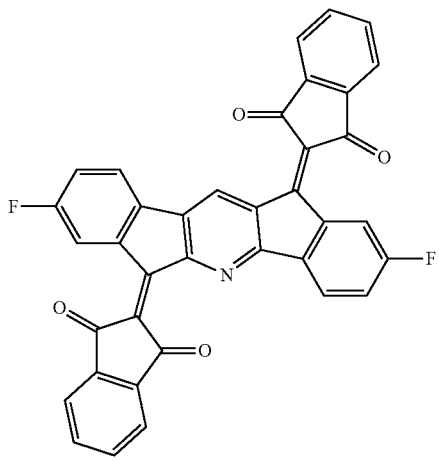
(A-31)
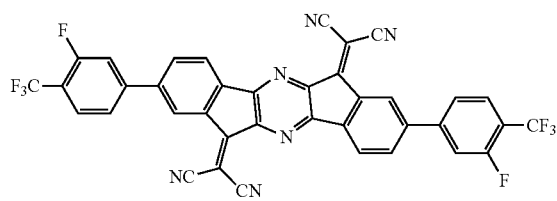
(A-32)
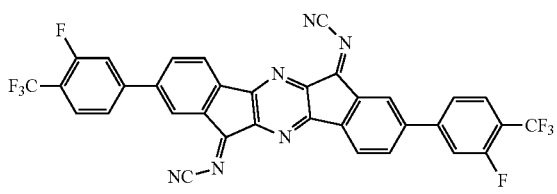
(A-33)
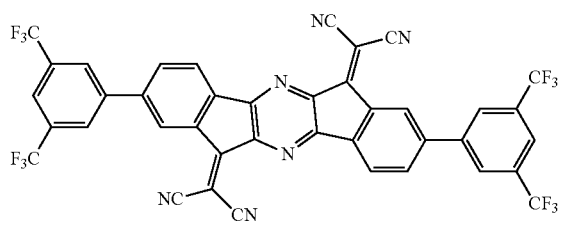
(A-34)
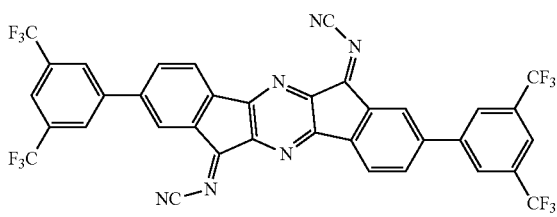
(A-35)
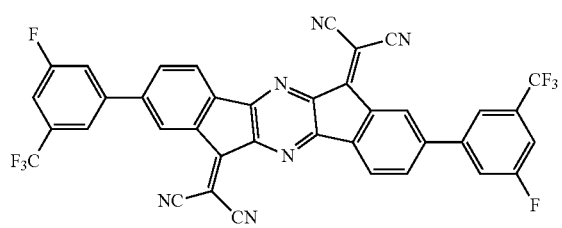
(A-36)
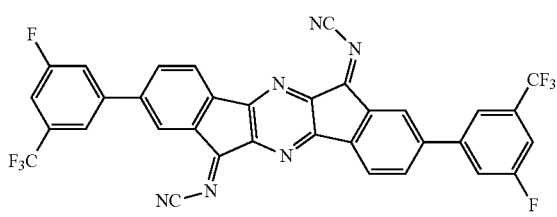
(A-37)
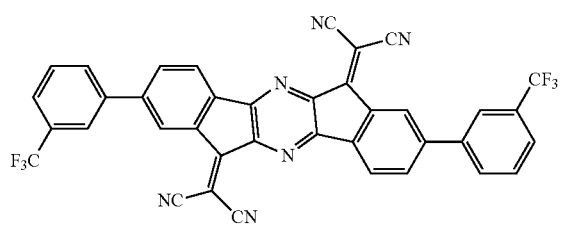
(A-38)
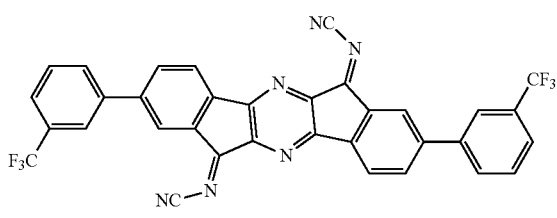
(A-39)
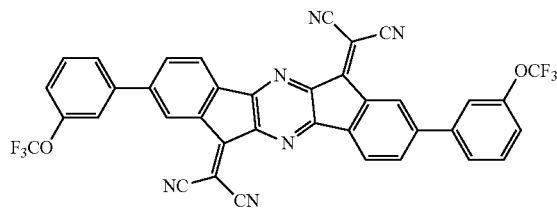
(A-40)
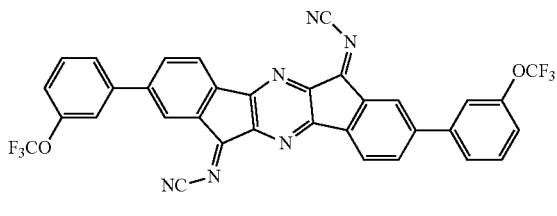

-continued
(A-41)
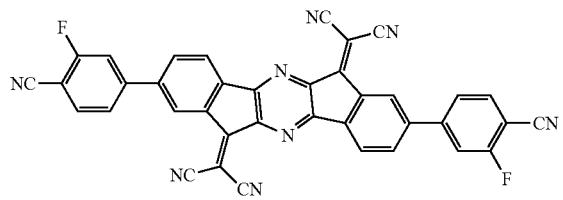
(A-42)
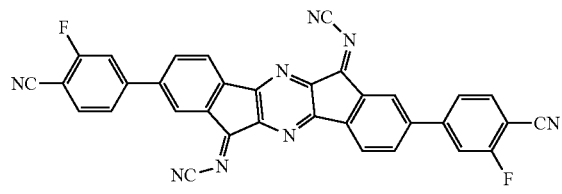
(A-43)
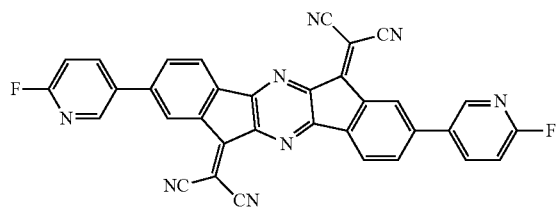
(A-44)
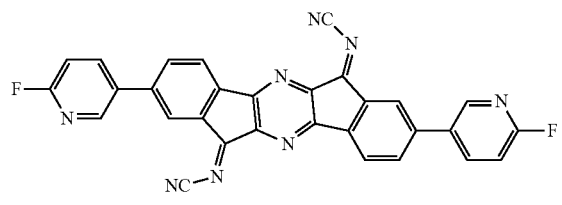
(A-45)
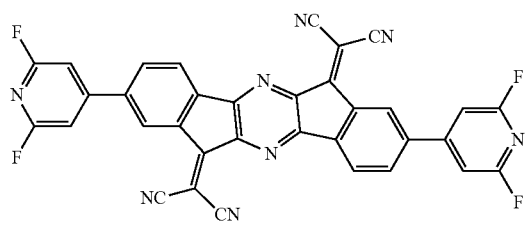
(A-46)
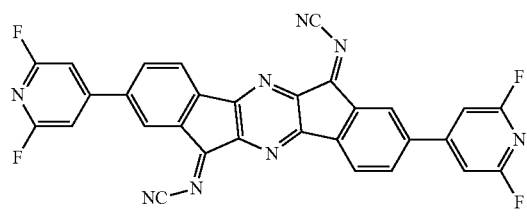
(A-47)
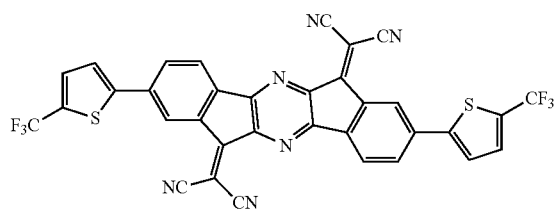
(A-48)
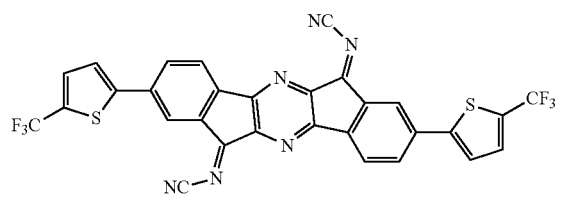
(A-49)
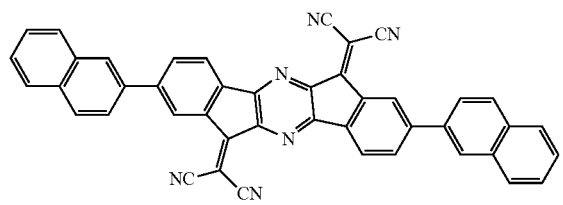
(A-51)
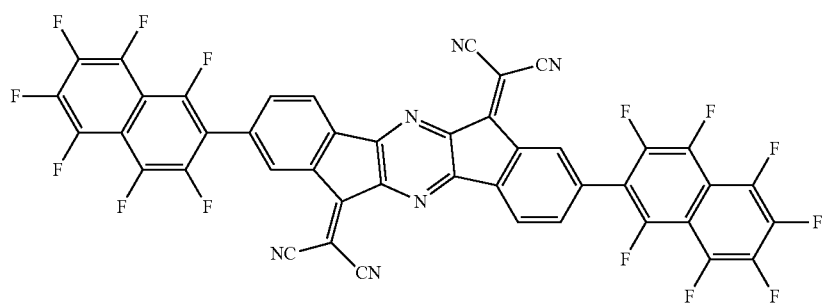

-continued
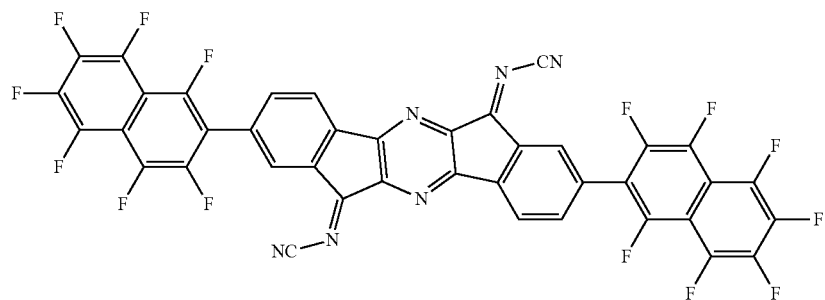
(A-52)
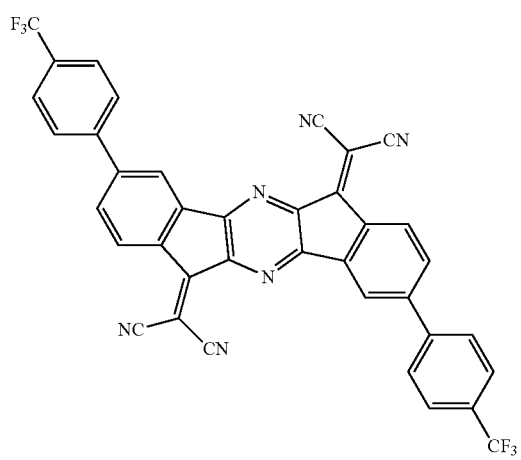
(A-53)
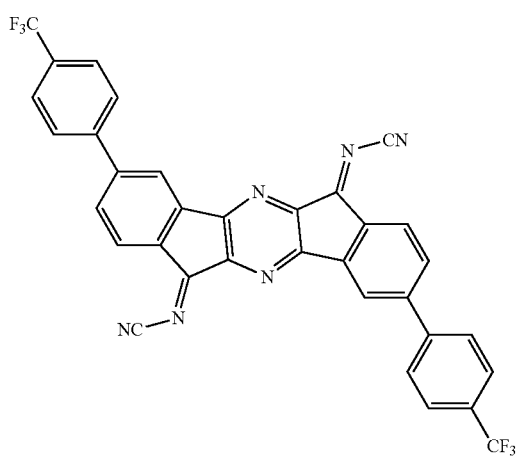
(A-54)
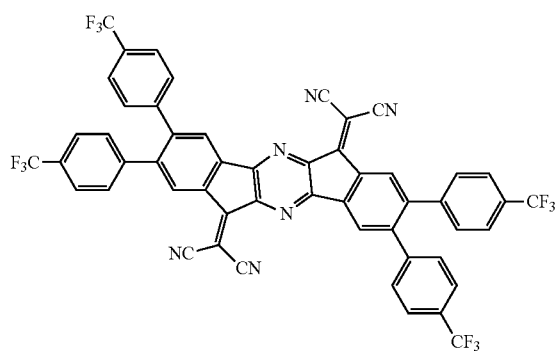
(A-55)
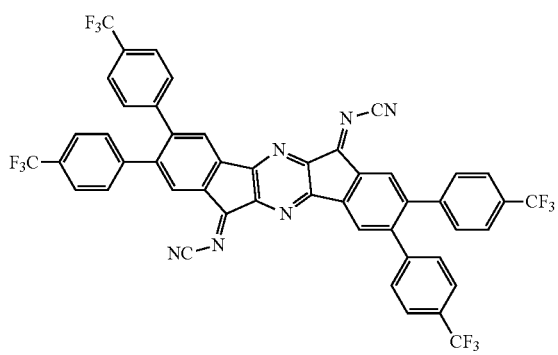
(A-56)
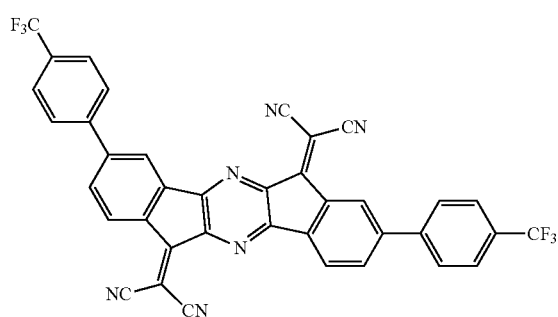
(A-57)
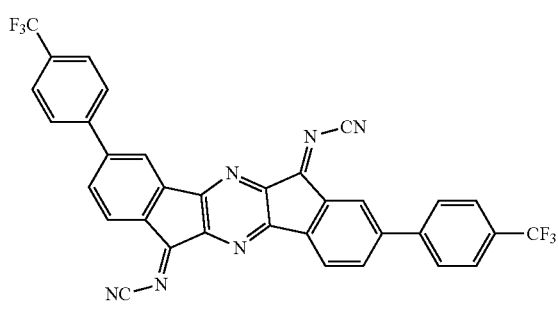
(A-58)

-continued
(A-59)
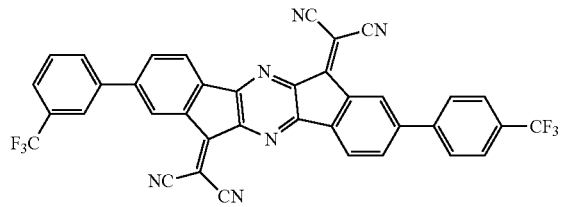
(A-60)
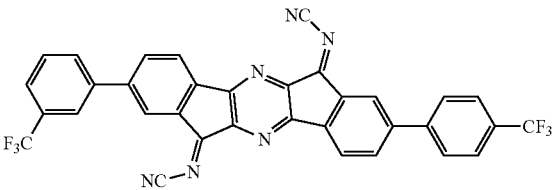
(A-61)
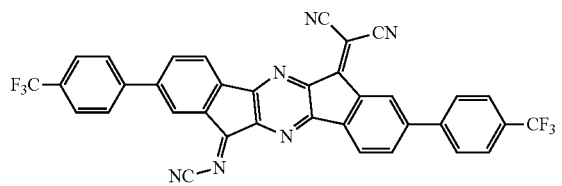
(B-1)
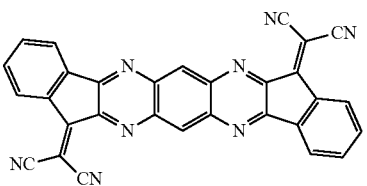
(B-2)
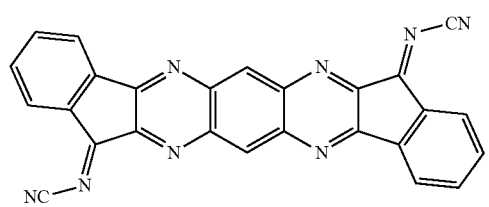
(B-3)
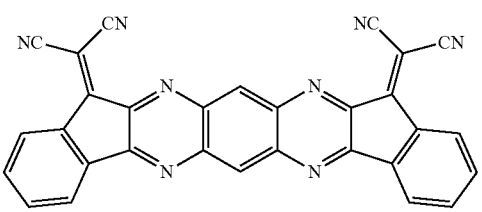
(B-4)
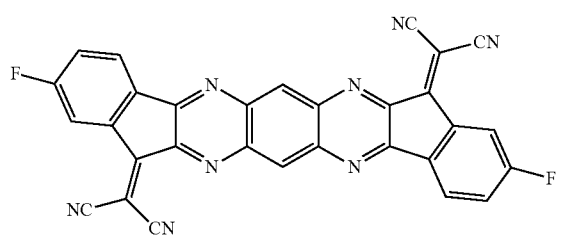
(B-5)
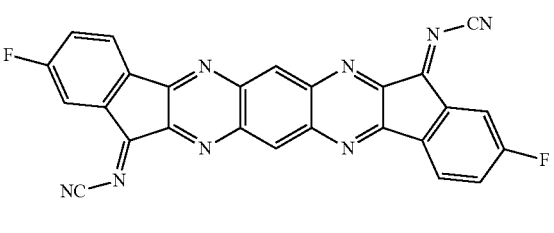
(B-6)
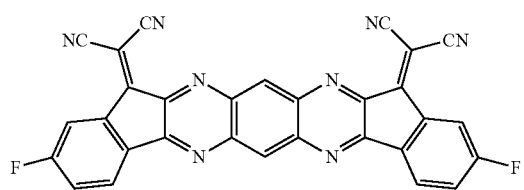
(B-7)
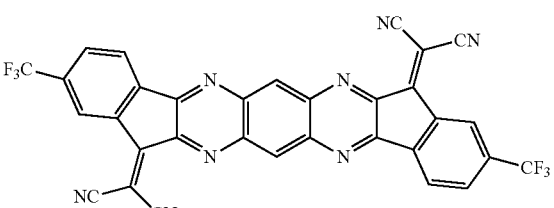
(B-8)
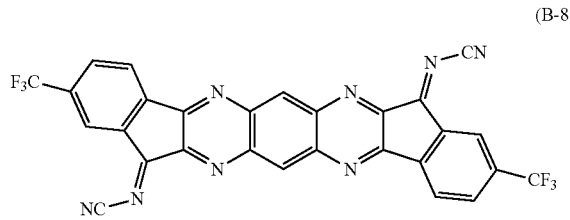
(B-9)
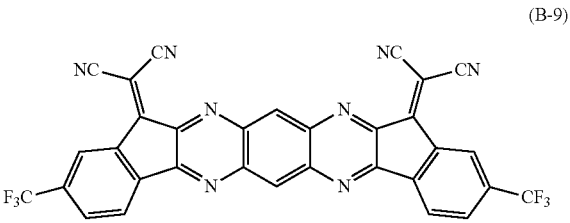
(B-10)
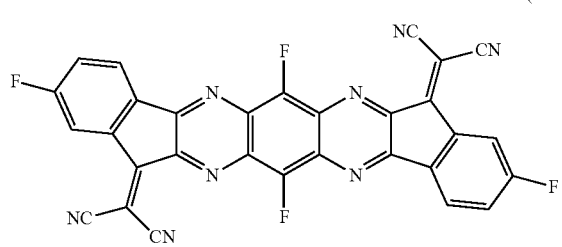
(B-11)
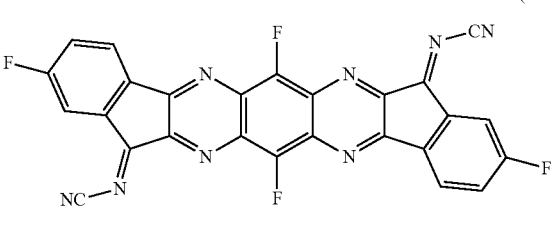

-continued
(B-12)
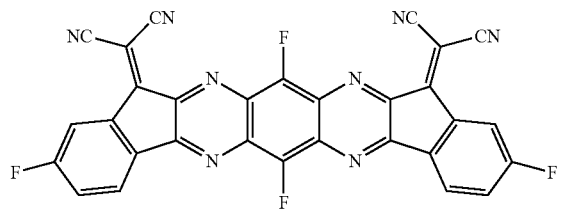
(B-13)
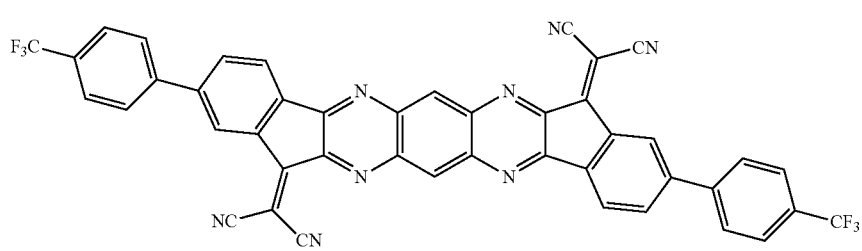
(B-14)
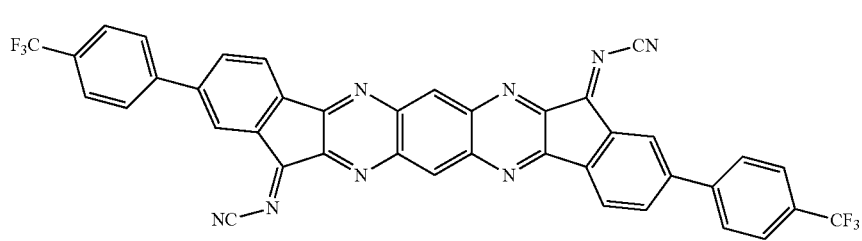
(B-15)
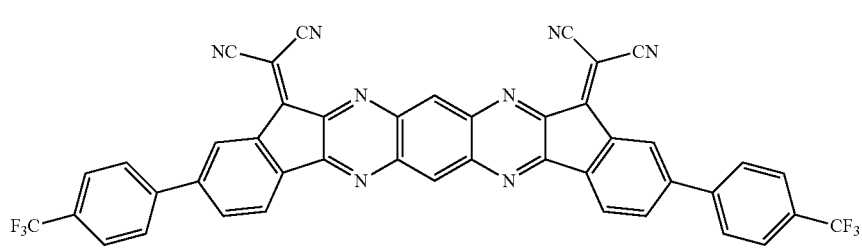
(B-16)
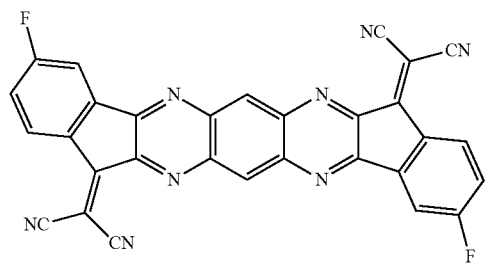
(B-17)
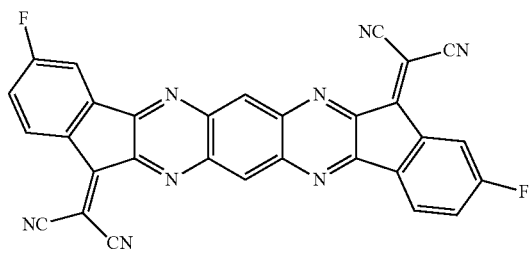
(B-18)
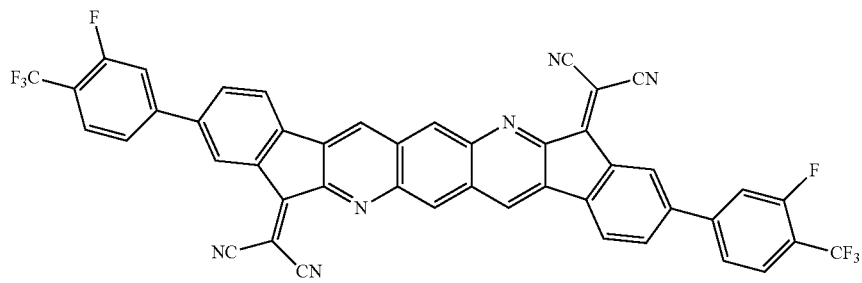

-continued
(B-19)
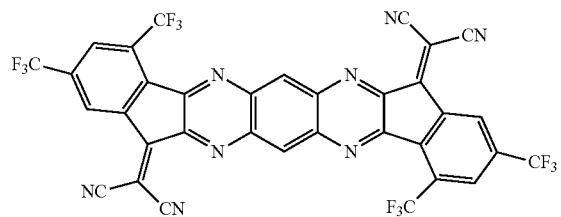
(B-20)
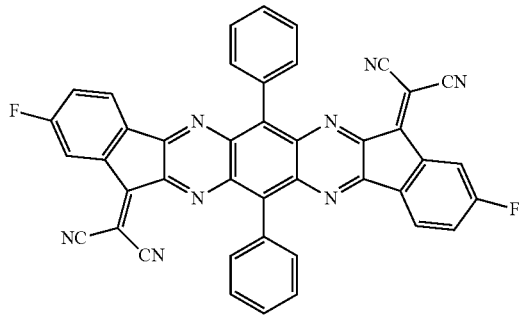
(A'-1)
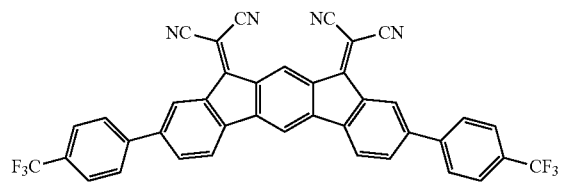
(A'-2)
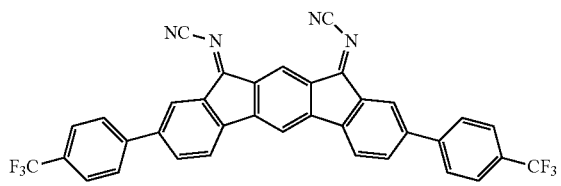
(A'-3)
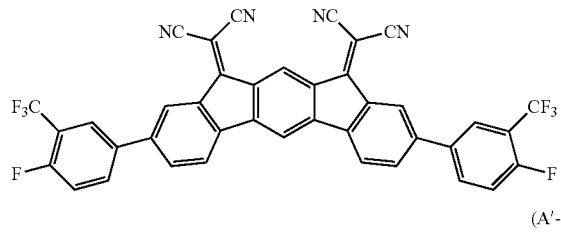
(A'-4)
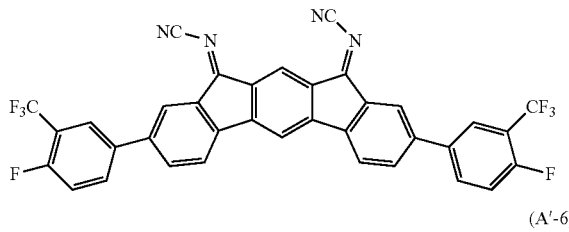
(A'-5)
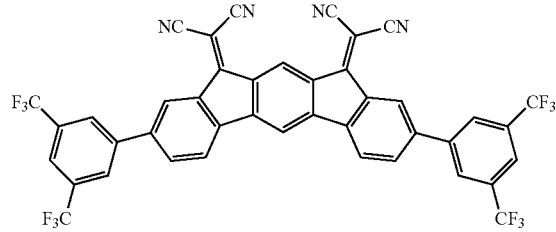
(A'-6)
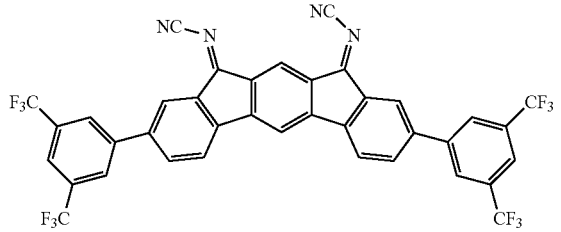
(A'-7)
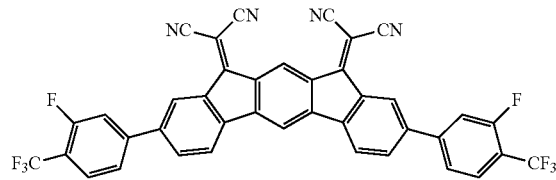
(A'-8)
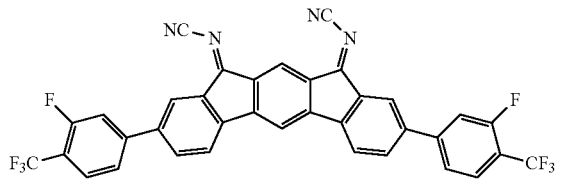
(A'-9)
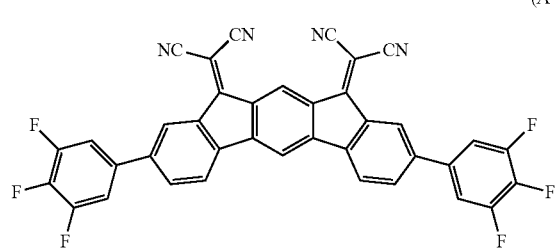
(A'-10)
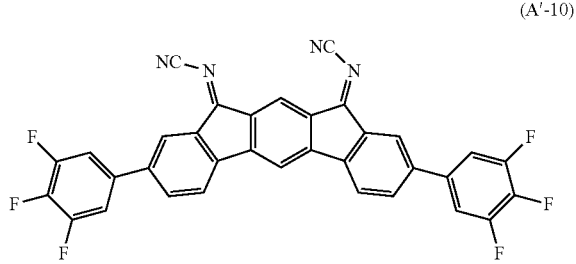

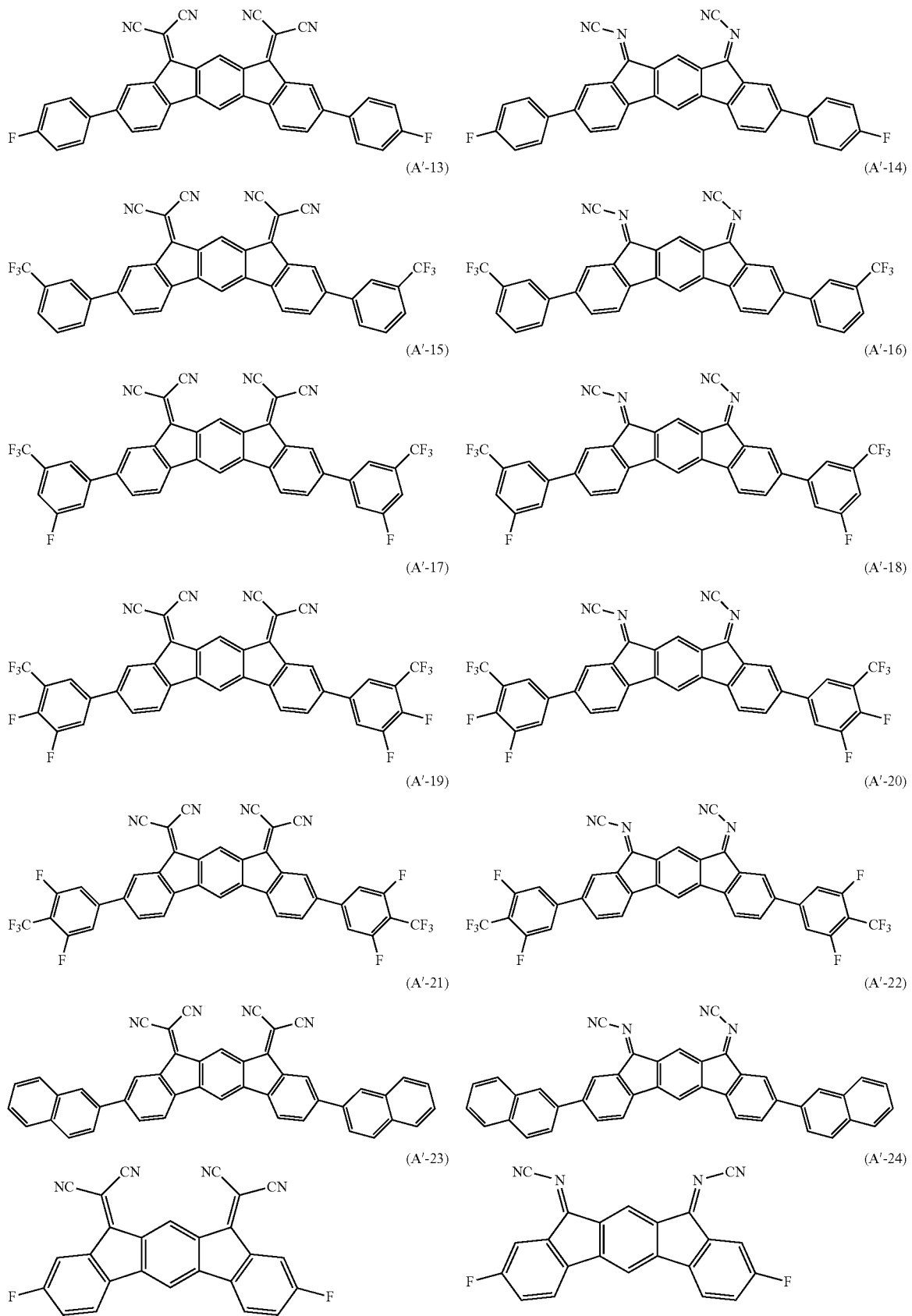

-continued
(A'-25) 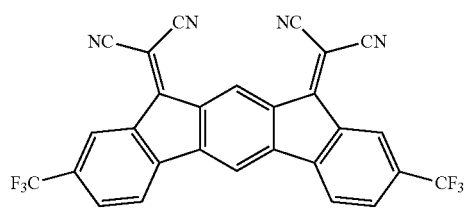
(A'-26) 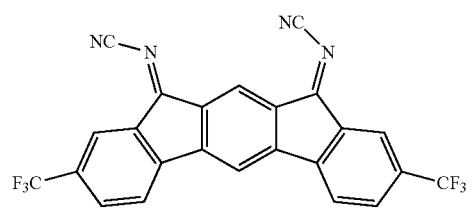
(A'-27) 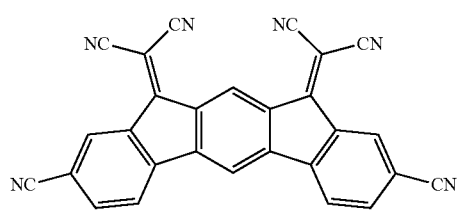
(A'-28) 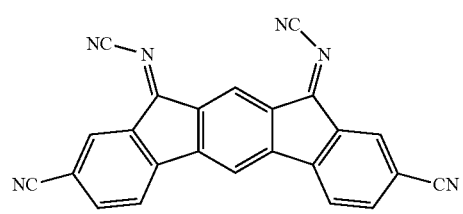
(A'-29) 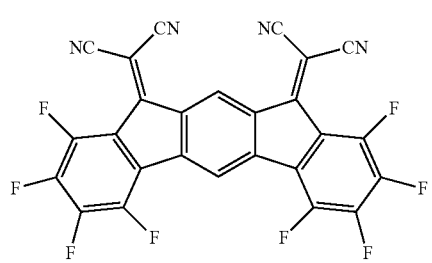
(A'-30) 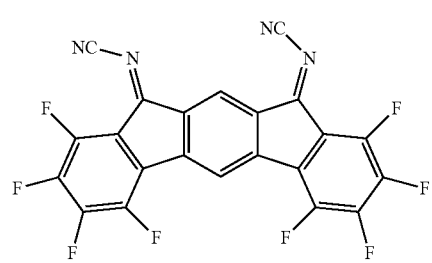
(A'-31) 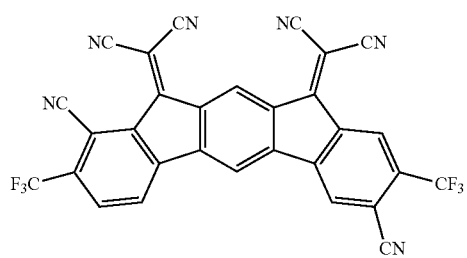
(A'-32) 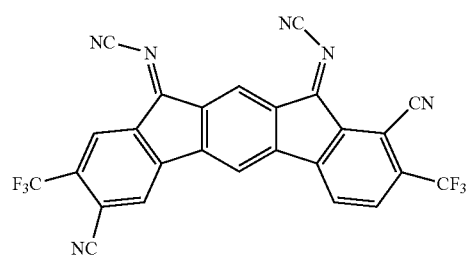
(A'-43) 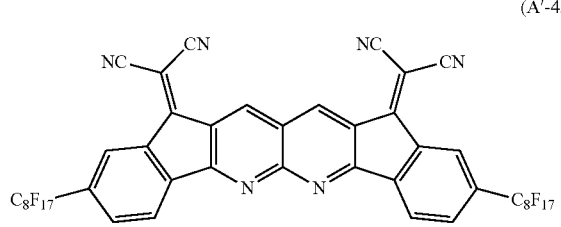
(A'-44) 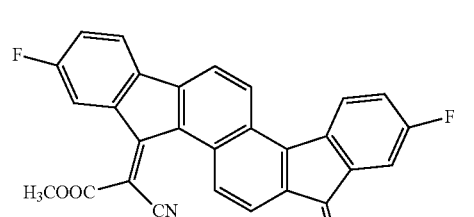
(A'-45) 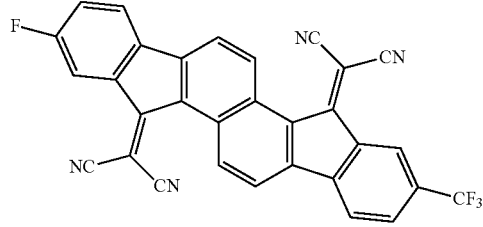
(A'-46) 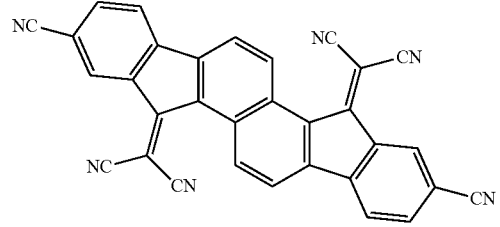

-continued
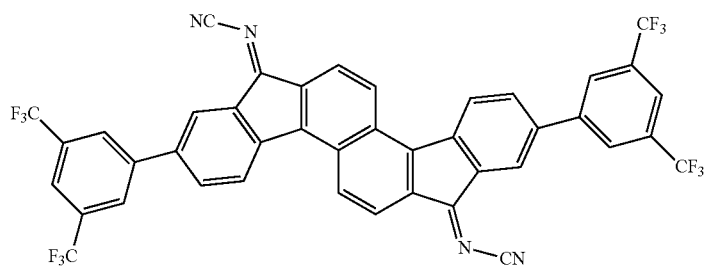
(A'-47)
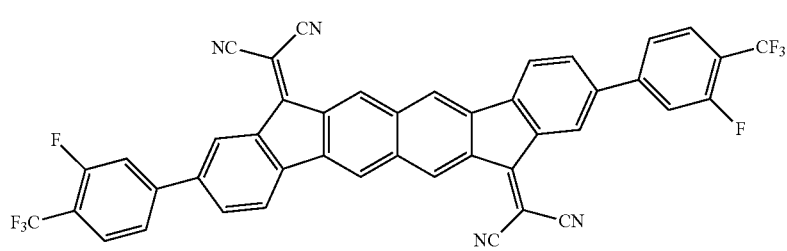
(A'-48)
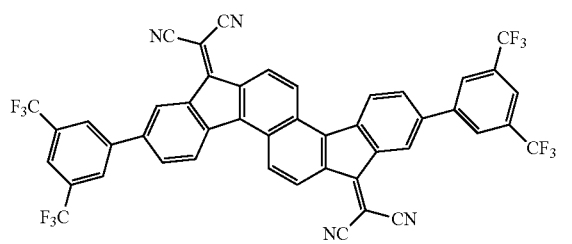
(A'-49)
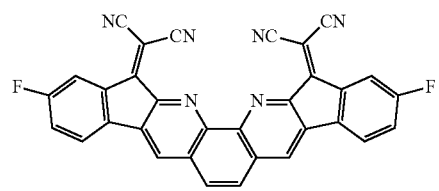
(A'-50)
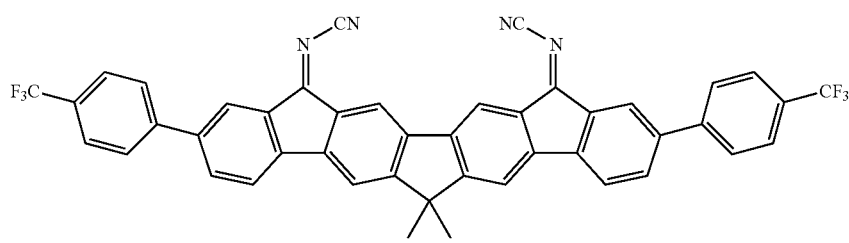
(A'-51)
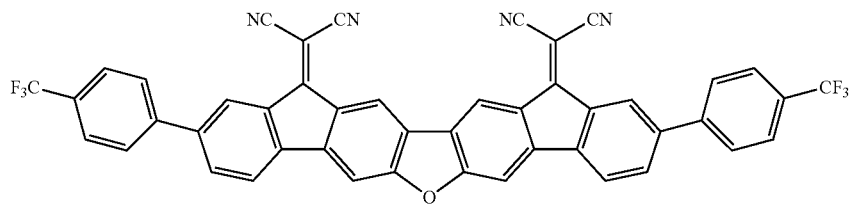
(A'-52)
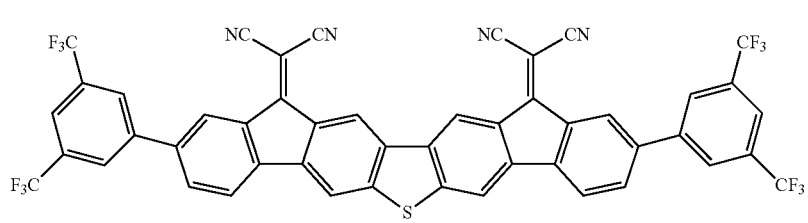
(A'-53)

-continued
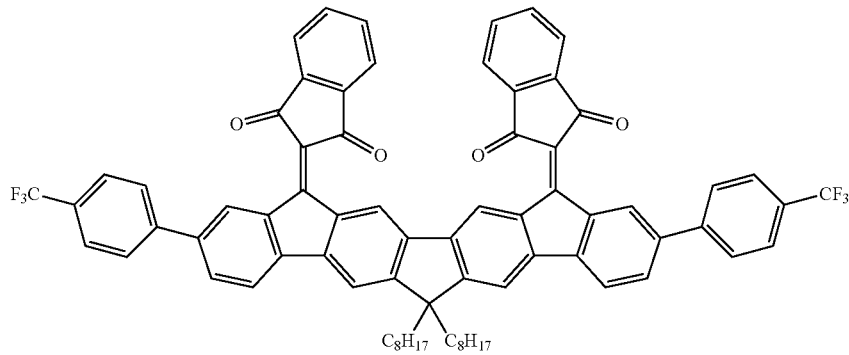
(A'-54)
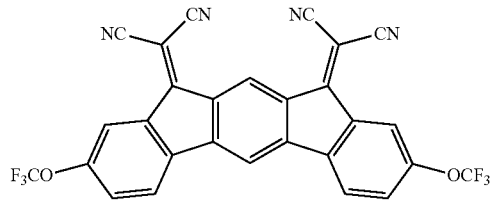
(A'-55)
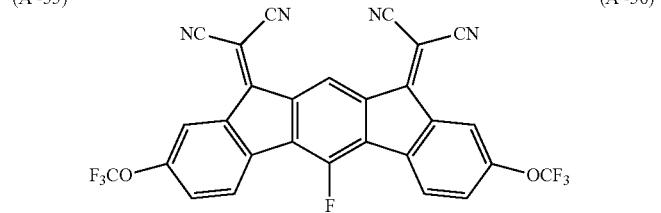
(A'-56)
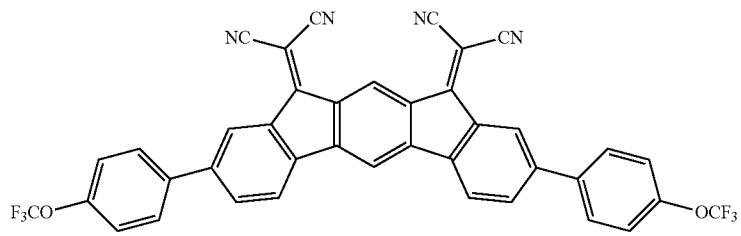
(A'-57)
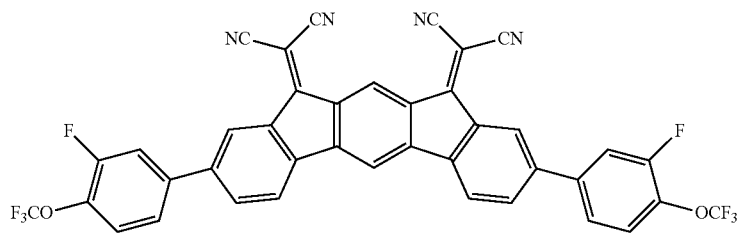
(A'-58)
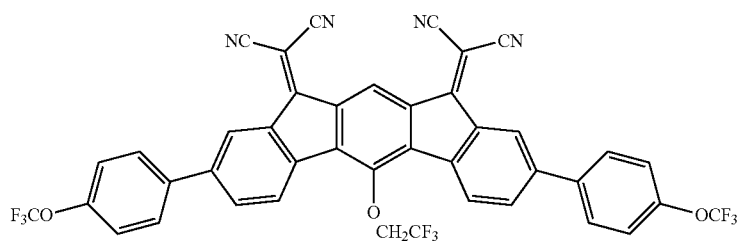
(A'-59)
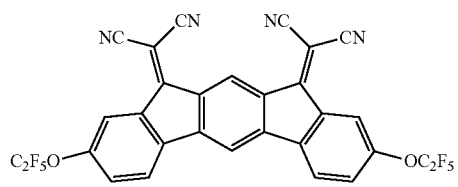
(A'-60)
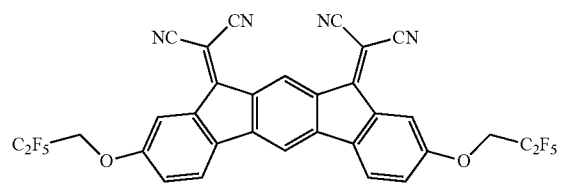
(A'-61)

-continued

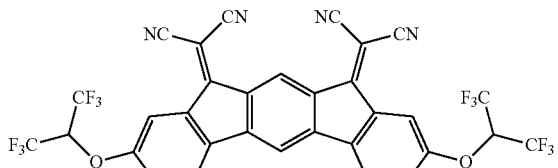
(A'-62)

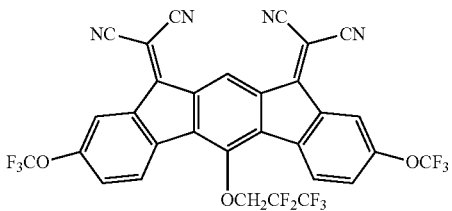
(A'-63)

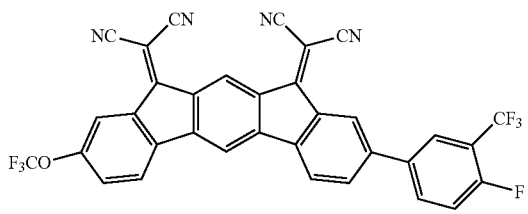
(A'-64)

(A'-65)

(A'-66)

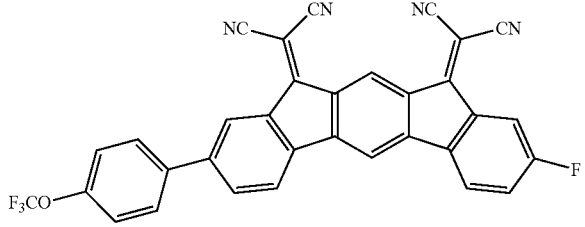

(Space Layer)

For example, in the case where a fluorescent light emitting layer and a phosphorescent light emitting layer are laminated, a space layer is disposed between the fluorescent light emitting layer and the phosphorescent light emitting layer to prevent the diffusion of excitons generated in the phosphorescent light emitting layer to the fluorescent light emitting layer or to control the carrier balance. The space layer may be disposed between two or more phosphorescent light emitting layers.

Since the space layer is disposed between the light emitting layers, a material having both the electron transporting ability and the hole transporting ability is preferably used for forming the space layer. To prevent the diffusion of triplet energy in the adjacent phosphorescent light emitting layer, the triplet energy of the material for the space layer is preferably 2.6 eV or more. The materials described above with respect to the hole transporting layer are usable as the material for the space layer. As the material for the space layer, the compound of the present invention may also be used.

(Blocking Layer)

The organic EL device of one embodiment of the present invention preferably has a blocking layer, such as an electron blocking layer, a hole blocking layer, and a triplet blocking layer, which is disposed adjacent to the light emitting layer. The electron blocking layer is a layer which prevents the diffusion of electrons from the light emitting layer to the hole transporting layer. The hole blocking layer is a layer which prevents the diffusion of holes from the light emitting layer to the electron transporting layer. As the material for the hole blocking layer, the compound of the present invention may be used.

The triplet blocking layer prevents the diffusion of triplet excitons generated in the light emitting layer to adjacent layers and has a function of confining the triplet excitons in the light emitting layer, thereby preventing the deactivation of energy on molecules in the electron transporting layer other than the emitting dopant.

If a phosphorescent device having a triplet blocking layer satisfies the following energy relationship: $E^T_d < E^T_{TB}$, wherein $E^T_d$ is the triplet energy of the phosphorescent dopant in the light emitting layer and $E^T_{TB}$ is the triplet energy of the compound forming the triplet blocking layer, the triplet excitons of phosphorescent dopant are confined (not diffuse to other molecules). Therefore, the energy deactivation process other than the emission on the phosphorescent dopant may be prevented to cause the emission with high efficiency. However, even in case of satisfying the relationship of $E^T_d < E^T_{TB}$, the triplet excitons may move into other molecules if the energy difference ($\Delta E^T = E^T_{TB} - E^T_d$) is small, because the energy difference $\Delta E^T$ may be overcome by the absorption of ambient heat energy when driving a device at around room temperature as generally employed in practical drive of device. As compared with the fluorescent emission, the phosphorescent emission is relatively likely to be affected by the diffusion of excitons due to the heat absorption because the lifetime of triplet excitons is longer. Therefore, as for the energy difference $\Delta E^T$, the larger as compared with the heat energy of room temperature, the better. The energy difference $\Delta E^T$ is more preferably 0.1 eV or more and particularly preferably 0.2 eV or more. In fluorescent devices, the material for organic EL device in one embodiment of the present invention is usable as the material for triplet blocking layer of the TTF device described in WO 2010/134350.

The electron mobility of the material for the triplet blocking layer is preferably $10^{-6}$ cm$^2$/Vs or more at an electric field strength of 0.04 to 0.5 MV/cm. There are several methods for measuring the electron mobility of organic material, for example, Time of Flight method. In the present invention, the electron mobility is determined by impedance spectroscopy.

The electron mobility of the electron injecting layer is preferably $10^{-6}$ cm$^2$/Vs or more at an electric field strength of 0.04 to 0.5 MV/cm. Within the above range, the injection of electrons from the cathode to the electron transporting layer is promoted and the injection of electrons to the adjacent blocking layer and light emitting layer is also promoted, thereby enabling to drive a device at lower voltage.

The present invention is not limited to the above description, and any modification within the scope not overstepping the spirit of the present invention is contained in the present invention. For example, the following modifications are preferred modification examples of the present invention.

In the present invention, it is also preferable that the above light emitting layer contains a charge injection auxiliary agent.

In the case where a host material having a broad energy gap is used to form the light emitting layer, the difference between the ionization potential (Ip) of the host material and Ip of the hole transporting layer or the like is large so that hole injection into the light emitting layer would be difficult and the driving voltage for realizing sufficient brightness would increase.

In the case, incorporating a hole transporting charge injection auxiliary agent in the light emitting layer could facilitate hole injection into the light emitting layer and could lower the driving voltage.

As the charge injection auxiliary agent, for example, any general hole transporting material, hole injecting material or the like is usable.

Specific examples of the materials include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, fluorenone derivatives, hydrazone derivatives, stilbene derivatives, silazane derivatives, polysilane copolymers, aniline copolymers, conductive high-molecular oligomers (especially thiophene oligomers), etc.

As the material having hole injecting capability (hole injecting material), the above are mentioned, and porphyrin compounds, aromatic tertiary amine compounds and styrylamine compounds, especially aromatic tertiary amine compounds are preferred.

In addition, there are further mentioned those having two condensed aromatic ring in the molecule, for example, 4,4'-bis(N-(1-naphthyl)-N-phenylamino)biphenyl [this may be referred to as NPD], as well as 4,4',4''-tris(N-(3-methylphenyl)-N-phenylamino)triphenylamine (this may be referred to as MTDATA) in which the three triphenylamine units are connected like a starburst, etc.

Further, hexaazatriphenylene derivatives and the like are also favorably used as the hole injecting material.

In addition, inorganic compounds such as p-type Si, p-type SiC and the like are also usable as the hole injecting material.

The method for forming each layer of the organic EL device of the present invention is not specifically limited. Any known method, such as a vapor deposition method, a spin coating method or the like may be used. The organic thin film layer containing the above-mentioned compound of the present invention for use in the organic EL device of the present invention may be formed according to a known method such as a vapor deposition method, a molecular beam evaporation method (MEB method), or a coating method of a dipping method, a spin coating method, a casting method, a bar coating method, a roll coating method or the like using a solution of the compound dissolved in a solvent.

The thickness of each organic layer of the organic EL device of the present invention is not specifically limited, but in general, when the thickness is too small, there may readily form defects such as pin holes and the like, but when too large, a high application voltage is needed and the efficiency worsens. In general, therefore, the thickness is preferably within a range of a few nm to 1 μm.

The method for forming each layer of the organic EL device of one embodiment of the present invention is not specifically limited. Any known forming method of a vapor deposition method, a spin coating method or the like may be used. The organic thin film layer containing the compound of the other embodiment of the present invention for use in the organic EL device of one embodiment of the present invention may be formed according to a known method such as a vapor deposition method, a molecular beam evaporation method (MBE method), or a coating method of a dipping method, a spin coating method, a casting method, a bar coating method, a roll coating method or the like using a solution of the compound dissolved in a solvent.

[Electronic Equipment]

The organic EL device produced using the compound of the present invention can be used in electronic equipments, for example, as display parts, such as organic EL panel module etc., display devices of television sets, mobile phones, personal computer, etc., and light emitting sources of lighting equipment and vehicle lighting equipment, etc.

EXAMPLES

The present invention will be described below in more detail with reference to Examples and Comparative examples. However, it should be noted that the present invention is not limited at all by the contents described in these Example.

Synthesis Example 1

Synthesis of Compound 1

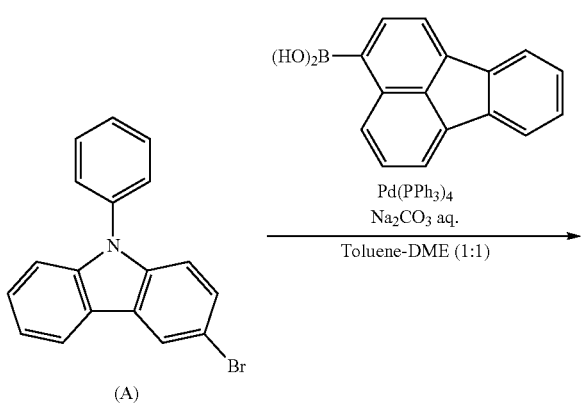

-continued

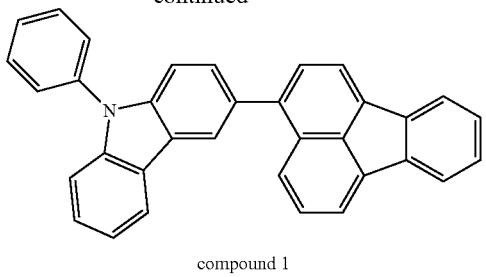

compound 1

In an argon atmosphere, 4.53 g of the above-mentioned starting compound (A), 4.00 g of 3-fluorantheneboronic acid synthesized according to a known method, 250 mg of tetrakis(triphenylphosphine)palladium, 25 mL of aqueous 2-mol sodium carbonate solution, 35 mL of toluene, and 35 mL of dimethyl ether (DME) were put in a 300-mL flask, and heated with stirring under reflux for 4 hours.

After cooled to room temperature, the reaction solution was extracted with dichloroethane, and filtered through Celite. The filtrate was concentrated, and the residue was purified through silica gel column chromatography to give the compound 1 (3.85 g, yield 62%). As a result of mass spectrometry, m/e=443 with respect to the molecular weight 443 of the compound 1.

Synthesis Example 2

Synthesis of Compound 2

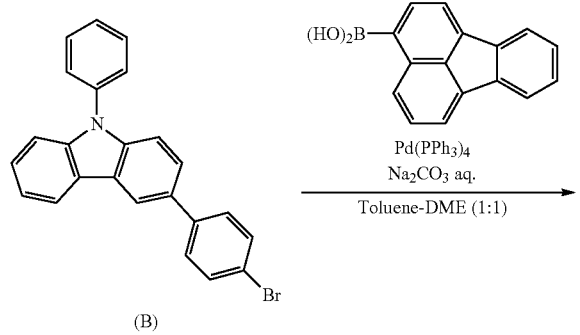

compound 2

In an experiment according to the same method as in Synthesis Example 1, except that the above-mentioned starting compound (B) synthesized according to a known method was used in place of the starting compound (A), the compound 2 was obtained. As a result of mass spectrometry, m/e=519 with respect to the molecular weight 519 of the compound 2.

Synthesis Example 3

Synthesis of Compound 3

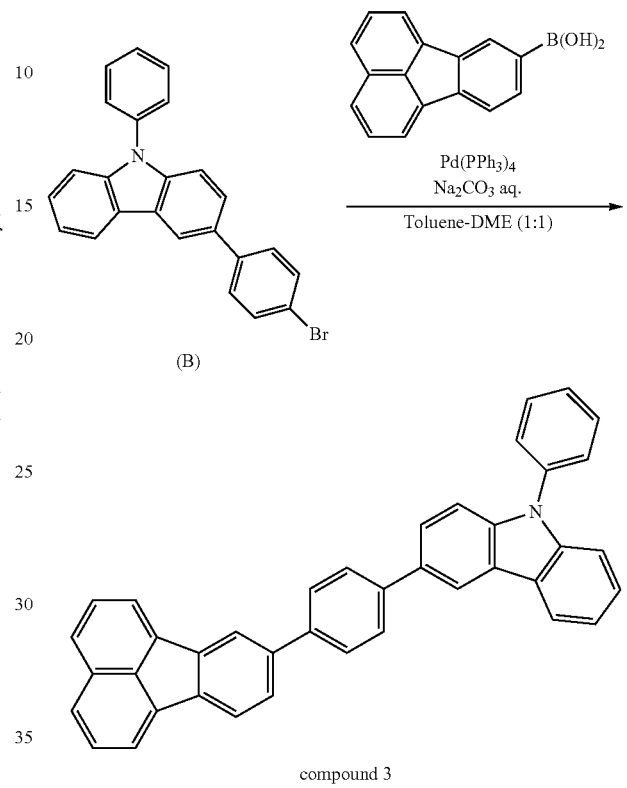

compound 3

In an experiment according to the same method as in Synthesis Example 2, except that 8-fluorantheneboronic acid was used in place of 3-fluorantheneboronic acid, the compound 3 was obtained. As a result of mass spectrometry, m/e=519 with respect to the molecular weight 519 of the compound 3.

Synthesis Example 4

Synthesis of Compound 4

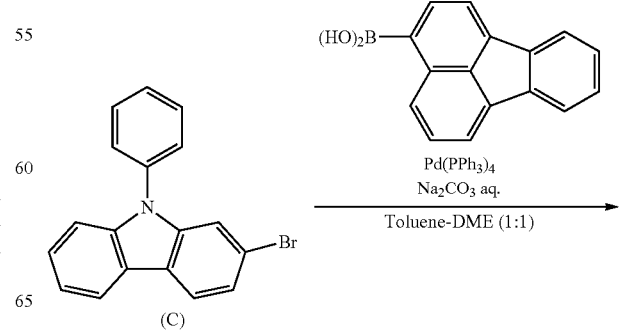

Synthesis Example 6

Synthesis of Compound 6

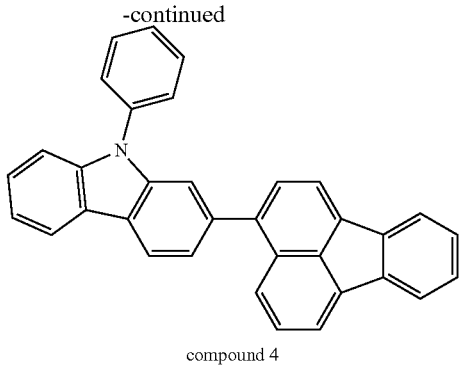

compound 4

In an experiment according to the same method as in Synthesis Example 1, except that the above-mentioned starting compound (C) synthesized according to a known method was used in place of the starting compound (A), the compound 4 was obtained. As a result of mass spectrometry, m/e=443 with respect to the molecular weight 443 of the compound 4.

Synthesis Example 5

Synthesis of Compound 5

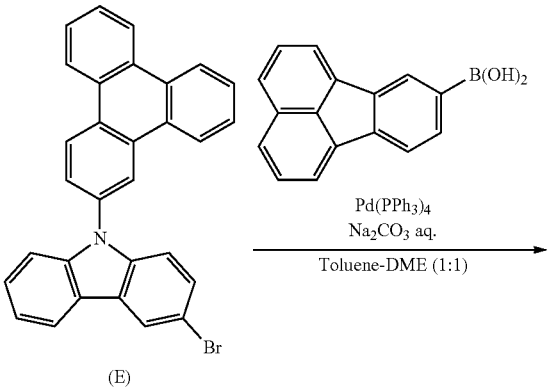

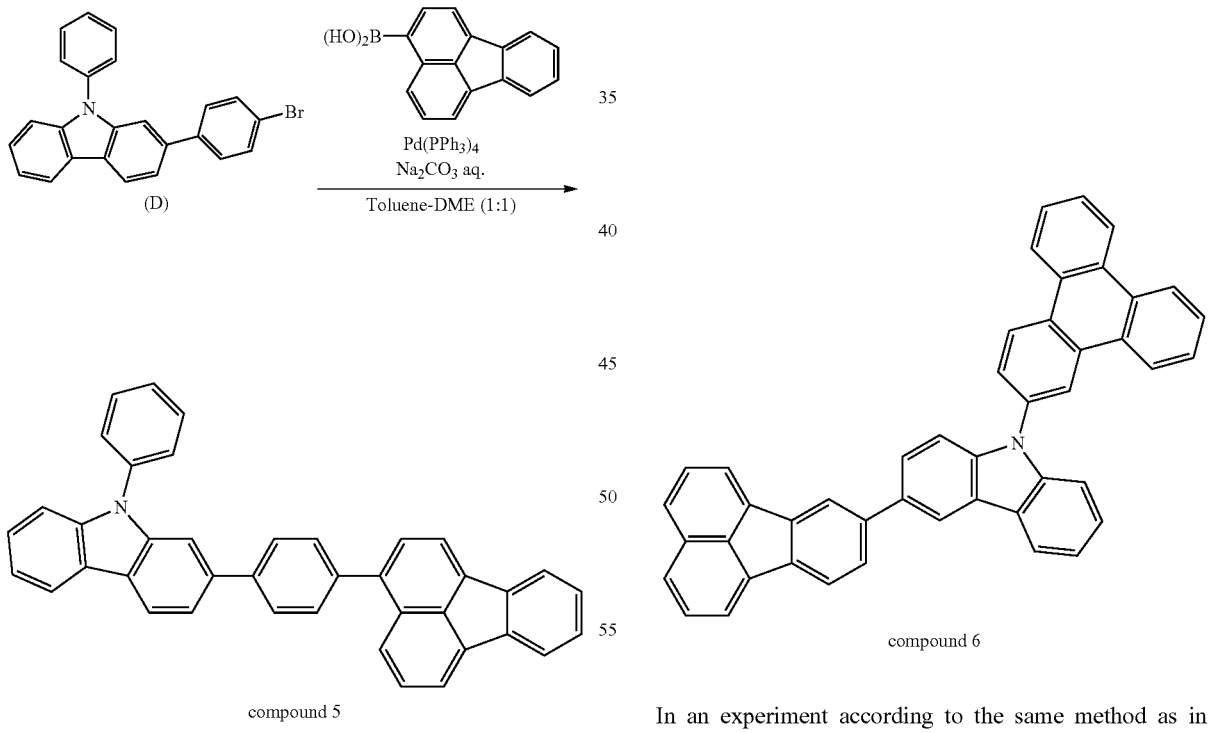

compound 5

In an experiment according to the same method as in Synthesis Example 4, except that the above-mentioned starting compound (D) synthesized according to a known method was used in place of the starting compound (C), the compound 5 was obtained. As a result of mass spectrometry, m/e=519 with respect to the molecular weight 519 of the compound 5.

compound 6

In an experiment according to the same method as in Synthesis Example 3, except that the above-mentioned starting compound (E) synthesized according to a known method was used in place of the starting compound (B), the compound 6 was obtained. As a result of mass spectrometry, m/e=593 with respect to the molecular weight 593 of the compound 6.

Synthesis Example 7

Synthesis of Compound 7

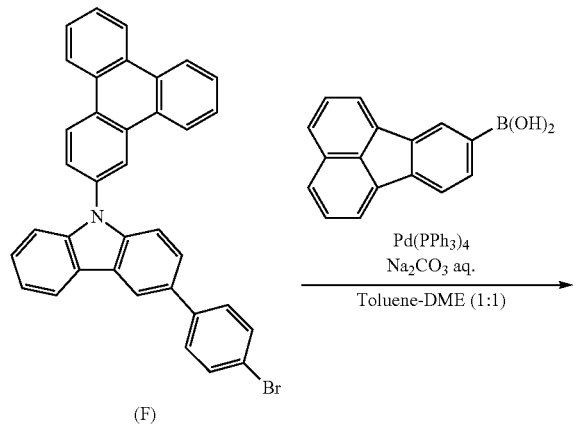

(F)

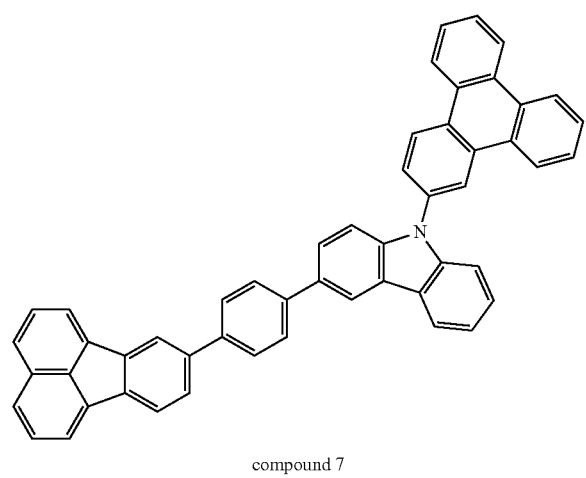

compound 7

In an experiment according to the same method as in Synthesis Example 6, except that the above-mentioned starting compound (F) synthesized according to a known method was used in place of the starting compound (E), the compound 7 was obtained. As a result of mass spectrometry, m/e=669 with respect to the molecular weight 669 of the compound 7.

Synthesis Example 8

Synthesis of Compound 8

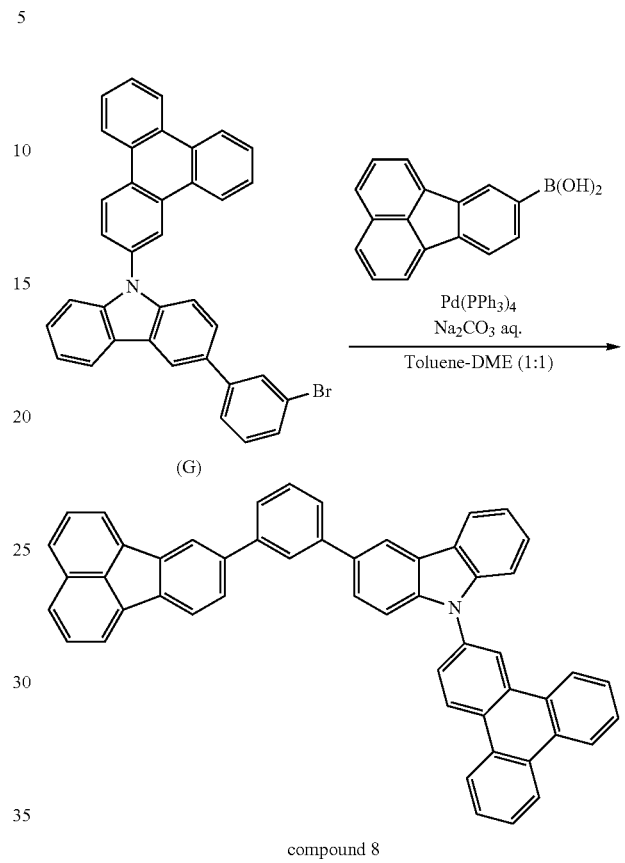

(G)

compound 8

In an experiment according to the same method as in Synthesis Example 7, except that the above-mentioned starting compound (G) synthesized according to a known method was used in place of the starting compound (F), the compound 8 was obtained. As a result of mass spectrometry, m/e=669 with respect to the molecular weight 669 of the compound 8.

Synthesis Example 9

Synthesis of Compound 9

(H)

-continued

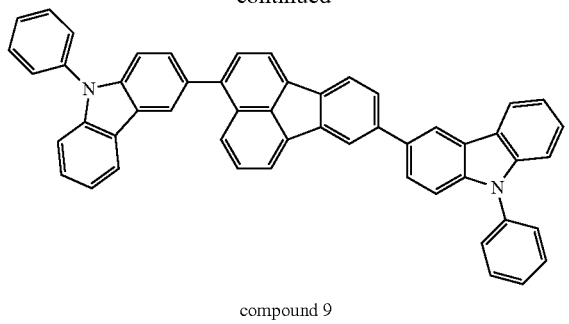

compound 9

In an experiment according to the same method as in Synthesis Example 1, except that 2 equivalents of the above-mentioned starting compound (H) synthesized from the compound (A) according to a known method was used in place of the starting compound (A), and 3,8-dibromo-fluoranthene produced according to a known method was used in place of 3-fluorantheneboronic acid, the compound 9 was obtained. As a result of mass spectrometry, m/e=684 with respect to the molecular weight 684 of the compound 9.

Synthesis Example 10

Synthesis of Compound 10

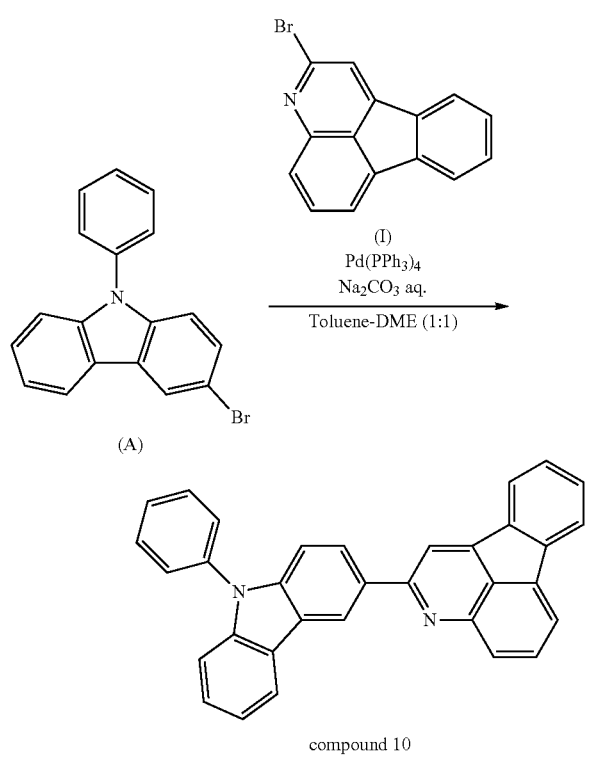

compound 10

In an experiment according to the same method as in Synthesis Example 1, except that the starting compound (A) and the compound (I) obtained according to a known method (for example, see WO2008/078824, p. 68) were used, the compound 10 was obtained. As a result of mass spectrometry, m/e=444 with respect to the molecular weight 444 of the compound 10.

Example 1

Production and Evaluation of Organic EL Device

A glass substrate provided with an ITO transparent electrode which had a size of 25 mm×75 mm and a thickness of 1.1 mm (product of Geomatec Company) was cleaned by ultrasonic cleaning in isopropyl alcohol for 5 min and then UV ozone cleaning for 30 min. The thickness of the ITO transparent electrode was 100 nm.

The cleaned glass substrate having a transparent electrode line was mounted on a substrate holder in a vacuum vapor deposition apparatus. The following acceptor material (K-1) was vapor-deposited on the surface having the transparent electrode line formed thereon, so as to cover the transparent electrode to form an acceptor layer with a thickness of 5 nm. Successively after forming the acceptor layer, the following aromatic amine compound HT-1 was vapor-deposited to form a first hole transporting layer with a thickness of 220 nm. After the formation of the first hole transporting layer, the following compound HT-2 was vapor-deposited to form a second hole transporting layer with a thickness of 10 nm.

Next, on the second hole transporting layer, the compound 1 obtained in Synthesis Example 1 (host material) and the following compound RD-1 (dopant material) were co-deposited to form a co-deposited film with a thickness of 40 nm. The concentration of the compound RD-1 was 5.0% by mass. The co-deposited film functions as a light emitting layer.

With that, the following compound ET-1 (50% by mass) and a reducing dopant Liq(8-hydroxy-quinolinolato-lithium) (50% by mass) was dual-deposited on the light emitting layer to form thereon an ET-1 film with a thickness of 36 nm, thereby forming an electron transporting layer.

Next, LiF was vapor-deposited on the ET-1 film at a film-forming speed of 0.1 angstrom/min to form an LiF film with a thickness of 1 nm, thereby forming an electron injecting electrode (cathode).

A metal Al was vapor-deposited on the LiF film to form a metal Al film with a thickness of 80 nm as a metal Al cathode, thereby constructing an organic EL device.

(Evaluation of Organic EL Device)

The produced organic EL device was driven to emit light by direct current application thereto, and the driving voltage (V) at a current density of 10 mA/cm² was measured to evaluate the the external quantum efficiency (EQE). The results are shown in Table 1.

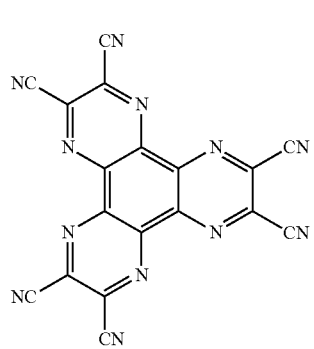

K-1

-continued

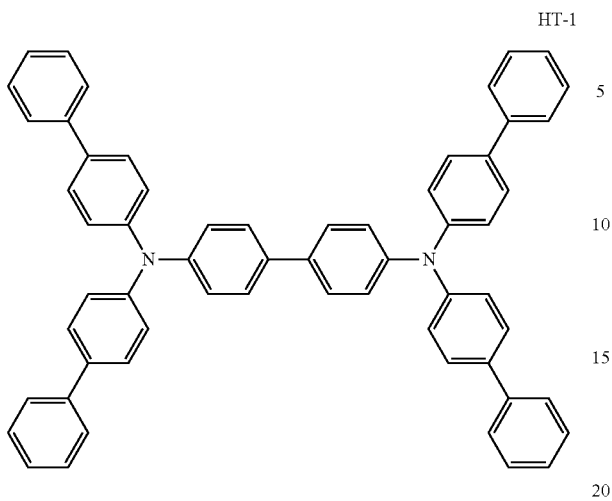
HT-1

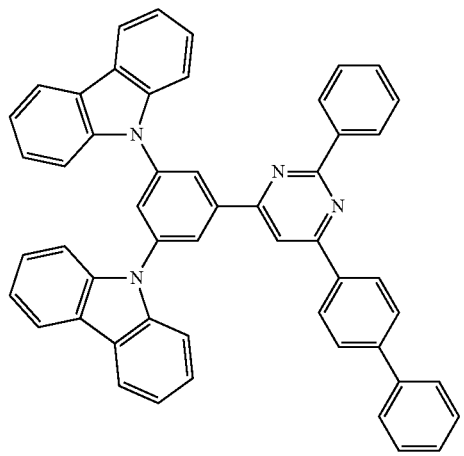
ET-1

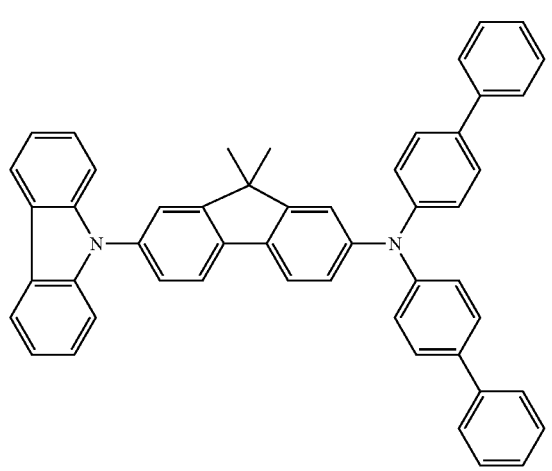
HT-2

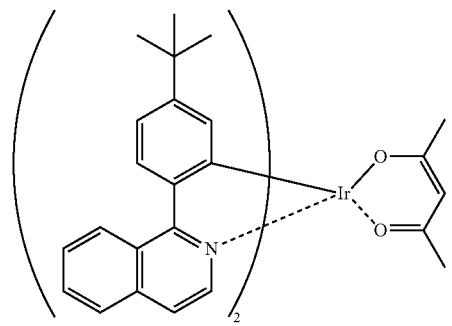
RD-1

Comparative Examples 1 and 2

Production of Organic EL Device

Organic EL devices were produced in the same manner as in Example 1 except that the compound listed in Table 1 was used in place of the compound 1 to form the light emitting layer.

The results in measurement of the driving voltage and the external quantum efficiency (EQE) are shown in Table 1.

TABLE 1

|  |  | Physical Properties | | Evaluation Results | |
| --- | --- | --- | --- | --- | --- |
|  | Host Material | Ionization Potential (eV) | Electron Affinity Af (eV) | Driving Voltage (V) | EQE (%) |
| Example 1 | Compound 1 | 5.61 | 2.97 | 4.61 | 15.4 |
| Comparative Example 1 | Comparative Compound 1 | 5.92 | 3.25 | 6.17 | 7.2 |
| Comparative Example 2 | Comparative Compound 2 | 5.64 | 2.91 | 4.99 | 10.9 |

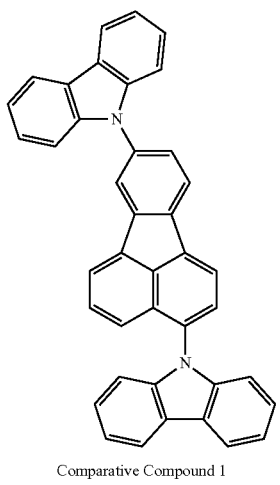 [SMILES: c1cc2c3c(ccc(-n4c5ccccc5c5ccccc54)c3c1)-c1ccc(-n3c4ccccc4c4ccccc43)cc1-2]
Comparative Compound 1

TABLE 1-continued

| | Physical Properties | | Evaluation Results | |
|---|---|---|---|---|
| Host Material | Ionization Potential (eV) | Electron Affinity Af (eV) | Driving Voltage (V) | EQE (%) |

Comparative Compound 2

In Comparative Example 1 using the comparative compound 1 where two carbazolyl groups present as a substituent on the fluoranthene skeleton at the 9-position of the carbazolyl group, the driving voltage greatly increased and the external quantum efficiency drastically lowered as compared with Example 1.

As compared with the results in Example 1 using the compound 1 having one fluoranthene skeleton, the driving voltage greatly increased and the external quantum efficiency drastically lowered in Comparative Example 2 using the comparative compound 2 having two fluoranthene skeletons.

The reason for the above-mentioned results could be presumed as follows. That is, the compound (comparative compound 1) having two carbazole skeletons each bonding to fluoranthene at the 9-position of the carbazole, like the comparative compound 1, tends to have a deep (large) ionization potential (Ip) (the ionization potential of the comparative compound 1 is around 6.0 eV), and therefore it is presumed that the hole injecting performance thereof may lower to break down the carrier balance and the driving voltage would increase to lower the emission efficiency. The compound having two fluoranthene skeletons (comparative compound 2) has a deep (large) ionization potential and tends to have a shallow (small) electron affinity (Af) and, in addition, the hole injecting performance and the electron injecting performance thereof lower, as compared with that of the compound having one fluoranthene skeleton like the compound 1, and therefore it is presumed that the driving voltage would increase and the emission efficiency would lower.

REFERENCE SIGNS LIST

1 Organic Electroluminescence Device
2 Substrate
3 Anode
4 Cathode
5 Phosphorescent Light Emitting Layer
6 Hole Transporting Layer
7 Electron Transporting Layer
10 Organic Thin Film Layer

The invention claimed is:
1. A compound represented by formula (1-3):

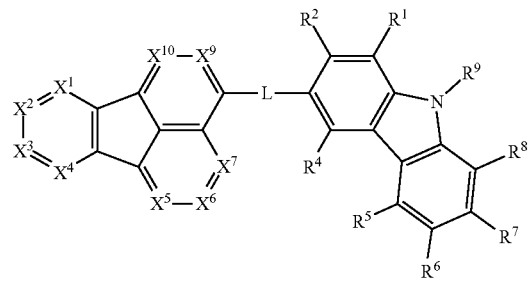

(1-3)

wherein $X^2$, $X^3$, $X^5$, $X^6$, $X^7$, and $X^9$ and $X^{10}$ each independently represent C—R where R represents a hydrogen atom, or a substituent;
$X^1$ and $X^4$ are each C—R wherein R is a hydrogen atom:
L represents a single bond, an unsubstituted phenylene group, an unsubstituted biphenylene group, an unsubstituted terphenylene group, an unsubstituted naphthalene group, or an unsubstituted pyrenylene group, wherein L does not comprise a heteroatom;
$R^1$ to $R^2$ and $R^4$ to $R^8$ each independently represent a hydrogen atom, a fluorine atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkylthio group having 1 to 20 carbon atoms, a substituted or unsubstituted arylthio group having 6 to 30 ring carbon atoms, a silyl group represented by —Si($R^{100}$)$_3$ where $R^{100}$ represents a hydrogen atom, an alkyl group having 1 to 30 carbon atoms, or an aromatic hydrocarbon group having 6 to 60 ring carbon atoms, three $R^{100}$'s may be the same or different, a substituted or unsubstituted alkylamino group having 2 to 30 carbon atoms, a substituted or unsubstituted aryl amino group having 6 to 60 ring carbon atoms, a substituted or unsubstituted and group having 6 to 30 ring carbon atoms, or a heteroaryl group selected from the group consisting of a pyrrolyl group, a furyl group, a thienyl group, a pyridyl group, an imidazopyridyl group, apyridazinyl group, apyrimidinyl group, apyrazinyl group, a triazinyl group, an imidazolyl group, an oxazolyl group, a thiazolyl group, a pyrazolyl group, an isoxazolyi group, an isothiazolyl group, an oxadiazolyl group, a thiadiazolyl group, a triazolyl group, a tetrazolyl group, an indolyl group, an isoindolyl group, a benzofuranyl group, an isobenzofuranyl group, a benzothiophenyl group, an isobenzothiophenyl group, an indolidinyl group, a quinolidinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, aphenoxazinyl group and axanthenyl group, which each may be substituted or unsubstituted;

R⁹ represents a substituted or unsubstituted aryl group having 6 to 30 ring carbon atoms, wherein R⁹ does not comprise a heteroatom; and, when R⁹ is a substituted aryl group, the substituent to the and group is selected from the group consisting of an alkyl group having 1 to 20 carbon atoms; a cycloalkyl group having 3 to 20 ring carbon atoms; an aryl group having 6 to 30 ring carbon atoms; an aralkyl group having 7 to 30 carbon atoms and having an aryl group having 6 to 30 ring carbon atoms; with the proviso that the compound of formula (1-3) comprises one fluoranthrene structure.

2. The compound according to claim 1, wherein R⁹ is a substituted or unsubstituted phenyl group, a substituted or unsubstituted biphenyly group, a substituted or unsubstituted terphenylyl group, a substituted or unsubstituted naphthyl group, a substituted or unsubstituted anthryl group, or a substituted or unsubstituted pyrenyl group.

3. A material for an organic electroluminescence device comprising the compound according to claim 1.

4. An organic electroluminescence device having plural organic thin film layers which includes a light-emitting layer between a cathode and an anode, wherein at least one layer of the organic thin film layers contains the compound according to claim 1.

5. The organic electroluminescence device according to claim 4, wherein the light emitting layer contains said compound.

6. The organic electroluminescence device according to claim 5, wherein the light emitting layer further contains a phosphorescent material.

7. The organic electroluminescence device according to claim 6, wherein the phosphorescent material is an ortho-metalated complex with a metal atom selected from the group consisting of iridium (Ir), osmium (Os) and platinum (Pt).

8. The organic electroluminescence device according to claim 4, which has an electron injecting layer between the cathode and the light emitting layer and wherein the electron injecting layer contains a nitrogen-containing cyclic derivative.

9. The organic electroluminescence device according to claim 4, which has a hole transporting layer between the anode and the light emitting layer and wherein the hole transporting layer contains an aromatic amine compound.

10. The organic electroluminescence device according to claim 9, wherein the hole transporting layer comprises two layers.

11. The organic electroluminescence device according to claim 9, which has an acceptor layer containing an acceptor material between the anode and the hole transporting layer.

12. The organic electroluminescence device according to claim 4, which contains a reducing dopant in the interface between the cathode and the organic thin film layer.

13. An electronic equipment comprising the organic electroluminescence device according to claim 4.

14. A compound of formula (1-5):

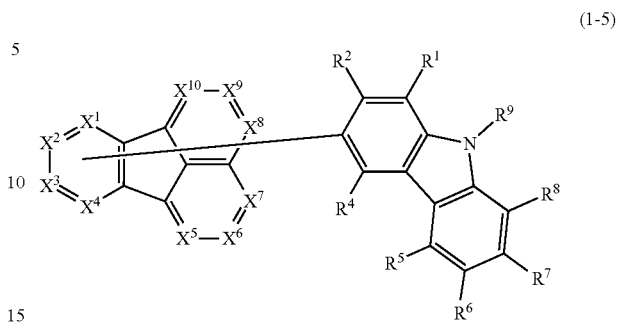

(1-5)

wherein $X^2$, $X^3$, and $X^5$ to $X^{10}$ each independently represent C—R where R represents a hydrogen atom, a substituent or a single bond;
$X^1$ and $X^4$ are each C—R wherein R is a hydrogen atom;
$R^1$ to $R^2$ and $R^4$ to $R^8$ each independently represent a hydrogen atom, a fluorine atom, a substituted or unsubstituted alkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 30 ring carbon atoms, a substituted or unsubstituted alkyithio group having 1 to 20 carbon atoms, a substituted or unsubstituted arylthio group having 6 to 30 ring carbon atoms, a silyl group represented by —Si(R¹⁰⁰)₃ where $R^{100}$ represents a hydrogen atom, an alkyl group having 1 to 30 carbon atoms, or an aromatic hydrocarbon group having 6 to 60 ring carbon atoms, three $R^{100}$'s may be the same or different, a substituted or unsubstituted alkyiamino group having 2 to 30 carbon atoms, a substituted or unsubstituted arylamino group having 6 to 60 ring carbon atoms, a substituted or unsubstituted aryl group having 6 to 30 ring carbon atoms, or a heteroaryl group selected from the group consisting of a pyrrolyl group, a furyl group, a thienyl group, a pyndyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isomdolyl group, a benzofuranyl group, an isobenzofuranyl group, a benzothiophenyl group, an isobenzothiophenyl group, an indolidinyl group, a quinolidinyl group, a qumolyl group, an isoquinolyl group, a cinnolyl group, a phthalazinyl group, a quinazolinyl group, a quinoxahnyl group, a benzimidazolyl group, a benzoxazolyl group, a benzothiazolyl group, an indazoivl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group and axanthenyl group, which each may be substituted or unsubstituted;
R⁹ represents a substituted or unsubstituted aryl group having 6 to 30 ring carbon atoms wherein R⁹ does not comprise a heteroatom and, when R⁹ is a substituted aryl group, the substituent to the aryl group is selected from the group consisting of an alkyl group having 1 to 20 carbon atoms; a cycloalkyl group having 3 to 20 ring carbon atoms; an aryl group having 6 to 30 ring carbon atoms; an aralkyl group having 7 to 30 carbon atoms and having an aryl group having 6 to 30 ring carbon atoms; with the proviso that the compound of formula (1-5) comprises one fluoranthrene structure.

15. The compound according to claim 14, which is represented by the following formula (1-9):

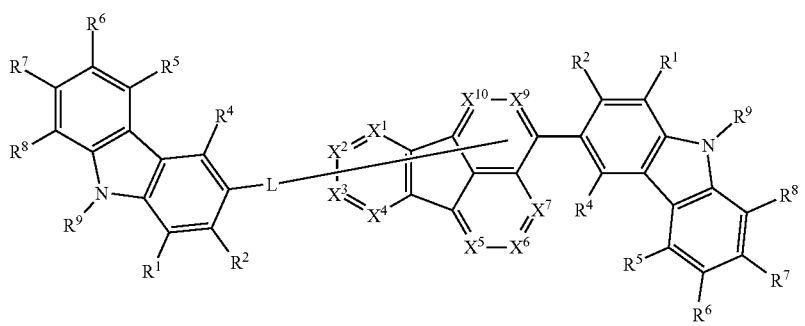

(1-9)

wherein L represents a single bond, a substituted or unsubstituted arylene group having 6 to 30 ring carbon atoms, a substituted or unsubstituted heteroarylene group having 5 to 30 ring carbon atoms, or a divalent group composed of 2 to 4 of the arylene group and the heteroarylene group bonding to each other;

$X^1$ to $X^7$, $X^9$ to $X^{10}$, $R^1$ to $R^2$ and $R^4$ to $R^9$ are the same as those defined with respect to claim 14, with the proviso that the compound of formula (1-9) comprises one fluoranthrene structure.

16. The compound according to claim 14, which is represented by the following formula (1-10):

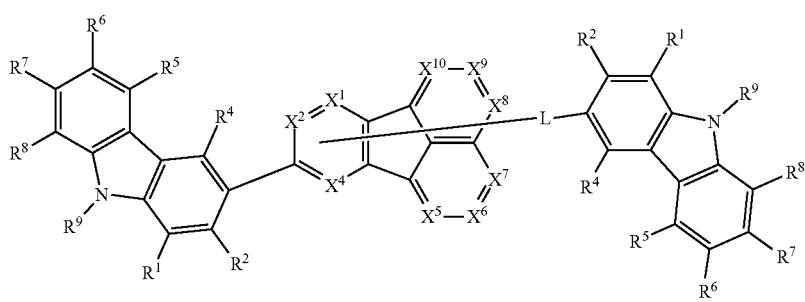

(1-10)

wherein L represents a single bond, a substituted or unsubstituted arylene group having 6 to 30 ring carbon atoms, a substituted or unsubstituted heteroarylene group having 5 to 30 ring carbon atoms, or a divalent group composed of 2 to 4 of the arylene group and the heteroarylene group bonding to each other;

$X^1$ to $X^2$, $X^4$ to $X^{10}$, $R^1$ to $R^2$ and $R^4$ to $R^9$ are the same as those defined with respect to claim 14, with the proviso that the compound of formula (1-10) comprises one fluoranthrene structure.

17. The compound according to claim 1, wherein R is selected from the group consisting of an alkyl group having 1 to 20 carbon atoms; a cycloalkyl group having 3 to 20 ring carbon atoms; an aryl group having 6 to 30 ring carbon atoms; an aralkyl group having 7 to 30 carbon atoms and having an aryl group having 6 to 30 ring carbon atoms; an amino group; a mono- or dialkylamino group having an alkyl group having 1 to 20 carbon atoms; a mono- or diarylamino group having an aryl group having 6 to 30 ring carbon atoms; an alkoxy group having an alkyl group having 1 to 30 carbon atoms; an aryloxy group having an aryl group having 6 to 30 ring carbon atoms; a mono-, di- or tri-substituted silyl group having a group selected from an alkyl group having 1 to 20 carbon atoms and an aryl group having 6 to 30 ring carbon atoms; a heteroaryl group having 5 to 30 ring carbon atoms and containing 1 to 5 hetero atoms; a haloalkyl group having 1 to 20 carbon atoms; a halogen atom; a cyano group; and a nitro group.

18. The compound of claim 1, wherein $R^9$ is an unsubstituted aryl group having 6 to 30 ring atoms.

19. The compound of claim 1, wherein $R^9$ is a substituted or unsubstituted phenyl group, and when $R^9$ is a substituted phenyl group, the substituent to the phenyl group is selected from the group consisting of an alkyl group having 1 to 20 carbon atoms; a cycloalkyl group having 3 to 20 ring carbon atoms; an aryl group having 6 to 30 ring carbon atoms; an aralkyl group having 7 to 30 carbon atoms and having an aryl group having 6 to 30 ring carbon atoms.

20. The compound of claim 19, wherein $R^9$ is an unsubstituted phenyl group.

21. The compound of claim 14, wherein $R^9$ is an unsubstituted aryl group having 6 to 30 ring atoms.

22. The compound of claim 14, wherein $R^9$ is a substituted or unsubstituted phenyl group, and when $R^9$ is a substituted phenyl group, the substituent to the phenyl group is selected from the group consisting of an alkyl group having 1 to 20 carbon atoms; a cycloalkyl group having 3 to 20 ring carbon atoms; an aryl group having 6 to 30 ring carbon atoms; an aralkyl group having 7 to 30 carbon atoms and having an aryl group having 6 to 30 ring carbon atoms.

23. The compound of claim 22, wherein $R^9$ is an unsubstituted phenyl group.

24. An organic electroluminescence device having plural organic thin film layers which includes a light-emitting layer between a cathode and an anode, wherein at least one layer of the organic thin film layers contains the compound according to claim 14.

25. The organic electroluminescence device according to claim 24, wherein the light emitting layer contains said compound.

26. The organic electroluminescence device according to claim 25, wherein the light emitting layer further contains a phosphorescent material.

27. The organic electroluminescence device according to claim 26, wherein the phosphorescent material is an ortho-metalated complex with a metal atom selected from the group consisting of iridium (Ir), osmium (Os) and platinum (Pt).

28. The organic electroluminescence device according to claim 24, which has an electron injecting layer between the cathode and the light emitting layer and wherein the electron injecting layer contains a nitrogen-containing cyclic derivative.

29. The organic electroluminescence device according to claim 24, which has a hole transporting layer between the anode and the light emitting layer and wherein the hole transporting layer contains an aromatic amine compound.

30. The organic electroluminescence device according to claim 29, wherein the hole transporting layer comprises two layers.

31. The organic electroluminescence device according to claim 29, which has an acceptor layer containing an acceptor material between the anode and the hole transporting layer.

32. The organic electroluminescence device according to claim 24, which contains a reducing dopant in the interface between the cathode and the organic thin film layer.

* * * * *